US009759725B2

(12) United States Patent
Nelson et al.

(10) Patent No.: US 9,759,725 B2
(45) Date of Patent: Sep. 12, 2017

(54) TREATMENT-INDUCED DAMAGE TO THE TUMOR MICRO-ENVIRONMENT PROMOTES CANCER THERAPY RESISTANCE THROUGH EXTRACELLULAR PROTEINS

(71) Applicant: Fred Hutchinson Cancer Research Center, Seattle, WA (US)

(72) Inventors: Peter S. Nelson, Seattle, WA (US); Yu Sun, Lynnwood, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 14/418,789

(22) PCT Filed: Aug. 2, 2013

(86) PCT No.: PCT/US2013/053425
§ 371 (c)(1),
(2) Date: Jan. 30, 2015

(87) PCT Pub. No.: WO2014/022774
PCT Pub. Date: Feb. 6, 2014

(65) Prior Publication Data
US 2015/0309037 A1 Oct. 29, 2015

Related U.S. Application Data

(60) Provisional application No. 61/678,972, filed on Aug. 2, 2012.

(51) Int. Cl.
A61K 48/00 (2006.01)
G01N 33/574 (2006.01)
A61K 31/00 (2006.01)
C12N 15/113 (2010.01)
C12Q 1/68 (2006.01)

(52) U.S. Cl.
CPC ....... *G01N 33/57488* (2013.01); *A61K 31/00* (2013.01); *C12N 15/113* (2013.01); *C12Q 1/6886* (2013.01); *G01N 33/57434* (2013.01); *G01N 33/57492* (2013.01); *C12N 2310/14* (2013.01); *C12N 2310/531* (2013.01); *C12Q 2600/118* (2013.01); *C12Q 2600/158* (2013.01); *G01N 2800/44* (2013.01); *G01N 2800/52* (2013.01); *G01N 2800/60* (2013.01)

(58) Field of Classification Search
CPC ...................................................... A61K 48/00
See application file for complete search history.

(56) References Cited

U.S. PATENT DOCUMENTS

2008/0267951 A1* 10/2008 You ................... A61K 31/00
424/133.1
2009/0075299 A1 3/2009 Mathew
2009/0285832 A1 11/2009 Teh
2011/0064739 A1 3/2011 Borlak
2011/0152106 A1 6/2011 Lee

OTHER PUBLICATIONS

International Search Report and Written Opinion of the International Searching Authority, mailed Nov. 1, 2013, in corresponding International Patent Application No. PCT/US2013/053425, filed Aug. 2, 2013, 12 pages.
Sun, J., et al., "Treatment-induced damage to the tumor microenvironment promotes prostate cancer therapy resistance through WNT16B," Nature Medicine 18(9)1359-1368, Aug. 5, 2012.

* cited by examiner

*Primary Examiner* — Kimberly Chong
(74) *Attorney, Agent, or Firm* — Christensen O'Connor Johnson Kindness PLLC

(57) ABSTRACT

The present disclosure provides methods for determining the effectiveness of a cancer therapy, as well as methods for increasing the effectiveness of that therapy and determining a prognosis for a patient receiving that therapy.

5 Claims, 88 Drawing Sheets

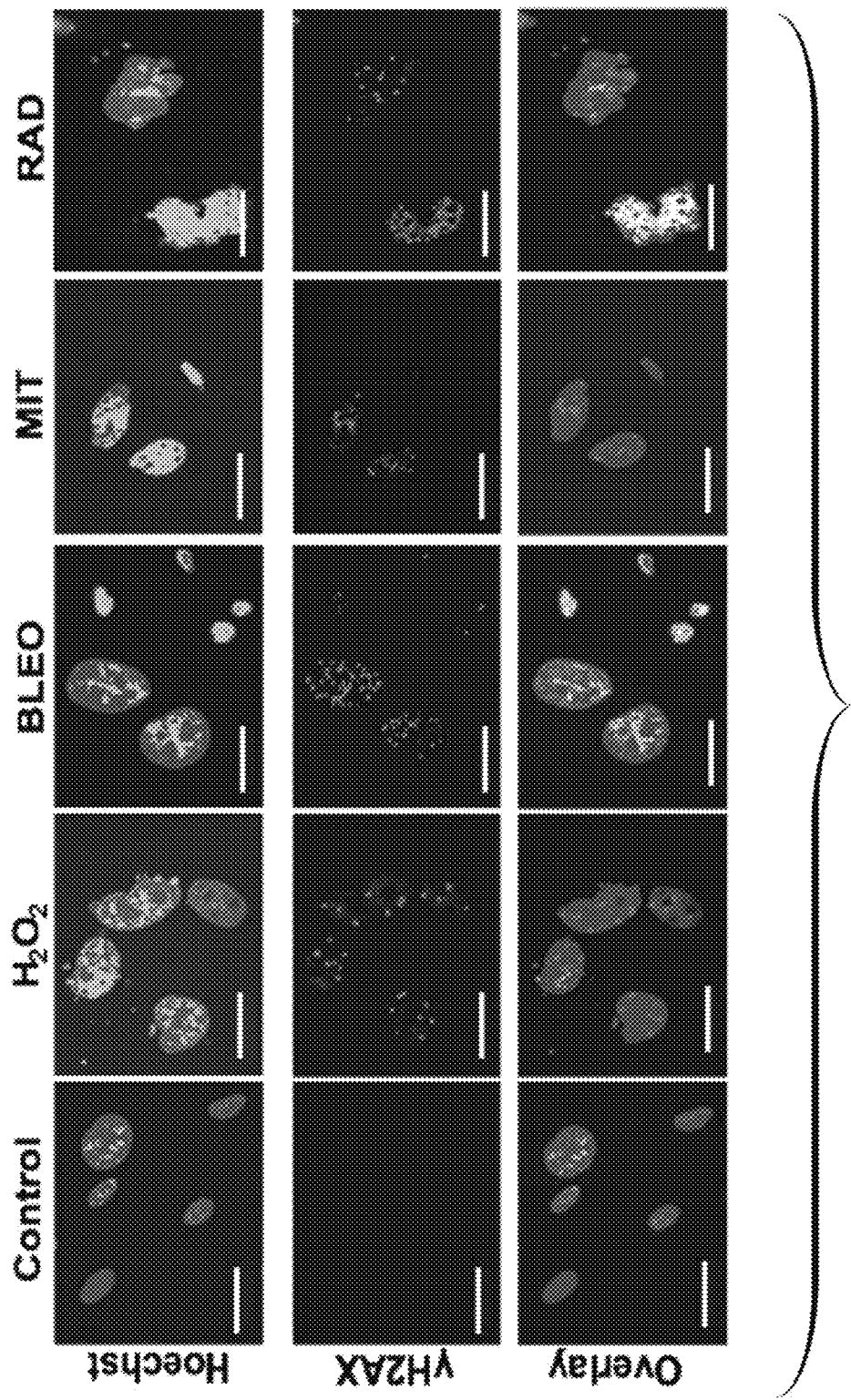

HBF1203
(Breast Fibroblast)

OVF28901
(Ovary Fibroblast)

PSC27
(Prostate Fibroblast)

PC3
(Prostate Epithelium)

TREATMENT-INDUCED DAMAGE TO THE TUMOR MICRO-ENVIRONMENT PROMOTES CANCER THERAPY RESISTANCE THROUGH EXTRACELLULAR PROTEINS

RELATED APPLICATIONS

The present application claims the benefit of U.S. provisional application Ser. No. 61/678,972, filed Aug. 2, 2012, the content of which is incorporated herein in its entirety.

STATEMENT OF GOVERNMENT LICENSE RIGHTS

This invention was made with government support under grant number CA126540 awarded by the National Institutes of Health. The government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 42895_SEQ_Final_2013-07-22.txt. The text file is 8 KB; was created on Jul. 22, 2013; and is being submitted via EFS-Web with the filing of the specification.

FIELD OF THE INVENTION

The present disclosure provides methods for enhancing the effectiveness of a cancer therapeutic by inhibiting the activity of a gene that encodes an extracellular protein, wherein after genotoxic treatment the gene is expressed at a level at least 3.5 fold above the level of expression without the genotoxic treatment. The extracellular proteins are collectively termed herein DNA damage secretory program (DDSP) polypeptides or proteins. In another embodiment the invention provides a method for determining a prognosis of cancer in a patient administered a genotoxic agent by observing expression changes in the production of extracellular proteins in the tumor microenvironment. By observing up regulation or down regulation of specified extracellular proteins, both the effectiveness of the genotoxic agent and a prognosis of cancer can be determined.

BACKGROUND

A major impediment to more effective cancer treatment is the ability of tumors to acquire resistance to cytotoxic and cytostatic therapeutics, a development that contributes to treatment failures exceeding 90% in patients with metastatic carcinomas (Longley and Johnston, *J. Pathol.* 205:272-292, 2005). Efforts focused on circumventing cellular survival mechanisms after chemotherapy have defined systems that modulate the import, export or metabolism of drugs by tumor cells (Wang et al., *Proc. Natl. Acad. Sci. USA* 101: 3089-3094, 2004; Schmitt et al., *Nat. Med.* 6:1029-1035, 2000; Helmrich et al., *Ocogene* 24:4174-4182, 2005; Redmond et al., *Front. Biosci.* 13:5138-5154, 2008; Wilson et al., *Ann. Oncol.* 17(Suppl.10):x315-x324. 2006). Enhanced damage repair and modifications to apoptotic and senescence programs also contribute to de novo or acquired tolerance to anti-neoplastic treatments (Schmitt et al., *Nat. Med.* 6:1029-1035, 2000; Lee and Schmitt, *Curr. Opin. Genet. Dev.* 13:90-96, 2003; Sakai et al., *Nature* 451:1116-1120, 2008). In addition, the finding that ex vivo assays of sensitivity to chemotherapy do not accurately predict responses in vivo indicate that tumor microenvironments also contribute substantially to cellular viability after toxic insults (Kobayashi et al., *Proc. Natl. Acad. Sci. USA* 90:3294-3298, 1993; Waldman et al., *Nat. Med.* 3:1034-1036, 1997; Samson et al., *J. Clin. Oncol.* 22:3618-3630, 2004). For example, cell adhesion to matrix molecules can affect life and death decisions in tumor cells responding to damage (Croix et al., *J. Natl. Cancer Inst.* 88:1285-1296, 1996; Kerbel, *Cancer Metastasis Rev.* 20:1-2, 2001; Wang et al., *J. Natl. Cancer Inst.* 94: 1494-1503, 2002). Further, the spatial organization of tumors relative to the vasculature establishes gradients of drug concentration, oxygenation, acidity and states of cell proliferation, each of which may substantially influence cell survival and the subsequent tumor repopulation kinetics (Kim and Tannnock, *Nat. Rev. Cancer* 5:516-525, 2005; Tredan et al., *J. Natl. Cancer Inst.* 99:1441-1454, 2007).

Most cytotoxic agents selectively target cancers by exploiting differential tumor cell characteristics, such as high proliferation rates, hypoxia and genome instability, resulting in a favorable therapeutic index. However, cancer therapies also affect benign cells and can disrupt the normal function and physiology of tissues and organs. To avoid host lethality, most anticancer regimens do not rely on single overwhelming treatment doses: both radiation and chemotherapy are administered at intervals to allow the recovery of vital normal cell types. However, gaps between treatment cycles also allow tumor cells to recover, activate and exploit survival mechanisms and resist subsequent therapeutic insults.

Here it is demonstrated that treatment-associated DNA damage responses in benign cells comprising the tumor microenvironment promote therapy resistance and subsequent tumor progression. Evidence of treatment-induced alterations in tumor stroma is provided that include the expression of a diverse spectrum of secreted cytokines and growth factors. Among these, the present disclosure shows that WNT16B is activated in fibroblasts through NF-κB and promotes an epithelial to mesenchymal transition (EMT) in neoplastic prostate epithelium through paracrine signaling. Further, WNT16B, acting in a cell non-autonomous manner, promotes the survival of cancer cells after cytotoxic therapy. In additional embodiments it is demonstrated that secreted fizzled-related protein 2 (SFRP2), serine peptidase inhibitor (Kazal type 1) (SPINK1), and glial cell derived neurotrophic factor (GDNF) are activated in the tumor microenvironment and are targets for intervention for improving cancer therapeutics. As such, the inventors provide herein methods targeting constituents of the tumor microenvironment in conjunction with conventional cancer therapeutics to enhance treatment responses.

SUMMARY

The present disclosure provides methods for determining the effectiveness of a cancer therapy, as well as methods for increasing the effectiveness of that therapy and determining the prognosis of a patient receiving that therapy. In one embodiment, the disclosure provides a method for enhancing the effectiveness of a cancer therapeutic by administering an agent that inhibits the activity of a gene encoding an extracellular polypeptide protein that is increased subsequent to treatment of a patient with a cancer therapeutic. In certain embodiment the cancer therapeutic is a genotoxic agent. Further, the extracellular polypeptide or protein can be at least one of matrix metallopeptidase 1 (interstitial collagenase) (MMP1), Wingless-type MMTV integration site family member 16B (WNT16B), secreted fizzled-related protein 2 (SFRP2), matrix metallopeptidase 12 (MMP12), serine peptidase inhibitor (Kazal type 1) (SPINK1), matrix metallopeptidase 10 (stromelysin 2) (MMP10), ectonucleotide pyrophosphatase/phosphodiesterase 5 (ENPP5), epiregulin (EREG), bone morphogenic protein 6 (BMP6), angiopoietin-like 4 (ANGPTL4), chondroitin sulfate N-acetylgalactosaminyltransferase (CSGALNACT), chemokine (C-C motif) ligand 26 (CCL26), ampiregulin (AREG), angioplastin 1 (ANGPT1), cholecystokinin (CCK), thrombomodulin (THBD), chemokine (C-X-C motif) ligand 14 (CXCL14), novoblastoma overexpressed protein (NOV), galanin prepropeptide (GAL), natriuretic peptide C (NPPC), family with sequence similarity 150, member B (FAM150B), cystatin SN (CST1), glial cell derived neurotrophic factor (GDNF), mucin-like 1 (MUCL1), neuronal pentaraxin II (NPTX2), transmembrane protein 155 (TMEM155), endothelin 1 (EDN1), pregnancy specific beta-1-glycoprotein 9 (PSG9), ADAM metallopeptidease with thrombospondin type 1 motif, 3 (ADAMTS3), CD24, pro-platelet basic protein (chemokine (C-X-C motif) ligand 7) (PPBP), chemokine (C-X-C motif) ligand 3 (CXCL3), matrix metallopeptidase 3 (stromelysin 1, progelatinase (MMP3), cystatin SA (CST2), pregnancy specific beta-1-glycoprotein 8 (PSG8), procollagen C-endopeptidase enhancer 2 (PCOLCE2), pregnancy specific beta-1-glycoprotein 7 (PSG7), tumor necrosis factor (ligand) superfamily, member 15 (TNFSF15), chromosome 17 open reading frame 67 (C17orf17), calcitonin-related polypeptide alpha (CALCA), fibroblast growth factor 18 (FGF18), bone morphogenic protein 2 (BMP2), matrilin 3 (MATN3), transferring pseudogene 1 (TFP1), serpin peptidase inhibitor, clade 1, member 1 (neuroserpin) (SERPINI1), tumor necrosis factor receptor superfamily, member 25 (TNFRSF25), or interleukin 23, alpha subunit p19 (IL23A). In a particular embodiment the at least one extracellular protein is selected from Wingless-type MMTV integration site family member 16B (WNT16B), secreted fizzled-related protein 2 (SFRP2), serine peptidase inhibitor (Kazal type 1) (SPINK1), and glial cell derived neurotrophic factor (GDNF).

In another embodiment, the present disclosure provides a method for determining the effectiveness of a cancer therapeutic in a patient comprising: i) obtaining a sample of a tumor microenvironment from the patient; ii) measuring the level of expression of at least one extracellular protein in the sample; and iii) assessing whether the level of the at least one extracellular protein is increased as compared with a control sample; wherein a decreased or unchanged level of the at least one extracellular protein is indicative of effectiveness of the cancer therapeutic and wherein an increased level of the at least one extracellular protein is indicative of a decreased effectiveness of the cancer therapeutic. In a particular embodiment provided herein the cancer therapeutic is a genotoxic agent. Further, the at least one extracellular protein is matrix metallopeptidase 1 (interstitial collagenase) (MMP1), Wingless-type MMTV integration site family member 16B (WNT16B), secreted fizzled-related protein 2 (SFRP2), matrix metallopeptidase 12 (MMP12), serine peptidase inhibitor (Kazal type 1) (SPINK1), matrix metallopeptidase 10 (stromelysin 2)(MMP10), ectonucleotide pyrophosphatase/phosphodiesterase 5 (ENPP5), epiregulin (EREG), bone morphogenic protein 6 (BMP6), angiopoietin-like 4 (ANGPTL4), chondroitin sulfate N-acetylgalactosaminyltransferase (CSGALNACT), chemokine (C-C motif) ligand 26 (CCL26), ampiregulin (AREG), angioplastin 1 (ANGPT1), cholecystokinin (CCK), thrombomodulin (THBD), chemokine (C-X-C motif) ligand 14 (CXCL14), novoblastoma overexpressed protein (NOV), galanin prepropeptide (GAL), natriuretic peptide C (NPPC), family with sequence similarity 150, member B (FAM150B), cystatin SN (CST1), glial cell derived neurotrophic factor (GDNF), mucin-like 1 (MUCL1), neuronal pentaraxin II (NPTX2), transmembrane protein 155 (TMEM155), endothelin 1 (EDN1), pregnancy specific beta-1-glycoprotein 9 (PSG9), ADAM metallopeptidease with thrombospondin type 1 motif, 3 (ADAMTS3), CD24, pro-platelet basic protein (chemokine (C-X-C motif) ligand 7) (PPBP), chemokine (C-X-C motif) ligand 3 (CXCL3), matrix metallopeptidase 3 (stromelysin 1, progelatinase (MMP3), cystatin SA (CST2), pregnancy specific beta-1-glycoprotein 8 (PSG8), procollagen C-endopeptidase enhancer 2 (PCOLCE2), pregnancy specific beta-1-glycoprotein 7 (PSG7), tumor necrosis factor (ligand) superfamily, member 15 (TNFSF15), chromosome 17 open reading frame 67 (C17orf17), calcitonin-related polypeptide alpha (CALCA), fibroblast growth factor 18 (FGF18), bone morphogenic protein 2 (BMP2), matrilin 3 (MATN3), transferring pseudogene 1 (TFP1), serpin peptidase inhibitor, clade 1, member 1 (neuroserpin) (SERPINI1), tumor necrosis factor receptor superfamily, member 25 (TNFRSF25), or interleukin 23, alpha subunit p19 (IL23A). In a particular embodiment the at least one extracellular protein is WNT16B, secreted fizzled-related protein 2 (SFRP2), serine peptidase inhibitor (Kazal type 1) (SPINK1), and/or glial cell derived neurotrophic factor (GDNF).

In yet another embodiment the present disclosure provides a method for determining a prognosis in a cancer patient treated with a cancer therapeutic; comprising: i) obtaining a sample of a tumor microenvironment from the patient; ii) measuring the level of expression of at least one extracellular protein in the sample; and iii) assessing whether the level of the at least one extracellular protein is increased as compared with a control sample; wherein a decreased or unchanged level of expression of the at least one extracellular protein is determinant of a more favorable or better prognosis, a longer survival period, and wherein an increase in the expression of the at least one extracellular protein is determinant of a less favorable prognosis and/or shorter period of survival. In certain embodiments disclosed herein the cancer therapeutic is a genotoxic agent. Further, the at least one extracellular protein can be matrix metallopeptidase 1 (interstitial collagenase) (MMP1), Wingless-type MMTV integration site family member 16B (WNT16B), secreted fizzled-related protein 2 (SFRP2), matrix metallopeptidase 12 (MMP12), serine peptidase inhibitor (Kazal type 1) (SPINK1), matrix metallopeptidase 10 (stromelysin 2)(MMP10), ectonucleotide pyrophosphatase/phosphodiesterase 5 (ENPP5), epiregulin (EREG), bone morphogenic protein 6 (BMP6), angiopoietin-like 4 (ANGPTL4), chondroitin sulfate N-acetylgalactosaminyltransferase (CSGALNACT), chemokine (C-C motif) ligand 26 (CCL26), ampiregulin (AREG), angioplastin 1 (ANGPT1), cholecystokinin (CCK), thrombomodulin (THBD), chemokine (C-X-C motif) ligand 14 (CXCL14), novoblastoma overexpressed protein (NOV), galanin prepropeptide (GAL), natriuretic peptide C (NPPC), family with sequence similarity 150, member B (FAM150B), cystatin SN (CST1), glial cell derived neurotrophic factor (GDNF), mucin-like 1 (MUCL1), neuronal pentaraxin II (NPTX2), transmembrane protein 155 (TMEM155), endothelin 1 (EDN1), pregnancy specific beta-1-glycoprotein 9 (PSG9), ADAM metallopeptidease with thrombospondin type 1 motif, 3 (ADAMTS3), CD24, pro-platelet basic protein (chemokine (C-X-C motif) ligand 7) (PPBP), chemokine (C-X-C motif) ligand 3 (CXCL3), matrix metallopeptidase 3 (stromelysin 1, progelatinase (MMP3), cystatin SA (CST2), pregnancy specific beta-1-glycoprotein 8 (PSG8), procollagen C-endopeptidase enhancer 2 (PCOLCE2), pregnancy specific beta-1-glycoprotein 7 (PSG7), tumor necrosis factor (ligand) superfamily, member 15 (TNFSF15), chromosome 17 open reading frame 67 (C17orf17), calcitonin-related polypeptide alpha (CALCA), fibroblast growth factor 18 (FGF18), bone morphogenic protein 2 (BMP2), matrilin 3 (MATN3), transferring pseudogene 1 (TFP1), serpin peptidase inhibitor, clade 1, member 1 (neuroserpin) (SERPINI1), tumor necrosis factor receptor superfamily, member 25 (TNFRSF25), or interleukin 23, alpha subunit p19 (IL23A). In a particular embodiment the at least one extracellular protein is WNT16B, secreted fizzled-related protein 2 (SFRP2), serine peptidase inhibitor (Kazal type 1) (SPINK1), and/or glial cell derived neurotrophic factor (GDNF).

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A. Schematic of the prostate cancer treatment regimen comprising a pretreatment prostate biopsy and four cycles of neoadjuvant DOC and MIT chemotherapy followed by radical prostatectomy. FIG. 1B. DNA damage foci in human prostate tissues collected before and after chemotherapy. Tissue sections were probed with antibodies recognizing γ-H2AX (lighter signals), and nuclei were counterstained with Hoechst 33342. Gl, gland lumen; e, epithelium; s, stroma. Scale bars, 50 µm. FIG. 1C. Analysis of gene expression changes in prostate fibroblasts by transcript microarray quantification. The heatmap depicts the relative mRNA levels after exposure to $H_2O_2$, BLEO or RAD compared to vehicle-treated cells. Columns are replicate experiments. WNT16B is highlighted in bold for emphasis. FIG. 1D shows a robust induction of GDNF in prostate fibroblasts following DNA damage. FIG. 1E shows a robust induction of SPINK1 in prostate fibroblasts following DNA damage. FIG. 1F. Measurements of WNT16B expression by qRT-PCR in prostate fibroblasts. Shown are the log 2 transcript measurements before (Pre) or after exposure to the indicated factors relative to vehicle-treated control cells. Data are mean±s.d. of triplicates. The P value was calculated by analysis of variance (ANOVA) followed by t test. FIG. 1G. WNT16B protein expression in prostate PSC27 fibroblast extracellular conditioned medium (CM) or in cell lysates (IC) after genotoxic exposures. β-actin is a loading control. FIG. 1H. Immunohistochemical analysis of WNT16B expression in prostate fibroblasts before (Pre) and after exposure to MIT or RAD. Brown chromogen indicates WNT16B expression. Scale bars, 50 µm. FIG. 1I. Expression of Wnt family members in prostate fibroblasts after exposure to DNA-damaging agents. Transcript quantification was determined by microarray hybridization. Columns represent independent replicate experiments. WNT16B is listed in bold for emphasis. FIG. 1J. WNT16B expression by qRT-PCR in PSC27 fibroblasts and prostate cancer cell lines after the indicated genotoxic exposure relative to pretreatment transcript amounts. Data are mean±s.d.

FIGS. 2A through 2E demonstrate an analysis of DNA damage responses (DDR) in prostate fibroblasts following DNA damaging cancer therapy. FIG. 2A. Quantitation of DNA damage foci before (Pre) and after DNA damaging treatments. DDR foci identified by immunofluorescence staining for γ-H2AX (see FIG. 2B) were recorded according to a 4-category scale. Data were averaged from readings of 3 independent fields, each with a total count of 100 nuclei. * represent significant differences P<0.01 compared to untreated (Pre). FIG. 2B. Analysis of DNA damage foci formation in prostate fibroblasts upon exposure to various DNA damaging agents. PSC27 prostate fibroblasts were treated with $H_2O_2$, bleomycin (BLEO) or gamma-irradiation (RAD). Immunofluorescence staining for γ-H2AX (bright foci), with nuclei counterstained by Hoechst 33342 (light gray). Scale bar, 15 µm. FIG. 2C. Analysis of gene expression changes in prostate fibroblasts by microarray hybridization. The heatmaps depict the relative mRNA levels after exposure to hydrogen peroxide ($H_2O_2$), Bleomycin (BLEO) or ionizing radiation (RAD) compared to vehicle treated cells. FIG. 2D. WNT16B transcript levels in specific cell populations microdissected from prostate tissues before and after exposure to cytotoxic chemotherapy. Measurements are by qRT-PCR. Log 2 fold changes are shown relative to the lowest measurement of untreated benign prostate epithelium. Each data-point represents an individual patient sample. FIG. 2E. Transcript levels of WNT family members in microdissected human prostate stroma acquired before and after exposure to chemotherapy as quantitated by microarray hybridization. Columns represent individual patients. Values for each gene are mean-centered across all samples.

FIG. 3A. Chemotherapy-induced gene expression changes in human prostate-cancer-associated stroma measured by qRT-PCR of microdissected cells. The amounts of transcript before treatment (x axis) are plotted against the amounts of transcript after chemotherapy (y axis) from the same individual. Each data point represents the measurements from an individual patient. The results are shown as PCR cycle number relative to ribosomal protein L13 (RPL13), which served as the reference control. The P values were calculated by Student's t test. FIG. 3B. IHC assessment of prostate stromal WNT16B expression in prostatectomy tissue samples from men with prostate cancer who were either untreated (n=30) or treated with chemotherapy (n=50). Patients were assigned to four categories based on their stromal WNT16B staining: 0, no expression; 1, faint or equivocal expression; 2, moderate expression; 3, intense reactivity. P<0.0001 by ANOVA. FIG. 3C. Representative example of intense WNT16B expression in prostate stroma after in vivo exposure to MIT and DOC. The black arrows denote areas of the stroma with fibroblasts and smooth muscle. Note the minimal WNT16B reactivity in the epithelium (gray arrows). Scale bars, 50 µm. FIG. 3D. Kaplan-Meier plot of biochemical (prostate-specific antigen) relapse-free survival based on the expression of WNT16B in prostate stroma after exposure to MIT and DOC chemotherapy (P=0.04 by log-rank test comparing WNT16B<1 with WNT16B≥2 survival distributions). DFI, disease-free interval from surgery. FIGS. 3E and 3F. WNT16B staining of breast (FIG. 3E) and ovarian (FIG. 3F) carcinoma from patients receiving neoadjuvant chemotherapy or no treatment before surgical resection. Staining is recorded on a 4-point scale: 0, no expression; 1, faint or equivocal expression; 2, moderate expression; 3, intense reactivity. Scale bars, 50 µm. The P values were calculated by ANOVA.

FIGS. 4A and 4B. Human prostate fibroblasts (HSP27), and newly derived breast (HBF1203) and ovarian (OVF28901) primary fibroblast lines express stromal but not epithelial markers. FIG. 4A. Concurrent immunofluorescence staining using vimentin (dark grey) and cytokeratin 8 (light grey) antibodies with PC3 cells serving as a positive control for epithelial cells. Scale bar, 15 µm. FIG. 4B. Western immunoblot of stromal and epithelial cell lines confirming expression of mesenchymal and epithelial proteins, respectively. FIG. 4C. WNT16B expression is induced by DNA damage in most, but not all human fibroblast isolates: HBF1203 (breast), OVF28901 (ovary), HS5 (bone marrow) and HS27A (bone marrow). CM, conditioned media; IC, intracellular lysates. FIG. 4D. Systemic chemotherapy induces WNT16B expression in diverse murine organs. Each tissue type was collected after three mitoxantrone treatments administered over eight weeks.

FIG. 5A. Immunofluorescence confirmation of WNT16B in PSC27 cells engineered to alter WNT16B: (1) PSC27 vector control (PSC27C); (2) PSC27 cells expressing WNT16B (PSC27WNT16B); (3) PSC27WNT16B with non-specific shRNA; (4, 5) PSC27WNT16B cells with WNT16B-specific shRNAs. Scale bar, 25 µm. Below: conditioned medium from PSC27C (1); PSC27WNT16B (2); PSC27WNT16B with control shRNA (3); and (4, 5) PSC27WNT16B with WNT16B-specific shRNAs. FIG. 5B. WNT16B shRNAs suppress the induction of WNT16B following genotoxic stress induced by irradiation (RAD) or mitoxantrone (MIT). Conditioned medium from PSC27WNT16B cells promotes the migration FIG. 5C and invasion FIG. 5D of tumor cells (n=3 replicates). FIG. 5E. Fibroblast derived WNT16B promotes the growth of prostate carcinoma in vivo. Subrenal capsule grafts comprised of BPH1 prostate epithelial cells alone, in combination with PSC27C control fibroblasts, or in combination with PSC27WNT16B fibroblasts are shown. Dashed lines denote the size of the tumor outgrowth from the kidney capsule. FIG. 5F. Histology of subrenal capsule grafts comprised of BPH1 or PC3 prostate cells in combination with control fibroblasts (PSC27C), or fibroblasts expressing WNT16B (PSC27WNT16B). Dashed lines demarcate the tumor (T) from the kidney parenchyma (K). SV40 and CD44 IHC mark BPH1 and PC3 prostate epithelial cells respectively in the kidney grafts. Black arrows indicate epithelial cells invading into the kidney parenchyma. Scale bar, 150 µm.

FIG. 6A. Conditioned medium from WNT16B-expressing prostate fibroblasts (PSC27$^{WNT16B}$) promotes the proliferation of neoplastic prostate epithelial cells. shRNA$^C$, control shRNA; shRNA$^{WNT16B}$#1 and shRNA$^{WNT16B}$#2, WNT16B-specific shRNAs. FIG. 6B. Scratch assay showing the enhanced motility of PC3 cells exposed to conditioned medium from prostate fibroblasts expressing a control vector (PSC27$^C$) or fibroblasts expressing WNT16B (PSC27$^{WNT16B}$). Scale bars, 100 µm. FIG. 6C. The full fibroblast DDSP induced by radiation (PSC27-RAD) promotes the proliferation of tumorigenic prostate epithelial cells. The proliferative effect is significantly attenuated by the suppression of damage-induced expression of WNT16B (PSC27-RAD+shRNA$^{WNT16B}$). FIG. 6D. The full paracrine-acting fibroblast DDSP induced by radiation (PSC27-RAD) promotes the invasion of neoplastic epithelial cells. Invasion is significantly attenuated by the suppression of damage-induced expression of WNT16B (PSC27-RAD+shRNA$^{WNT16B}$). Data in FIG. 6A, FIG. 6C and FIG. 6D are mean±s.e.m. of triplicates, with P values calculated by ANOVA followed by t test. FIG. 6E. Schematic of the xenograft cell recombination experiment to assess the ability of fibroblasts expressing WNT16B to influence prostate tumorigenesis in vivo. PFC, prostate fibroblast cells; PC, prostate cancer cells. FIG. 6F. Prostate fibroblasts engineered to express WNT16B promote the growth of prostate carcinoma in vivo. Subrenal capsule grafts comprised of PC3 prostate epithelial cells alone, PC3 cells in combination with PSC27$^C$ control fibroblasts or PC3 cells in combination with PSC27$^{WNT16B}$ fibroblasts are shown. The green dashed lines denote the size of the tumor outgrowth from the kidney capsule. FIG. 6G. Irradiated prostate fibroblasts (PSC27-RAD) promote the growth of prostate carcinoma cells in vivo, and this effect is significantly attenuated by the suppression of fibroblast WNT16B using WNT16B-specific shRNAs (PSC27-RAD+shRNA$^{WNT16B}$) (P<0.05). Shown are tumor volumes 8 weeks after renal capsule implantation of PC3 and PSC27 cell grafts. In FIG. 6F and FIG. 6G, horizontal lines denote the mean of each group of eight tumors, and P values were determined by ANOVA followed by t test.

FIG. 7A. Assay of canonical Wnt pathway signaling through activation of a TCF/LEF luciferase reporter construct (TOPflash) or a control reporter (FOPflash). Epithelial cells were exposed to conditioned medium (CM) from PSC27 prostate fibroblasts expressing WNT16B (PSC27$^{WNT16B}$) or control vector (PSC27$^C$). Data are mean±s.e.m. of triplicates, and P values were determined by ANOVA followed by t test. FIG. 7B. qRT-PCR assessment of the expression of β-catenin target genes in prostate cancer cell lines (BPH1, M12 and PC3) before and 72 h after exposure to PSC27$^{WNT16B}$-conditioned medium. Data represent the mean±s.e.m. fold change after as compared to before exposure for three replicates. FIG. 7C. Expression of β-catenin target genes in human prostate cancers in vivo after neoadjuvant treatment with MIT and DOC. Log$_2$ transcript amounts in carcinoma cells after and before chemotherapy are shown in relation to low or high WNT16B expression in the prostate stroma. Each data point represents an individual patient; n=8 patients. Horizontal bars are group means. *P<0.05, **P<0.01 by ANOVA followed by t test. FIG. 7D. The β-catenin pathway inhibitor XAV939 suppresses the proliferation of prostate cancer cells in response to PSC27$^{WNT16B}$ CM and attenuates the response to the full DDSP in PSC27-RAD-conditioned medium. Cell numbers were determined 72 hours after treatment. FIG. 7E. Quantification of transcripts in neoplastic prostate epithelial cells encoding proteins associated with a phenotype of EMT. Measurements are from epithelial cells exposed to control media (DMEM), media conditioned by PSC27 fibroblasts (PSC27$^C$) or PSC27 fibroblasts expressing WNT16B (PSC27$^{WNT16B}$). E-cad, E-cadherin; N-cad, N-cadherin. FIG. 7F. Analysis of EMT-associated protein expression by Western Blot. M12 or PC3 cells were exposed to control media, media conditioned by PSC27 fibroblasts (PSC27$^C$), PSC27 fibroblasts expressing WNT16B (PSC27$^{WNT16B}$) or PSC27 fibroblasts expressing WNT16B and shRNA targeting WNT16B (PSC27$^{shRNA-WNT16B}$). FIG. 7G. Chromatin immunoprecipitation assays identified NF-κB binding sites within the proximal promoter of the WNT16 gene. PCR reaction products from Mock (no DNA loading), NF-κB immunoprecipitation, input control DNA and no antibody (Ab) control before treatment (Pre) and after irradiation (Rad). p1, p2 and p3 indicate primer pairs corresponding to putative NF-κB binding regions in WNT16, IL-6 and IL-8, respectively (see Example for the primer sequences). FIG. 7H. Analysis of WNT16B transcript expression by qRT-PCR in PSC27 prostate fibroblasts with (PSC27$^{IκBα}$) or without (PSC27$^C$) inhibition of NF-κB signaling before and after DNA-damaging exposures. FIG. 7I. Inhibition of NF-κB signaling in fibroblasts responding to DNA damage attenuates the effect of the DDSP on tumor cell proliferation. Cell numbers were determined 72 h after RAD exposure to conditioned medium from fibroblasts with (PSC27$^{IκBα}$) or without (PSC27$^C$) inhibition of NF-κB signaling. Data in FIG. 7D, FIG. 7E, FIG. 7H and FIG. 7I are mean±s.e.m. of triplicates, and P values were determined by ANOVA followed by t test.

FIG. 8A. Immunohistochemical assessment of WNT16B and β-catenin expression in human prostate cancers with and without exposure to chemotherapy. Arrows in β-catenin panels show minimal staining in cancer glands that is localized to the cytoplasm or plasma membrane in untreated tissues with intense nuclear localization in carcinoma cells following chemotherapy treatment. FIG. 8B. The β-catenin pathway inhibitor XAV939 suppresses the invasion of prostate cancer cells in response to fibroblast WNT16B and attenuates the response to the full DNA damage secretory program. Cell numbers were determined after 24 h of treatment. FIGS. 8C and 8D. Western immunoblot analysis of proteins associated with an epithelial to mesenchymal transition. BPH1 and PC3 prostate (FIG. 8C), MDA MD-231 breast (FIG. 8(d)) and SKOV3 ovarian (FIG. 8D) epithelial cells were treated with conditioned medium from prostate (PSC), breast (HBF) or ovarian (OVF) fibroblasts expressing a vector control (PSC27C), WNT16B (PSC27WNT16B), WNT16B with WNT16B-specific shRNAs, or WNT16B fibroblast conditioned medium with the 0-catenin pathway inhibitor XAV939.

FIG. 9A. Analysis of NFκB regulatory regions in the WNT16B promoter by site-directed mutagenesis. (Left) WNT16B promoter constructs for each of the 10 putative NFκB binding sites in the WNT16B promoter, denoted by −181 through −3838 bp upstream of the transcriptions start site. Black boxes=wild type sequence; White boxes=mutated NFκB binding sites. (Right) Corresponding WNT16B promoter activity with and without γ-irradiation in HEK293 cells. Data are mean±s.d., of normalized luciferase signals (n=3). WNT16B and NFkB promoter reporter assays with genotoxic stress FIG. 9B and TNF-α FIG. 9C. Multiple NFkB binding sites maximize WNT16B promoter activity in prostate fibroblasts following irradiation or exposure to TNF-α. Constructs shown in FIG. 9A were used in assays of PSC27 fibroblasts. NAT11-Luc2CP is a NFκB promoter positive control construct. FIG. 9D. Analysis of NFκB activity following genotoxic stress with mitoxantrone or irradiation. FIG. 9E. IκBα expression in PSC27 fibroblasts suppresses DNA damage-induced NFκB activation. Analysis of nuclear translocation of NFκB protein in prostate fibroblasts following irradiation with and without expression of mutant IκBα (PSC27IκBα). Pre=prior to irradiation; RAD=72 h post-irradiation. β-actin and Histone H1 represent resident cytoplasmic and nuclear protein controls, respectively.

FIG. 10A. Viability of prostate cancer cells 3 d after treatment with a half-maximal inhibitory concentration (IC$_{50}$) of MIT and medium conditioned by fibroblasts with (PSC27$^{WNT16B}$) or without (PSC27$^C$) WNT16B. FIG. 10B. Bright field microscopic view of PC3 cells cultured with control or PSC27$^{WNT16B}$-conditioned medium photographed 24 h after exposure to vehicle or the IC$_{50}$ of MIT. Arrowheads denote apoptotic cell bodies. Scale bars, 50 μm. FIG. 10C. Acute tumor cell responses to chemotherapy in vitro. Quantification of apoptosis by assays reflecting combined caspase 3 and 7 activity measured 24 h after the exposure of PC3 cells to vehicle or the IC$_{50}$ of MIT. Data in a and c are mean±s.e.m. of triplicate experiments, and P values were determined by ANOVA followed by t test. RLU, relative luciferase unit. FIG. 10D. In vivo responses of PC3 tumors to MIT chemotherapy. Grafts were comprised of PC3 cells alone or PC3 cells combined with either PSC27 prostate fibroblasts expressing a control vector (PC3+PSC27$^C$) or PSC27 prostate fibroblasts expressing WNT16B (PC3+PSC27$^{WNT16B}$). MIT was administered every 2 weeks for three cycles, and grafts were harvested and tumor volumes determined 1 week after the final MIT treatment. Each data point represents an individual xenograft. Horizontal lines are group means of ten tumors, with P values determined by ANOVA followed by t test. FIG. 10E. Acute tumor cell responses to chemotherapy in vivo. Quantification of apoptosis by cleaved caspase 3 (C-caspase 3) IHC and of DNA damage by γ-H2AX immunofluorescence in PC3 and fibroblast xenografts measured 24 h after in vivo treatment with vehicle (C) or MIT. Values represent a minimum of 100 cells counted from each of 3-5 tumors per group. Data are mean±s.e.m., and P values were determined by ANOVA followed by t test.

FIG. 11A. Viability of prostate cancer cells across a range of mitoxantrone concentrations with (PSC27WNT16B) or without (PSC27C) WNT16B in fibroblast conditioned medium. Non-linear regression curves were calculated and plotted using GraphPad Prism. FIG. 11B. Acute viability assays of epithelial cells following 12 h of exposure to IC$_{50}$ concentrations of mitoxantrone and conditioned medium from PSC27 fibroblasts expressing a control vector (PSC27C) or WNT16B (PSC27WNT16B). FIG. 11C. Tumor volumes of subrenal capsule grafts comprised of MDA-MB-231 breast carcinoma cells in combination breast fibroblasts (HBF1203) expressing a control vector (HBF1203C) or WNT16B (HBF1023WNT16B) with or without treatment with three cycles of mitoxantrone (MIT). Tumor grafts were harvested one week after the 3rd cycle of treatment. Depicted are typical grafts from each treatment group with tumor masses outlined by green dashed line. Each datapoint represents the volume of a tumor resected from an individual mouse.

FIG. 12A. Viability of prostate cancer cells across a range of MIT concentrations with (PSC27-RAD+shRNA$^{WNT16B}$) or without (PSC27-RAD+shRNA$^C$) the suppression of WNT16B in irradiated-fibroblast-conditioned medium or with the addition of the β-catenin pathway inhibitor XAV939. Data are mean±s.e.m. of triplicates. FIG. 12B. Viability of prostate cancer cells 3 days after treatment with two times the IC$_{50}$ of MIT in the context of conditioned medium from irradiated prostate fibroblasts (PSC27-RAD) expressing shRNAs targeting and suppressing WNT16B (shRNA$^{WNT16B}$), a vector control (shRNA$^C$) or combined with the β-catenin pathway inhibitor XAV939. FIG. 12C. Viability of prostate cancer cells 3 days after treatment with the IC$_{50}$ of MIT in the context of conditioned medium from prostate fibroblasts pretreated with radiation (PSC27-RAD) or MIT (PSC27-MIT) and with (PSC27$^{IκBα}$) or without (PSC27$^C$) the suppression of NF-κB signaling. FIG. 12D. Acute tumor cell responses to chemotherapy in vitro. Quantification of apoptosis by caspase 3 and 7 activity measured 24 hours after the exposure of PC3 cells to vehicle or the IC$_{50}$ of MIT. Data for FIG. 12B, FIG. 12C and FIG. 12D are mean±s.e.m. of triplicates, and P values were determined by ANOVA followed by t test. FIGS. 12E and 12F. In vivo effects of MIT chemotherapy in the context of suppressing the induction of the expression of fibroblast WNT16B. Tumors comprised PC3 cells in combination with irradiated (PSC27-RAD) fibroblasts, FIG. 12E, or unirradiated (PSC27$^C$), FIG. 12F, prostate fibroblasts expressing shRNAs targeting WNT16B (shRNA$^{WNT16B}$) or a vector control (shRNA$^C$). MIT was administered every 2 weeks for three cycles, and grafts were harvested and tumor volumes determined 1 week after the final treatment. Each data point represents an individual xenograft. Tumor volumes of PSC27$^C$+shRNA$^C$ grafts in FIG. 12F averaged 20 mm$^3$, and tumor volumes of PSC27$^C$+shRNA$^{WNT16B}$ grafts averaged 12 mm$^3$ (P<0.001). Horizontal lines are group means, with n=8. P values were determined by ANOVA followed by t test. The bracket boundaries in f are the group means for PSC27$^C$+shRNA$^C$ grafts compared to PSC27$^C$+shRNA$^{WNT16B}$ grafts showing a 40% difference in size. FIG. 12G. Model for cell non-autonomous therapy-resistance effects originating in the tumor microenvironment in response to genotoxic cancer therapeutics. The initial round of therapy engages an apoptotic or senescence response in subsets of tumor cells and activates a DNA damage response (DDR) in DDR-competent benign cells (+DDR) comprising the tumor microenvironment. The DDR includes a spectrum of autocrine- and paracrine-acting proteins that are capable of reinforcing a senescent phenotype in benign cells and promoting tumor repopulation through progrowth signaling pathways in neoplastic cells. Paracrine-acting secretory components such as WNT16B also promote resistance to subsequent cycles of cytotoxic therapy. CEC, cancer epithelial cell; BEC, benign epithelial cell; FC, fibroblast cell; –DDR, DDR-incompetent benign cells.

FIG. 13A. Viability assays of prostate carcinoma cells exposed to prostate fibroblast conditioned medium and mitoxantrone chemotherapy. Epithelial cells were treated with 1050 concentrations of mitoxantrone in conditioned medium from irradiated PSC27 (PSC27C-RAD) prostate fibroblasts expressing a control shRNA or WNT16B-specific shRNAs and irradiated, or with the addition of the β-catenin pathway inhibitor XAV939. Epithelial viability was determined by trypan blue counting of cells 72 hours after chemotherapy. Bars represent means of 3 replicate experiments. FIG. 13B. Viability assays of breast and ovarian carcinoma cells exposed to fibroblast conditioned medium and mitoxantrone chemotherapy. Epithelial cells were treated with 1050 concentrations of mitoxantrone in conditioned medium from irradiated breast or ovarian fibroblasts expressing a control shRNA or WNT16B-specific shRNAs and irradiated, or with the addition of the β-catenin pathway inhibitor XAV939. Epithelial viability was determined by trypan blue counting of cells 72 hours after chemotherapy. Bars represent means of three replicate experiments. FIG. 13C. In vivo effects of WNT16B on breast tumor responses to mitoxantrone chemotherapy. Tumors comprised MDAMB-231 cells in combination with irradiated breast (HBF1203-RAD) fibroblasts expressing short hairpin RNAs targeting WNT16B or a vector control. Mitoxantrone was administered every 2 weeks for 3 cycles, and grafts were harvested and tumor volumes determined 1 week after the final treatment. Each datapoint represents an individual xenograft. FIG. 13D. In vivo effects of mitoxantrone chemotherapy in the context of suppressing the induction of fibroblast WNT16B. Tumors comprised PC3 cells in combination with untreated prostate fibroblasts expressing a control vector (PSC27C+shRNAC) or shRNAs targeting WNT16B (PSC27C+shRNAWNT16B). Mitoxantrone was administered every 2 weeks for 3 cycles, and grafts were harvested and tumor volumes determined 1 week after the final treatment. Each data point represents an individual xenograft.

FIG. 22A demonstrates gene expression microarray data of GDNF in human prostate stromal cells treated with hydrogen peroxide ($H_2O_2$), bleomycin (bleo) and irradiation (Rad) on a log scale. FIG. 22B shows qPCR data showing up-regulation of GDNF after irradiation between 6 and 16 days post treatment. FIG. 22C shows qPCR data showing up-regulation of GDNF after mitoxantrone treatment between days 17 and 15.

FIG. 23A. CaP cell expressiong GDNF receptors Ret and/or GFRA1 (top row) show increased proliferation upon GDNF stimulation in vitro with a maximum stimulation around 10 ng/ml GDNF in the culture medium (p<0.001) whereas Ret and GFRA1 negative cell (bottom ros) do not show any differences in proliferation after 3 or 5 days. FIG. 23B. GDNF responsive cells show activation of the Src and the Erk pathways upon GDNF stimulation.

FIG. 23A shows GDNF-V5 expression and secretion to the conditioned medium analyzed by Western Blot. FIG. 24B. ELISA measurement of GDNF secreted into the culture medium after 72 hours. FIG. 24C. GDNF expression in transduced PSC27 cell lysates measured by ELISA with normalized input of 62.5 µg/ml total protein starting concentration.

DETAILED DESCRIPTION

Figure 1A:
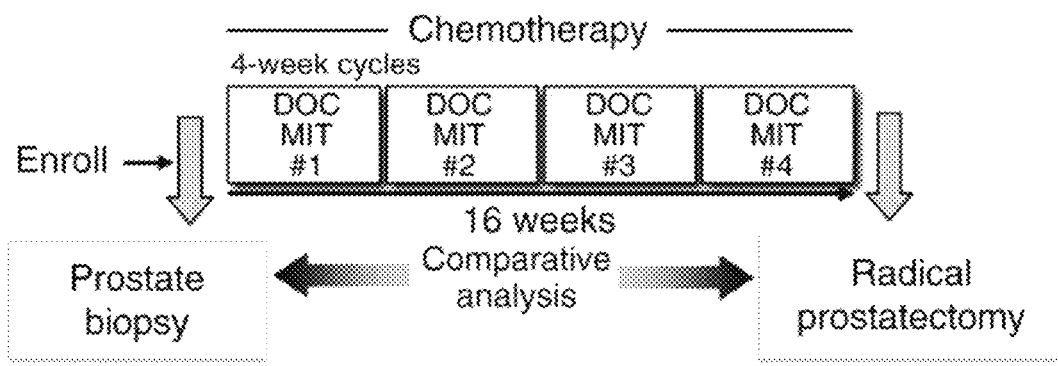
FIGS. 1A through 1J demonstrate that genotoxic damage to primary prostate fibroblasts induces expression of a spectrum of secreted proteins that includes WNT16B.

Unless defined otherwise, all technical and scientific terms used herein have the meaning commonly understood by one of ordinary skill in the art to which this invention belongs.

The present disclosure provides methods for the identification of proteins secreted into a tumor microenvironment in response to a genotoxic stress. Certain of these proteins have been found to attenuate the effects of cytotoxic therapy in vivo, promoting tumor cell survival and disease progression, herein collectively the polypeptides or proteins are termed DNA damage secretory program (DDSP) proteins. The methods include assessing for treatment-induced damage response in benign cells comprising the tumor microenvironment. The methods compare the changes in expression of the DDSP polypeptide or protein before and after tumor therapy, such as chemotherapy or radiation therapy, in benign cells, such as, for example, fibroblasts, smooth muscle cells, and the like. In an another embodiment the level of one or more of the DDSP polypeptides or proteins can be used to determine the effectiveness of the administered genotoxic agent or the prognosis for the cancer.

Expression of DNA damage secretory program proteins (DDSP proteins) can be reflected in the transcriptional activity of the cell (i.e., transcriptional state), in addition to the amount of protein translated from the resulting mRNA molecules (i.e., translational state). Therefore, the level of DDSP proteins in the subject can be determined at the nucleic acid or protein levels. The transcriptional state of DDSP proteins can be conveniently determined by measuring transcript abundance by any of several existing gene expression technologies that are well-known in the art. The translational state includes the identities and abundance of the constituent polypeptide species in the sample generated by the ribosomal machinery using the mRNA template described above. The translational state, i.e., level of constituent DDSP proteins, can also be conveniently determined by various technologies that are well-known in the art.

In a particular method, primary tissues can be collected from patients before and after a genotoxic treatment. The treatment can be, for example, chemotherapy, radiation therapy, or a combination thereof. RNA transcripts from the samples can be collected by any method well known in the art. A comparison of the RNA transcripts from the patient samples collected before and after treatment can then be carried out by any standard method, such as, for example, whole-genome microarray analysis. One specific embodiment of this particular method is set forth in the examples herein.

Of particular interest in the present disclosure are proteins and factors with clear paracrine effects on tumor cells, and specifically genes with at least 3.5-fold elevated expression in the primary tissues after the genotoxic treatment that encode extracellular proteins (DNA damage secretory program proteins). The DDSP proteins from prostate tissue can include, for example, and not by limitation, matrix metallopeptidase 1 (interstitial collagenase) (MMP1), Wingless-type MMTV integration site family member 16B (WNT16B), secreted fizzled-related protein 2 (SFRP2), matrix metallopeptidase 12 (MMP12), serine peptidase inhibitor (Kazal type 1) (SPINK1), matrix metallopeptidase 10 (stromelysin 2) (MMP10), ectonucleotide pyrophosphatase/phosphodiesterase 5 (ENPP5), epiregulin (EREG), bone morphogenic protein 6 (BMP6), angiopoietin-like 4 (ANGPTL4), chondroitin sulfate N-acetylgalactosaminyltransferase (CSGALNACT), cheokine (C-C motif) ligand 26 (CCL26), ampiregulin (AREG), angioplastin 1 (ANGPT1), cholecustokinin (CCK), thrombomodulin (THBD), chemokine (C-X-C motif) ligand 14 (CXCL14), novoblastoma overexpressed protein (NOV), galanin prepropeptide (GAL), natriuretic peptide C (NPPC), family with sequence similarity 150, member B (FAM150B), cystatin SN (CST1), glial cell derived neurotrophic factor (GDNF), mucin-like 1 (MUCL1), neuronal pentaraxin II (NPTX2), transmembrane protein 155 (TMEM155), endothelin 1 (EDN1), pregnancy specific beta-1-glycoprotein 9 (PSG9), ADAM metallopeptidase with thrombospondin type 1 motif, 3 (ADAMTS3), CD24, pro-platelet basic protein (chemokine (C-X-C motif) ligand 7) (PPBP), chemokine (C-X-C motif) ligand 3 (CXCL3), matrix metallopeptidase 3 (stromelysin 1, progelatinase (MMP3), cystatin SA (CST2), pregnancy specific beta-1-glycoprotein 8 (PSG8), procollagen C-endopeptidase enhancer 2 (PCOLCE2), pregnancy specific beta-1-glycoprotein 7 (PSG7), tumor necrosis factor (ligand) superfamily, member 15 (TNFSF15), chromosome 17 open reading frame 67 (C17orf17), calcitonin-related polypeptide alpha (CALCA), fibroblast growth factor 18 (FGF18), bone morphogenic protein 2 (BMP2), matrilin 3 (MATN3), transferring pseudogene 1 (TFP1), serpin peptidase inhibitor, clade 1, member 1 (neuroserpin) (SERPINI1), tumor necrosis factor receptor superfamily, member 25 (TNFRSF25), interleukin 23, alpha subunit p19 (IL23A), and the like. See FIG. 1. A similar spectrum of secreted proteins can be identified for other tissues. Some of the proteins identified can be either the same or different from those identified above.

In one embodiment, a PCR method such as a quantitative RT PCR (qRT PCR or qPCR), can be used to compare specifically identified DDSP protein mRNA levels between treated and untreated samples, and thus determine the difference in a DDSP protein gene expression level. As one example herein, the level of WNT16B was determined. In one illustrative technique, for which there are commercially available kits such as Taqman® (Perkin Elmer, Foster City, Calif.), qPCR is performed with a transcript-specific antisense probe. A PCR is prepared with a quencher and fluorescent reporter probe complexed to the 5' end of the oligonucleotide. When Taq DNA polymerase is activated, it cleaves off the fluorescent reporters of the probe bound to the template by virtue of its 5' to 3' exonuclease activity. In the absence of the quenchers, the reporters now fluoresce providing a quantifiable signal to ascertain template abundance at every round of amplification. An alternative technique is to use an intercalating dye such as the commercially available QuantiTect™ SYBR® Green PCR (Qiagen, Valencia, Calif.). RT-PCR is performed using SYBR® green as a fluorescent label which is incorporated into the PCR product during the PCR stage and produces a fluorescence proportional to the amount of PCR product.

In another embodiment, nuclease protection assays (including both ribonuclease protection assays and S1 nuclease assays) can be used to detect and quantitate an identified DDSP protein mRNA level. In nuclease protection assays, an antisense probe (labeled with, e.g., radiolabeled or nonisotopic label) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations. The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to the target RNA to prevent cleavage of the probe-target hybrid by the nuclease. For instance, the antisense probe can correspond to any section of the WNT16B mRNA sequence.

In another embodiment, standard Northern blot assays are used to detect and ascertain the relative amounts of RNA, such as mRNA, in a sample according to conventional Northern hybridization techniques known in the art. Briefly, RNA samples are obtained and separated by size via electrophoresis. The RNA is transferred to a membrane, cross-linked and hybridized with a labeled probe that hybridizes specifically to the target mRNA under defined hybridization conditions. The probe can be labeled by any of the many different methods known to those skilled in this art. The labels most commonly employed for these studies are radioactive elements, enzymes, chemicals that fluoresce when exposed to ultraviolet light, and others.

In additional embodiments, RNA need not be extracted from the sample. For example, fluorescent in situ hybridization can be used to determine the presence, relative quantity, and spatial distribution of target mRNA in a cell. In an illustrative example, Single Molecule RNA FISH (Biosearch Technologies, Novato, Calif.) uses multiple short, singly-labeled oligonucleotide probes complementary to distinct portions of the target sequence. When each probe binds to the single stranded mRNA template, it causes cooperative unwinding of the mRNA, promoting the binding of the additional probes. The net result is the binding of a large multitude of fluorescent labels to a single molecule of mRNA template, providing sufficient fluorescence to reliably locate each target mRNA in a wide-field fluorescent microscopy image.

In additional embodiments, the gene expression level can be determined by assessing the translational state of an identified DDSP gene. In these embodiments, standard techniques can be used for determining the amount of the DDSP polypeptide or protein present in a sample. For example, immunoassays such as Western blot involve immunoprecipitation of protein from a sample according to methods well-known in the art. This is followed by sodium dodecyl sulfate polyacrylamide gel electrophoresis (SDS-PAGE) of the protein sample. After separation of the proteins, immunocytochemistry and the like can be used to determine the amount of the protein or proteins of interest present in a sample. A typical agent for detecting a protein of interest is a detectable antibody, or fragment thereof, capable of binding to the protein of interest.

In another embodiment, antibodies, or fragments thereof, can be employed to detect levels of in identified DDSP polypeptide, including splice variant isoforms, in a sample by techniques such as with an enzyme-linked immunosorbent assay (ELISA). Briefly, an antibody or fragment thereof that specifically binds to a portion of the DDSP polypeptide or protein is immobilized on a solid substrate. The sample is contacted to the solid substrate and any DDSP polypeptides or proteins present in the sample are permitted to bind to the immobilized (capture) antibody. A second antibody that also binds to the DDSP polypeptide or protein is also contacted with the biological sample and/or solid substrate and permitted to bind to the OPN polypeptide. The second antibody usually comprises a detectable label or signal. The label can be detected directly, or it may be a component of a signal-generating system, which are well-known in the art. The level of the DDSP polypeptide or protein is determined by assaying the detectable signal after the solid substrate has been rinsed of unbound sample and antibody.

Additionally, antibodies, or fragments thereof, can be employed histologically, as in immunofluorescence or immunoelectron microscopy, for in situ detection of a protein of interest. In situ detection can be accomplished by obtaining a histological specimen (e.g., a biopsy specimen or immobilized cell culture) and applying thereto a labeled antibody that is directed to the target protein. The antibody (or fragment) is preferably applied onto a biological sample, such as liver cells from a section or biopsy. Through the use of such a procedure, it is possible to determine not only the presence of the protein of interest, but also its distribution, and/or its presence in lymphocytes within the sample. A wide variety of well-known histological methods (such as staining procedures) can be utilized in order to achieve such in situ detection.

Antibodies can be generated utilizing standard techniques well known to those of skill in the art. Such antibodies can be polyclonal, or more preferably, monoclonal. An intact antibody, or an antibody fragment (e.g., Fab or $F(ab')_2$), that specifically binds to a portion of the DDSP polypeptide or protein can be used.

A wide variety of known signaling mechanisms are available for the described immunoassays. To illustrate, an enzyme bound to the antibody will react with an appropriate substrate, preferably a chromogenic substrate, in such a manner as to produce a chemical moiety which can be detected, for example, by spectrophotometric, fluorometric or by visual means. The detection can be accomplished by colorimetric methods which employ a chromogenic substrate for the enzyme. Detection can also be accomplished by radioactively labeling the antibodies or antibody fragments, and detecting the protein of interest through the use of a radioimmunoassay. It is also possible to label the antibody with a fluorescent compound which fluoresces upon stimulation by light of a proper wavelength. Among the most commonly used fluorescent labeling compounds are fluorescein isothiocyanate, rhodamine, phycoerythrin, phycocyanin, allophycocyanin, o-phthaldehyde fluorescamine, and the like.

Once the DDSP gene has been identified and the polypeptide or protein expressed by the gene recognized. An agent as used in the present disclosure is a molecule that inhibits the expression of the identified DDSP gene or inhibits the activity of the polypeptide or protein expressed by the identified DDSP gene. The identified agent can be, for example, an antibody that specifically binds to and inactivates the DDSP polypeptide or protein, a polynucleotide that inhibits the expression of the identified DDSP gene, or any protein or small molecule that blocks the activity of the identified DDSP polypeptide or protein or a pathway modulated by the identified DDSP polypeptide or protein that promotes genotoxic therapy resistance.

In one aspect the agent that inhibits the activity of the identified DDSP is an antisense nucleic acid capable of inhibiting transcription of the DDSP gene or translation of the corresponding messenger RNA. The antisense nucleic acid can comprise all or part of the sequence of the DDSP gene, or of a sequence that is complementary thereto. The antisense sequence can be a DNA, an RNA (e.g., siRNA), a ribozyme, and the like. It may be single-stranded or double stranded. It can also be a RNA encoded by an antisense gene. When an antisense nucleic acid comprising part of the sequence of the gene or messenger RNA under consideration is being used, it is preferred to use a part comprising at least 10 consecutive bases from the sequence, more preferably at least 15, in order to ensure specific hybridization. In the case of an antisense oligonucleotide, it typically comprises less than 100 bases, for example in the order of 10 to 50 bases. This oligonucleotide can be modified to improve its stability, its nuclease resistance, its cell penetration, and the like. Perfect complementarily between the sequence of the antisense molecule and that of the target gene or messenger RNA is not required, but is generally preferred.

According to another embodiment, the inhibitor compound is a polypeptide. It can be, for example, a peptide comprising a region of the DDSP polypeptide or protein, and capable of antagonizing its activity. A peptide advantageously comprises from 5 to 50 consecutive amino acids of the primary sequence of the identified DDSP polypeptide or protein, typically from 7 to 40. The polypeptide can also be an antibody that specifically binds the identified DDSP polypeptide or protein, or a fragment or derivative of such an antibody, for example a Fab fragment, a CDR region, or, more preferably, a single chain antibody (e.g., a scFv). Single chain antibodies are particularly advantageous insofar as they can act in a specific and intracellular fashion to modulate the activity of a target protein. Such antibodies, fragments, or derivatives can be produced by conventional techniques comprising immunizing an animal and recovering the serum (polyclonal) or spleen cells (in order to produce a hybridoma by fusion with appropriate cell lines).

Methods for producing polyclonal antibodies in various species are described in the prior art. Typically, the antigen, the identified DDSP polypeptide or protein, or a portion thereof, is combined with an adjuvant (e.g., Freund's adjuvant) and administered to an animal, typically by subcutaneous injection. Repeated injections can be performed. Blood samples are collected and the immunoglobulin or serum is separated. Conventional methods for producing monoclonal antibodies comprise immunizing of an animal with an antigen, followed by recovery of spleen cells, which are then fused with immortalized cells, such as myeloma cells. The resulting hybridomas produce monoclonal antibodies and can be selected by limiting dilution in order to isolate individual clones. Fab or $F(ab')_2$ fragments can be produced by protease digestion, according to conventional techniques.

According to another embodiment, the inhibitor is a chemical compound, of natural or synthetic origin, particularly an organic or inorganic molecule, capable of modulating the expression or the activity of the identified DDSP polypeptide or protein.

In another embodiment of the present disclosure provides for the administration to a subject of a therapeutically effective amount of an agent that inhibits the activity of the identified DDSP polypeptide or protein as an adjuvant to a cancer therapy. The agent of the present disclosure can be administered as a pharmaceutical composition comprising a therapeutically effective amount of the inhibitory agent together with a pharmaceutically acceptable carrier. In the context of the present disclosure, a "therapeutically effective amount" is understood as the amount of an agent inhibiting the expression and/or activity of an identified DDPS polypeptide or protein of interest that is necessary to achieve the desired effect which, in this specific case, is the increase in the effectiveness of a genotoxic therapy. Generally, the therapeutically effective amount of the inhibitory agent according to the present disclosure to be administered will depend, among other factors, on the individual to be treated, on the severity of the disease said individual suffers, on the chosen dosage form, and the like. For this reason, the doses mentioned in the present disclosure must be considered only as a guideline for the person skilled in the art, and the latter must adjust the doses according to the previously mentioned variables. Nevertheless, an inhibitory agent according to the present disclosure can be administered one or more times a day, for example, 1, 2, 3 or 4 times a day, in a typical total daily amount comprised between 0.1 and 1000 mg/kg body mass/day, preferably 10 mg/kg body mass/day. In the context of the present disclosure, the term "treatment" or "treating" means the administration of an inhibitory agent according to the disclosure to effectively decrease the expression of activity of the DDPS polypeptide or protein of interest such that it no longer promotes resistance to a genotoxic therapy.

The subject can be a human or non-human animal, a vertebrate, and is typically an animal, including but not limited to, cows, pigs, horses, chickens, cats, dogs, and the like. More typically, the subject is a mammal, and in a particular embodiment, human.

Various delivery systems are well known to the skilled artisan and can be used to administer the inhibitory agent, such as, for example, by infusion, injection (e.g., intradermal, intramuscular or intraperitoneal), oral delivery, nasal delivery, intrapulmonary delivery, rectal delivery, transdermal delivery, interstitial delivery or subcutaneous delivery. In a specific embodiment, it can be desirable to administer the inhibitory agent locally to the area in need of treatment, e.g., the tumor bed, into the tumor, and the like; this administration can be achieved by, for example, and not by way of limitation, local infusion, topical application, by injection (e.g., intra-testicular or intra-prostatic), by means of a catheter, or by means of an implant, the implant being for example, a porous, non-porous, gelatinous or polymeric material, including membranes such as silastic membranes or fibers. In one embodiment, administration can be by direct injection at the target site, for example, into a tumor.

Pharmaceutical compositions containing the inhibitory agent can be formulated according to the desired delivery system. Such pharmaceutical compositions typically comprise a therapeutically effective amount of the inhibitory agent and a pharmaceutically acceptable carrier. The term "pharmaceutically acceptable" means approved by a regulatory agency of the Federal or a state government or listed in the U.S. Pharmacopeia or other generally recognized pharmacopeia for use in vertebrates, typically animals, and more typically in humans. The term "carrier" refers to a diluent, adjuvant, excipient, stabilizer, preservative, viscogen, or vehicle with which the inhibitory agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Suitable excipients include starch, glucose, lactose, sucrose, gelatin, malt, rice, flour, chalk, silica gel, sodium stearate, glycerol monostearate, talc, sodium chloride, dried skim milk, glycerol, propylene glycol, ethanol, and the like. The composition, if desired, can also contain minor amounts of a wetting or emulsifying agent, or a pH buffering agent.

Suitable preservatives include, for example, sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, potassium benzoate, potassium metabisulfite, potassium sorbate, sodium bisulfite, sulfur dioxide, organic mercurial salts, phenol and ascorbic acid. Suitable viscogens include, for example, carboxymethylcellulose, sorbitol, dextrose, and polyethylene glycols. Other examples of suitable pharmaceutical carriers are described in, for example, Remington's Pharmaceutical Sciences (Gennaro (ed.), Mack Publishing Co., Easton, Pa. (1990)).

The selected inhibitory agent can also be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

In one embodiment, the selected inhibitory agent can be formulated in accordance with routine procedures as a pharmaceutical composition adapted for intravenous administration to human beings. For intravenous delivery, water is a typical carrier. Saline, aqueous dextrose and glycerol solutions can also be employed as liquid carriers, particularly for injectable solutions. Typically, compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Orally deliverable compositions can take the form of solutions, suspensions, emulsions, tablets, pills, capsules, powders, sustained-release formulations, and the like. Oral formulations can include standard carriers such as pharmaceutical grades of mannitol, lactose, starch, magnesium stearate, sodium saccharine, cellulose, magnesium carbonate, and the like.

The inhibitory agent can also be formulated for other methods of delivery using well known formulations. These can included, but are not limited to, intranasal, rectal, intrathecal, controlled release systems, and the like. Controlled release systems can include, pumps, gels, skin patches, and the like.

The following examples are merely illustrative and should not be construed to limit the invention.

EXAMPLES

Example 1

The present example provides methods and determines those DDSP proteins increased by at least 3.5-fold in response to a genotoxic agent. Further, the example provides confirmation of the effectiveness of inhibiting the activity of one of those DDSP proteins, Wnt16B, in increasing the effectiveness of a cancer therapeutic agent.

Experimental Procedures

Cell Lines and Cultures.

Cells of a primary normal human prostate fibroblast strain, PCS27, were cultured in prostate stromal cell (PSC) complete medium as described previously (Bavik et al. Cancer Res. 66:794-802, 2006). Human prostate epithelial cell lines DU145, PC3 and LNCaP were from American Type Culture Collection (ATCC, Manassas, Va.) and routinely subcultured under RPMI 1640 with 5% fetal bovine serum (FBS) conditions as recommended by the vendor. The prostatic epithelial line BPH1 was kindly provided by Dr. Simon Hayward and was derived from nonmalignant prostatic tissue with benign hyperplasia, immortalized by SV40-LT antigen, and cultured as previously described (Hayward et al., In vitro Cell Dev. Biol. Anim. 31:14-24, 1995). The neoplastic metastatic M12 human prostate epithelial cell line was provided by Dr. Joy Ware and maintained as previously described (Bae, et al., Prostate 34:275-282, 1998). BPH1 and M12 cells were transfected with a plasmid pIRES2-GFP, with cells passaged and subsequently flow-sorted in a FACSVantage. Cancer lines from other human cancer types including lung (A549), colon (HCT116), breast (MDA-MB-231, T47D), cervix (HeLa) and ovary (SKOV3, OVCAR3) were obtained from ATCC and cultured according to supplied instructions.

Establishment of Primary Fibroblast Lines.

Fresh human breast and ovarian tissues were acquired through Institutional Review Board-approved collection protocols from discarded surgical specimens. Tissue samples were washed in sterile PBS and gently agitated in RPMI/10% Fetal Bovine Serum media, with 1000 U/ml collagenase type IA. Samples were placed on the lid of a 100-mm tissue culture dish and dissected into small (2 to 3 mm) squares, and 5 to 10 tissue pieces were placed in the center of a 35-mm tissue culture dish or 6-well plate. A sterile 22-mm glass coverslip was placed gently over the tissue specimens, forming a sandwich. A few drops of 4° C. complete growth medium (DMEM or RPMI) was added under the coverslip. The culture was placed in a humidified 37° C., 5% $CO_2$ incubator, with fibroblast outgrowth checked every 3 to 4 days under an inverted phase-contrast microscope, and growth medium was changed after each assessment. Upon confluent growth, the coverslips were removed and the dish (or well) was washed twice with 4° C. PBS. Trypsin/EDTA (0.25%) was used to detach cells and fibroblasts were collected by centrifugation for 10 min at 150×g, 4° C. in a 15-ml polypropylene centrifuge tube. About 3 to $10\times10^4$ viable cells were placed in 5 ml of fresh complete growth medium in a T25 flask. Cells attached to the new flask within 2 to 3 hour and began to exhibit the characteristic spindle shape within 24 hour. Medium was changed every 3 to 4 days until the culture was confluent, and fibroblasts were passaged two additional times following the procedure described above. To confirm the fibroblast phenotype and assess culture purity, immunofluorescence staining was used and Western blot analysis with antibodies against vimentin (abcam), smooth muscle α-actin (abcam), E-cadherin (Genetex), CD44 (R&D systems) and cytokeratin 8 (Santa Cruz). The breast fibroblast line was designated HBF1023 and the ovarian fibroblast line was designated OVF28901.

Plasmids and Lentiviral Infection.

Lentiviral agents were produced by transfecting 293FT packaging cells, with virus-containing culture medium harvested and filtered through 0.45-μm syringe filters 48 to 96 hours post-transfection. PSC27 fibroblasts were infected by exposure to virus-containing medium for 12 to 16 hours, maintained in PSC complete medium, followed by selection in puromycin. For gene-specific silencing with small hairpin RNA (shRNA), the sequences targeting WNT16B gene were cloned in a lentiviral vector pGIPZ (Thermo Scientific). Transfection of 293FT cells and subsequent infection of PSC27 cells were carried out as above, with the interference of target gene expression confirmed by immunofluorescence and immunoblot analysis.

Cell Treatments with DNA Damaging Agents.

PSC27 cells were grown until 80% confluent (PSC27-Pre) and treated with 0.6 mM hydrogen peroxide (PSC27-$H_2O_2$), 100 μg/mL bleomycin (PSC27-BLEO) (Bavik et al., Cancer Res. 66:794-802, 2006), 1 μM Mitoxantrone (PSC27-MIT) or ionizing-radiated by a $^{137}Cs$ source at 743 rad/min (PSC27-RAD). After treatment, the cells were rinsed 3 times with PBS and left to recover for 3 days in PSC medium.

Immunofluorescence Analysis and Assessments of DNA-Damage Foci.

Cells growing on coverslips were rinsed, subjected to fixation in 4% paraformaldehyde and permeabilization with 0.1% Triton-X100 prior to immunostaining Primary mouse monoclonal anti-phospho-Histone H2A.X (Ser139) (clone JBW301) and secondary antibody Alexa Fluor® 488 (or 594)-conjugated $F(ab')_2$ goat anti-mouse IgG were sequentially applied. Nuclei were counterstained with 2 μg/ml of 4',6-diamidino-2-phenylindole (DAPI) and coverslips were mounted onto glass slides. Upon visual examination of the DNA damage extent with immunofluorescence microscopy, DDR foci were recorded with a 4-category counting strategy, namely 4 classes: 0 foci, 1 to 3 foci, 4 to 10 foci, and >10 foci. Data from each cell line/treatment were averaged from a pool of 3 independent fields counting 100 nuclei per pool.

Epithelial and Fibroblast Co-Cultures.

For direct in vitro co-culture, BPH1-GFP cells were mixed with various proportions of PSC27 cells expressing vector control ($PSC27^C$) or WNT16B ($PSC27^{WNT16B}$). The cultures were incubated for 3 days after which cells were detached with trypsin and the total cell number was determined by direct counting with hemacytometer. The PSC27/BPH1-GFP proportion was determined on a FACScan using GFP fluorescence as a marker for BPH1-GFP cells. M12-GFP cells were mixed with PSC27 cells and analyzed as above. For indirect co-culture, or culture of prostate epithelial cells with treated (e.g., irradiated), or WNT16-overexpressing fibroblast-conditioned medium, confluent cultures of PSC27 cells were rinsed thrice in PBS and incubated for 3 days in DMEM+0.5% FCS. The supernatant was harvested, filtered, concentrated and either stored frozen at −80° C. or applied immediately. BPH1-GFP, PC3 and other cell lines were seeded in conditioned medium or fresh DMEM+0.5% FBS, and grown for specific time periods and the total number of cells was determined by direct counting.

Characterization of Cell Phenotypes.

Assays of cell proliferation were performed with the Cell-Titer96® $A_{Queous}$ One Solution Cell Proliferation Assay (MTS) with signals captured using a 96-well plate reader. Serum-starved cells for trans-well migration and invasion assays were added to the top chambers of Cultrex® 24-well Cell Migration Assay plates (8 μm size) coated with or without basement membrane extract (BM) prepared as 0.5× of stock solution. After 12 or 24 hours, migrating or invading cells in the bottom chambers were stained and plate absorbance was recorded. In the two-dimensional in vitro "wound healing" assay, cells were seeded before cell monolayers were incised. Photographs were taken at specific time points with the relative distance traveled by cells at the acellular front measured by microscopy.

Chemoresistance assays were performed using epithelial cells cultured with either DMEM and low serum (0.5% FCS) (abbreviated as "DMEM"), or conditioned medium (CM) generated from PSC27, GHF1023 or OVF28901 cells expressing vector controls, WNT16B, or siRNAs. Cells received Mitoxantrone treatment for 12 hours, 1 or 3 days at concentrations near individual cell line's $IC_{50}$. Cell viability was then assayed, and the percentage of viable cells was calculated by comparing each experiment to vehicle-treated cells. Each assay was repeated a minimum of 3 times with results reported as mean±s.e.m.

Western Blot Analysis.

Conditioned Medium (CM) or cell lysates from PSC27 cells exposed to DNA damaging treatments (radiation, Bleomycin, hydrogen peroxide, Mitoxantrone) or vehicle controls were concentrated before SDS-PAGE by trichloroacetic acid (TCA) precipitation as described (Bavik et al., *Cancer Res.* 66:794-802, 2006). After drying, the CM samples were dissolved, reduced, and separated on a NuPAGE® 4-12% gel. Primary antibodies were applied to the semi-dry-transferred blots before horseradish peroxidase (HRP)-linked secondary antibodies (Thermo Scientific, Rockford, Ill.) were used.

Human Transcript Microarray Analysis.

Total RNA from experimental samples was isolated using the RNeasy® maxi kit (Qiagen Inc, Valencia, Calif.), incorporating on-column DNase treatment using the RNase-Free DNase Set (Qiagen Inc, Valencia, Calif.). To provide a reference standard RNA for use on two-color microarrays, pooled equal amounts were of total RNA isolated from LNCaP, DU145, PC3, and CWR22 cell lines (ATCC) growing at log phase in dye-free RPMI-1640 medium supplemented with 10% FBS (Invitrogen, Carlsbad, Calif.) were used. Reference RNA was purified using TRIzol® (Invitrogen, Carlsbad, Calif.) following the manufacturer's protocol. Reference RNA was then further purified by RNeasy® maxi kit incorporating on-column DNAse treatment using the RNase-Free DNase Set. Experimental total RNA samples were amplified one round while the reference RNA was amplified two rounds using the Ambion MessageAmp™ aRNA Kit (Ambion Inc, Austin, Tex.), incorporating amino-allyl UTP into amplified antisense RNA. Sample quality and quantity were assessed by agarose gel electrophoresis and absorbance at A260 and A280 using the Nanodrop® 1000 spectrophotometer (Thermo Fisher Scientific Wilmington, Del.)

Amplified amino-allyl aRNA (825 ng) from each experimental sample was labeled with Cy3 fluorescent dye (reference amino-allyl aRNA was labeled with Cy5) and hybridized to Agilent 44K whole human genome expression oligonucleotide microarray slides (Agilent Technologies, Inc., Santa Clara, Calif.) following the manufacturer's suggested protocols. Fluorescence array images were collected for Cy3 and Cy5 using the Agilent DNA microarray scanner G2565BA (Agilent Technologies, Inc., Santa Clara, Calif.), and Agilent Feature Extraction software was used to grid, extract, and normalize data. Spots of poor quality or average intensity levels <300 were removed from further analysis. The Significance Analysis of Microarray (SAM) method (Tusher et al., *Proc. Natl. Acad. Sci. USA* 98:5116-5121, 2001) was used to analyze expression differences between groups. Unpaired, two-sample t tests were calculated for all probes passing filters and controlled for multiple testing by estimation of q-values using the false discovery rate (FDR) method. These results were reduced to unique genes by eliminating all but the highest scoring probe for each gene.

Accession Codes.

Microarray data are deposited in the Gene Expression Omnibus database with accession code GSE26143.

RNA Isolation and Quantitative RT-PCR.

Cell cultures and human tissue samples were individually homogenized in Trizol (Invitrogen, Carlsbad Calif.) and total RNA was isolated using the RNeasy® Kit (Qiagen Inc, Valencia, Calif.). RNA was quantitated in a Gene-Spec III spectrophotometer (Hitachi, Tokyo), and amplified using the MessageAmp™ RNA amplification kit (Ambion). cDNA was generated by a reverse transcription reaction, and quantitative PCR (qRT-PCR) analyses were performed in triplicate using an Applied Biosystems 7700 sequence detector with approximately 5 ng of cDNA, 1 µM of designated primer pairs and SYBR Green PCR master mix (Applied Biosystems, Foster City, Calif.). The mean cycle threshold (Ct) for each gene was normalized to levels of RPL13A in the same sample (delta Ct). Unpaired two sample t-tests were used to determine differences in mean delta Ct's between treatment groups. The fold change was calculated by the delta-delta CT method (fold=$2^{DDCt}$). P values <0.05 were considered significant.

Analyses of Human Clinical Biospecimens.

Patients with high-risk localized prostate cancer were enrolled and treated on a phase I-II clinical neoadjuvant chemotherapy trial at the Oregon Health & Science University, Portland VA Medical Center, Kaiser Permanente Northwest Region, Legacy Health System, and University of Washington (Beer et al., *Clin. Cancer Res.* 10:1306-1311, 2004). Patients provided signed informed consent approving the use of their tissues for research purposes. From each patient, prostate biopsies were obtained prior to chemotherapy. At the time of radical prostatectomy following chemotherapy, cancer-containing tissue samples were obtained and snap-frozen in liquid nitrogen. Frozen sections (7 µm) were cut from OCT blocks, stained with Mayer's hematoxylin, dehydrated in 100% ethanol and xylene, and used for laser-capture microdissection (LCM) using an Arcturus PixCell® IIe microscope (Arcturus, Mountain View, Calif.). Stroma, cancerous epithelium, benign epithelium, and stroma from untreated biopsy and post-treated prostatectomy specimens were captured separately and the histology of acquired cells was verified by review of hematoxylin and eosin-stained sections from each sample and review of the LCM images.

Samples of breast carcinoma and ovarian carcinoma were collected under IRB-approved protocols. Ovarian and breast cancer specimens were selected based on either no treatment prior to surgical resection or genotoxic chemotherapy (e.g., cisplatin) prior to surgical resection.

Tissue Microarrays:

Tissue microarrays (TMA's) were constructed using prostates from 2 sets of patients with prostate adenocarcinoma—50 patients (median age 63 years old; range 62 to 74 y.o.) who received neoadjuvant chemotherapy (Mitoxantrone and docetaxel) prior to radical prostatectomy and 30 patients (median age 61 years old (y.o.); range 45 to 77 y.o.) who had no history of neoadjuvant chemotherapy prior to radical prostatectomy. Details of the neoadjuvant chemotherapy trial have been published. Duplicate cores from each set of radical prostatectomies were used in the TMAs. Carcinoma was confirmed in sections adjacent to those used for WNT16B immunostaining by immunostaining for a basal cell marker. An antibody to basal cell proteins high molecular weight keratins 1, 5, 10 and 14 (a mouse monoclonal antibody raised human stratum corneum; product number MS-1447-R7 clone 34betaE12, Thermo Fisher Scientific) was used in an indirect immunoperoxidase procedure.

Immunohistochemistry:

Antibodies to WNT16B (a mouse monoclonal antibody raised against human WNT16B recombinant protein; product number 552595 clone F4-1582, BD Pharmingen) and anti-β-catenin (Clone 14/Beta-Catenin, BD Transduction), were used at dilutions of 1:16,000 or 1:1000, respectively. These titers were selected to minimize nonspecific staining and specificity was confirmed by omission of the primary antibody. Immunolocalization was done using an indirect three-step avidin-biotin-peroxidase method. In brief, deparaffinized sections were re-hydrated in phosphate-buffered saline. Sections were then incubated sequentially in solutions of 5% albumin in PBS, 10% hydrogen peroxide in water, primary antibody, secondary anti-mouse IgG (biotinylated anti-mouse IgG (BA-2000, Vector Labs, Burlingame, Calif.) at 1:500 in PBS, and avidin-biotin-peroxidase solution (Vectastain ABC Elite kit at 1:100 in PBS, Vector Labs, Burlingame, Calif.) with interval washes in phosphate buffered saline. Reaction product was detected by incubating sections in a solution of the 0.05% diaminobenzidine and 0.3% hydrogen peroxide for 7 minutes. Sections were briefly counterstained with hematoxylin.

Interpretation of Immunohistochemical Stains:

The level of expression of WNT16B by prostate fibromuscular stromal cells in each core of each TMA was recorded on a 4-point scale as 3 "intensely", 2 "moderately", 1 "faintly/equivocally" or 0, for which there was no expression by any stromal cells. Statistical analysis testing the probability that there was unlikely to be a difference in expression level by the 2 types of patients (those who received neoadjuvant chemotherapy and those who did not receive neoadjuvant chemotherapy) was performed using 2-sample unpaired t-tests or logistic regression as previously described (Lucas et al., *J. Pathol.* 215:118-125, 2008). Analyses of WNT16B staining in breast and ovarian carcinoma samples followed these procedures.

Biochemical Recurrence Free Survival Analysis:

Prostate cancer patients treated with neoadjuvant chemotherapy were partitioned into 3 groups based on stromal WNT16B expression determined by IHC: those with WNT16B average score higher than and equal to 0 but less than 1; those with WNT16B average score higher than and equal to 1 but less than 2; and those with WNT16B average score higher than and equal to 2 but less than 3. Clinical outcome data were collected following surgical prostatectomy, specifically measures of serum prostate specific antigen (PSA) as a metric of disease recurrence. Biochemical relapse was defined as a confirmed serum PSA concentration >0.4 ng/ml. Kaplan-Meier survival curves were plotted with the program GraphPad® Prism, with p-value calculated and output designated as percent biochemical relapse-free survival. Of the 55 patients enrolled in the Phase I/II clinical study, 49 had cores present on the TMA and 6 patients had frozen specimens embedded in optimal cutting temperature (OCT). The positive control for WNT16B expression was PSC27-RAD cells and the negative control was IgG isotype antibody.

NFκB Studies.

To assess the WNT16B responses due to inhibition of NFκB nuclear translocation, the retroviral construct encoding a mutant form of IκBα, pBabe-Puro-IκBα-Mut (super repressor) that harbors two IKK phosphorylation sites genetically modified as S32A and S34A (Boehm et al., *Cell* 129:1065-1079, 2007), was used for retroviral production with the PHOENIX™ packaging cell line. Infections of PSC27 fibroblasts were performed serially using drug selection (2 μg/ml of puromycin) to isolate cell populations. The established cell strain was subsequently subjected to ionizing radiation or MIT. Conditioned medium was collected as described above and used to treat epithelial cells, and gene expression was assessed by qRT-PCR or Western blot.

Analyses of Cell Proliferation, Migration, Invasion and Chemotherapy Resistance.

All assays were performed at least three times and reported as mean values. Assays of cell proliferation were performed with the CellTiter96® AQ$_{ueous}$ One Solution Cell Proliferation Assay (MTS) with signals captured using a 96-well plate reader or by direct counting using a hemacytometer. For trans-well migration and invasion assays, serum-starved cells in serum-free medium were added to the top chambers of Cultrex 24-well Cell Migration Assay plates (8 μm size) coated with or without basement membrane extract (BM) prepared as 0.5× of stock solution. CM from fibroblasts or regular epithelial media containing 10% fetal calf serum (FCS) were added to the bottom chambers. Migrating or invading cells in the bottom chambers were stained and plate absorbance was recorded at 485/520 nm emission. Each assay was performed in triplicate and measured at 24 hour time points over 3 days and presented as the average absorbance of migrating cells and invading cells, with human HeLA cervical cancer cell line (ATCC) used as a reference positive control.

For the two-dimensional in vitro "wound healing" assay, cells were seeded, allowed to establish growth and high-density areas were incised. Detached cells were removed and fresh medium was added. Photographs were taken at 0, 12 and 24 hours, and the relative distance traveled by the cells at the acellular front was measured by microscopy.

For chemoresistance assays, various neoplastic epithelial cells were cultured with either DMEM of low serum (0.5% FBS) only (abbreviated as "DMEM"), or CM generated from PSC27, HBF1023 or OVF28901 in various states (e.g., WNT16B overexpression, WNT16B knockdown, irradiated). Cells received Mitoxantrone (MIT) treatment for 1 or 3 days at a range of concentrations bracketing individual cell line's $IC_{50}$ levels. Cell viability was assayed by MTS or direct counting with trypan blue, and the percentage of viable cells was calculated by normalizing absorbance of each experiment to untreated cells. To assess the influence of WNT16B across a range of MIT concentrations, a series of drug concentrations were applied bracketing the $IC_{50}$ dose, with percent survival plotted against MIT dose at a 3-day time point. Non-linear regression curves were plotted using GraphPad Prism.

For apoptosis assays, $0.2 \times 10^6$ PC3 cells were dispensed into 6-well culture plates and co-cultured with media conditioned from PSC27 sublines. Twelve hours later, Mitoxantrone was added to the media at the $IC_{50}$ concentration of the PC3 line, with distilled water applied in parallel as control. To measure cell apoptosis, lysates were prepared 24 hours post treatment from each group, and apoptosis quantitated using a Caspase-Glo 3/7 assay (Promega) that luminescently measures caspase-3 and -7 activities against a tetrapeptide sequence DEVD that is cleaved to release aminoluciferin, upon apoptosis in cultures. For the morphological analysis, bright field pictures were taken for PC3 cells with inverted phase-contrast microscopy.

TOPFLASH Reporter Assay and β-Catenin Inhibition.

Epithelial cells were transfected with the standardized pair of Super16×TOPFLASH and Super16×FOPFLASH (Addgene), each with a Renilla control luciferase plasmid applied for signal normalization. Empty vector pDNA3.1 was used as control plasmid to adjust for equal DNA concentrations per transfection. A construct encoding the full-length sequence of β-catenin was used as positive control of the canonical Wnt signaling pathway. Luciferase assays were performed using a Dual-Luciferase Reporter Assay kit, and fold induction for each cell line was calculated as normalized relative light units of TOPFLASH divided by those of FOPFLASH. To inhibit the β-catenin pathway, a small molecule compound XAV939 (Miltenyi Biotec) (Huang et al., Nature 461:614-620, 2009) (0.25 to about 0.50 μM) was applied to cultures of epithelial cells treated with conditioned medium from various fibroblast manipulations and with MIT chemotherapy.

WNT16B Promoter Analyses.

A 4000 base pair (bp) region immediately upstream of the human WNT16B gene (Genbank accession NM_016087.2) was analyzed for core NF-κB binding sites using the Consite computerized DNA-binding motif search program. Three PCR primer sets were designed to amplify small regions within the proximal promoter sequence (primer set #1 (−502 to −201) forward 5'-CAGGAAAGGTCATGACACACC-3' (SEQ ID NO: 1), reverse 5'-AGAGCAGCCTGGGGATCT-3' (SEQ ID NO: 2); primer set #2 (−947 to −618) forward 5'-TCTCAGGGACTGCAGGAAAT-3' (SEQ ID NO: 3), reverse 5'-CCCACCAACATCTGGGTTAC-3' (SEQ ID NO: 4); primer set #3 (−1356 to −1024) forward 5'-CTCCAGGGAGTACCCTGCTA-3' (SEQ ID NO: 5), reverse 5'-TGTGCTCTGATCTTTTTCTCCA-3' (SEQ ID NO: 6), and two additional primer sets were employed to amplify regions within the promoters of the human IL-6 (Naugler and Karin, Curr. Opin. Genet. Dev. 18:19-26, 2008) (forward 5'-AAATGCCCAACAGAGGTCA-3' (SEQ ID NO: 7), reverse 5'-CACGGCTCTAGGCTCTGAAT-3' (SEQ ID NO: 8)) and IL-8 (Martone et al., Proc. Natl. Acad. Sci. USA 100:12247-12252, 2003) (forward 5'-ACAGTTGAAAAC-TATAGGAGCTACATT-3' (SEQ ID NO: 9), reverse 5'-TCGCTTCTGGGCAAGTACA-3' (SEQ ID NO: 10)) genes, respectively, which encompass known NF-κB binding sites. ChIP assays were then performed on PSC27 cells of early passage (p8) and those that had undergone γ-irradiation at a 10-Gy dose, with detailed procedures carried out as per previously published methods (Nelson et al., Methods Mol. Biol. 567:45-57, 2009). A sample of formalin-fixed sheared chromatin (DNA fragments at about 500 bp in average) from these cells was used as 'input DNA' for control amplifications. Fixed chromatin was immunoprecipitated using monoclonal mouse anti-p65 antibody and DNAs were extracted from the immunoprecipitates and amplified using the primer sets described above. Control immunoprecipitations was carried out without antibody as control, which yielded no reaction products for any of the primer sets.

The immediate 5' upstream sequences containing putative NF-κB binding elements of the WNT16B gene were amplified from genomic DNA extracted from PSC27 cells by a DNeasy Blood and Tissue kit (QIAGEN). PCR products were cloned into pCR2.1-TOPO vector (Invitrogen) and each insert was sequenced for confirmation. PCR fragments were then double-digested and subcloned into a reporter luciferase vector pGL4.22 vector. Constructs containing one or multiple mutant NF-κB binding sites were generated from the reporter vector series by site-directed mutagenesis. The NAT11-Luc2CP-IRES-nEGFP control construct that contains large copy numbers of NF-κB binding sequences and an optimized IL-2 minimal promoter as part of NFκB-activated transgene (NAT) system was kindly provided by Dr. Hatakeyama (Hokkaido University). All constructs were confirmed by DNA sequencing in both directions. Reporter vectors were co-transfected with pRL-TK vector for transfection efficiency controls and internal normalization for gene expression measurements. Cells were either treated with 20 ng/ml TNF-α for 90 min, exposed to 10 Gy γ-irradiation or 1 μM Mitoxantrone for 1 day. PSC27 line over-expressing IκBα mutant/NF-κB super repressor was tested in parallel under above conditions for luciferase signals. Luciferase activity was measured using the Luciferase Assay System and normalized luciferase activities were calculated as light units normalized to renilla luciferase activity present in each specimen.

Animal and Xenograft Studies.

All animal studies were performed in accordance with protocols approved by the Institutional Animal Care and Use Committee (IACUC) of Fred Hutchinson Cancer Research Center, and were carried out in accordance with the NIH Guide for laboratory animals. Mouse care/welfare and veterinary oversight were provided by the center animal care. ICR SCID mice (Taconic, Inc.) at an age of approximately 6 weeks (25 g body weight) were used. Rat tail collagen (high concentration, type I) was prepared before the ice-cold collagen solution was neutralized and adjusted to the proper osmolarity by adding a mixture of NaOH and ×10 PBS. To prepare tissue recombinants, fibroblasts (PSC27 strain) and epithelial cells (PC3, BPH1 or MDA-MB-231) were mixed at a ratio of 1:1, with each recombinant comprised of 250,000 cells of each line. After polymerization, the cell/collagen mixture was overlaid with growth medium and incubated at 37° C. for 1 hour before implantation.

Xenografting was performed under isoflurane anesthesia. A pocket beneath the back skin was formed using surgical scissors, with an oblique incision (<1 cm) made on the capsule surface parallel and adjacent to the long axis of each kidney. Cells were injected under the capsule with a blunt 25-gauge needle and a glass Hamilton syringe via a transrenal injection, forming a starting tumor with a volume of 1 to 2 $mm^3$. The kidney was returned to the retroperitoneal space and the skin was closed with surgical staples. The growth of xenografts was assessed at weekly intervals using ultrasound instruments. Animals were sacrificed at 2-8 weeks post transplantation, based on the tumor burden and pathological progression of tested animals. Upon dissection, tumor volume (V) was measured and calculated according to the tumor length (l) and width (w) by the following formula: $V=(\pi/6)\times((l+w)/2)^3$ (Anand et al., Nat. Genet 31:301-305, 2002). Tumors were snap-frozen or processed conventionally for formalin fixation. Resulting sections were used for hematoxylin/eosin staining, and immunostaining for selected gene expression markers.

For chemoresistance studies, ICR SCID mice received subrenal capsule xenografts by implantation according to the procedure described above. After surgery, mice were given standard laboratory diets and water ad libitum for 2 weeks, to allow tumor uptake and growth initiation. Starting from the 3rd week (when tumor sizes reached from about 4 to about 8 mm in diameter), mice received Mitoxantrone at a dose of 0.2 mg/kg by i.p. injection, or vehicle control, on day 1 of week 3, week 5, and week 7 (Alderton et al., Cancer Res. 52:194-201, 1992). Between 8 and 12 mice were randomly assigned to each study arm. A total regimen of 3 2-week cycles was administered. After the final treatment cycle the mice were sacrificed, kidneys were removed for tumor measurement and histological analysis. The cumulative Mitoxantrone dose received per mouse was 0.6 mg/kg. Each experimental arm comprised 5-8 mice per treatment cohort.

To determine the systemic effects of MIT treatment on Wnt16b expression, parallel experiments involved administering MIT or vehicle as per the treatment schema above, to cohorts of mice (n=6) without xenografts. At the completion of the 8-week treatment regimen, mice were euthanized and various tissues were rapidly resected and snap frozen or fixed in formalin. Following protein isolations, Western immunoblot analysis was performed for Wnt16b expression, as described above.

For assessments of the acute effects of chemotherapy, mice harboring xenografts of PC3 cells combined with PSC27 fibroblasts were treated with Mitoxantrone 0.2 mg/kg by i.p. injection, or vehicle control. Xenografts were collected 24 hour after treatment and tissues were processed for IHC. Apoptosis was assessed by staining with anti-caspase 3 antibody (cleaved, BioCare Medical). On adjacent sections, immunostaining with anti-γH2AX (Upstate) was performed to quantitate cells with DNA-damage.

Statistical Analysis.

Analyses of microarray experiments are described above. In vitro studies of cell proliferation, viability, or invasion were performed a minimum of 3 times and data reported as ±s.e.m. Statistical analyses was performed on raw data for each group by one-way analysis of variance or a two-tailed Student's t-test. A p<0.05 was considered significant.

TABLE 1

PCR Primers

| GENE SYMBOL[1] | GENE NAME[1] | PRIMERS | SEQUENCES |
|---|---|---|---|
| WNT16 | Wingless-type MMTV integration site family member 16 | Forward | 5'-GCTCCTGTGCTGTGAA AACA-3' (SEQ ID NO: 11) |
| | | Reverse | 5'-TGCATTCTCTGCCTTG TGTC-3' (SEQ ID NO: 12) |
| p16/ CDKN2A/ INK4A | Cyclin-dependent kinase inhibitor 2A | Forward | 5'-GACATCCCCGATTGAA AGAA-3' (SEQ ID NO: 13) |
| | | Reverse | 5'-TTTACGGTAGTGGGGG AAGG-3' (SEQ ID NO: 14) |
| p21/ CDKN1A/ CIP1 | Cyclin-dependent kinase inhibitor 1A | Forward | 5'-GACACCACTGGAGGGT GACT-3' (SEQ ID NO:15) |
| | | Reverse | 5'-CAGGTCCACATGGTCT TCCT-3' (SEQ ID NO: 16) |
| IL-8/ CXCL8 | Interleukin 8 | Forward | 5'-GTGCAGTTTTGCCAAG GAGT-3' (SEQ ID NO: 17) |
| | | Reverse | 5'-CTCTGCACCCAGTTTT CCTT-3' (SEQ ID NO: 18) |
| E-cadherin/ CDH1 | E-cadherin (epithelial) | Forward | 5'-TGCCCAGAAAATGAAA AAGG-3' (SEQ ID NO: 19) |
| | | Reverse | 5'-GTGTATGTGGCAATGC GTTC-3' (SEQ ID NO: 20) |

TABLE 1-continued

PCR Primers

| GENE SYMBOL[1] | GENE NAME[1] | PRIMERS | SEQUENCES |
|---|---|---|---|
| N-cadherin/ CDH2 | N-cadherin (neuronal) | Forward | 5'-GACAATGCCCCTCAAG TGTT-3' (SEQ ID NO: 21) |
| | | Reverse | 5'-CCATTAAGCCGAGTGA TGGT-3' (SEQ ID NO: 22) |
| VIM | Vimentin | Forward | 5'-GAGAACTTTGCCGTTG AAGC-3' (SEQ ID NO: 23) |
| | | Reverse | 5'-TCCAGCAGCTTCCTGT AGGT-3' (SEQ ID NO: 24) |
| TWIST1 | Twist homolog 1 | Forward | 5'-GTCCGCAGTCTTACG AGGAG-3' (SEQ ID NO: 25) |
| | | Reverse | 5'-CCAGCTTGAGGGTCT GAATC-3' (SEQ ID NO: 26) |
| SNAIL2 | Snail homolog 2 | Forward | 5'-CTTTTTCTTGCCCTCA CTGC-3' (SEQ ID NO: 27) |
| | | Reverse | 5'-ACAGCAGCCAGATTCC TCAT-3' (SEQ ID NO: 28) |
| TWIST2 | Twist homolog 2 | Forward | 5'-AGCAAGAAGTCGAGCG AAGA-3' (SEQ ID NO: 29) |
| | | Reverse | 5'-CAGCTTGAGCGTCTG GATCT-3' (SEQ ID NO: 30) |
| AXIN2 | Axin2 | Forward | 5'-CCTGCCACCAAGACC TACAT-3' (SEQ ID NO: 31) |
| | | Reverse | 5'-CTTCATTCAAGGTGGG GAGA-3' (SEQ ID NO: 32) |
| SP5 | Sp5 | Forward | 5'-ACTTTGCGCAGTACCA GAGC-3' (SEQ ID NO: 33) |
| | | Reverse | 5'-ACGTCTTCCCGTACAC CTTG-3' (SEQ ID NO: 34) |
| c-Myc/MYC | v-myc viral oncogene ho-molog (avian) | Forward | 5'-TTCGGGTAGTGGAAAA CCAG-3' (SEQ ID NO: 35) |
| | | Reverse | 5'-CAGCAGCTCGAATTTC TTCC-3' (SEQ ID NO: 36) |
| Cyclin D1/CCND1 | Cyclin D1 | Forward | 5'-AACTACCTGGACCGCT TCCT-3' (SEQ ID NO: 37) |
| | | Reverse | 5'-CCACTTGAGCTTGTTC ACCA-3' (SEQ ID NO: 38) |

TABLE 1-continued

PCR Primers

| GENE SYMBOL[1] | GENE NAME[1] | PRIMERS | SEQUENCES |
|---|---|---|---|
| RPL13A | Ribosomal protein L13a | Forward | 5'-GTACGCTGTGAAGGCA TCAA-3' (SEQ ID NO: 39) |
| | | Reverse | 5'-CGCTTTTTCTTGTCGT AGGG-3' (SEQ ID NO: 40) |

1. According to the HUGO Gene Nomenclature Committee.

Results

Therapy Induces Damage Responses in Tumor Microenvironments

Figure 1B:
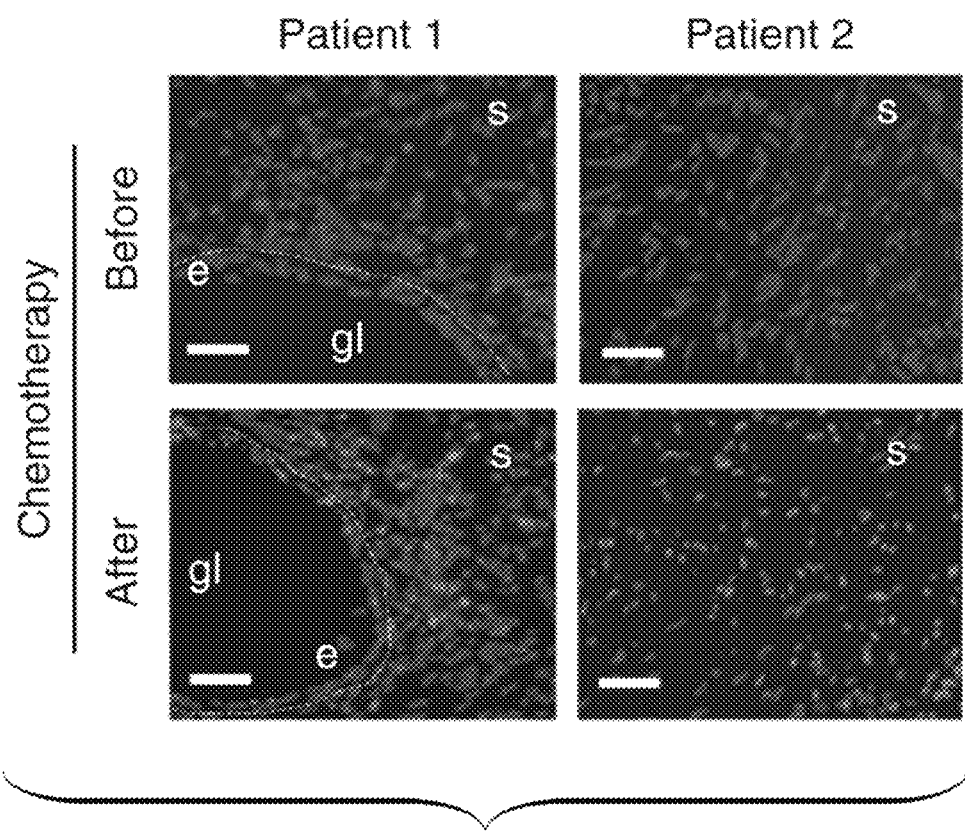
Figure 1C:
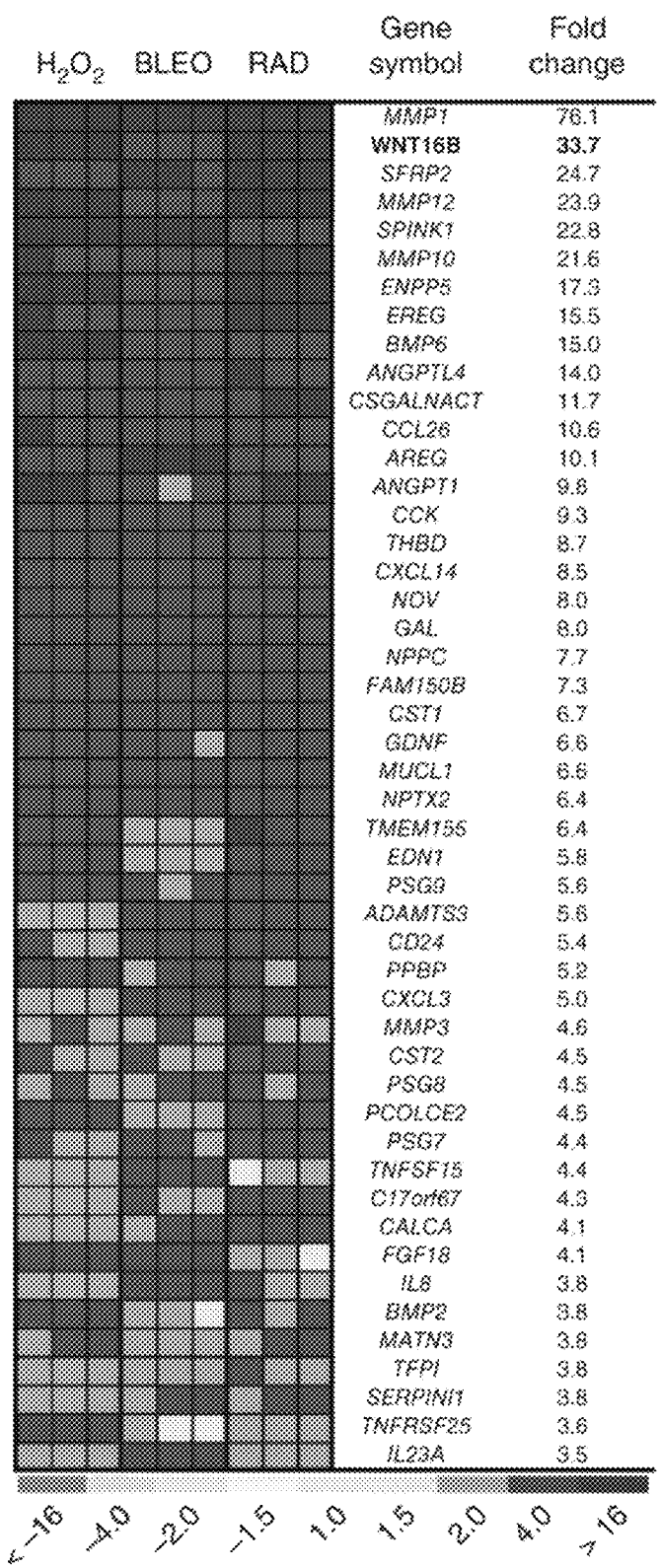
Figure 1D:
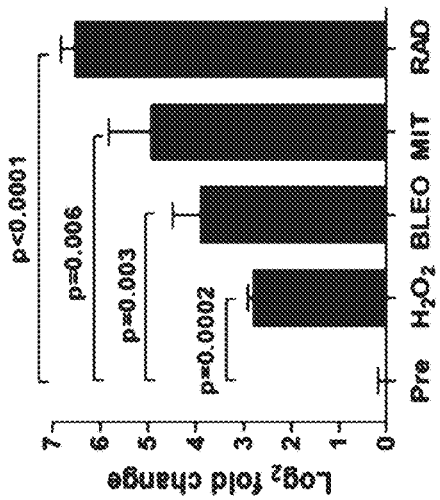
Figure 1F:
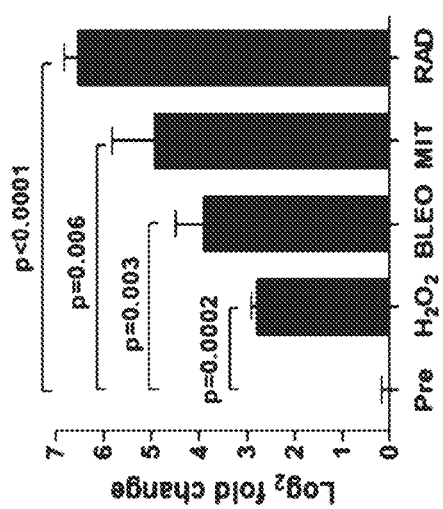
Figure 1E:
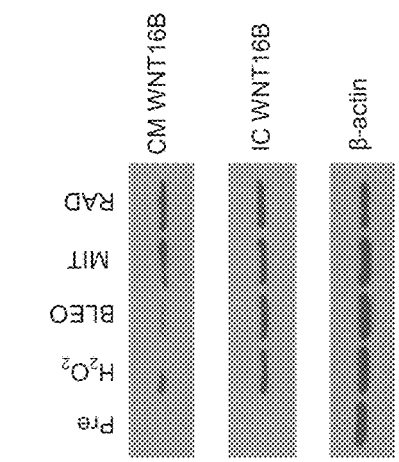
Figure 2A:
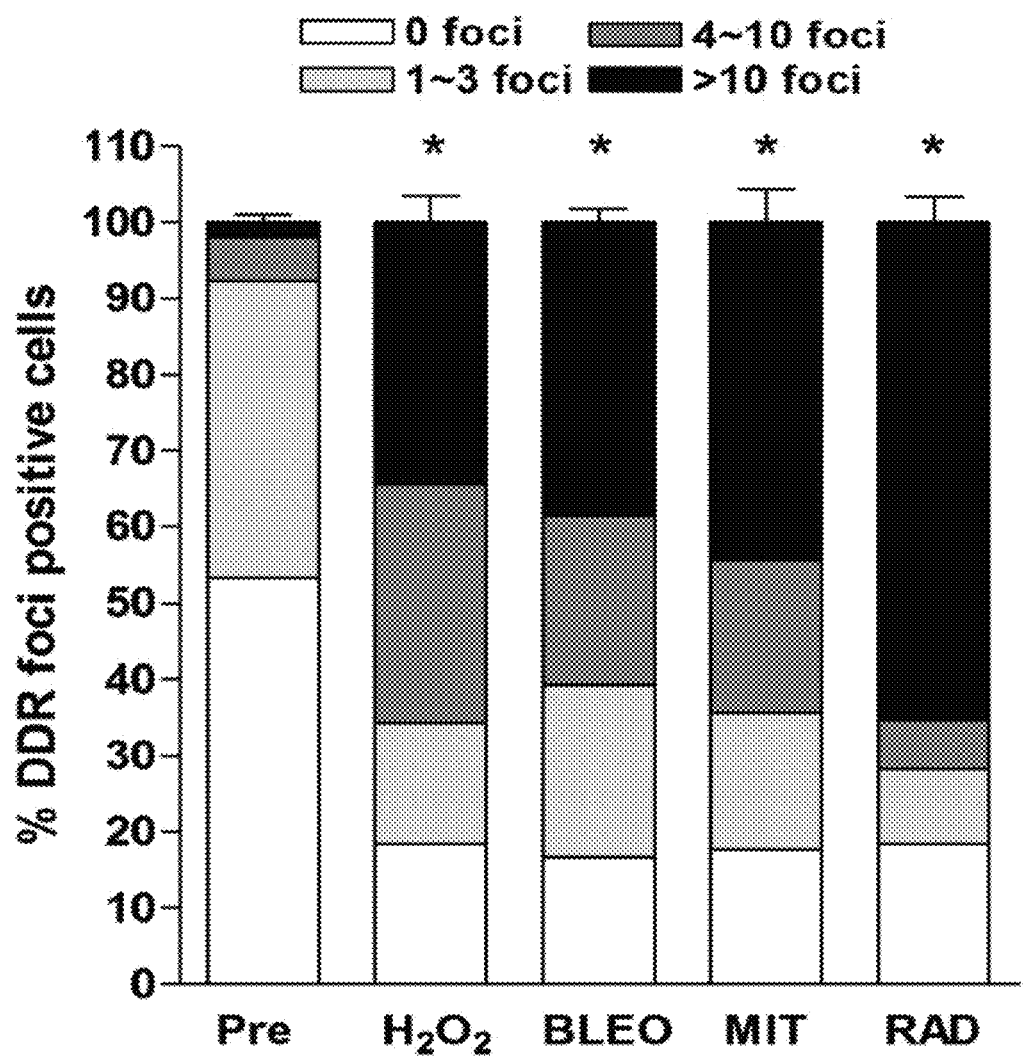
Figure 2C:
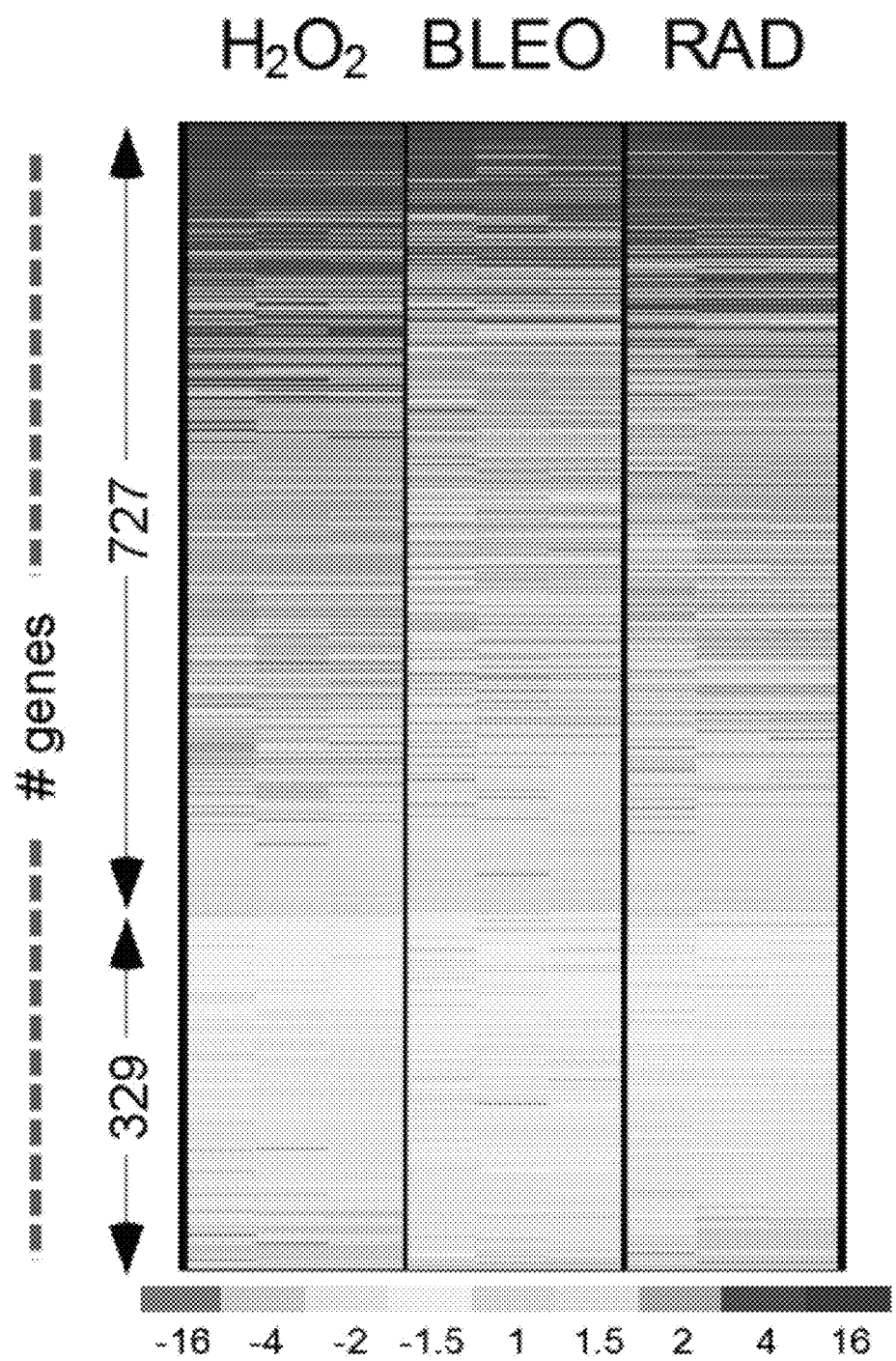

To assess for treatment-induced damage responses in benign cells comprising the tumor microenvironment, tissues collected before and after chemotherapy exposure were examined in men with prostate cancer enrolled in a neoadjuvant clinical trial combining the genotoxic drug mitoxantrone (MIT) and the microtubule poison docetaxel (DOC) (FIG. 1A) (Garzotto et al., Urol. Oncol. 24:254-259, 2006; Beer et al., Clin. Cancer Res. 10:1306-1311, 2004). After chemotherapy, evidence of DNA damage in fibroblasts and smooth muscle cells comprising the prostate stroma was found, as determined by the phosphorylation of histone H2AX on Ser139 (γ-H2AX) (FIG. 1B). To ascertain the molecular consequences of DNA damage in benign cells, primary prostate fibroblasts (PSC27 cells) were treated with MIT, bleomycin (BLEO), hydrogen peroxide ($H_2O_2$) or gamma radiation (RAD), each of which substantially increased the number of γ-H2AX foci (FIGS. 2A and 2B). Whole-genome microarrays were used to quantify transcripts in PSC27 cells and determined that the levels of 727 and 329 mRNAs were commonly increased and decreased, respectively (false discovery rate of 0.1%), as a result of these genotoxic exposures (FIG. 2C). To focus the present studies on those factors with the clear potential for paracrine effects on tumor cells, genes with at least 3.5-fold elevated expression after genotoxic treatments that encode extracellular proteins were evaluated, here collectively termed the DNA damage secretory program (DDSP) (FIG. 1C). Consistent with previous studies, transcripts encoding matrix metalloproteinases, such as MMP1, and chemokines, such as CXCL3, were substantially elevated in damaged cells. (Bavik et al., Cancer Res. 66:794-802, 2006; Coppe et al., PLos Biol. 6:2853-2868, 2008) Of particular interest, peptide growth factors with known roles or the potential to influence the growth of prostate cancer were upregulated including epidermal growth factor receptor (EGFR) ligands epiregulin (EREG), induced 15 fold, and amphiregulin (AREG), induced 10 fold. Surprisingly, the serine protease inhibitor SPINK1, recently shown to promote EGFR signaling in prostate cancinoma, was induced 20 fold (FIG. 1D). The RET oncogene ligand GDNF was induced 6 fold (FIG. 1E). Also, it was notable that the expression of WNT16B increased between eightfold and 64-fold as a result of these treatments (P<0.005) (FIGS. 1C and 1F).

Figure 1G:
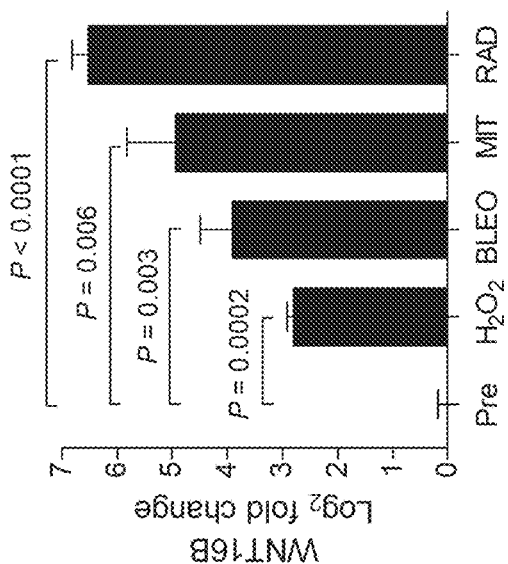
Figure 1H:
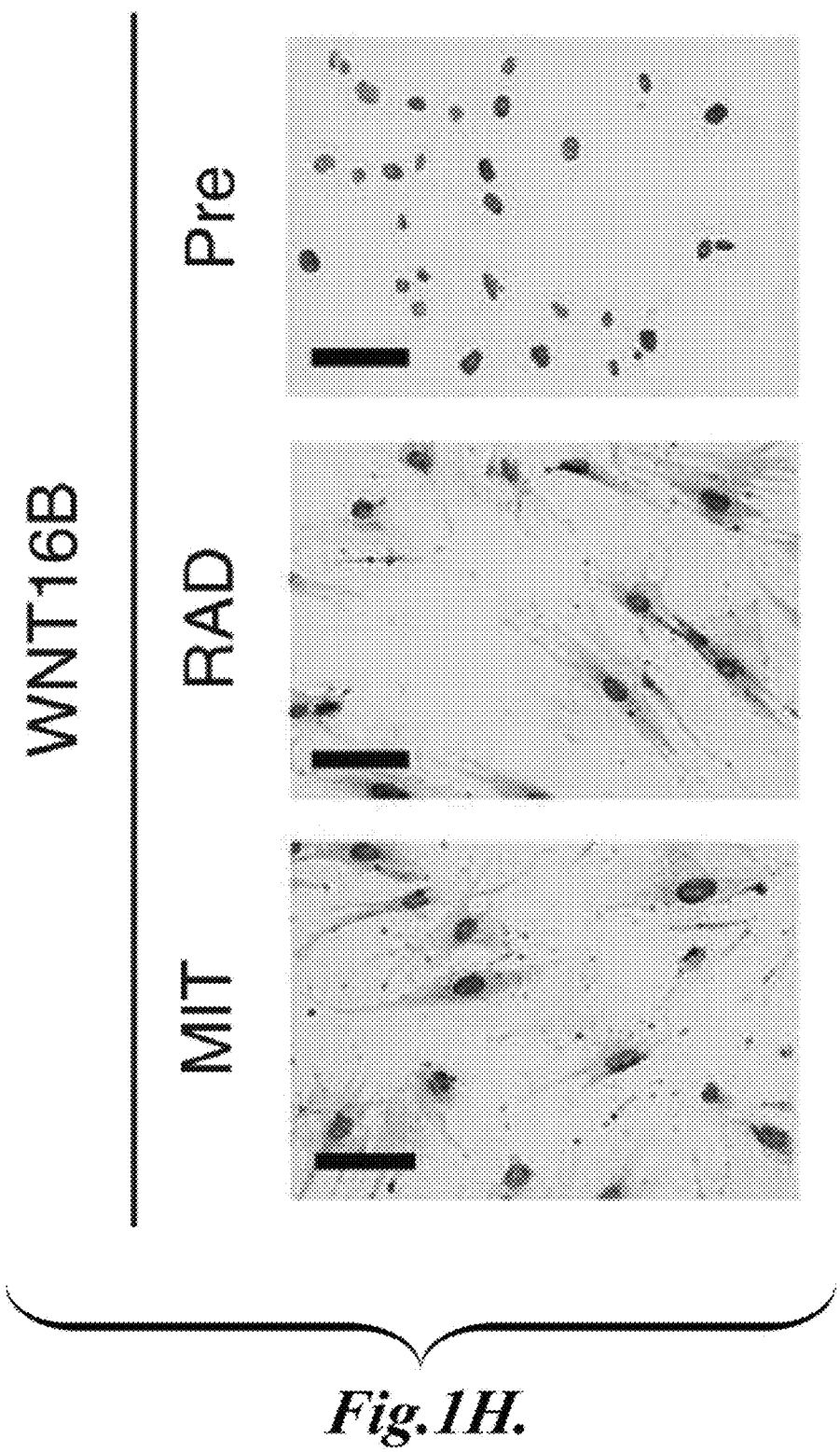
Figure 1I:
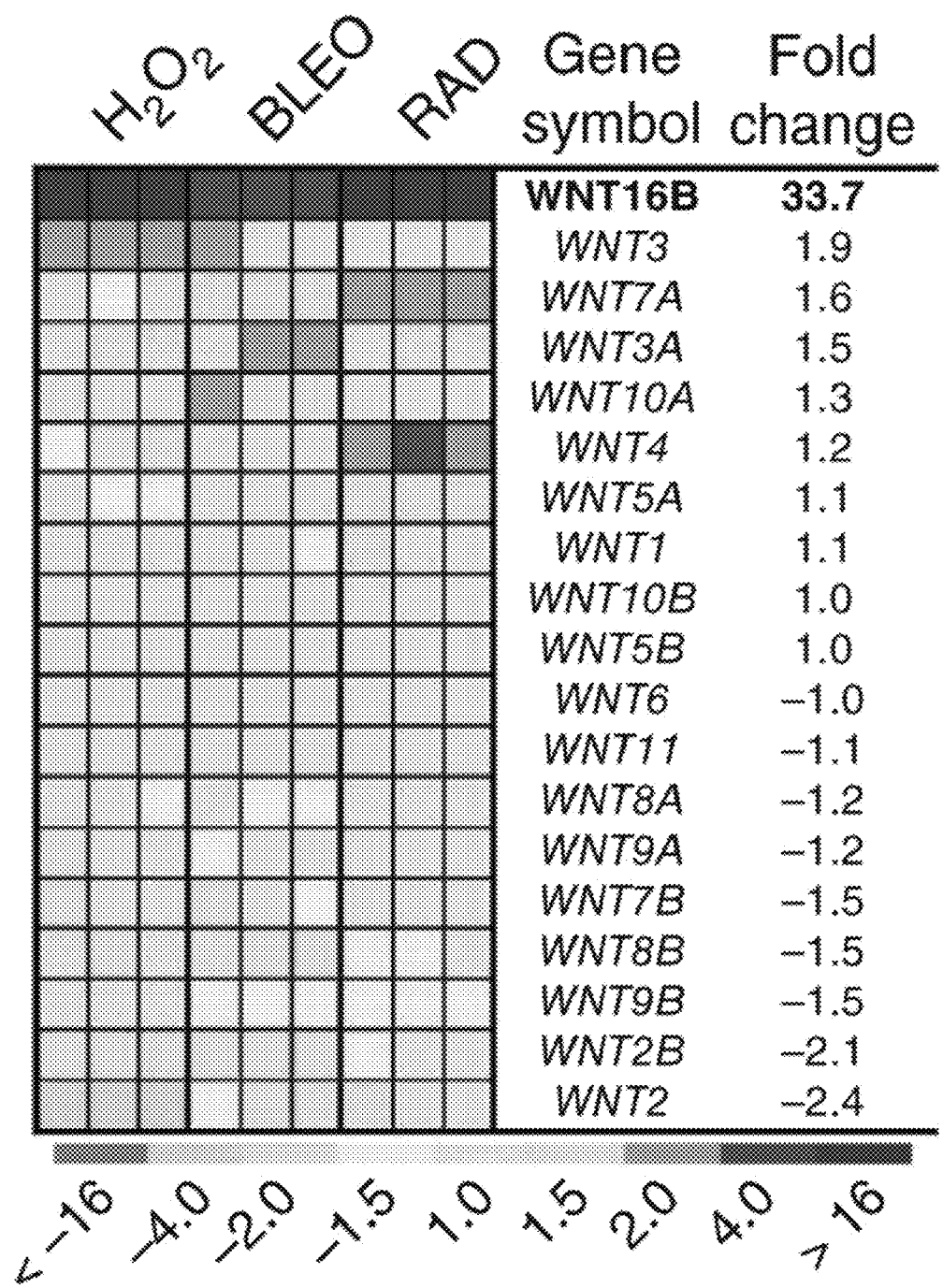
Figure 1J:
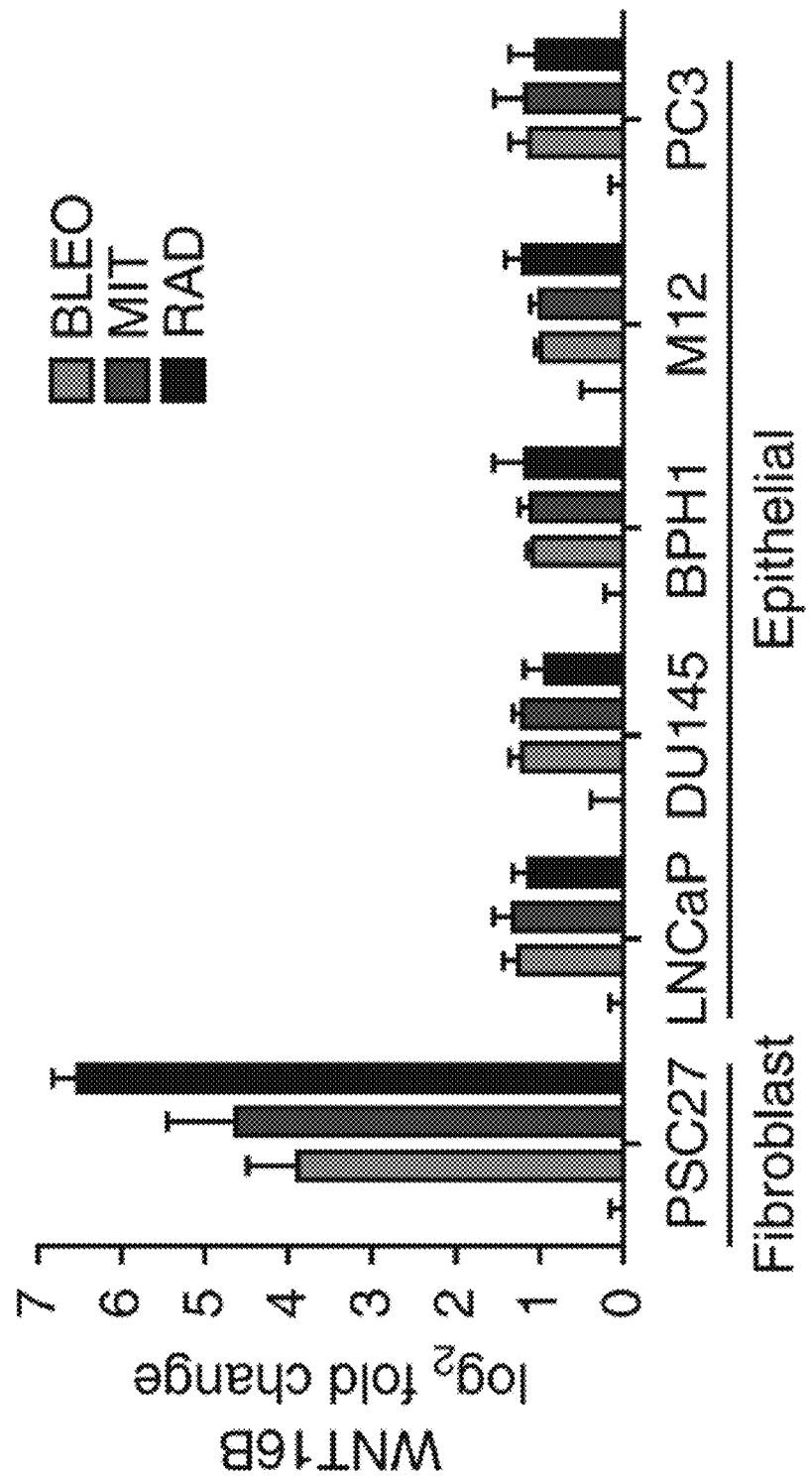

Wnt family members participate in well-described mesenchymal and epithelial signaling events that span developmental biology, stem cell functions and neoplasia (Clevers, Cell 127:469-480. 2006). Though little information links Wnt signaling to DNA damage responses, a previous study reported WNT16B overexpression in the context of stress- and oncogene-induced senescence (Binet et al., Cancer Res. 69:9183-9191, 2009). DNA damage increased WNT16B protein expression was confirmed and elevated amounts of extracellular WNT16B were found in conditioned medium from prostate fibroblasts after chemotherapy or radiation (FIGS. 1G and 1H). Transcripts encoding other Wnt family members were not substantially altered in the prostate fibroblasts studied here (FIG. 1I). In contrast to the WNT16B responses in fibroblasts, little induction of WNT16B expression was observed in epithelial cells (FIG. 1J).

Figure 2D:
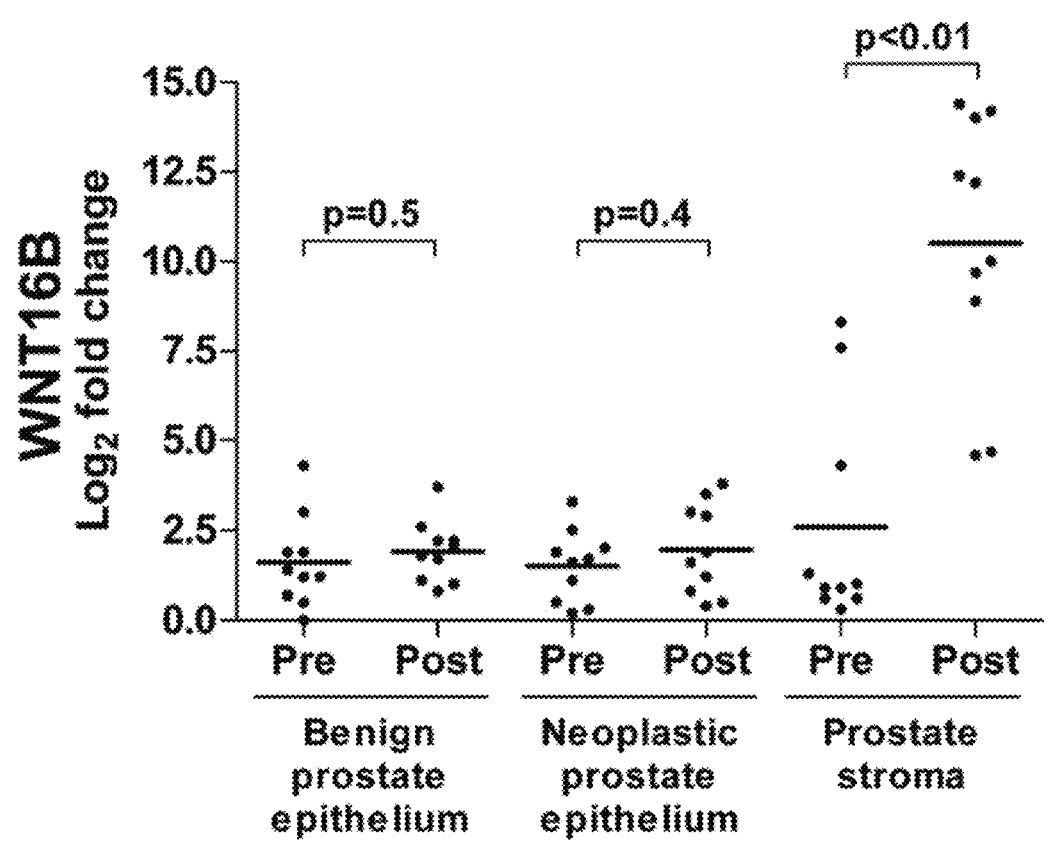
Figure 2E:
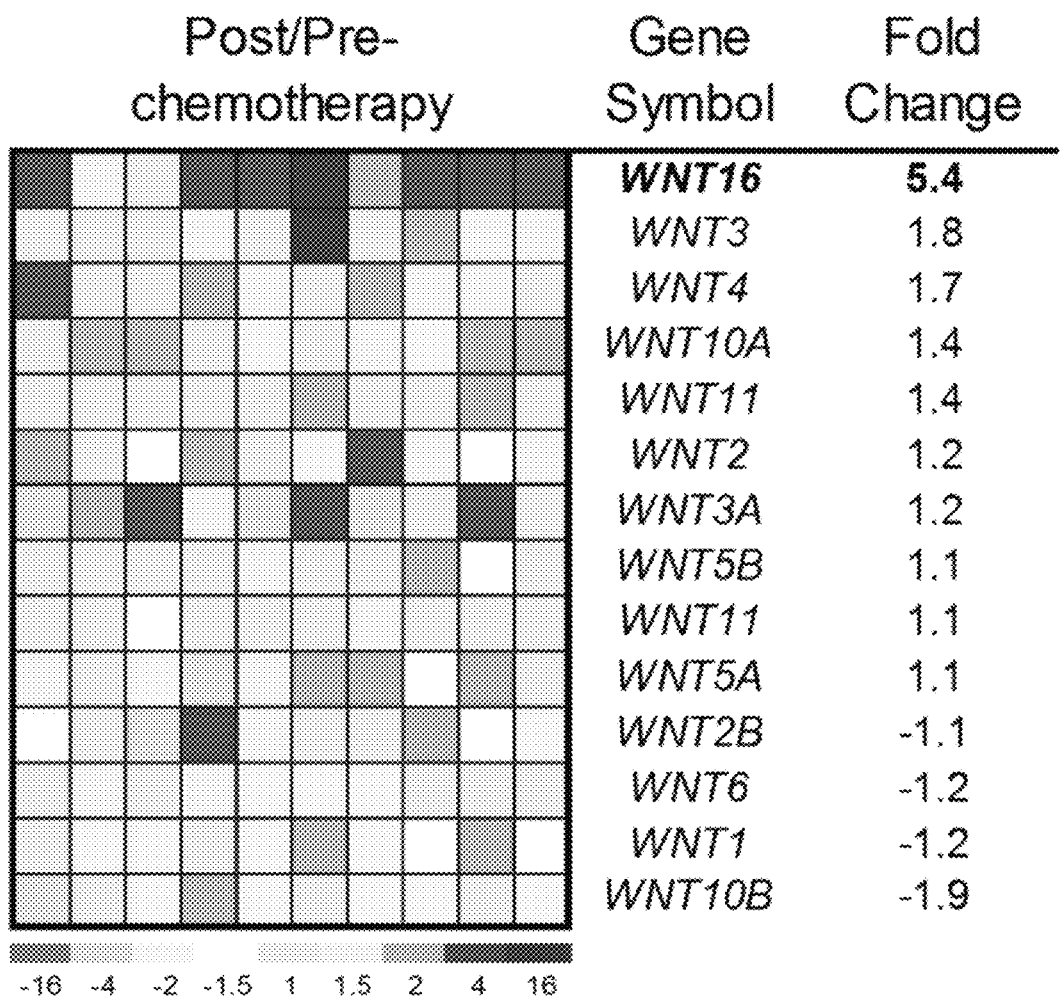
Figure 3A:
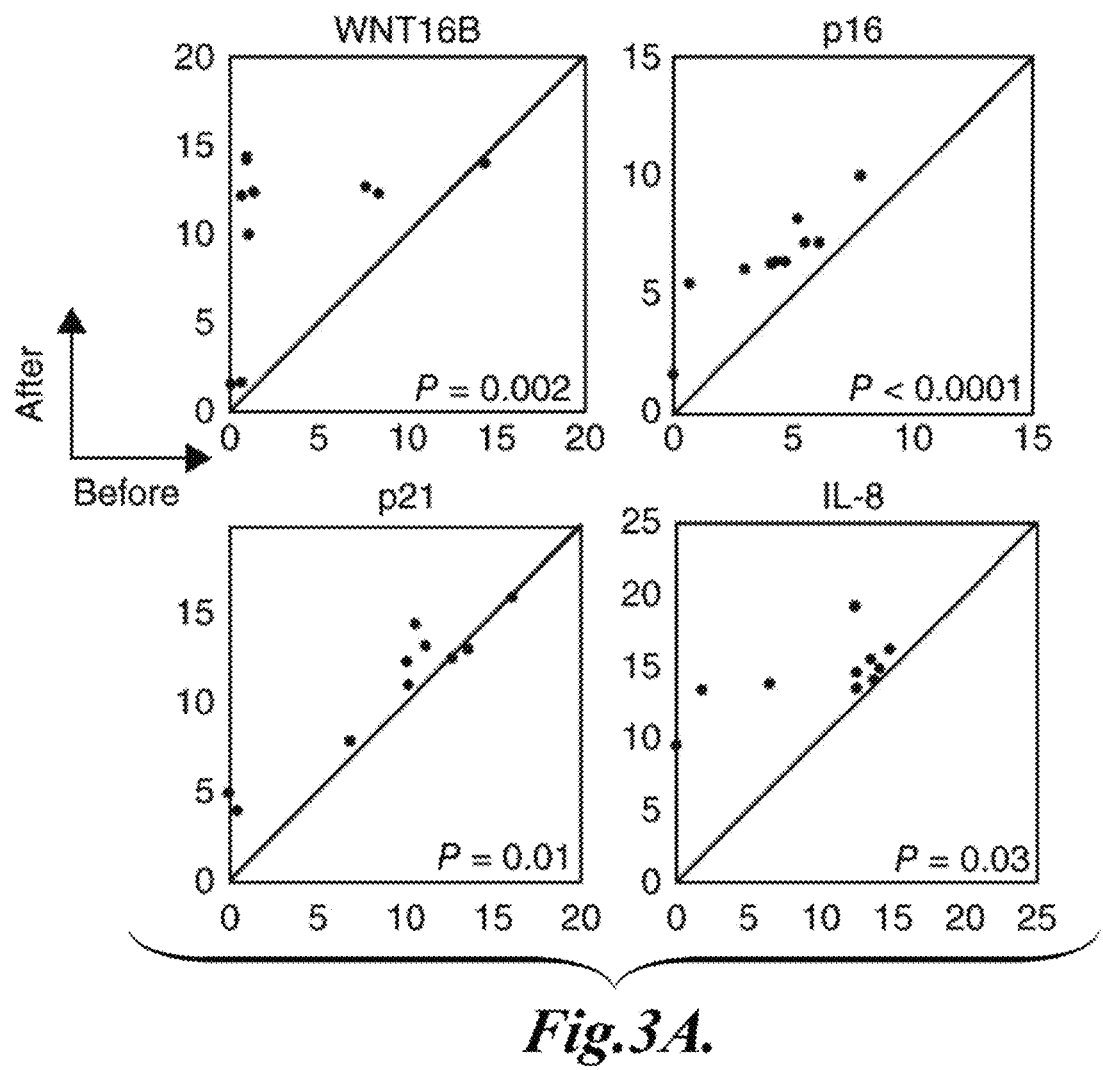
FIGS. 3A through 3F demonstrate that cytotoxic chemotherapy induces WNT16B expression in the tumor microenvironment.
Figure 3B:
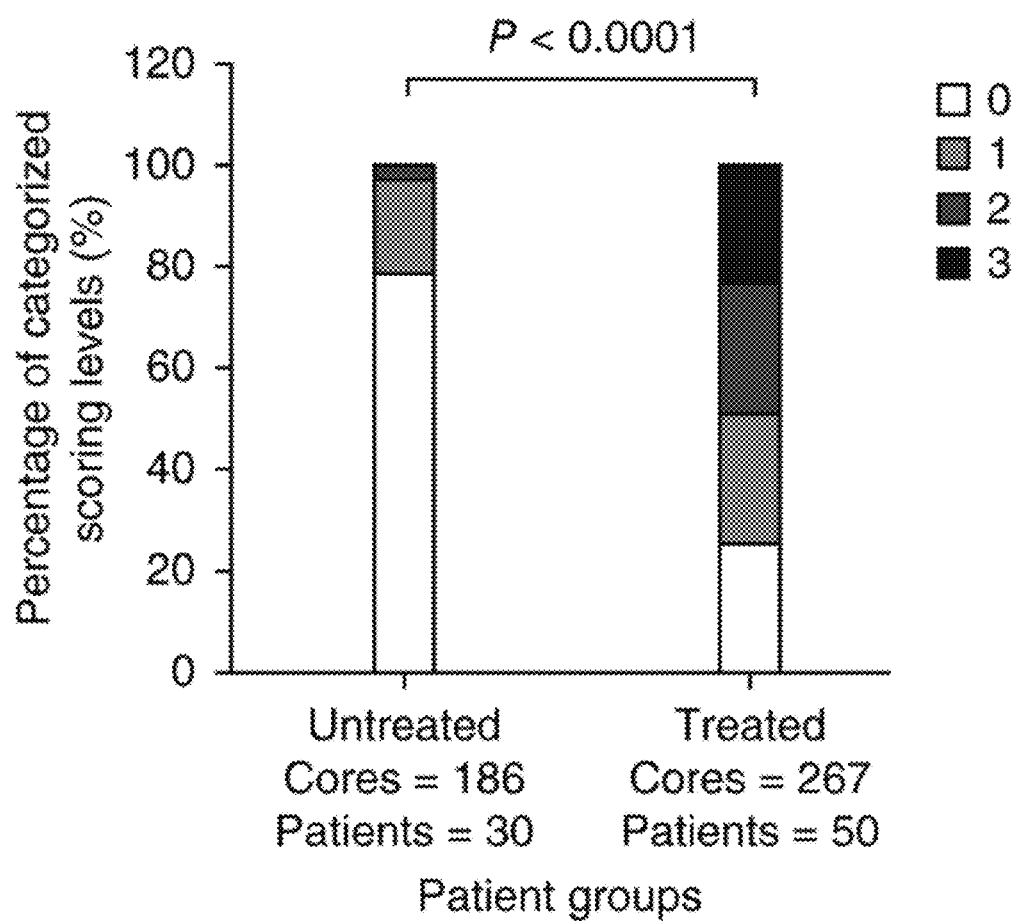
Figure 3C:
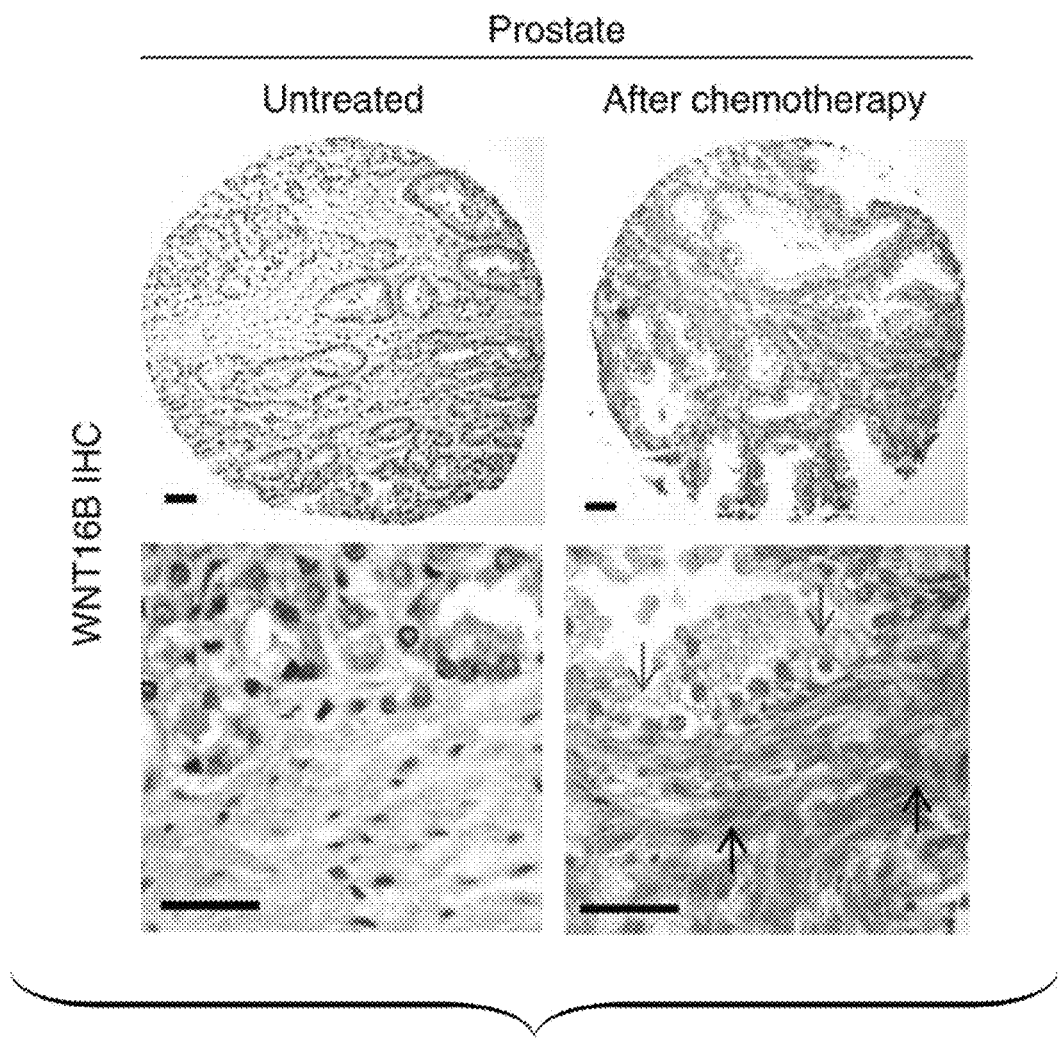

Next confirmation that expression of WNT16B is induced by genotoxic therapy in vivo was sought. Laser-capture microdissection was used to separately isolate stroma and epithelium and determined by quantitative RT-PCR (qRT-PCR) that the number of WNT16B transcripts increased by approximately sixfold in prostate stroma after chemotherapy (P<0.01) (FIG. 3A and FIG. 2D). The expression of other genes known to respond to DNA damage, including CDKN2A (also known as p16), CDKN1A (also known as p21) and IL8, also increased in response to chemotherapy in prostate stroma (FIG. 3A) (Coppe et al., PLos Biol. 6:2853-2868, 2008; Acosta et al., Cell 133:1006-1018, 2008). Next, induction of WNT16B protein expression was confirmed by immunohistochemistry. Compared to untreated prostate tissue, WNT16B protein was substantially and significantly increased after chemotherapy in the periglandular stroma, which included fibroblasts and smooth muscle cells (P<0.01) (FIGS. 3B and 3C). In contrast, very limited WNT16B expression was observed in benign or neoplastic epithelium, and mRNAs encoding other Wnt family proteins were not substantially altered in prostate stroma (FIGS. 2D and 2E).

Figure 3D:
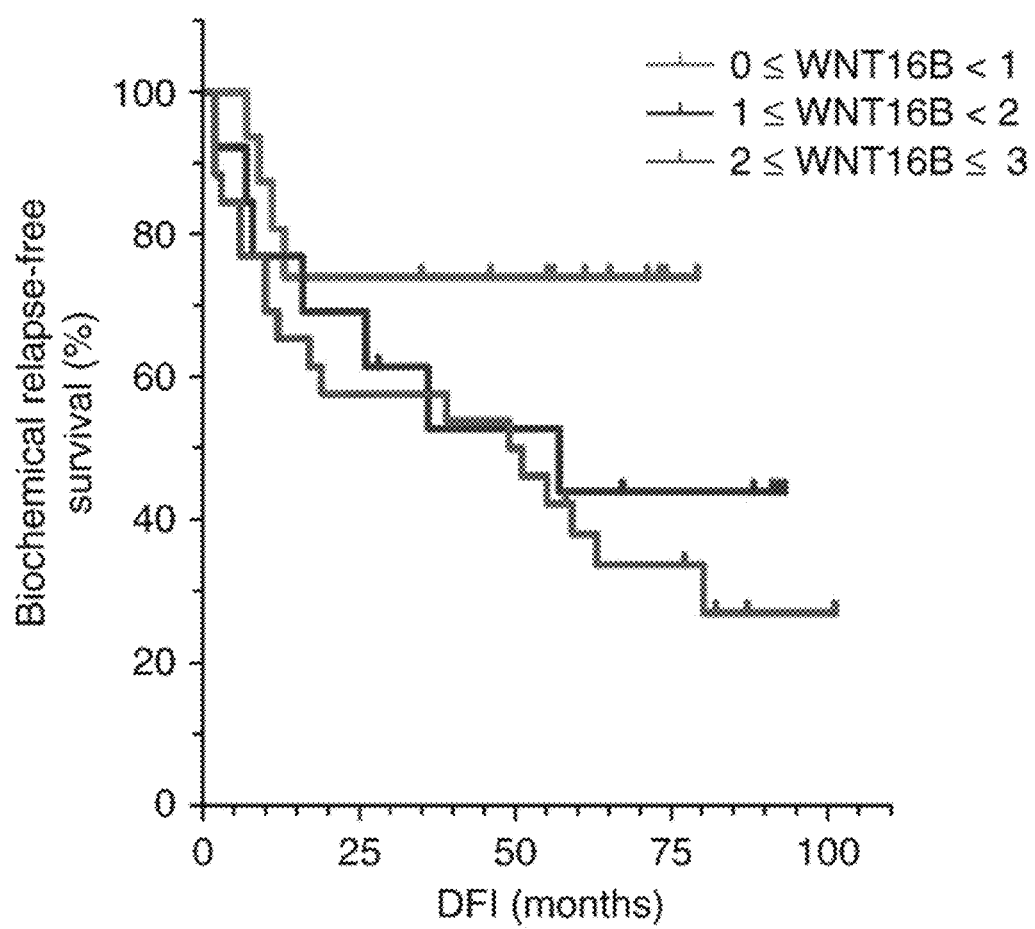
Figure 3E:
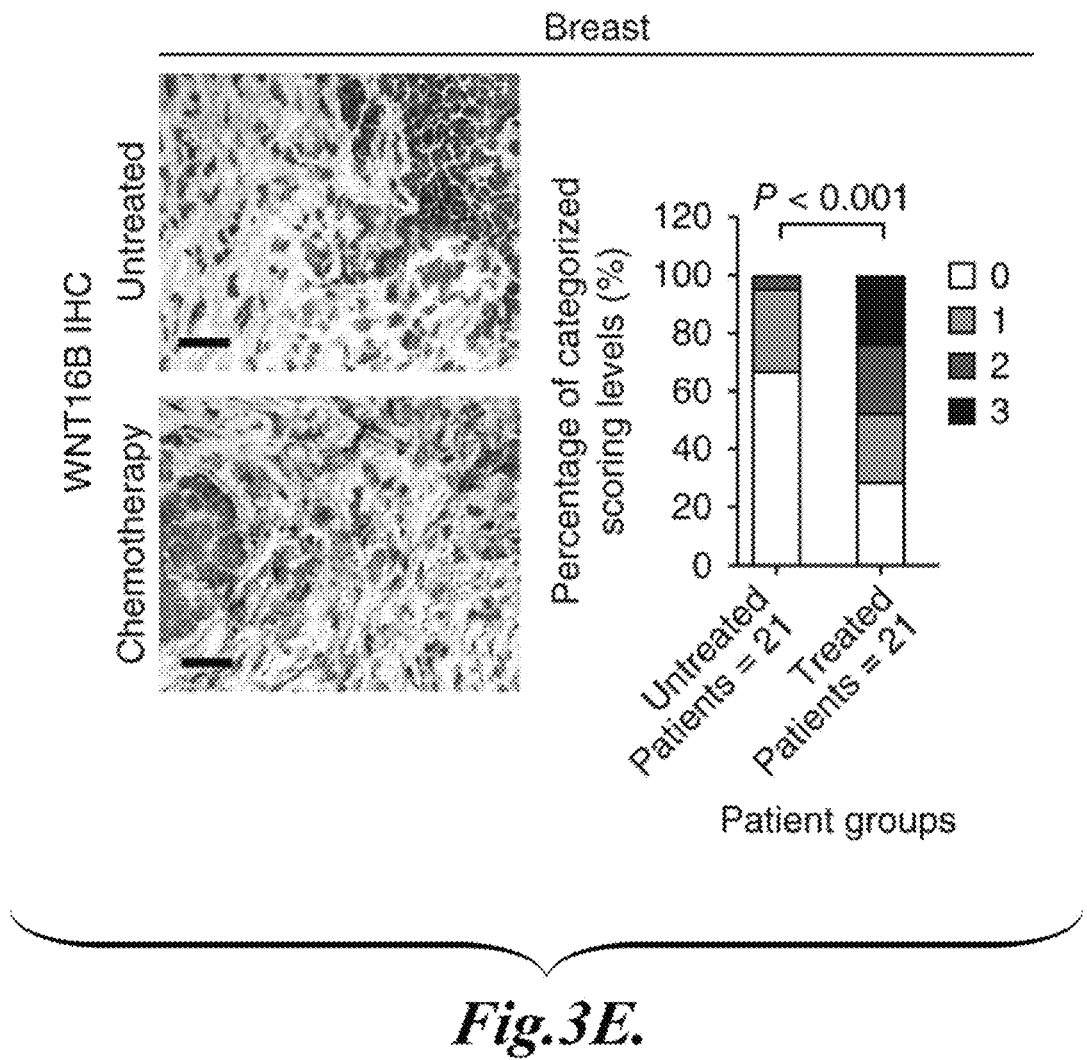
Figure 3F:
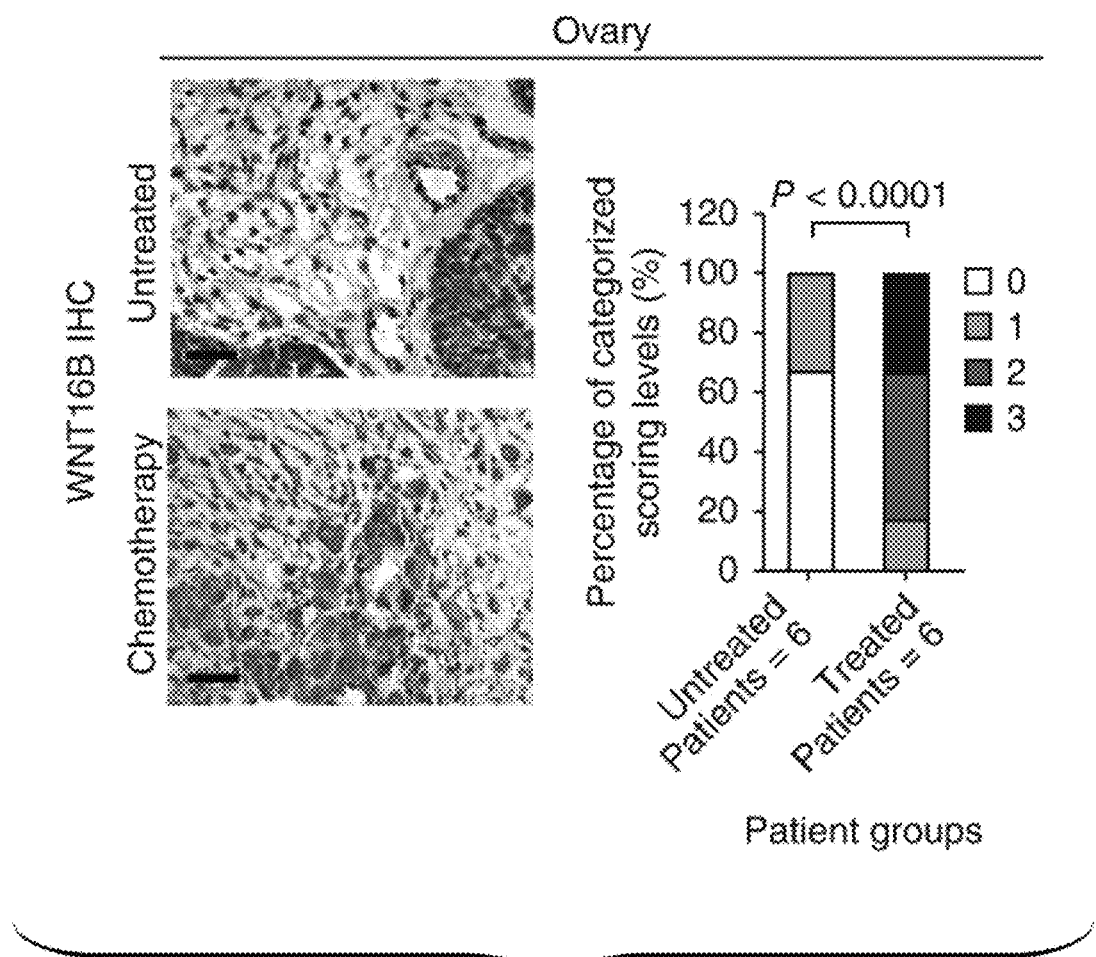
Figure 4A:
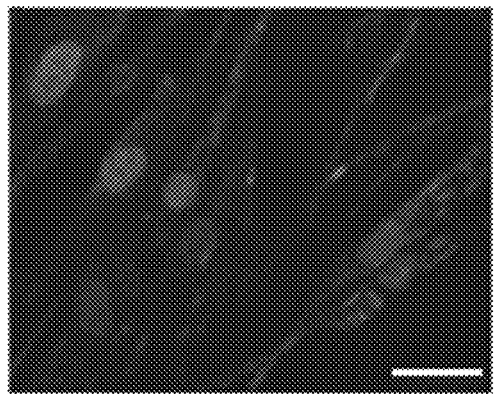
FIGS. 4A through 4D show that DNA damage induces WNT16B expression in a spectrum of human fibroblasts and murine organs.
Figure 4A:
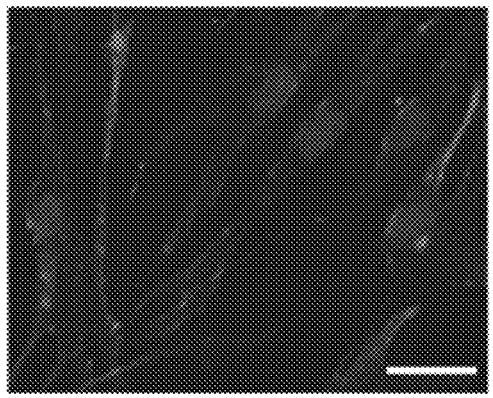
Figure 4A:
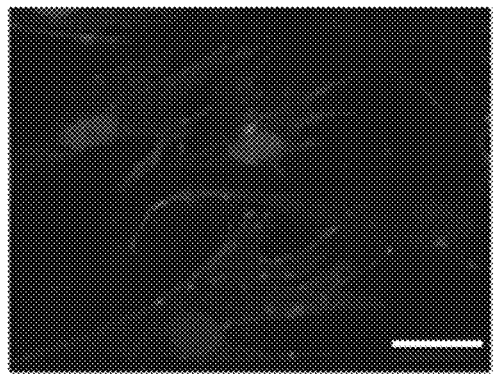
Figure 4A:
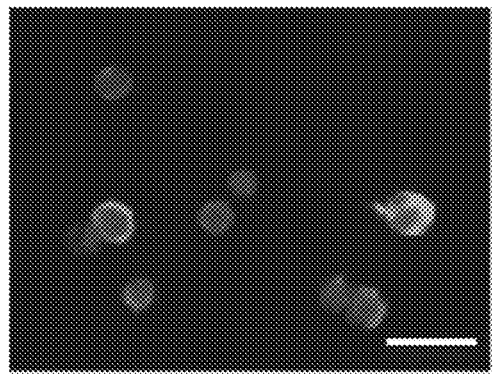
Figure 4B:
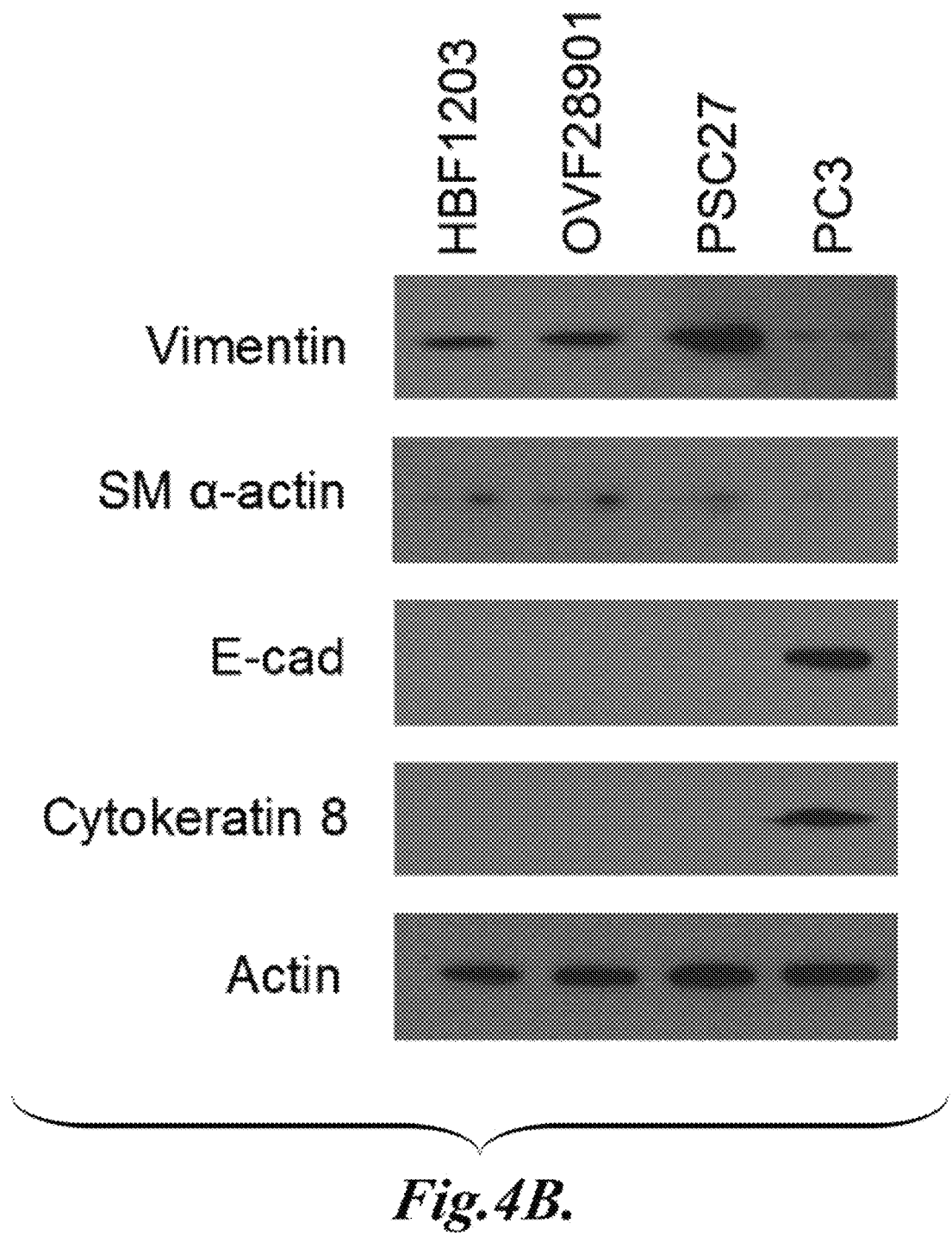
Figure 4C:
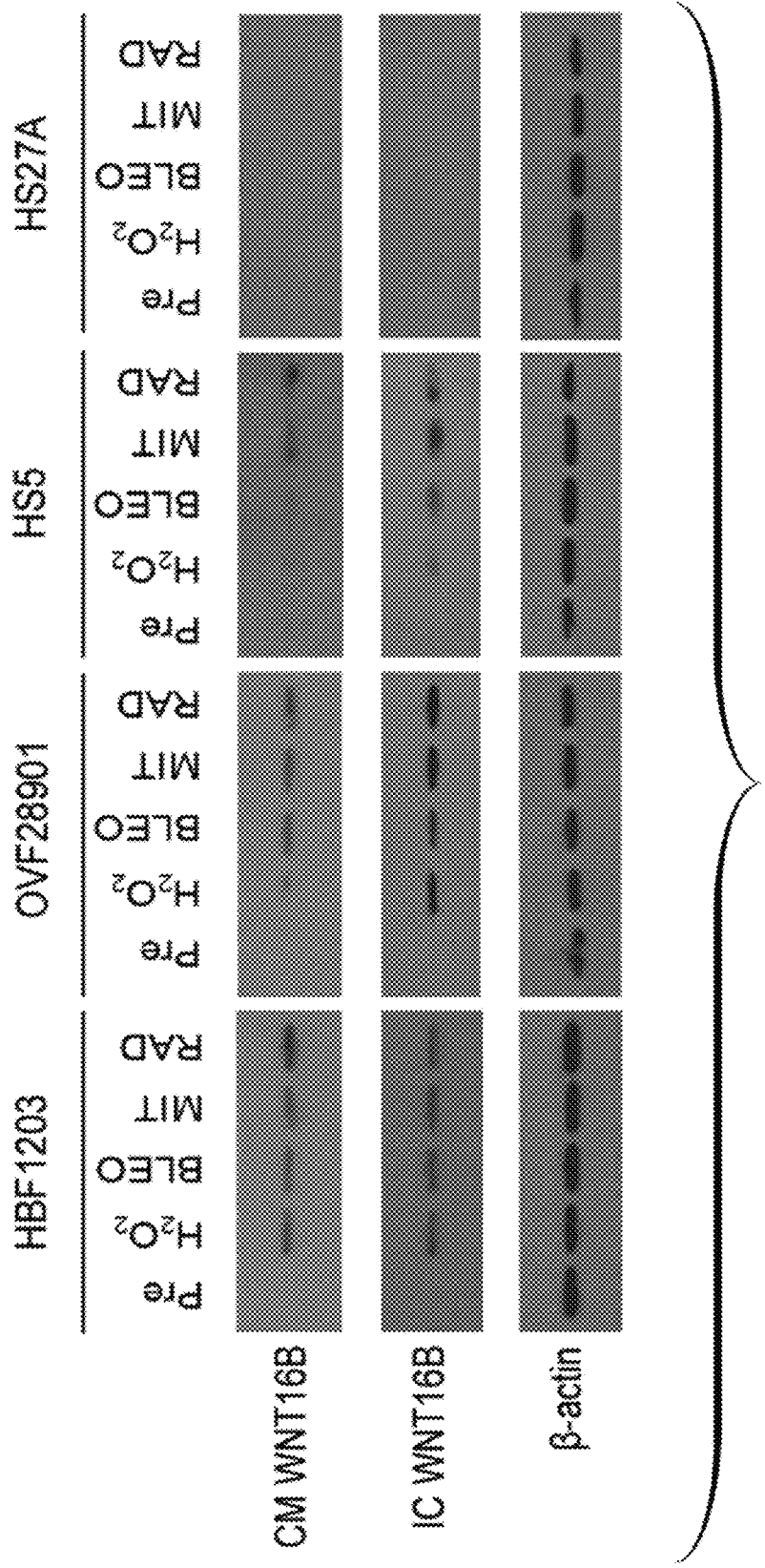
Figure 4D:
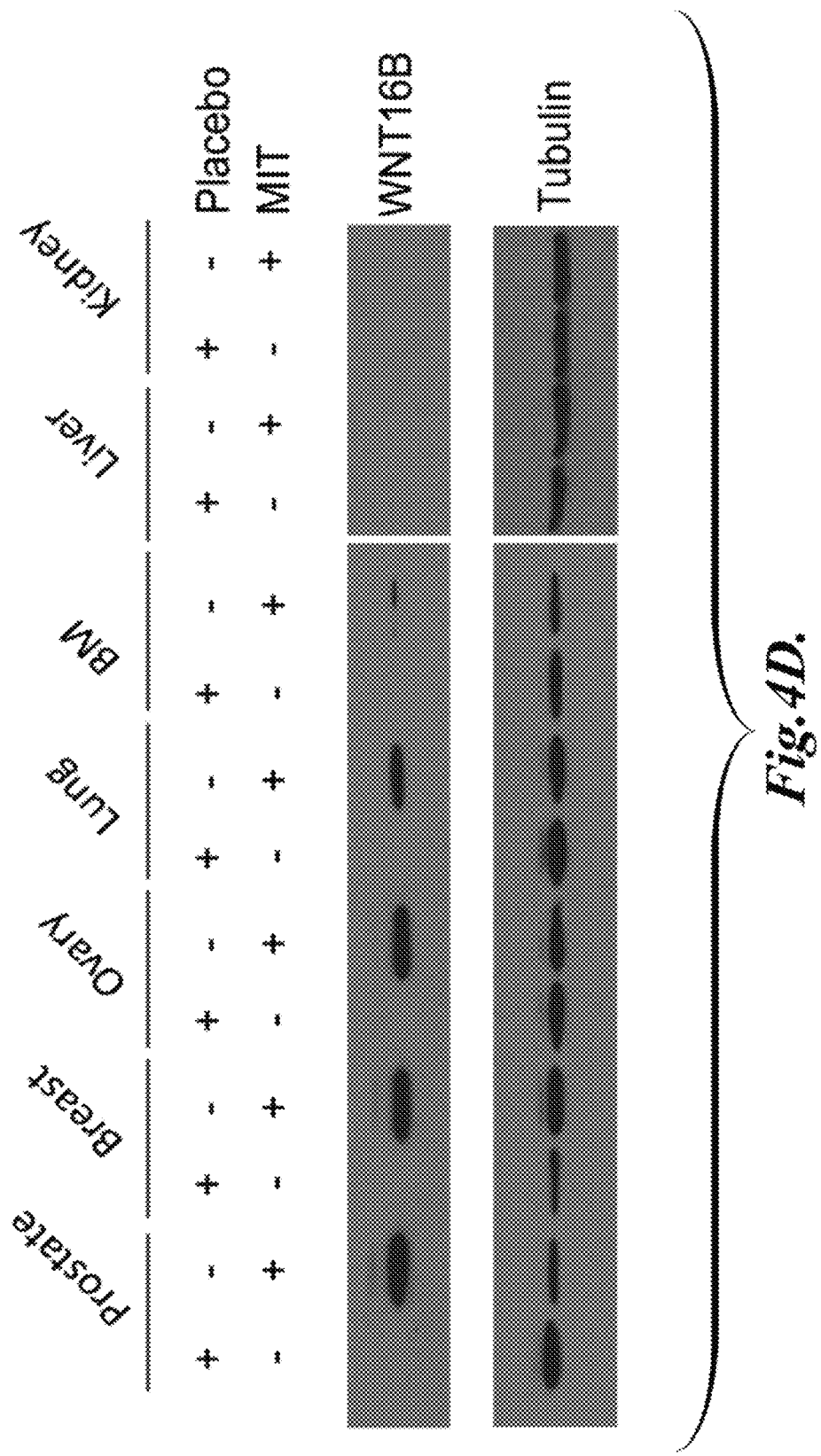

These findings were confirmed in breast and ovarian carcinomas, two other malignancies commonly treated with cytotoxic chemotherapy. Genotoxic treatments induced the expression of WNT16B protein in primary human fibroblasts isolated directly from breast and ovarian tissues and in the prostates, breasts and ovaries of mice treated with MIT (FIGS. 4A through 4D). WNT16B protein expression was significantly elevated in the stroma of human breast and ovarian cancers treated with neoadjuvant chemotherapy compared with tumors from patients that did not receive treatment (P<0.001) (FIG. 3). Notably, in each of the tumor types evaluated, a range of absent to robust WNT16B expression was evident. Because responses to chemotherapy also varied, whether WNT16B expression was associated with clinical outcome was evaluated. In patients with prostate cancer treated with neoadjuvant chemotherapy, higher WNT16B immunoreactivity in prostate stroma after treatment was associated with a significantly greater likelihood of cancer recurrence (P=0.04) (FIG. 3D). Next, the mechanism(s) by which WNT16B could contribute to treatment failure was sought.

WNT16B Promotes Cancer Cell Proliferation and Invasion

Figure 5A:
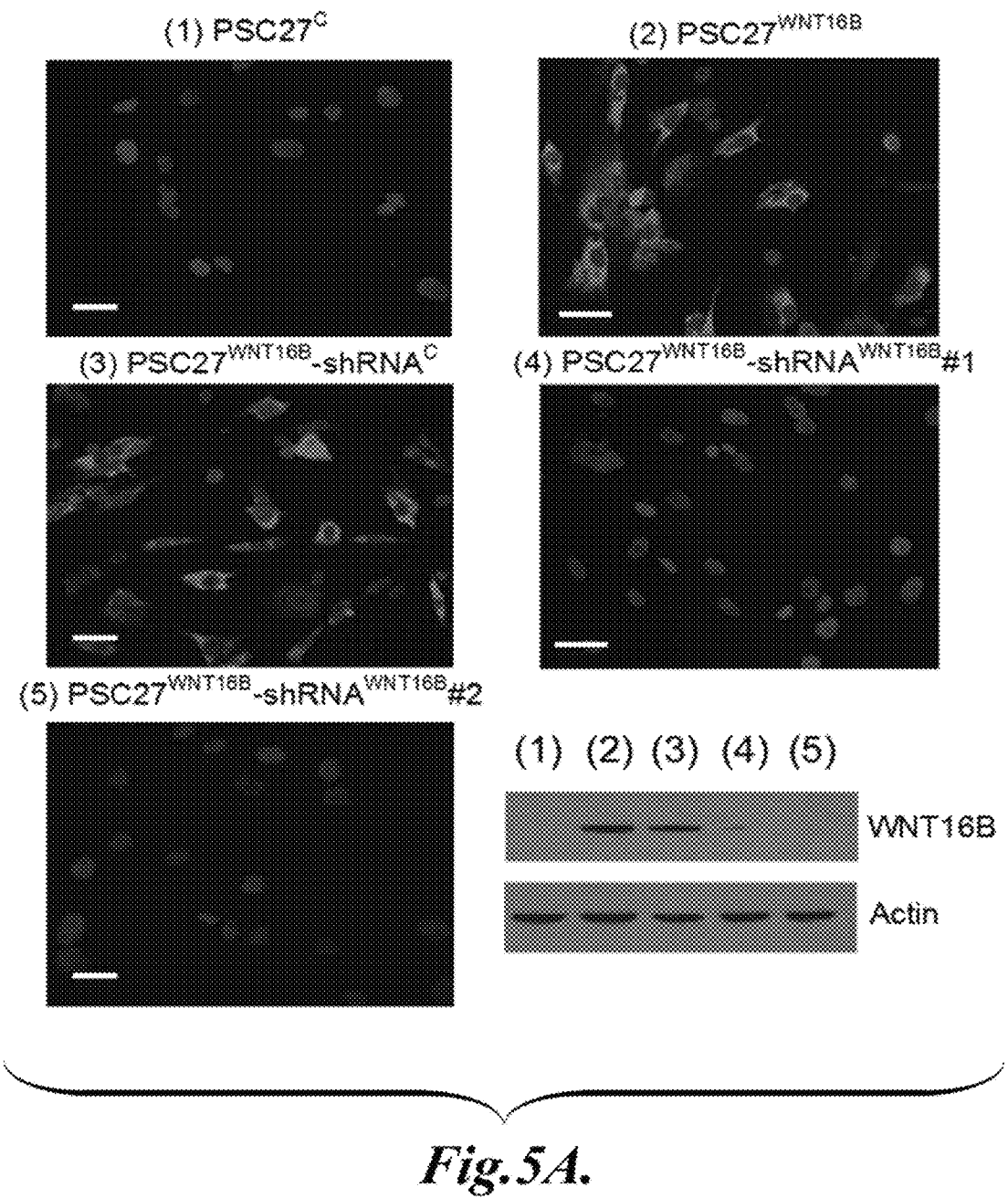
FIGS. 5A through 5F demonstrate that epithelial cell phenotypes are altered by fibroblast-derived paracrineacting WNT16B.
Figure 5B:
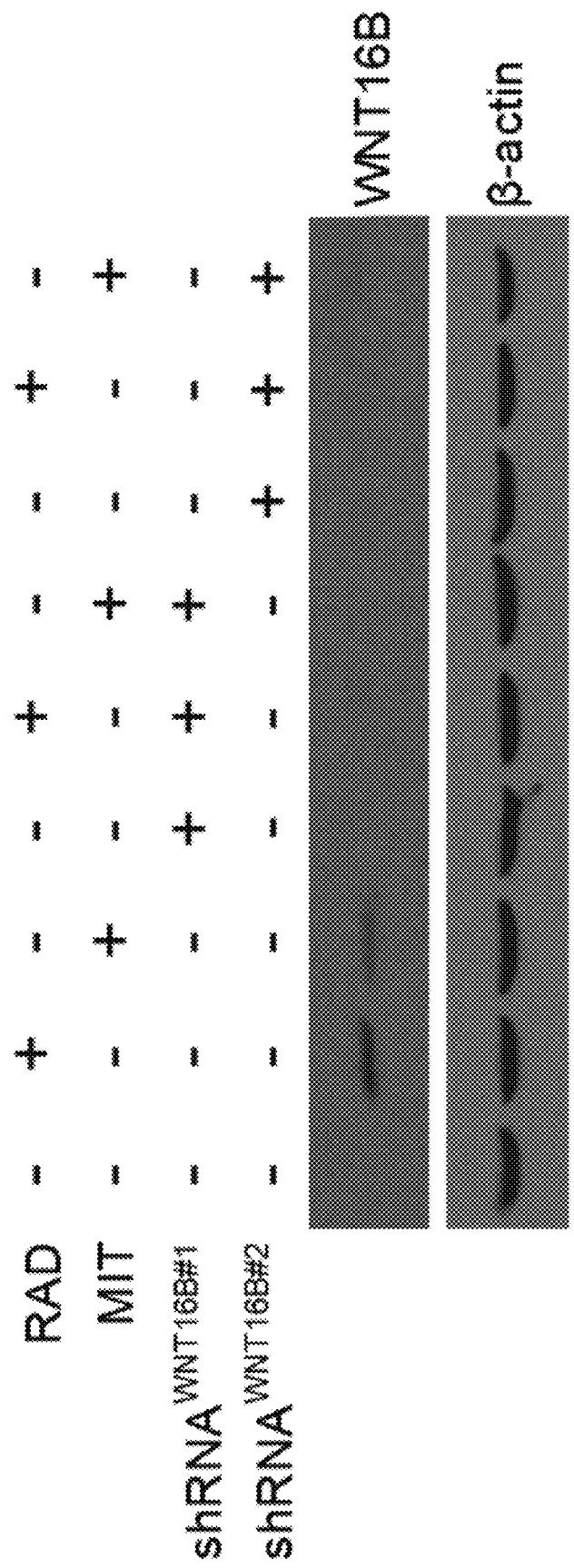
Figure 5C:
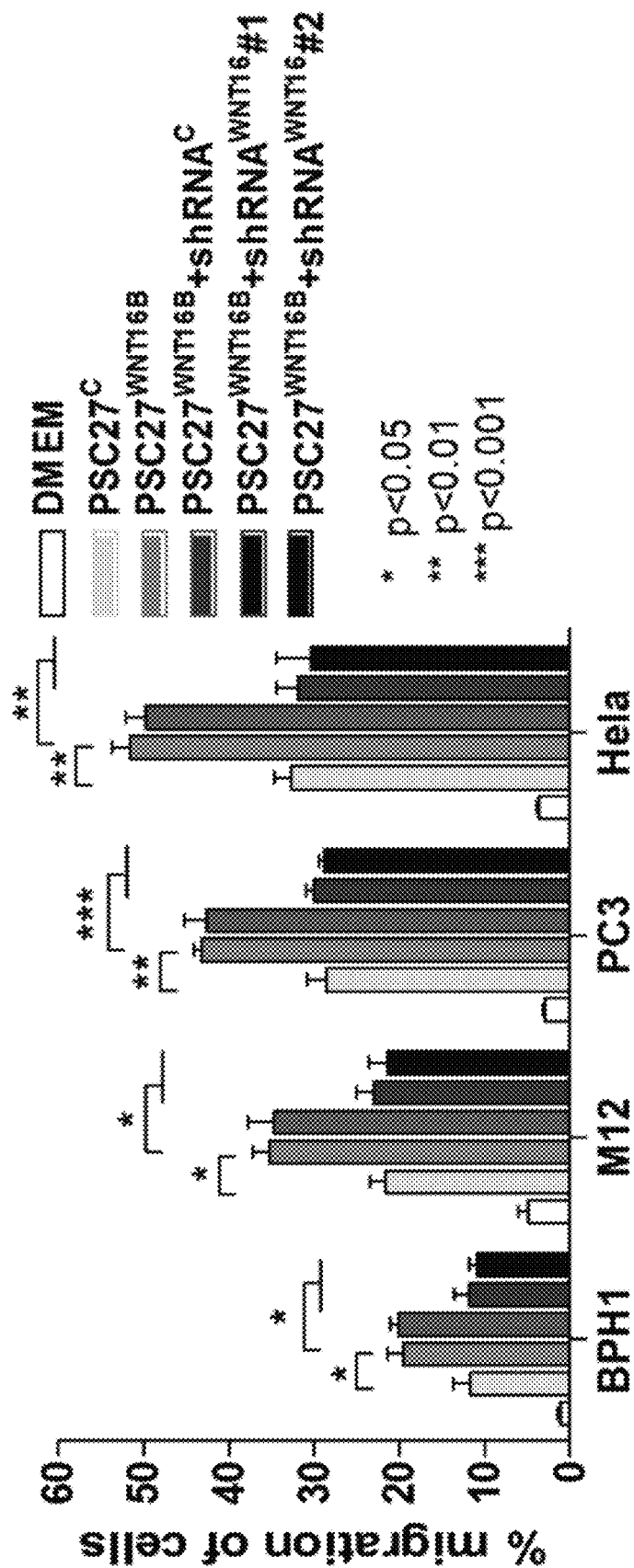
Figure 5D:
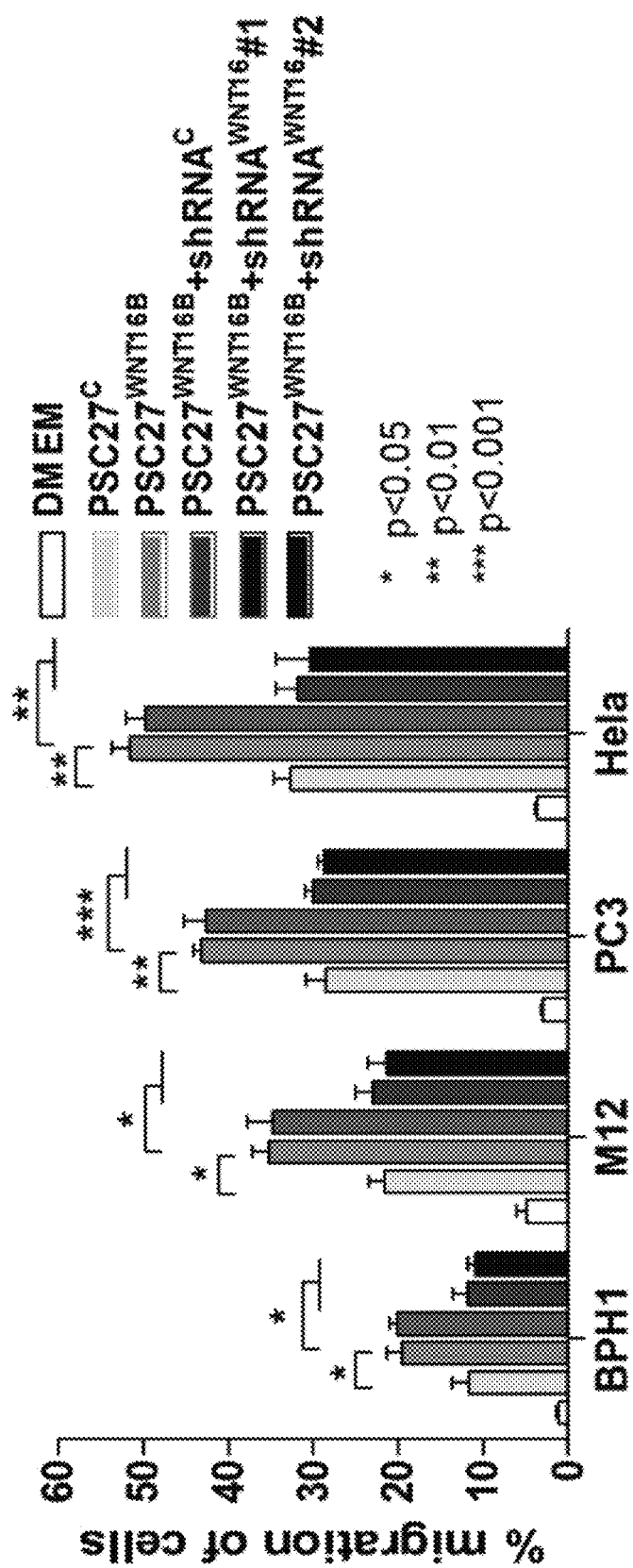
Figure 6A:
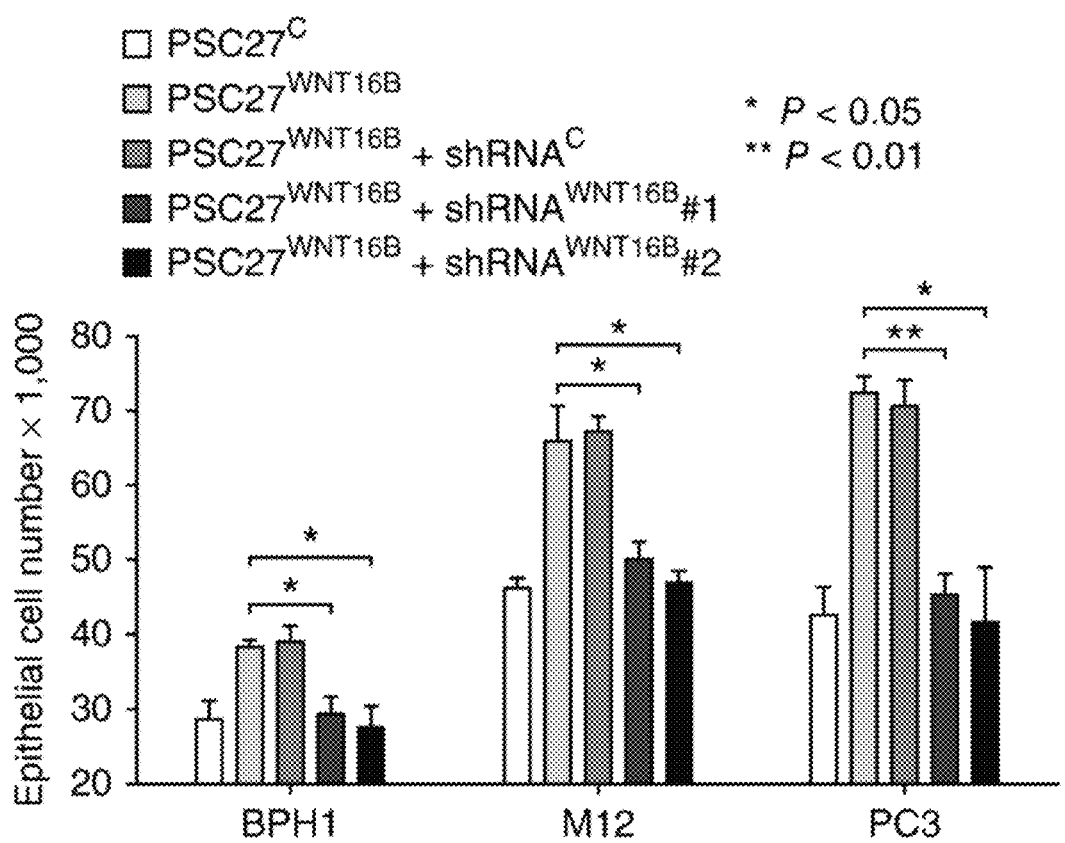
FIGS. 6A through 6G demonstrate that WNT16B is a major effector of the full DDSP and promotes the growth and invasion of prostate carcinoma.
Figure 6B:
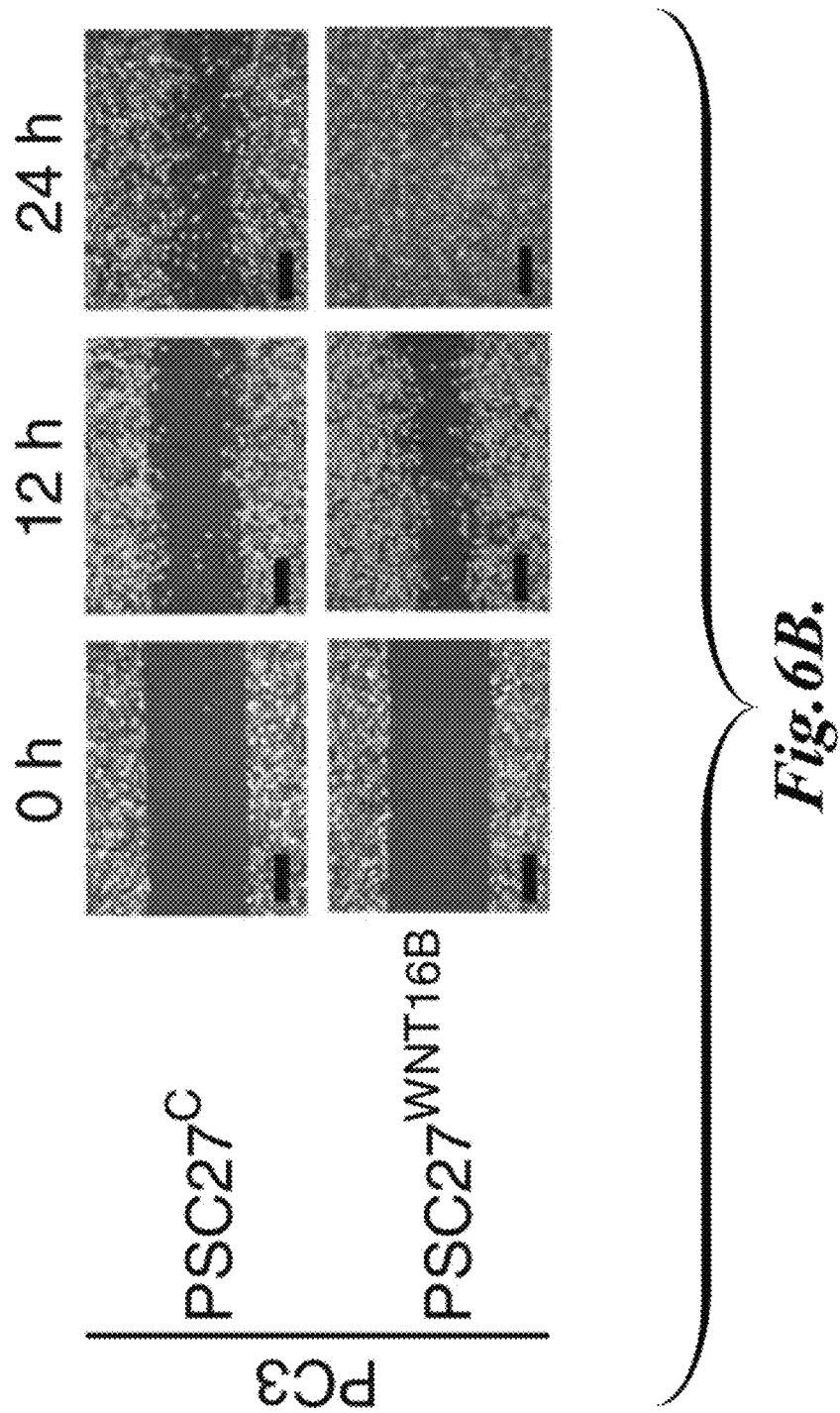

Members of the Wnt family influence cellular phenotypes through β-catenin-dependent and -independent pathways (Clevers, Cell 127:469-480, 2006). A prostate fibroblast cell strain with stable expression of WNT16B (PSC27$^{WNT16B}$) and fibroblast strains that expressed a short hairpin (sh) RNAs specific to WNT16B (shRNA$^{WNT16B}$) were generated, which blocked the induction of WNT16B expression by RAD and MIT (FIGS. 5A and 5B). PSC27$^{WNT16B}$-conditioned medium significantly enhanced prostate cancer cell growth (P<0.01) (FIG. 6A) and increased cellular migration and invasion of PC3 cells (P<0.05) compared to conditioned medium from PSC27 vector controls (PSC27$^C$) (FIG. 6B and FIGS. 5C and 5D), confirming that WNT16B can promote phenotypic changes in tumor cells through paracrine mechanisms.

Figure 6C:
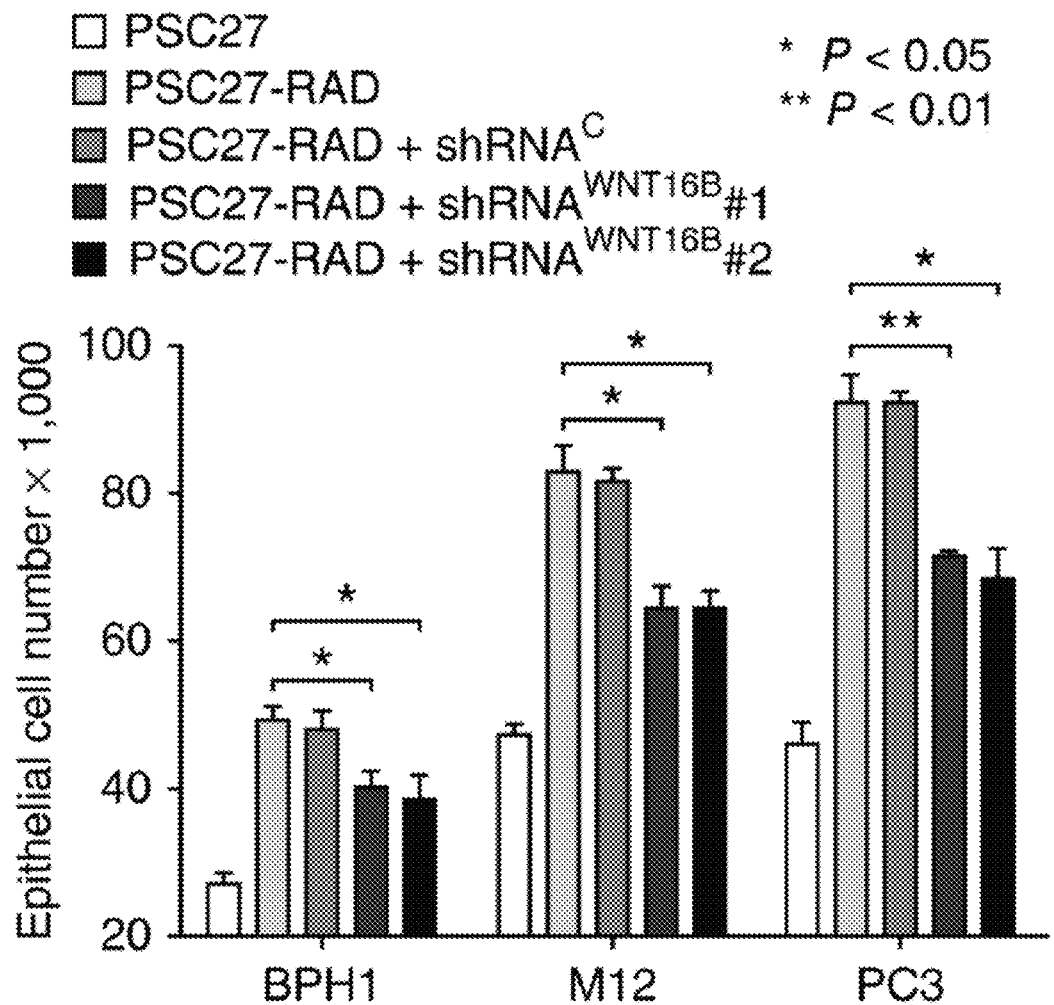
Figure 6D:
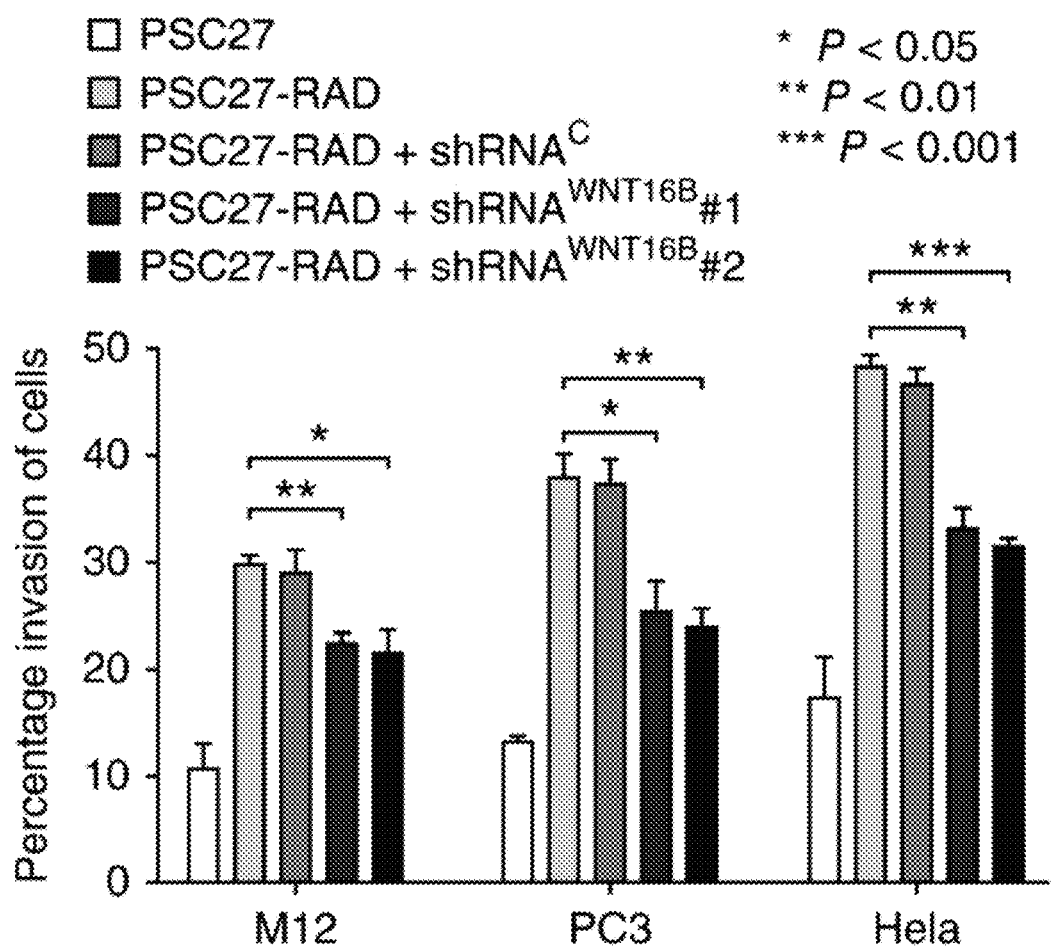

The DDSP comprises a diverse spectrum of secreted proteins with the potential to alter the phenotypes of neighboring cells (FIG. 1C). Next sought was to determine to what extent WNT16B is responsible for such effects in the context of the amalgam of factors induced by DNA damage. Conditioned medium from irradiated PSC27 fibroblasts (PSC27-RAD), representing the full DDSP, increased the proliferation (between 1.5-fold and twofold, P<0.05) and invasiveness (between threefold and fourfold, P<0.05) of neoplastic epithelial cells compared to conditioned medium from untreated PSC27 fibroblasts (FIGS. 6C and 6D). Compared to irradiated PSC27 cells expressing control shRNAs, conditioned medium from PSC27-RAD+shRNA$^{WNT16B}$ fibroblasts reduced these responses to the full DDSP by between 15% and 35%, depending on the cell line (P<0.05) (FIGS. 6C and 6D).

Figure 5E:
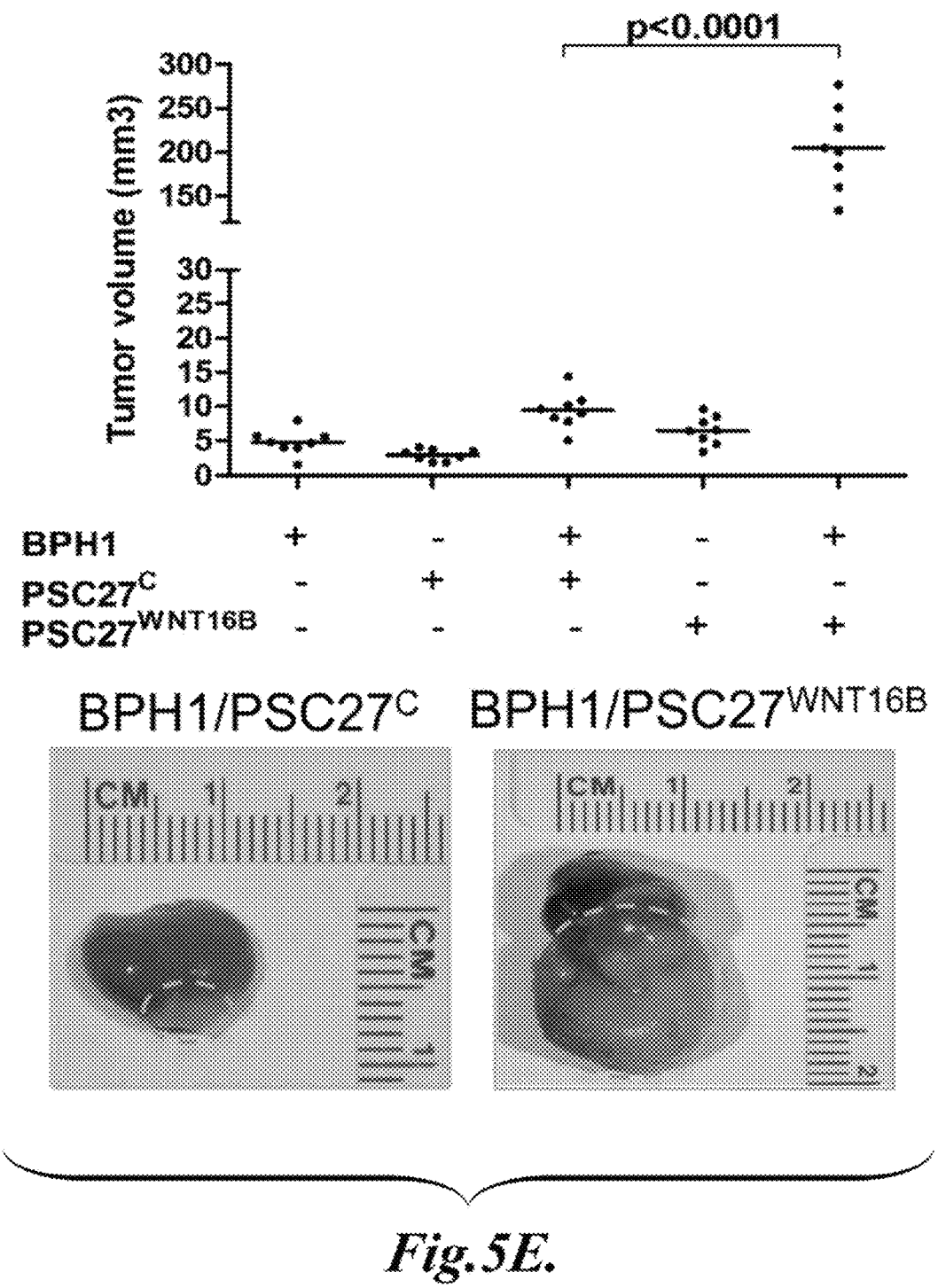
Figure 5F:
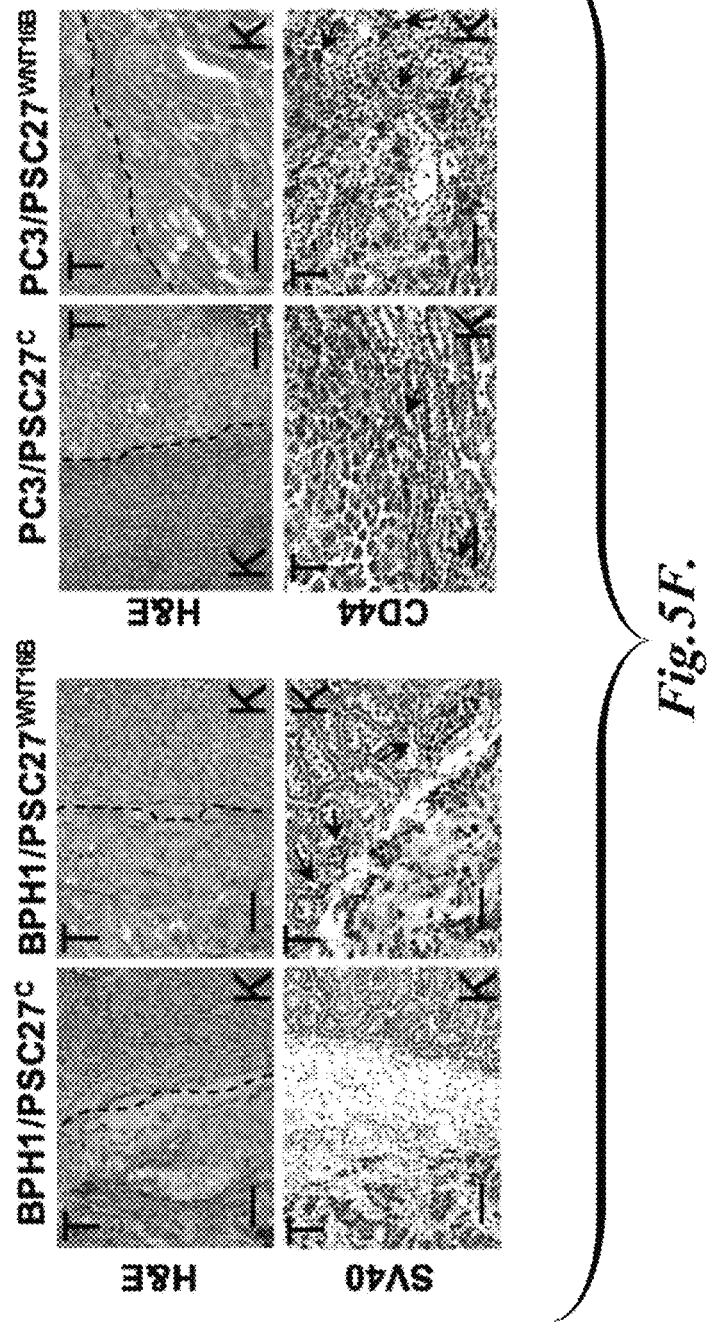
Figure 6E:
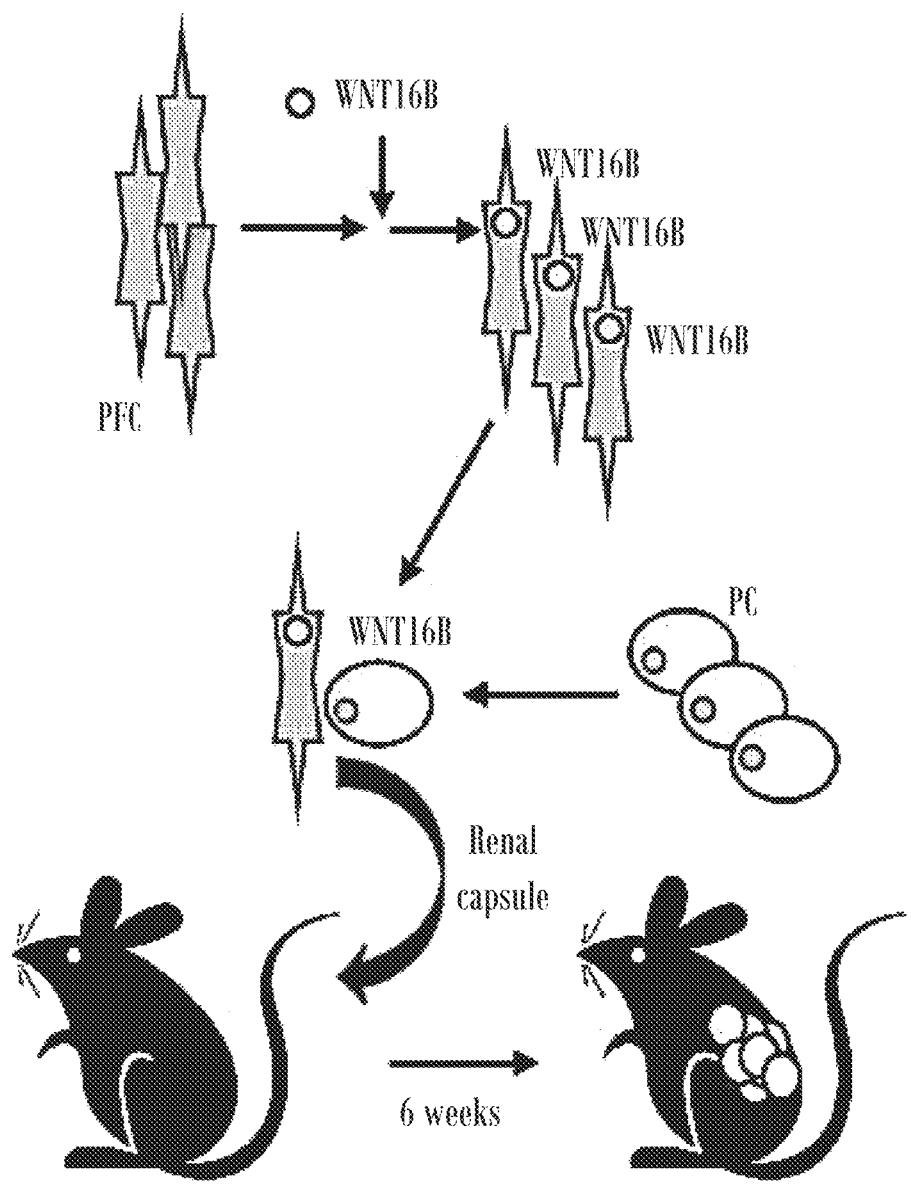
Figure 6F:
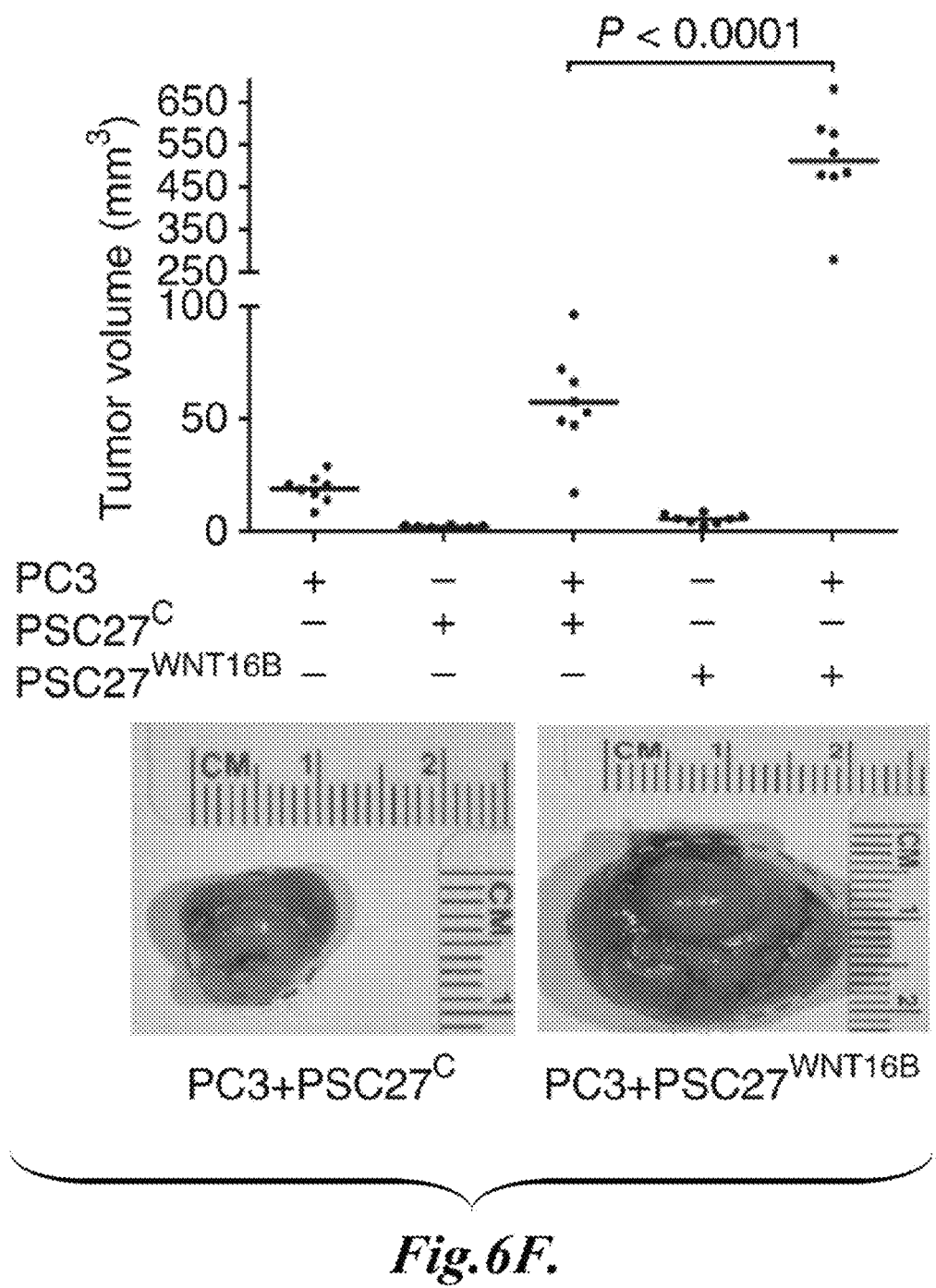

To investigate the in vivo consequences of WNT16B expression in the tumor microenvironment, non-tumorigenic BPH1 or tumorigenic PC3 cells were combined with PSC27$^{WNT16B}$ (BPH1+PSC27$^{WNT16B}$ and PC3+PSC27$^{WNT16B}$, respectively) or control PSC27 (BPH1+PSC27$^C$ and PC3+PSC27$^C$, respectively) fibroblasts and implanted the recombinants under the renal capsule of recipient mice (FIG. 6E). At 8 weeks after implantation, BPH1-PSC27$^{WNT16B}$ grafts were larger than BPH1+PSC27$^C$ grafts (approximately 200 mm$^3$ compared to approximately 10 mm$^3$, respectively; P<0.001) (FIG. 5E). As expected, grafts of PC3 cells alone formed tumors, and the tumors from PC3+PSC27C cells were of comparable size. In contrast, PC3+PSC27$^{WNT16B}$ recombinants generated very large poorly differentiated and invasive tumors with an average size of 500 mm$^3$, which were substantially larger than any of the control tumors (P<0.001) (FIG. 6F and FIG. 5F).

Figure 6G:
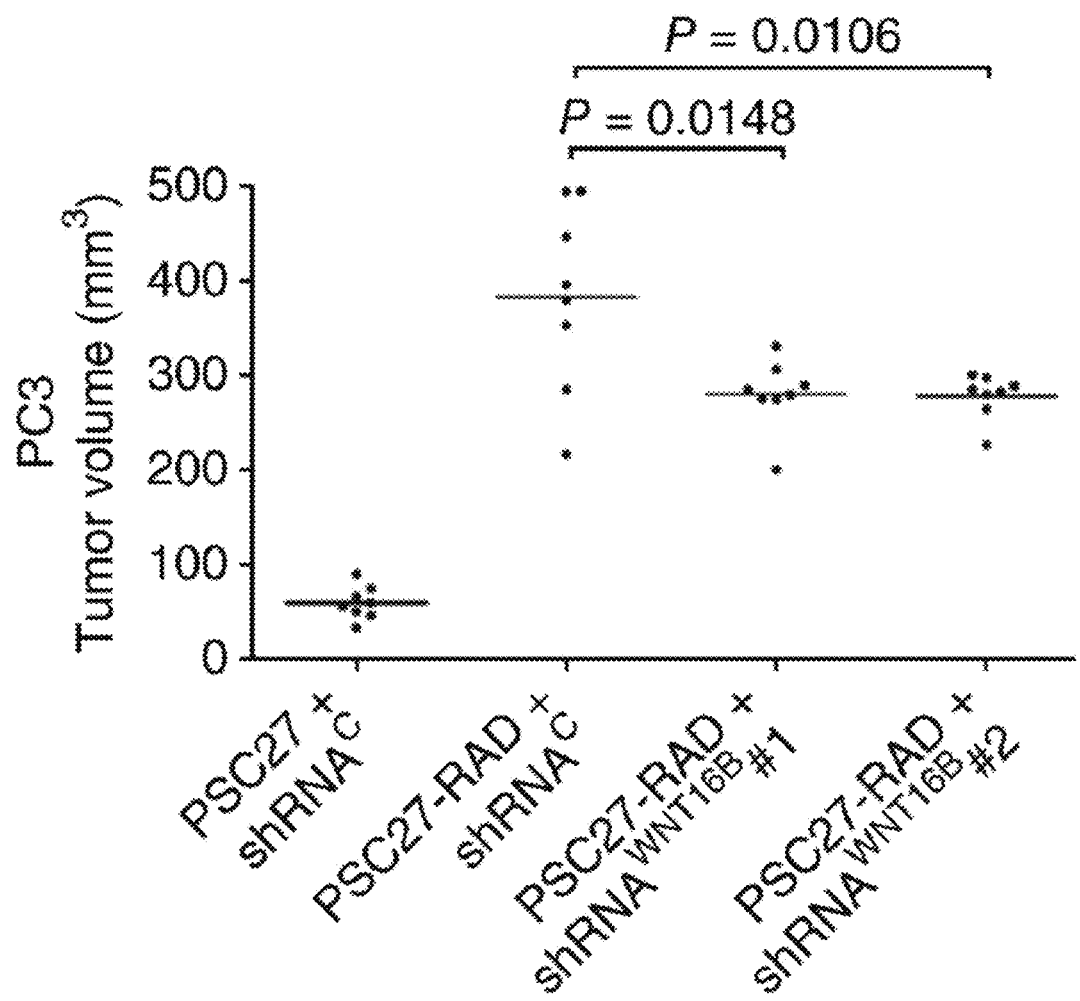

In vivo, PC3 cells combined with PSC27-RAD cells expressing the full fibroblast DDSP resulted in substantially larger tumors than PC3 cells combined with untreated PSC27 control fibroblasts (P<0.001) (FIG. 6G). Reducing the fibroblast contribution of WNT16B attenuated the PSC27-RAD effects: grafts of PC3+PSC27-RAD averaged 380 mm$^3$, whereas PC3 cells combined with PSC27-RAD+shRNA$^{WNT16B}$ averaged 280 mm$^3$, an approximately 25% reduction in tumor size when fibroblast WNT16B was suppressed (P<0.02) (FIG. 6G). Taken together, these findings show that paracrine WNT16B activity can promote tumor growth in vivo and accounts for a substantial component of the full DDSP effect on neoplastic epithelium.

WNT16B Signals Through β-Catenin and Induces an EMT

Figure 7A:
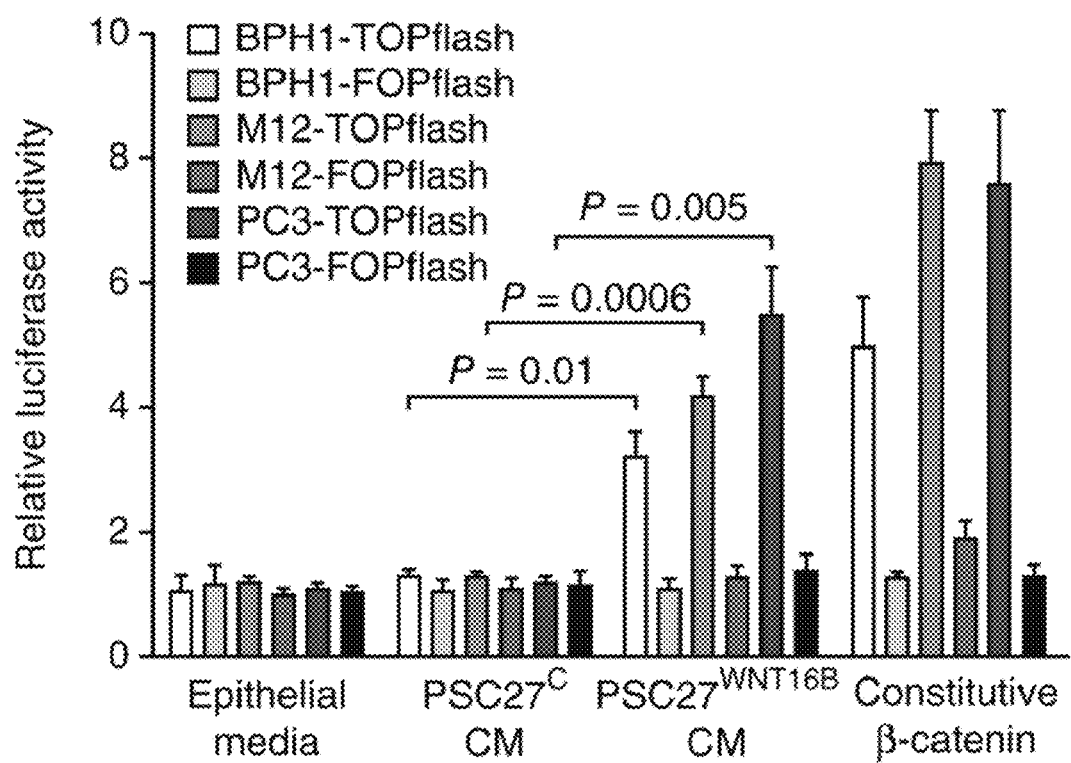
FIGS. 7A through 7I demonstrate that genotoxic stress upregulates WNT16B through NF-κB and signals through the canonical Wnt-β-catenin pathway to promote tumor cell proliferation and the acquisition of mesenchymal characteristics.
Figure 7B:
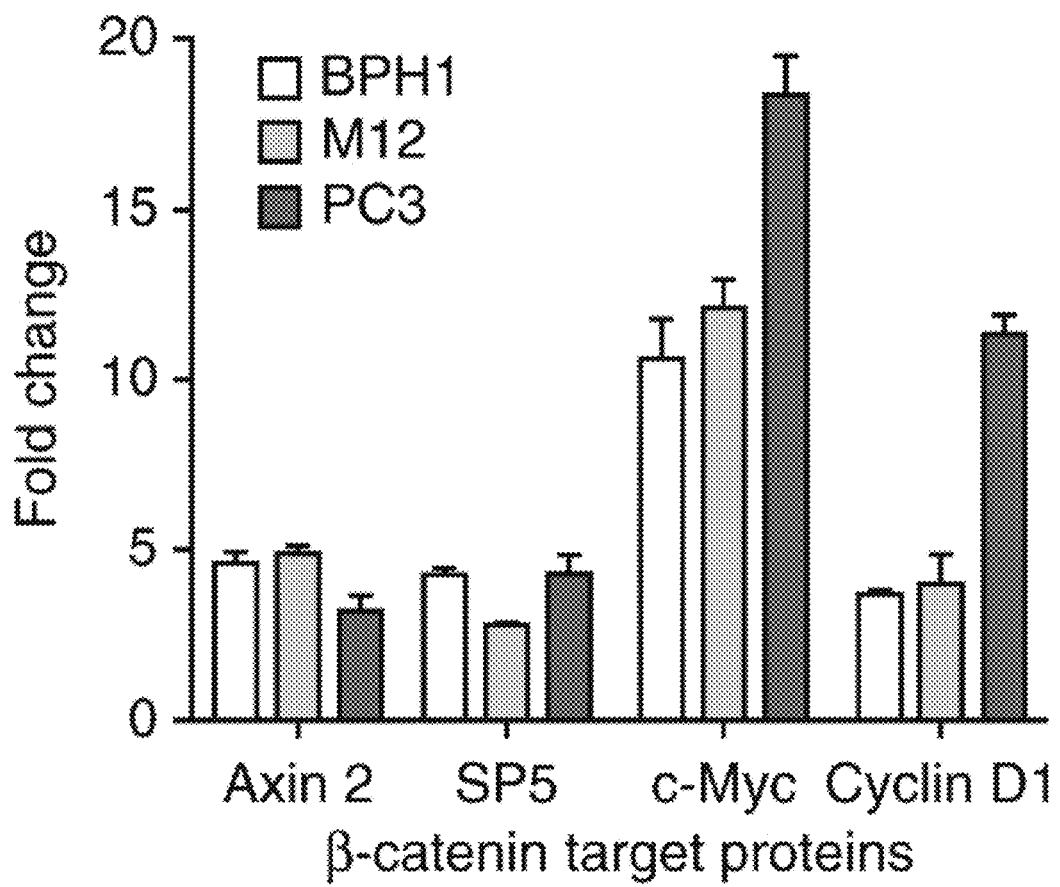
Figure 7C:
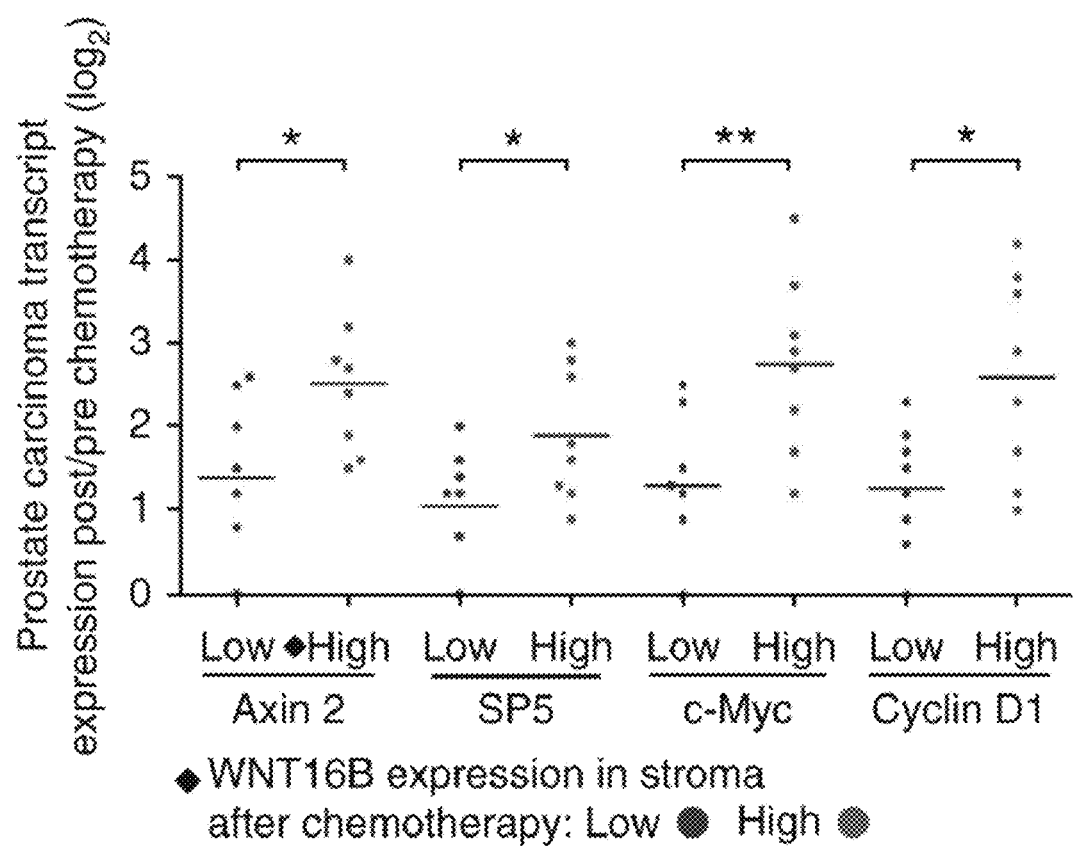
Figure 7D:
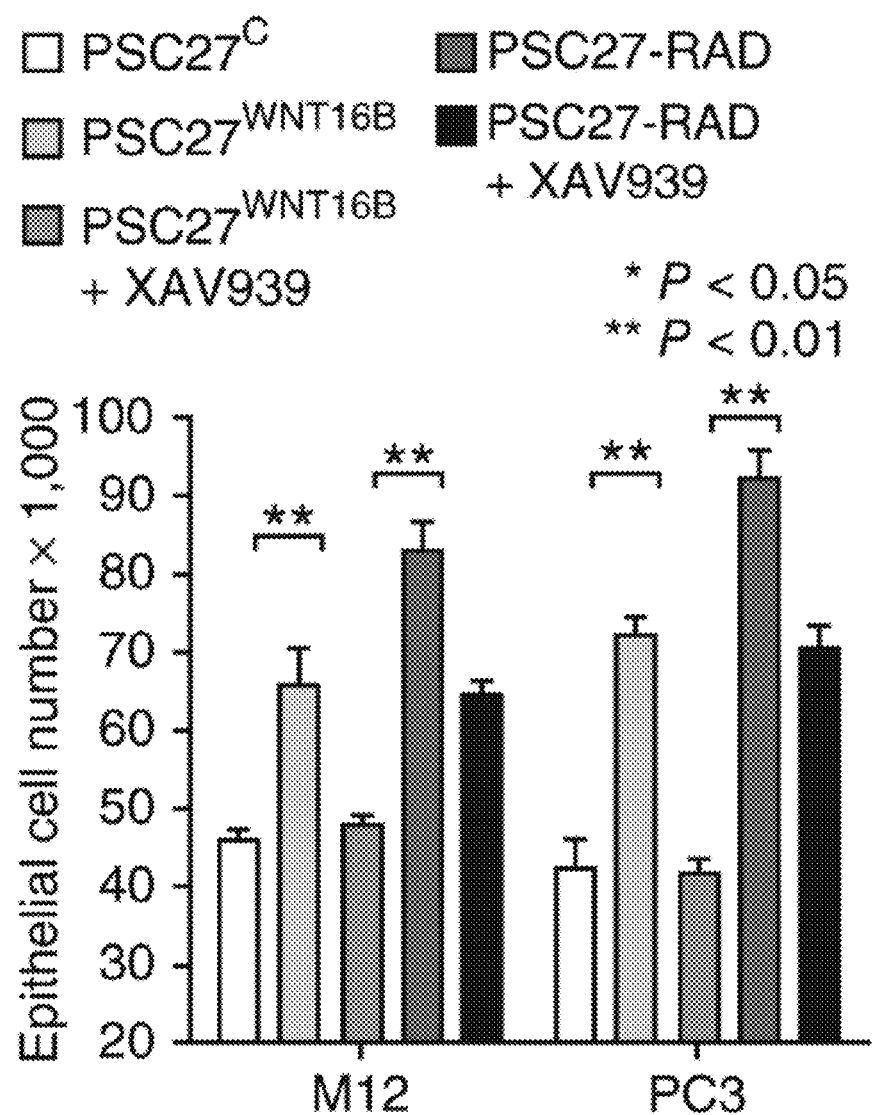
Figure 8A:
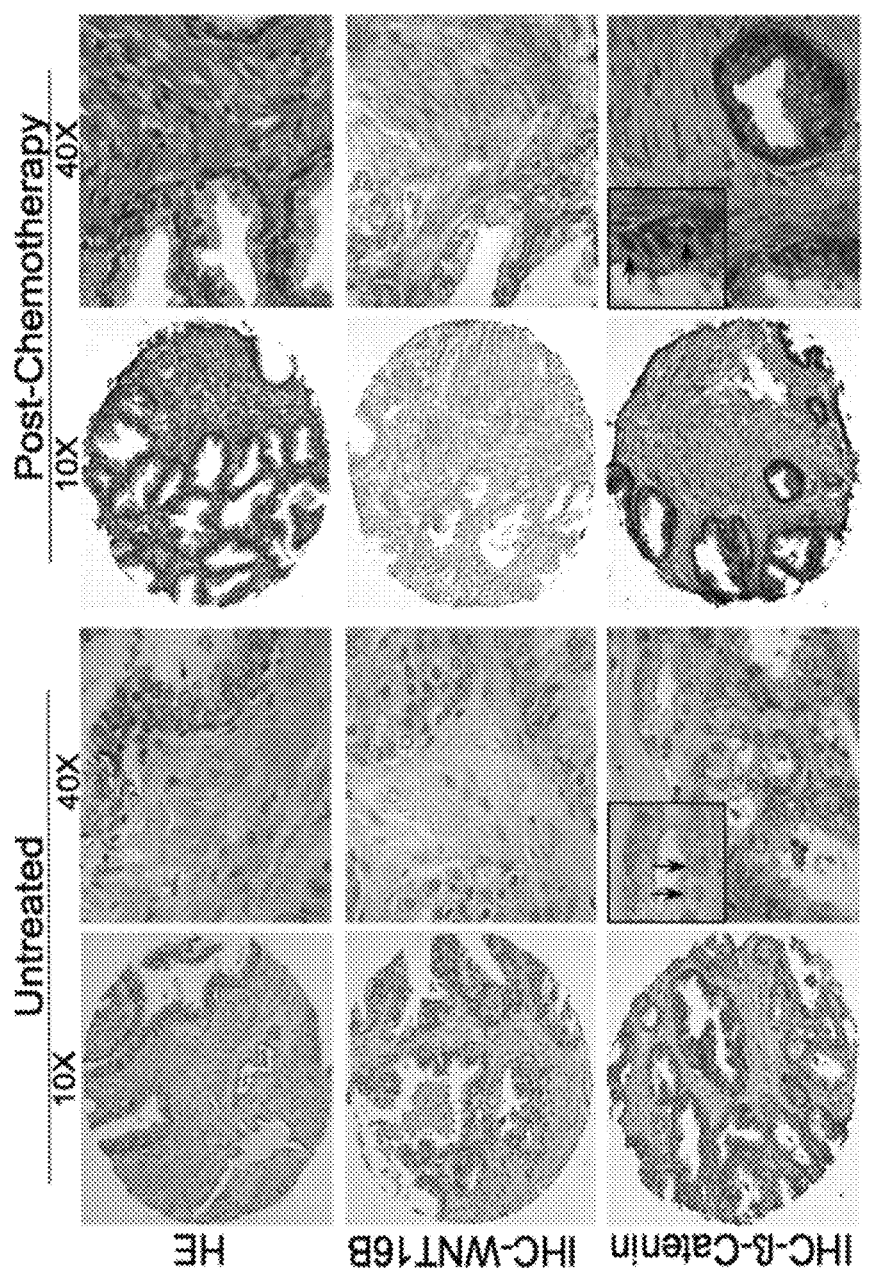
FIGS. 8A through 8D demonstrate that paracrine WNT16B induces a mesenchymal phenotype in vivo.
Figure 8B:
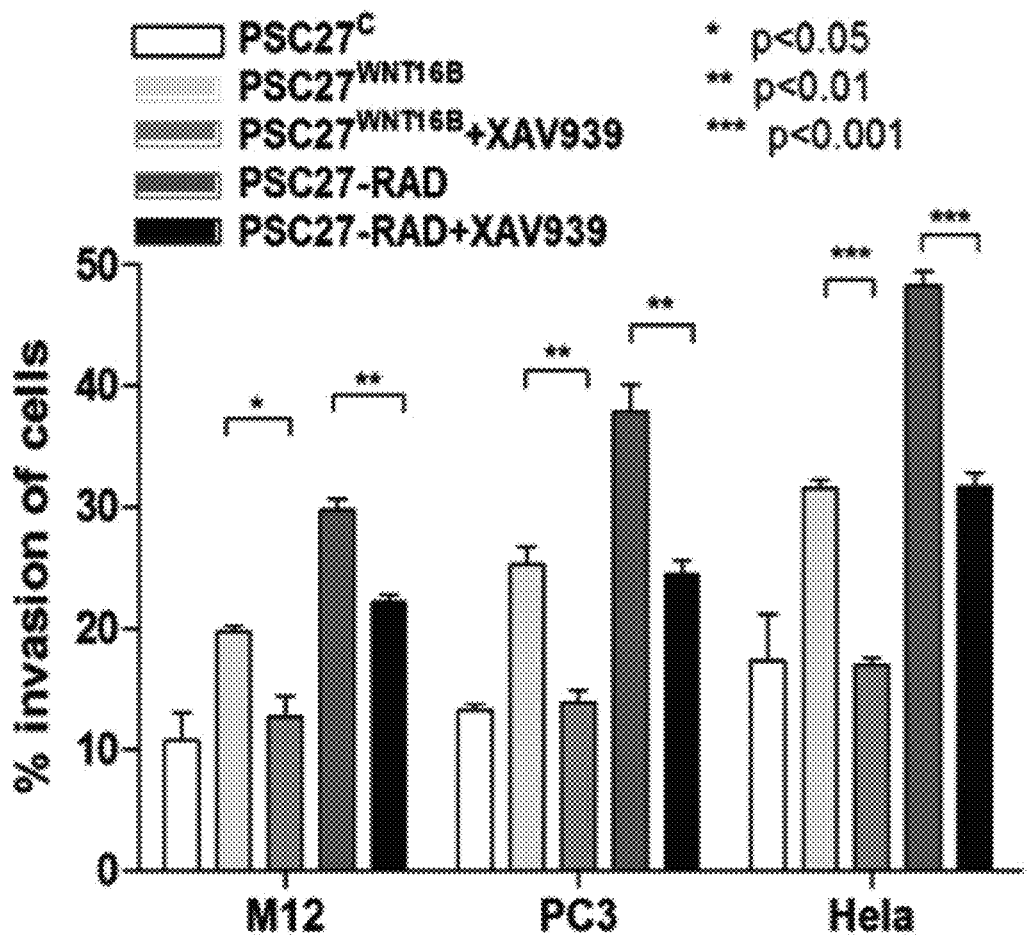

Having established that WNT16B can promote tumor growth through paracrine signaling, determination of the mechanism(s) by which it does so was sought. PSC27$^{WNT16B}$-conditioned medium activated canonical Wnt signaling in BPH1, PC3 and M12 prostate cancer cells, as measured by assays of β-catenin-mediated transcription through T cell factor/lymphoid enhancer binding factor (TCF/LEF) binding sites (FIG. 7A). Known β-catenin target genes, including AXIN2 and MYC, were upregulated (approximately fivefold and over tenfold, respectively) after exposure to WNT16B-enriched conditioned medium (FIG. 7B). In human prostate cancers treated with chemotherapy, β-catenin localized in the nucleus of tumor cells (FIG. 8A). It was also found that β-catenin target genes were expressed more highly in tumors with elevated stromal WNT16B expression relative to those with low WNT16B expression (P<0.05) (FIG. 7C). To confirm that β-catenin signaling contributed to the epithelial phenotypes resulting from exposure to PSC27-RAD-conditioned medium, prostate cancer cells were treated with the tankyrase inhibitor XAV939, which stabilizes axin and inhibits β-catenin-mediated transcription (Huang et al., Nature 461:614-620, 2009). XAV939 completely suppressed the proliferative and invasive responses induced by WNT16B and markedly attenuated the effects of the PSC27-RAD DDSP (FIG. 7D and FIG. 8B).

Figure 7E:
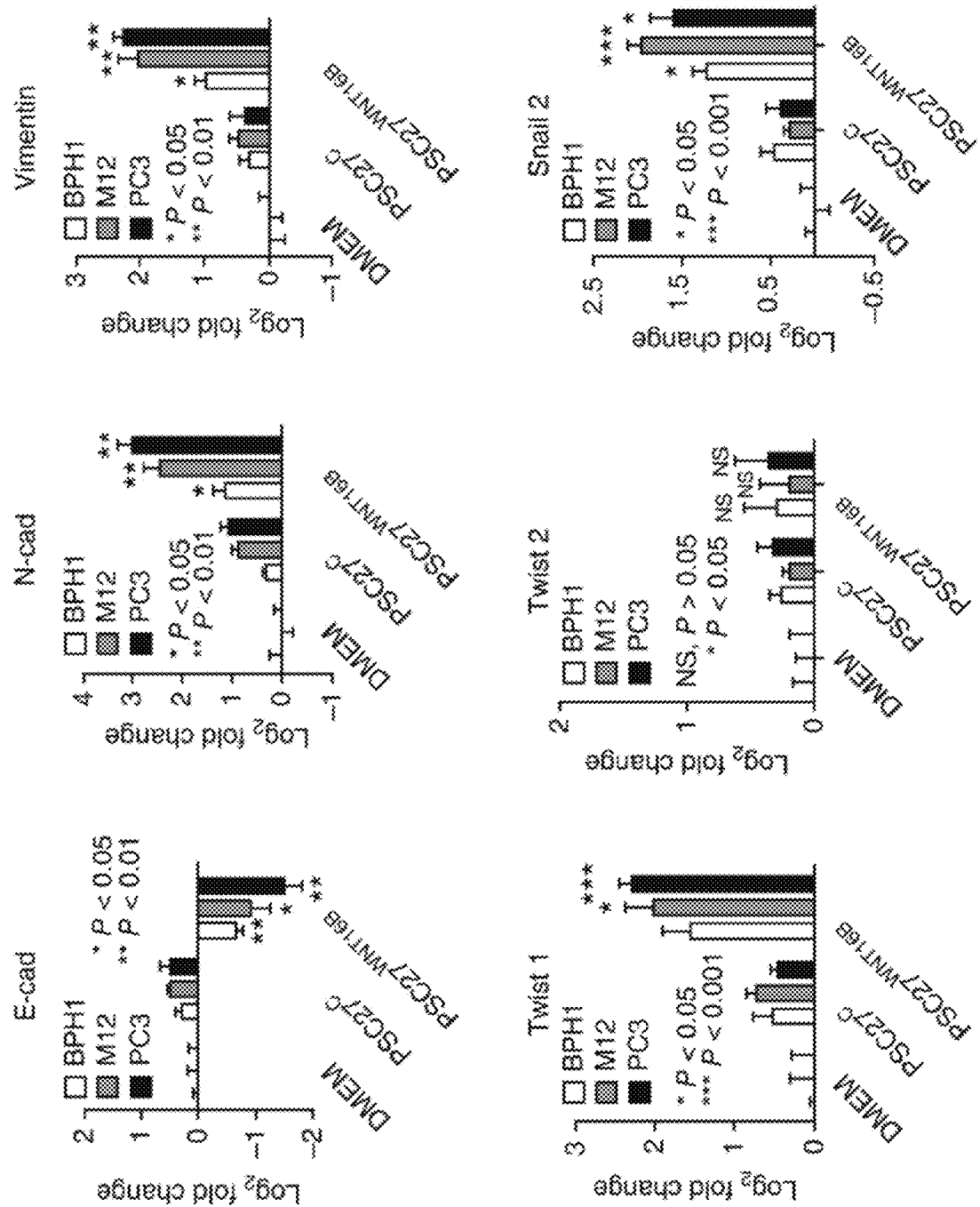
Figure 7F:
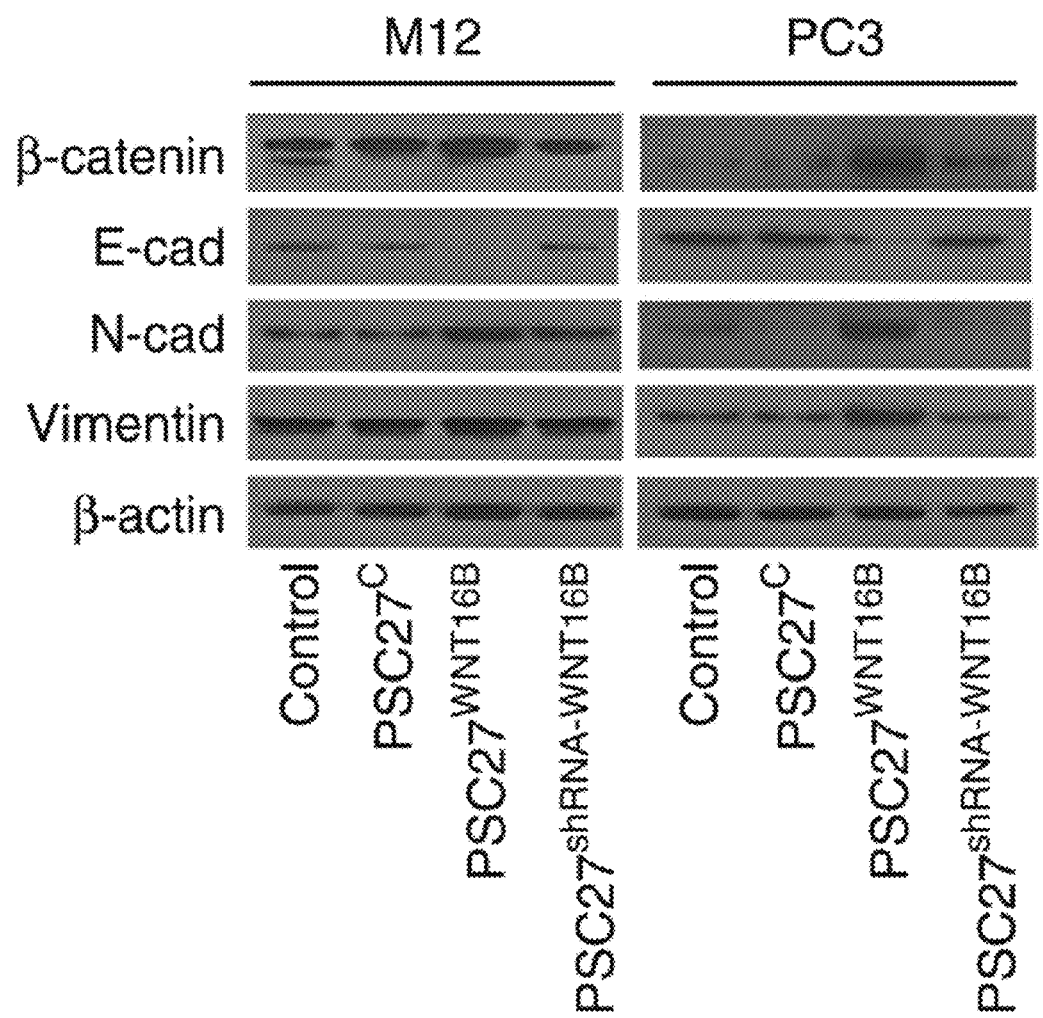
Figure 7G:
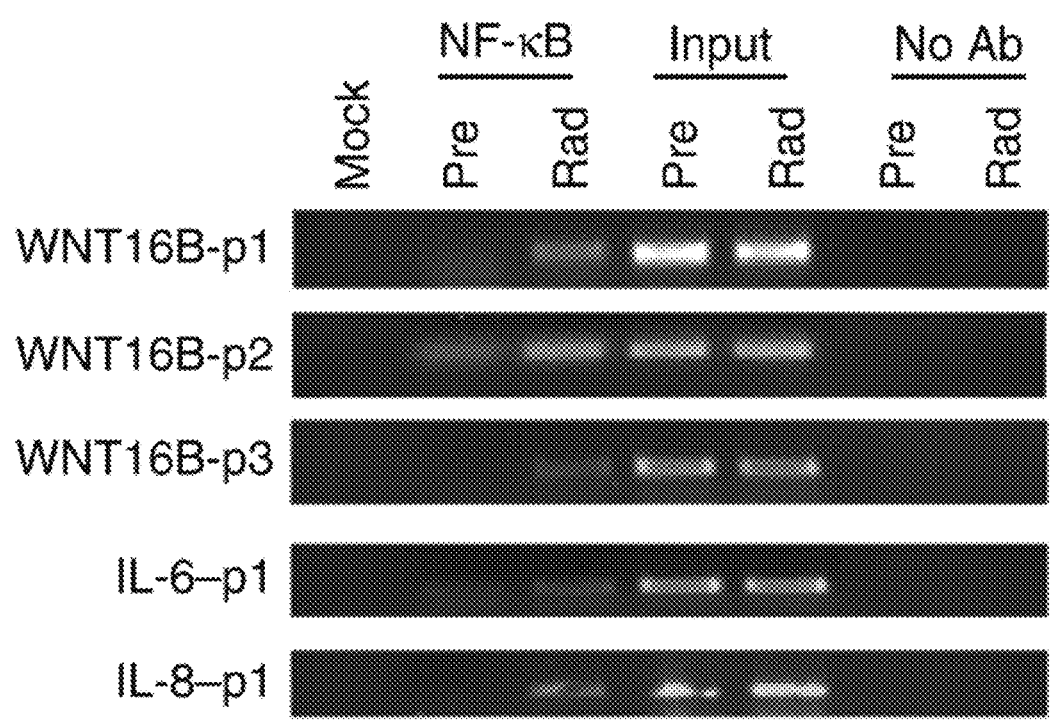
Figure 8C:
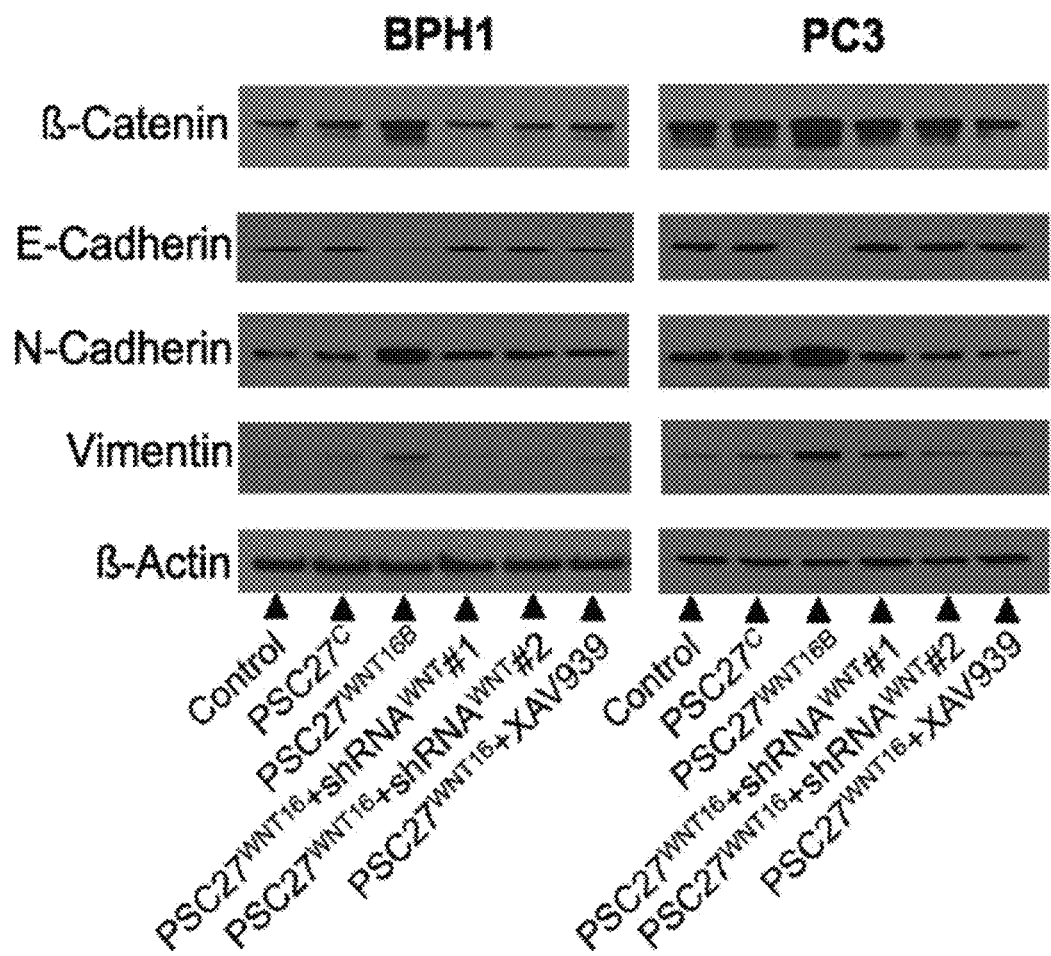
Figure 8D:
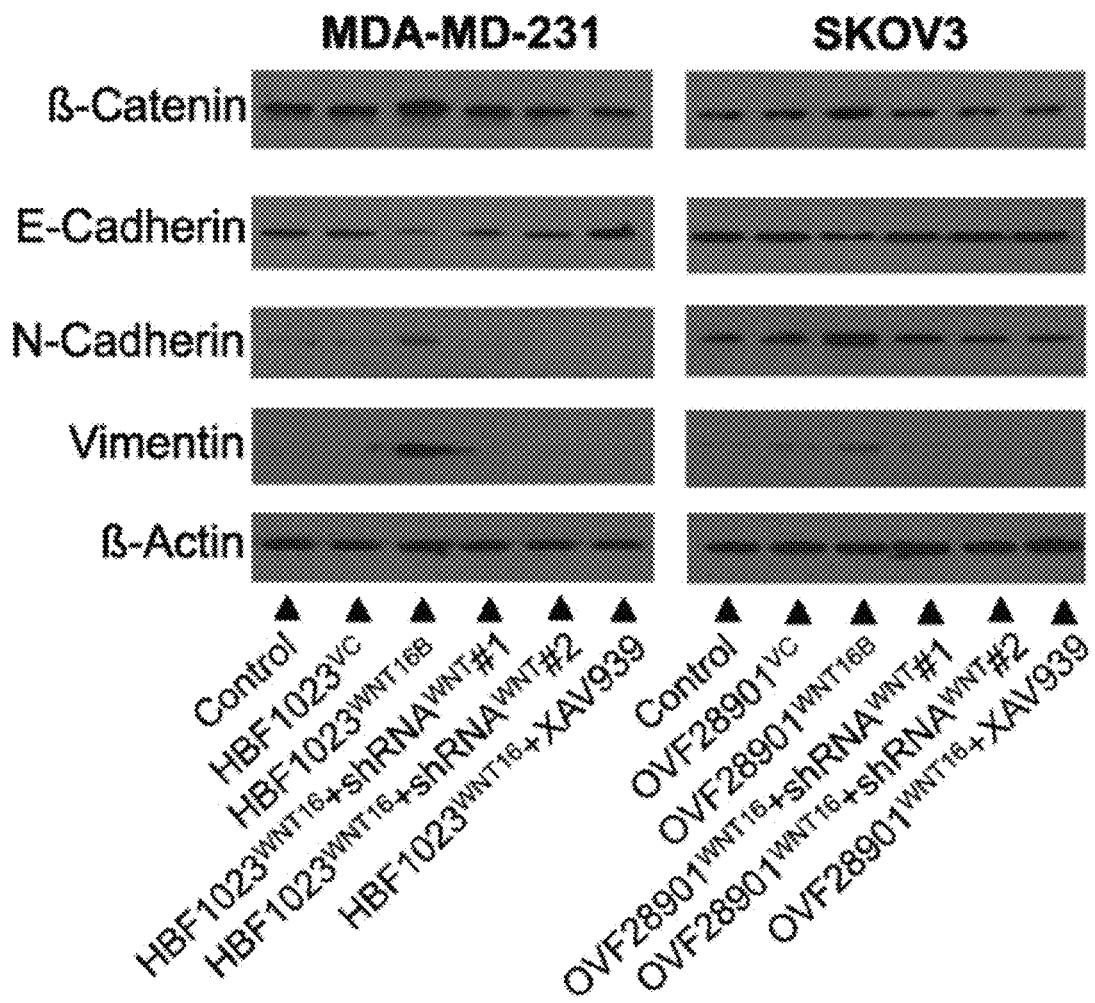

Wnt signaling is known to promote the acquisition of mesenchymal cell characteristics that can influence the migratory and invasive behavior of epithelial cells through an EMT (Thiery et al., Cell 139:871-890, 2009; Yook et al., Nat. Cell Biol. 8:1398-1406, 2006; Vincan and Barker, Clin. Exp. Metastasis 25:657-663, 2008). Loss of CDH1 (also known as E-cadherin), the prototypic epithelial adhesion molecule in adherens junctions, and gain of CDH2 (also known as N-cadherin) expression are among the main hallmarks of an EMT (Wu and Bonavida, Crit. Rev. Immunol. 29:241-254, 2009; Peinado et al., Nat. Rev. Cancer 7:415-428, 2007). After exposure of PC3 cells to PSC27$^{WNT16B}$-conditioned medium, the number of E-cadherin transcripts decreased 64%, whereas the number of N-cadherin transcripts increased fourfold (P<0.05). Similar alterations occurred in M12 and BPH1 cells (FIGS. 7E and 7F). Inhibiting β-catenin pathway signaling with XAV939 in epithelial cells blocked the WNT16B-induced EMT-associated gene expression (FIG. 8C). Exposure to PSC27$^{WNT16B}$-conditioned medium also promoted mesenchymal characteristics in MDA-MD-231 breast cancer and SKOV3 ovarian cancer cells (FIG. 8D).

Genotoxic Stress Induces WNT16B Expression Through NF-κB

Figure 7H:
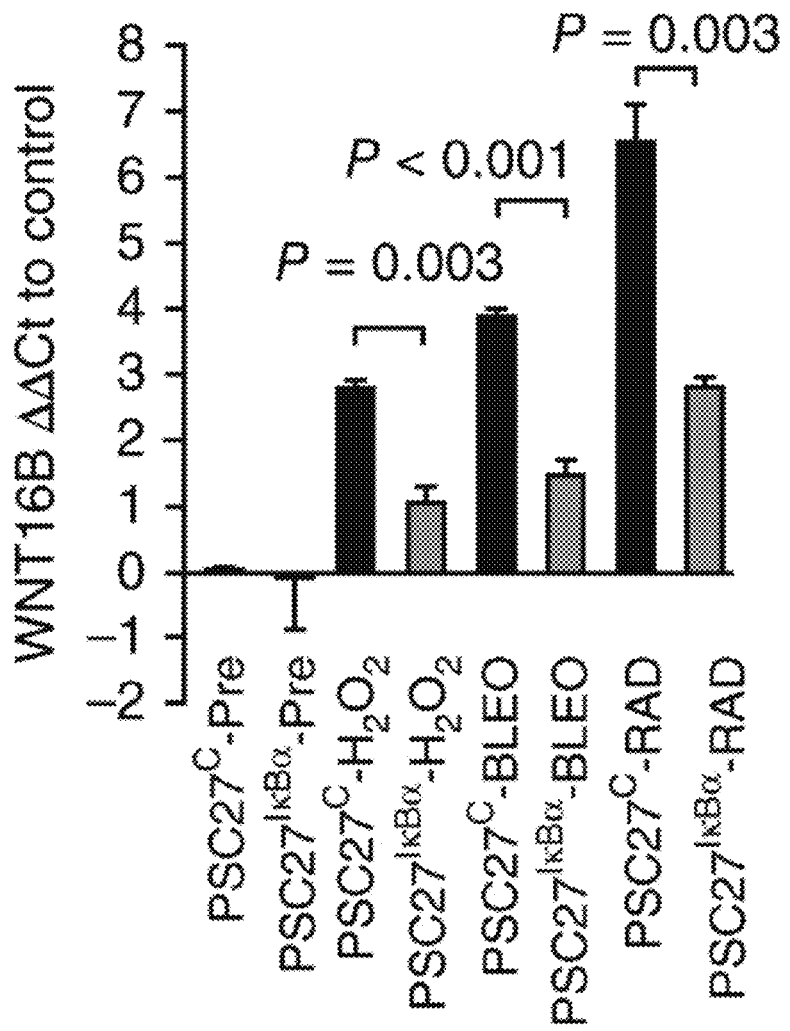
Figure 9A:
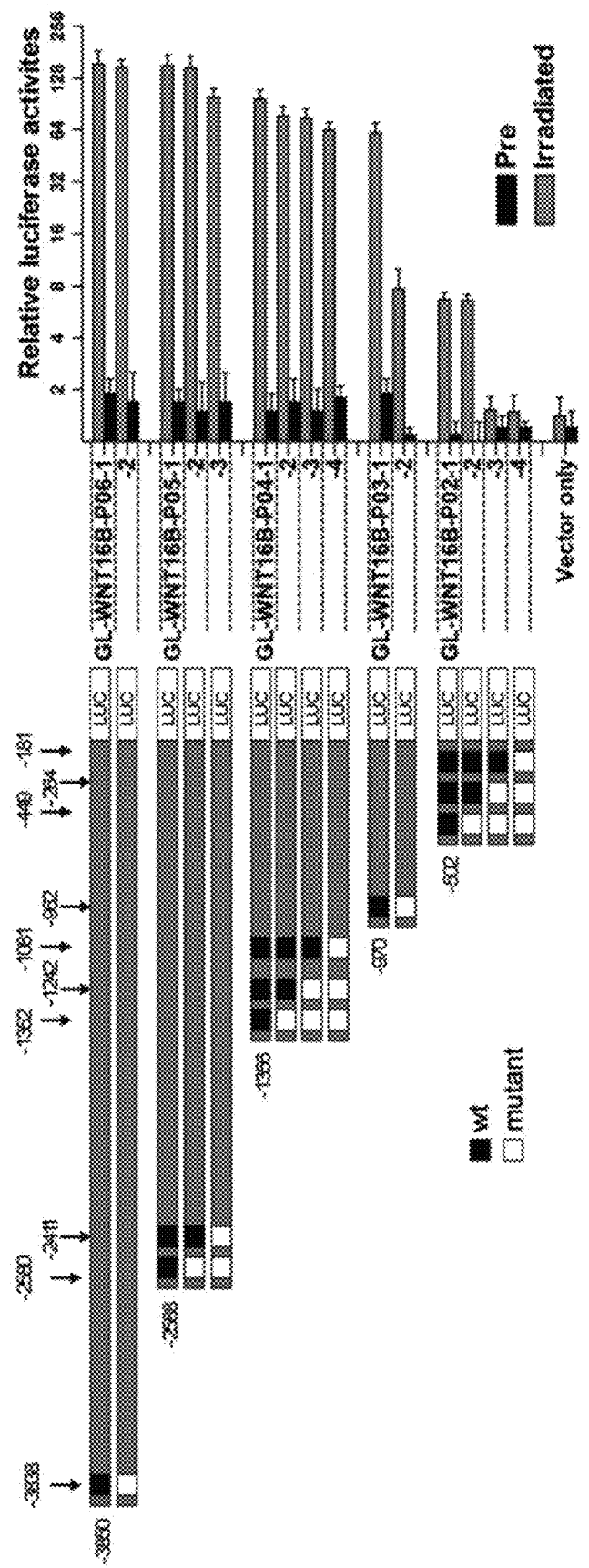
FIGS. 9A through 9E demonstrate that WNT16B expression is regulated by NFkB.
Figure 9B:
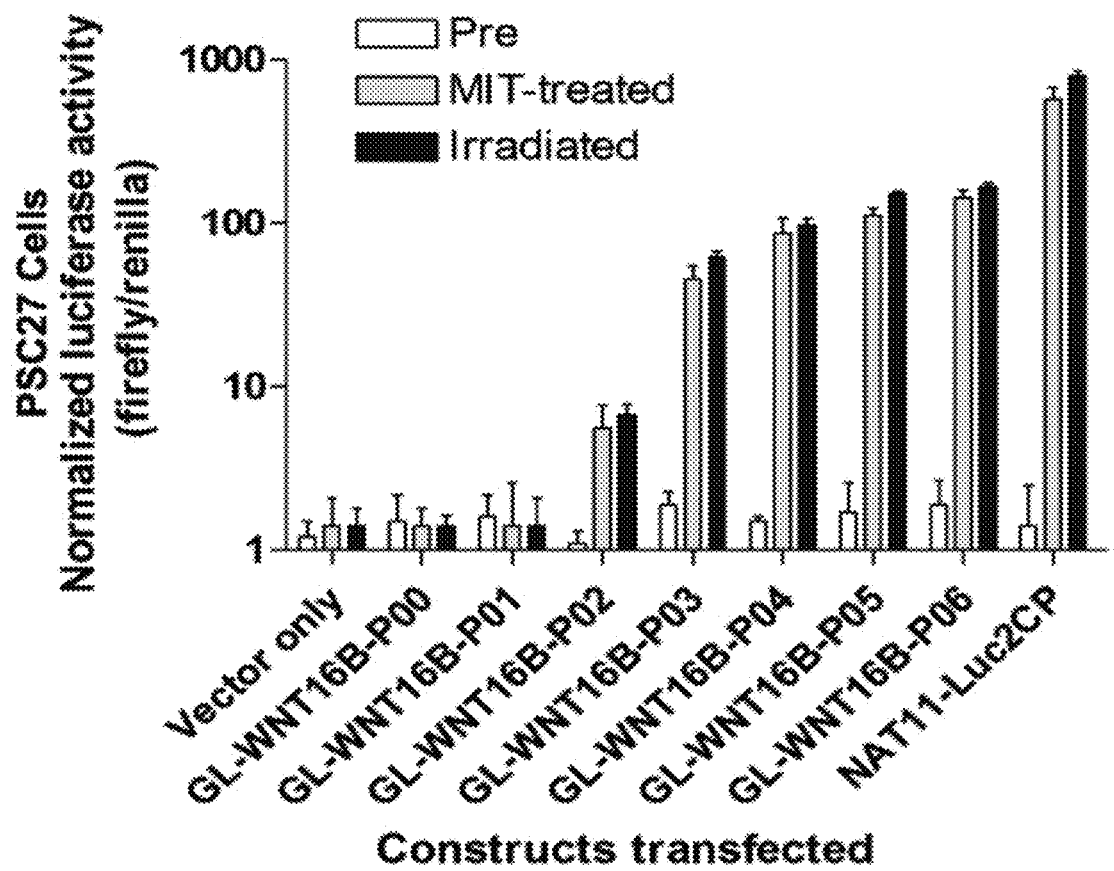
Figure 9C:
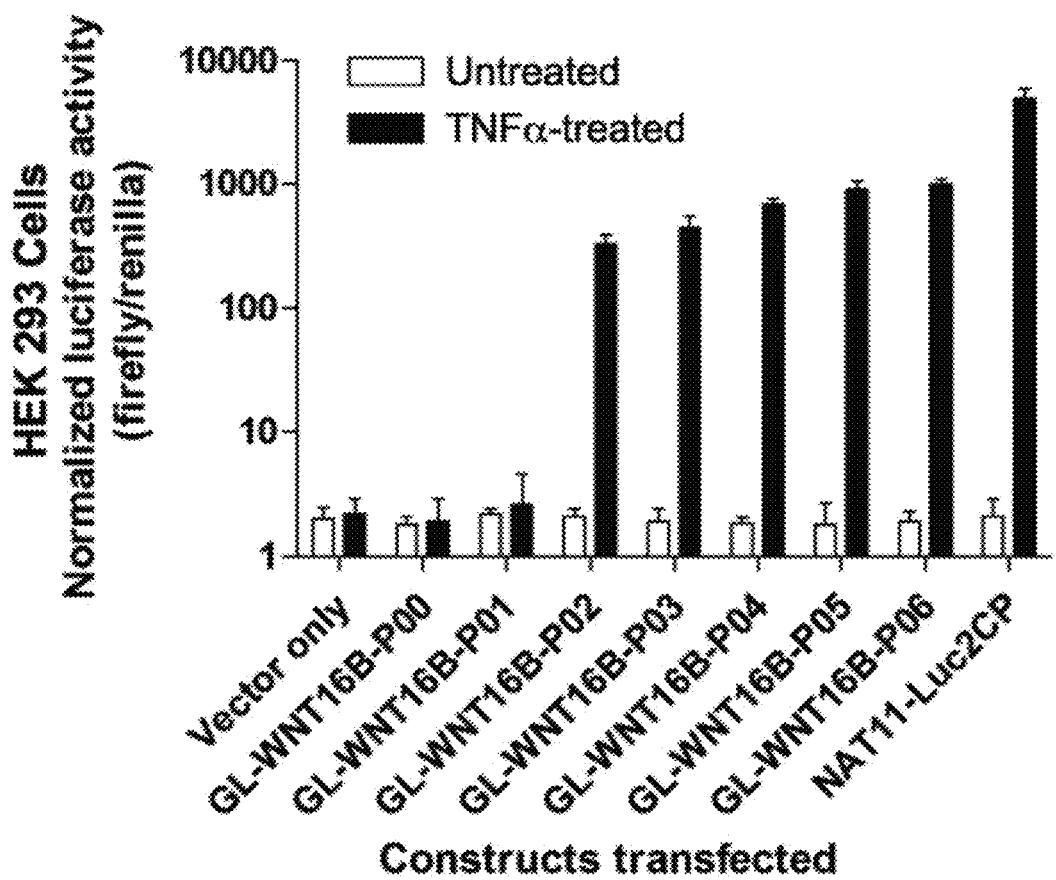
Figure 9D:
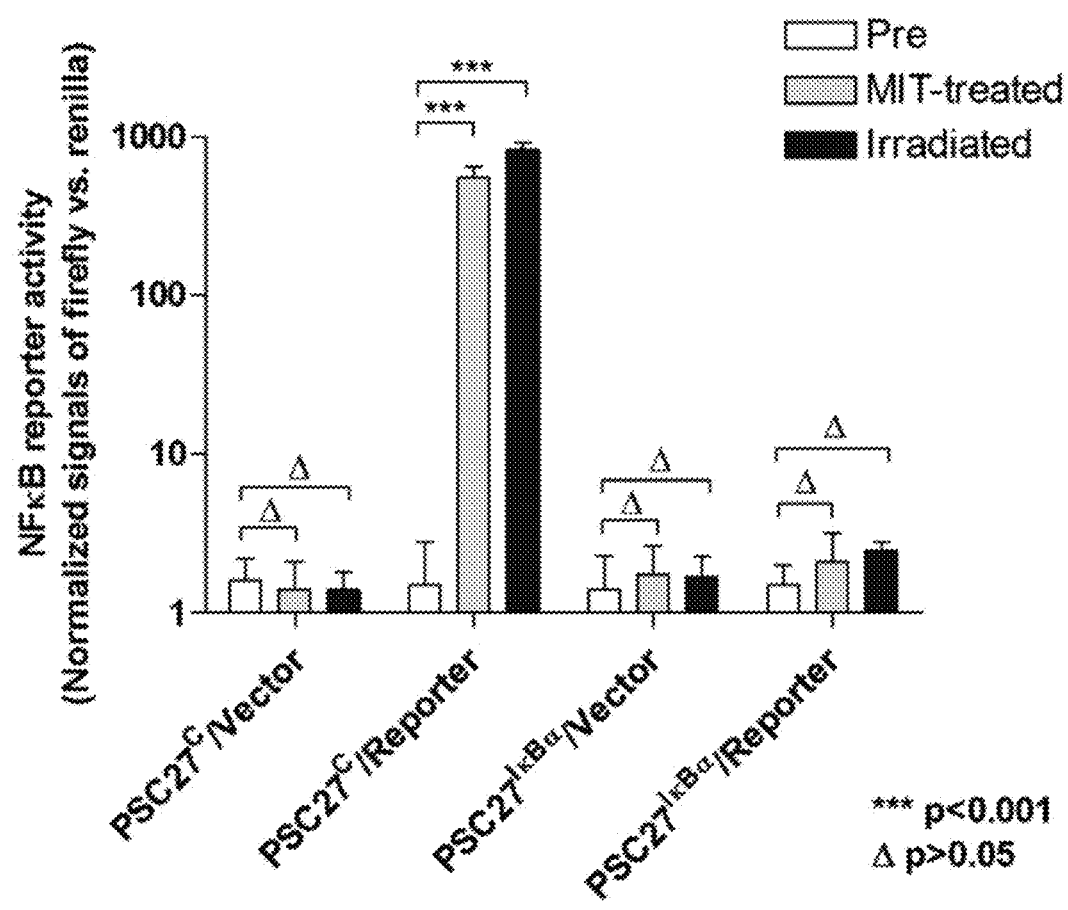
Figure 9E:
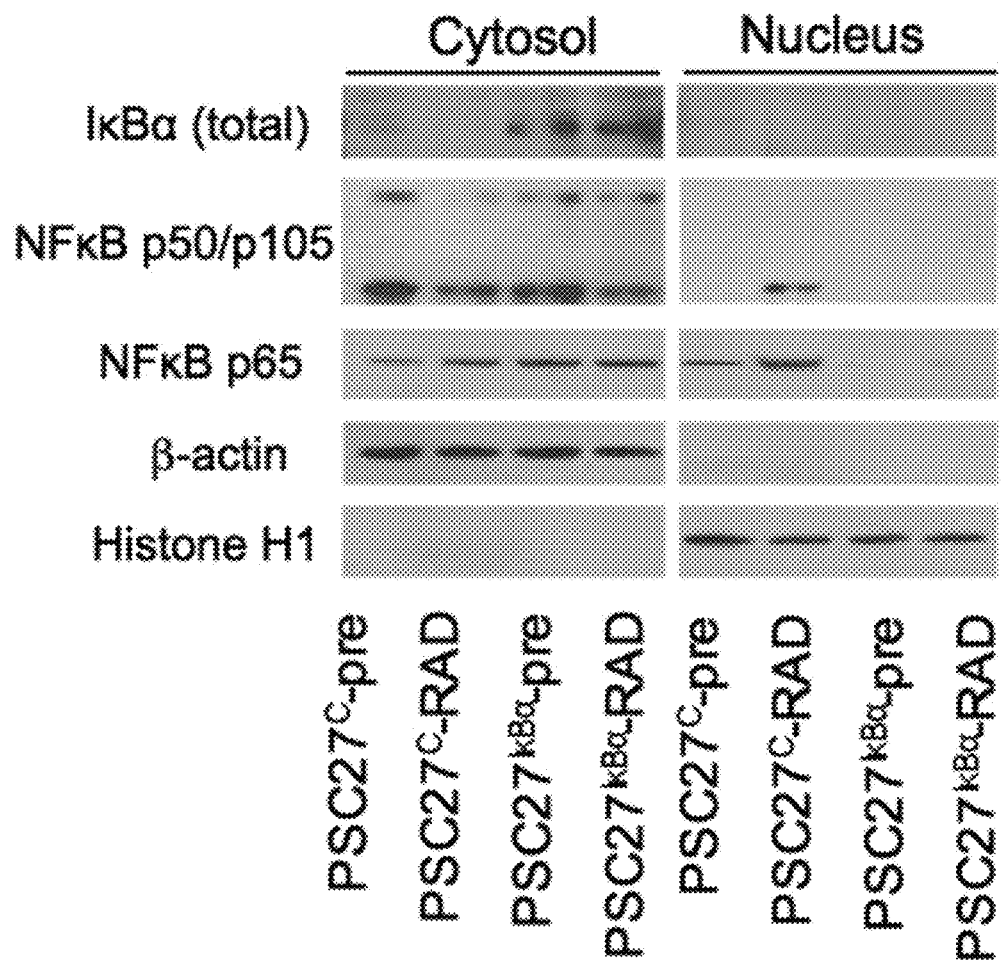

A key pathway linking DNA damage with apoptosis, senescence and DNA repair mechanisms involves activating the NF-κB complex (Bernard et al., Cancer Res. 64:472-481, 2004; Berchtold et al., Mol. Cell. Biol. 27:497-509, 2007). NF-κB is also pivotal in mediating the stress-associated induction of inflammatory networks, including the upregulation and secretion of interkeukin-6 (IL-6) and IL-8 (Acosta et al., Cell 133:1006-1018, 2008; Kuilman et al., Cell 133:1019-1031, 2008). It was therefore sought to determine whether DNA-damage-induced WNT16B expression is mediated by NF-κB. NF-κB binding motifs were identified in the WNT16B promoter region and their function was confirmed using WNT16B promoter constructs. Compared to untreated cells, both RAD and tumor necrosis factor α (TNF-α), which are known NF-κB activators, induced WNT16B reporter activity (P<0.01) (FIG. 7G and FIGS. 9A through 9E). Next, PSC27 prostate fibroblasts were generated with stable expression of a mutant nuclear factor of κ light polypeptide gene enhancer in B cells inhibitor, α (IκBα) (PSC27$^{IκBα}$), which prevents IκB kinase (IKK)-dependent degradation of IκBα and attenuates NF-κB signaling. After irradiation of PSC27 cells, NF-κB translocated to the nucleus and induced NF-κB reporter activity >100-fold (FIGS. 9D and 9E). In comparison, the amount of nuclear NF-κB in PSC27$^{IκBα}$-RAD cells was markedly lower. The PSC27$^{IκBα}$ cells with impaired NF-κB activation had a significant attenuation of induction of WNT16B expression after treatment with H$_2$O$_2$, BLEO or RAD (P<0.05) (FIG. 7H).

It was next determined whether suppressing fibroblast NF-κB signaling in response to DNA damage would attenuate the pro-proliferative effects of the PSC27-RAD DDSP.

Figure 7I:
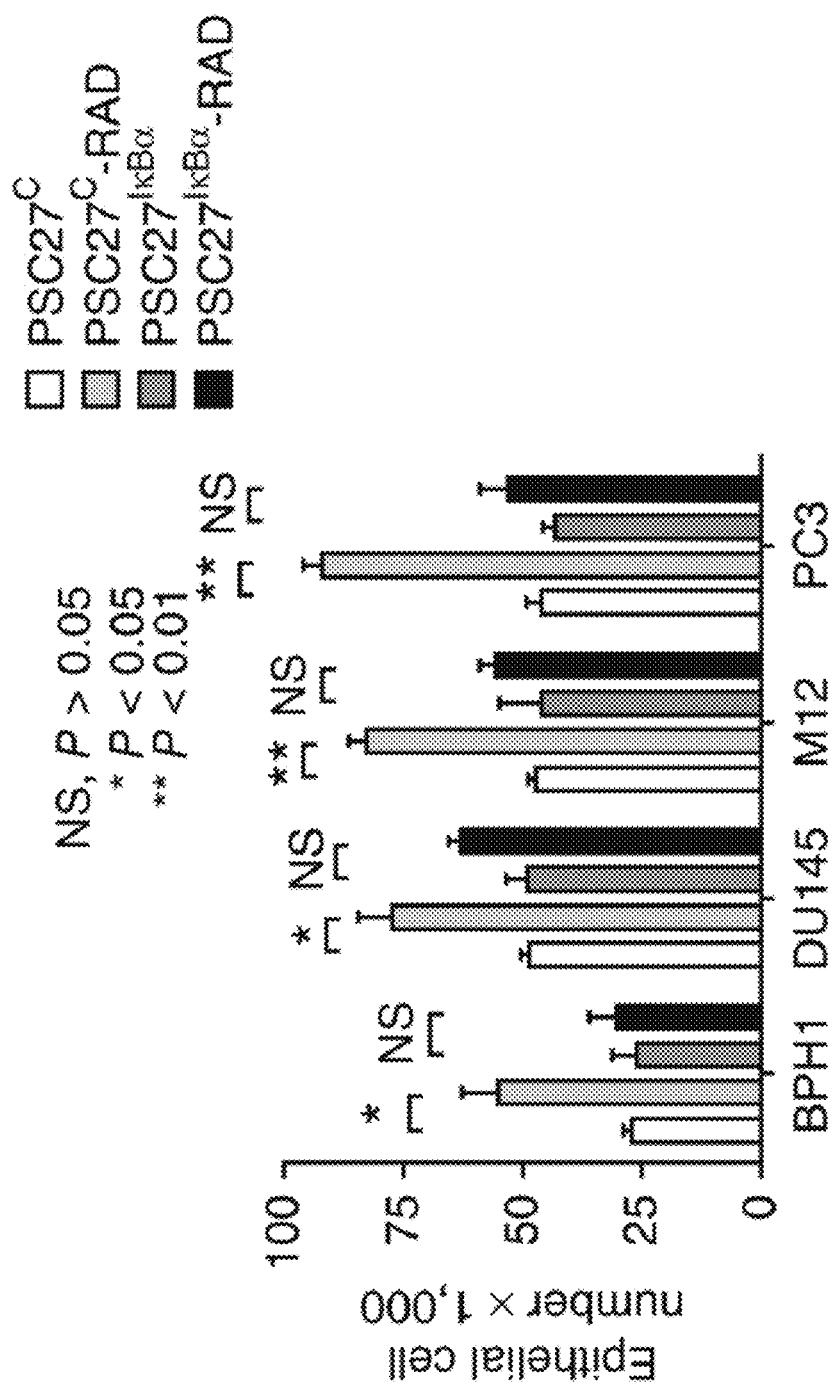

Whereas PSC27-RAD-conditioned medium promoted prostate epithelial cell proliferation, conditioned medium from PSC27$^{IκBα}$-RAD cells failed to do so (FIG. 7I). These experiments identify WNT16B as a new member of the cellular genomic program that is regulated by NF-κB signaling in response to DNA damage.

Paracrine WNT16B Attenuates the Effect of Cytotoxic Therapy

Figure 10A:
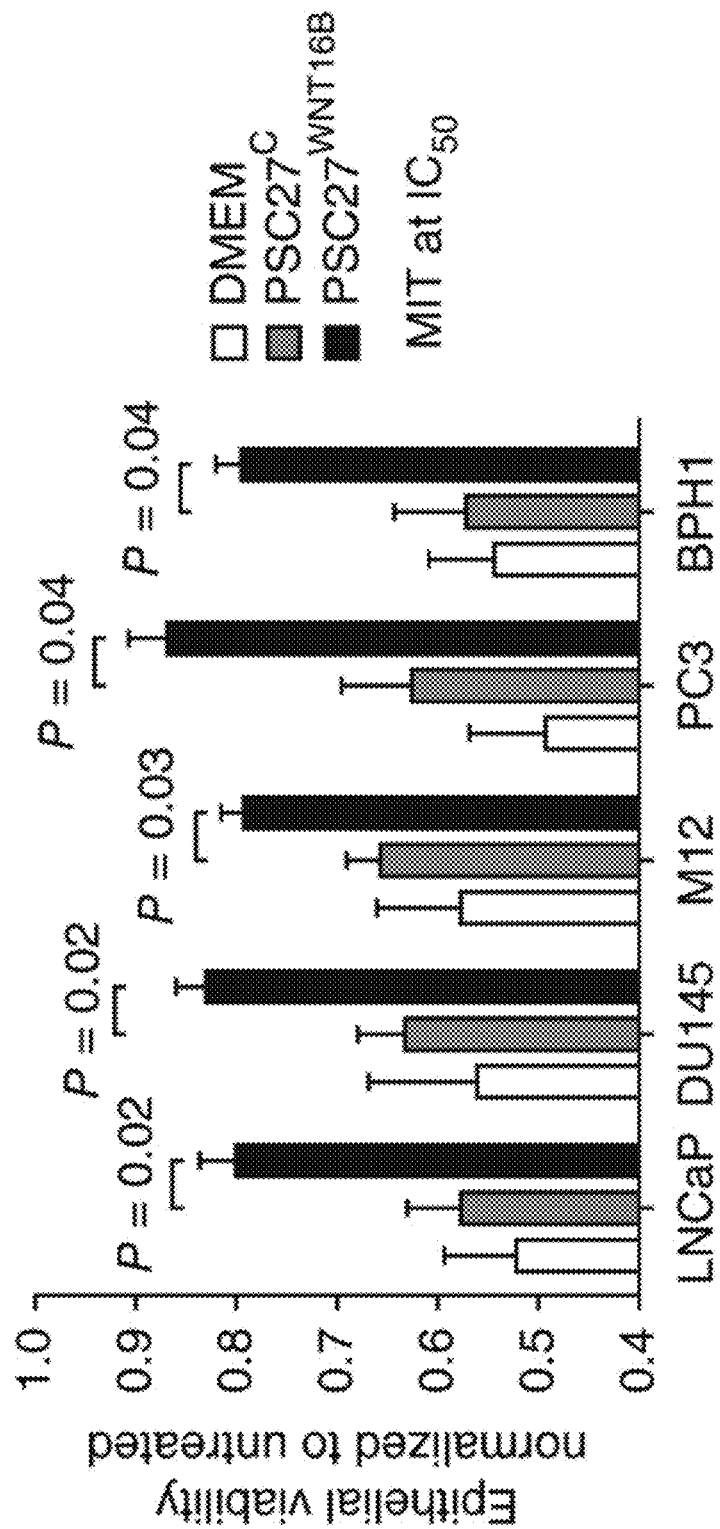
FIGS. 10A through 10E demonstrates that paracrine-acting WNT16B promotes the resistance of prostate carcinoma to cytotoxic chemotherapy.
Figure 11A:
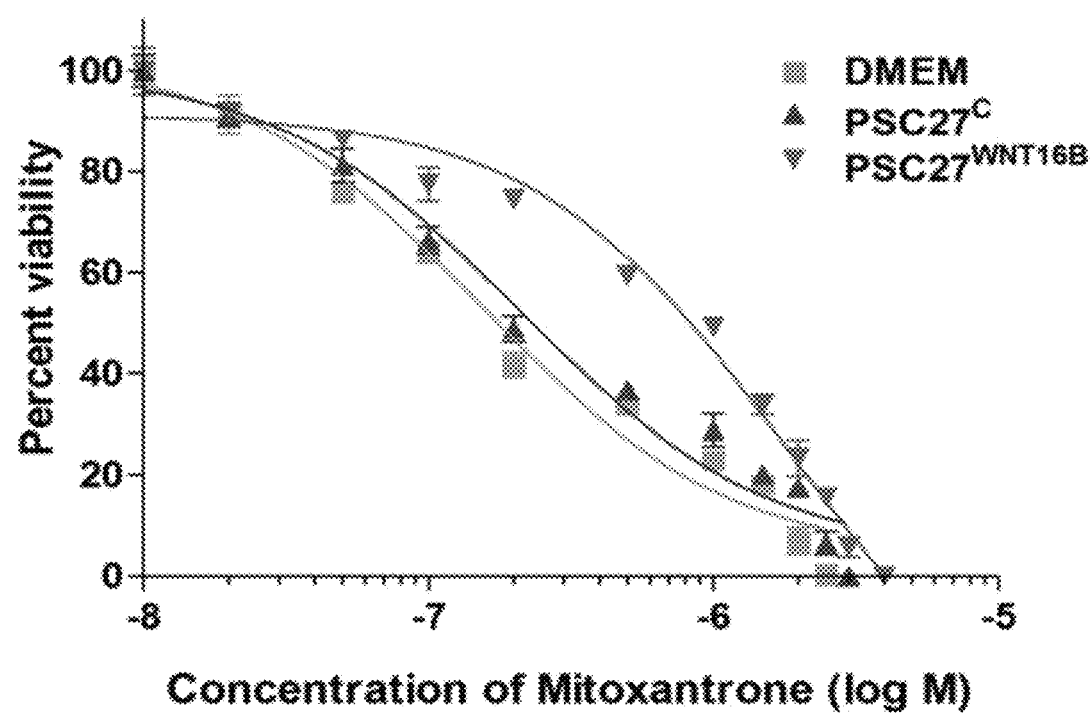
FIG. 11A through 11C demonstrate the modulation of chemotherapy resistance by paracrine WNT16B.

The preceding data suggested that in addition to tumor-promoting effects, paracrine-acting WNT16B may influence the responses of tumors to genotoxic cancer therapeutics. To evaluate this possibility, MIT, a type 2 topoisomerase inhibitor that produces DNA strand breaks, leading to growth arrest, senescence or apoptosis, which is in clinical use for the treatment of advanced prostate cancer was studied. Prostate cancer cells exposed to PSC27$^{WNT16B}$-conditioned medium compared to control medium consistently showed significant attenuation of chemotherapy-induced cytotoxicity across a range of MIT concentrations after 3 d ($P<0.05$) (FIG. 10A and FIG. 11A).

Figure 10B:
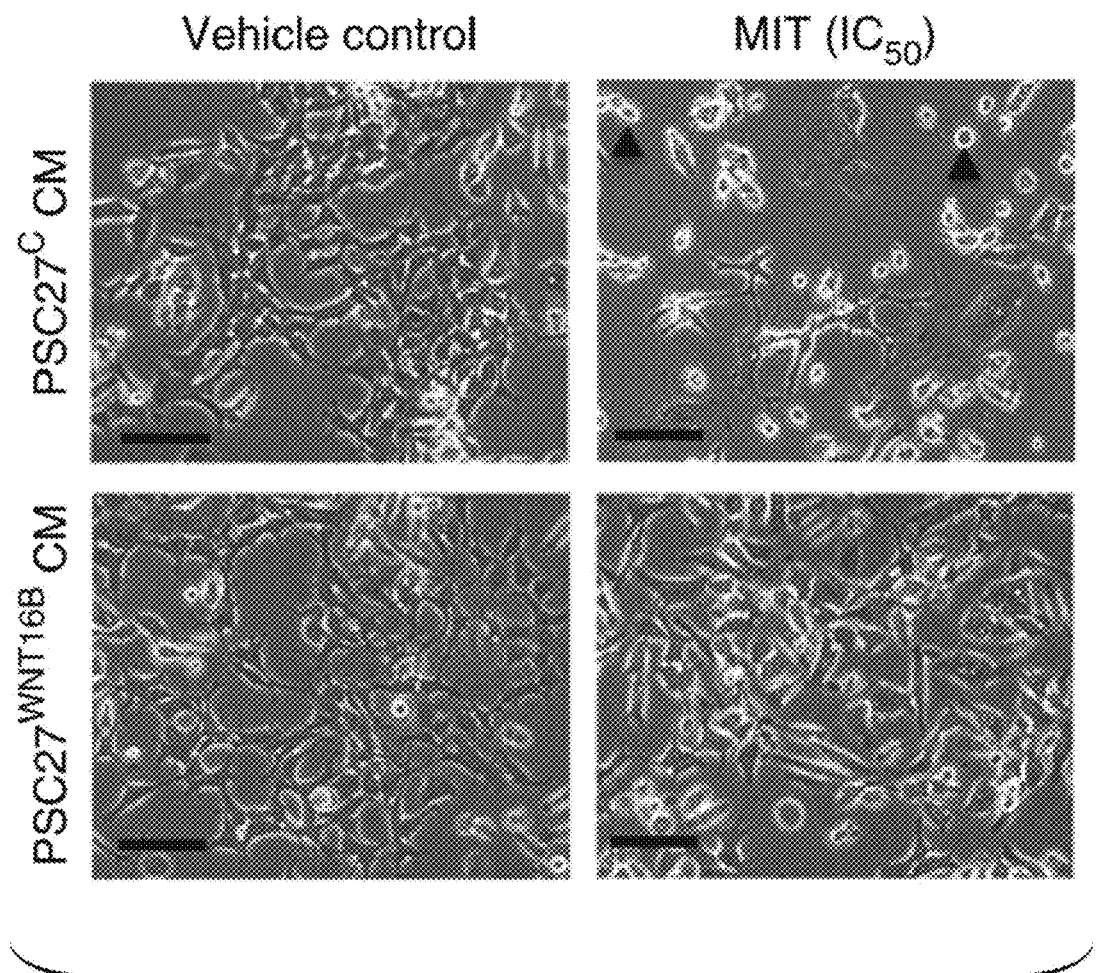
Figure 10C:
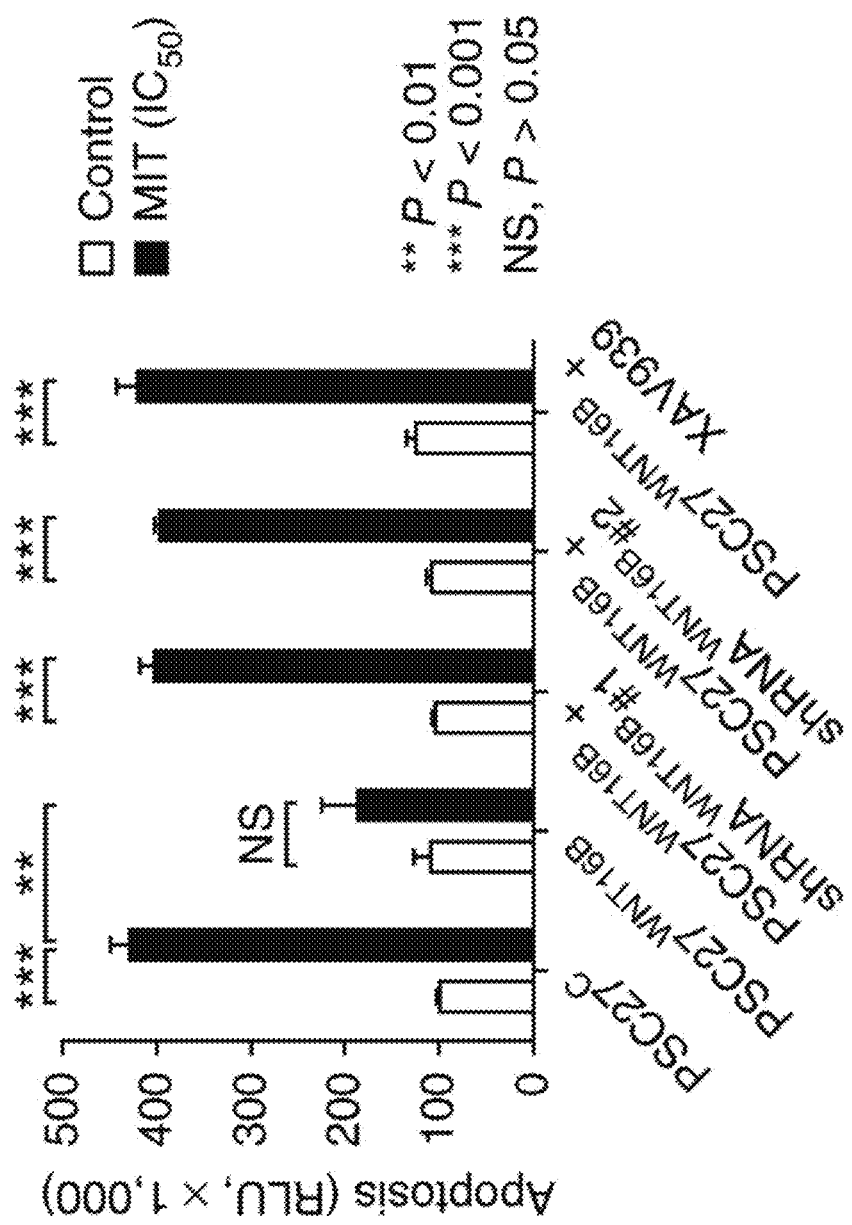
Figure 10D:
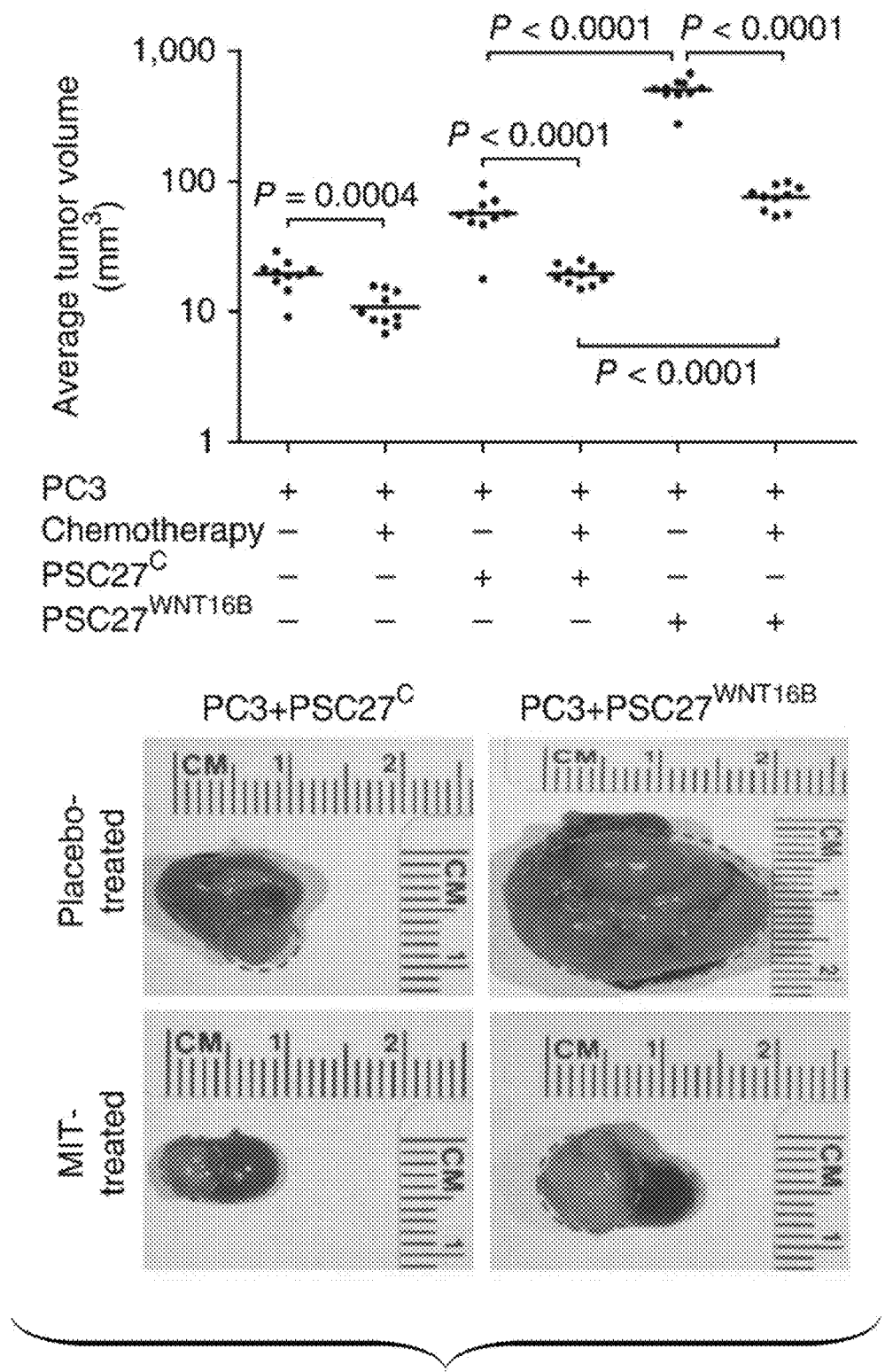
Figure 10E:
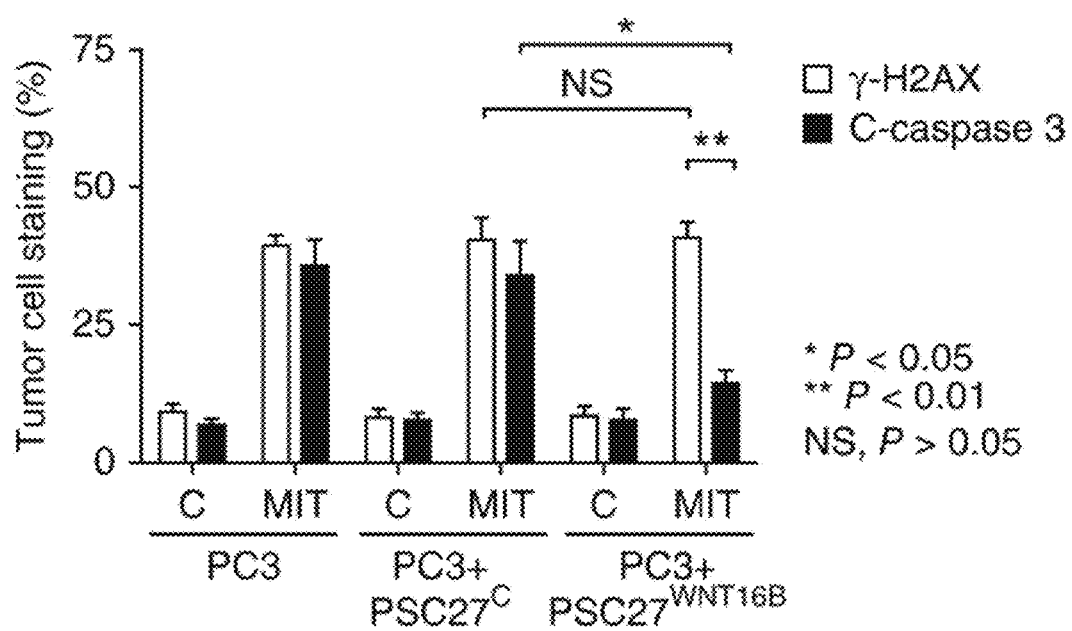
Figure 11B:
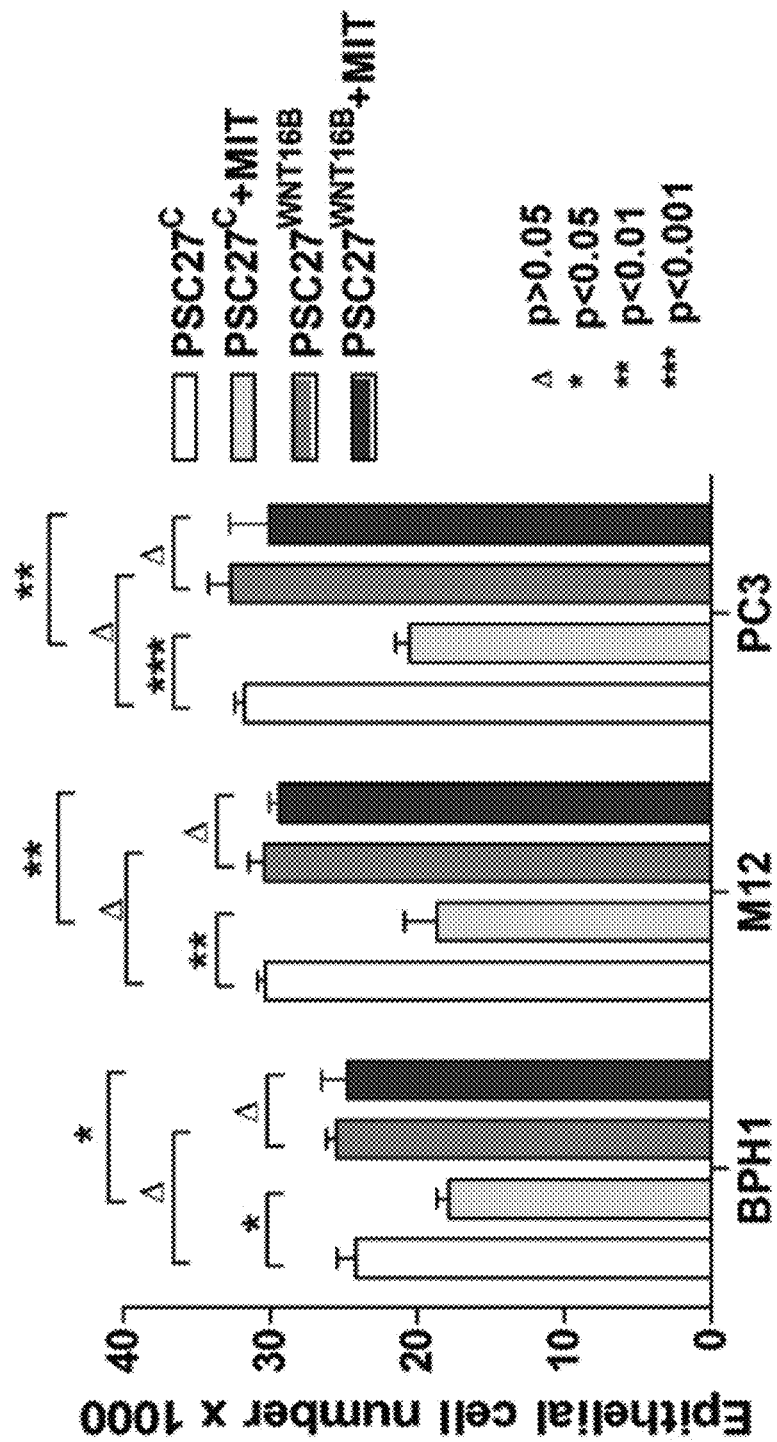
Figure 11C:
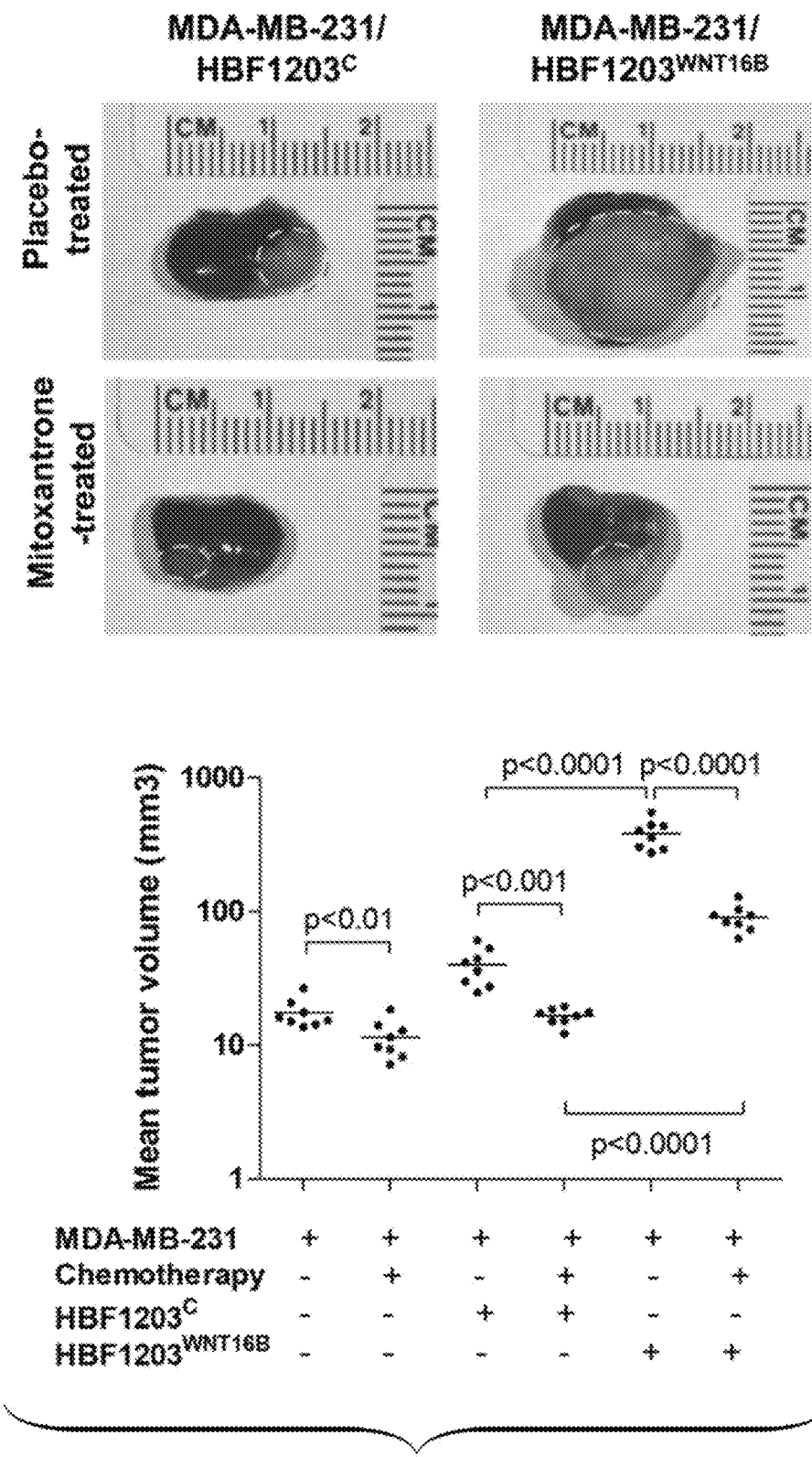

Short-term cell viability assays confirmed that, compared to controls, PSC27$^{WNT16B}$-conditioned medium improved cancer cell survival after acute 12 hour exposures to MIT ($P<0.01$) (FIG. 11B). Apoptotic responses measured after 24 hour of MIT exposure were substantially attenuated by PSC27$^{WNT16B}$-conditioned medium ($P<0.01$), an effect that was blocked by treatment with XAV939 (FIGS. 10B and 10C). To determine whether these observations were of relevance to tumor therapy in vivo, mice with tumor grafts comprised of BPH-1 or PC3 cells plus PSC27$^{WNT16B}$ or PSC27$^C$ fibroblasts were treated with three cycles of MIT given every other week. MIT treatment significantly reduced the tumor volumes ($P<0.001$). However, grafts of tumor cells with PSC27$^{WNT16B}$ fibroblasts attenuated the tumor inhibitory effects of MIT compared to tumor cells grafted with control PSC27 fibroblasts: PC3+PSC27$^C$ and PC3+PSC27$^{WNT16B}$ tumors averaged 13 mm$^3$ and 78 mm$^3$, respectively ($P<0.001$) (FIG. 10D). Experiments using MDA-MB-231 breast cancer cells plus breast fibroblasts produced similar results (FIG. 11C). To evaluate the influence of WNT16B on the acute effects of chemotherapy, cohorts of PC3+PSC27$^C$ and PC3+PSC27$^{WNT16B}$ xenografts were examined 24 hours after MIT treatment to quantify DNA damage using γ-H2AX immunofluorescence and apoptosis using cleaved caspase 3 immunohistochemistry (IHC). Compared to PC3+PSC27$^C$ grafts, there was no difference in the number of DNA damage foci in PC3+PSC27$^{WNT16B}$ tumors, but significantly fewer apoptotic cells were present (34% compared to 14%, respectively; $P<0.05$) (FIG. 10E).

Figure 12A:
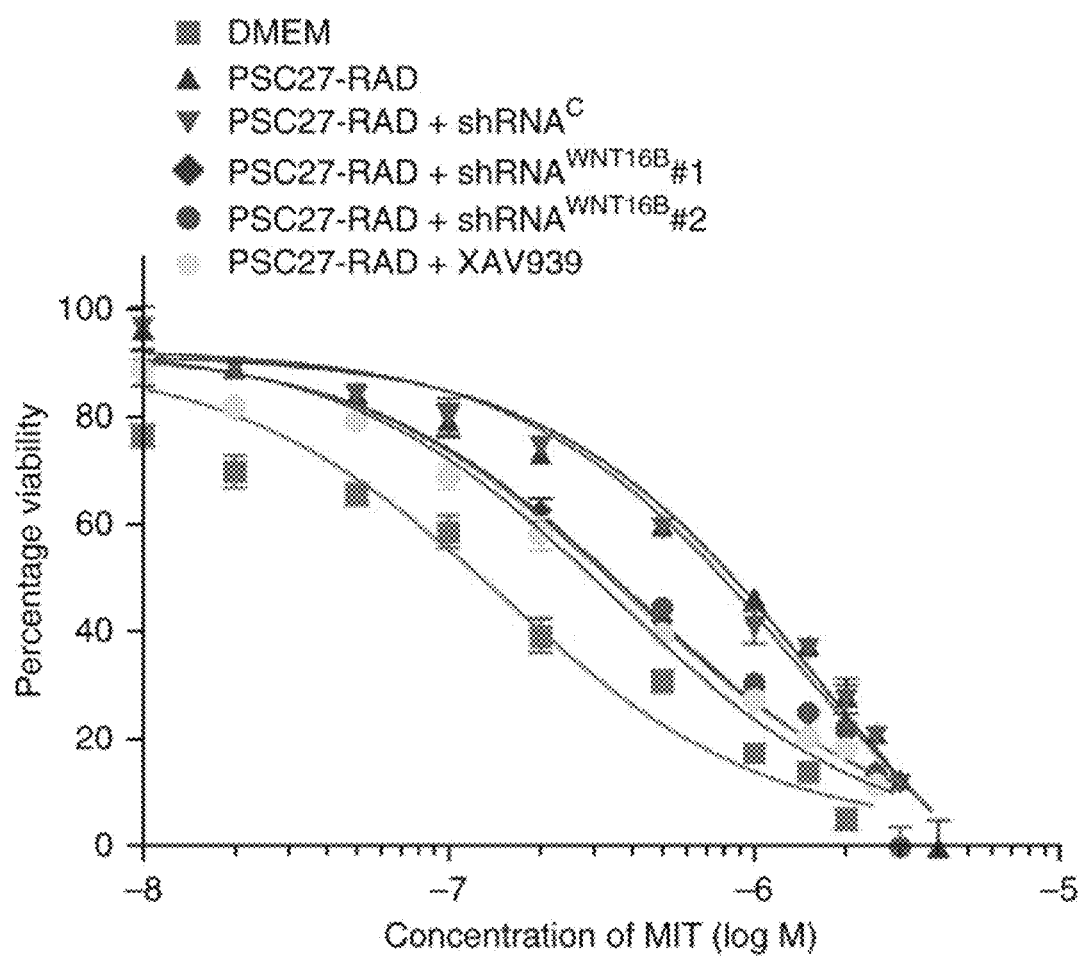
FIGS. 12A through 12G. Chemotherapy resistance promoted by damaged fibroblasts is attenuated by blocking WNT16B, β-catenin or NF-κB signaling.
Figure 12B:
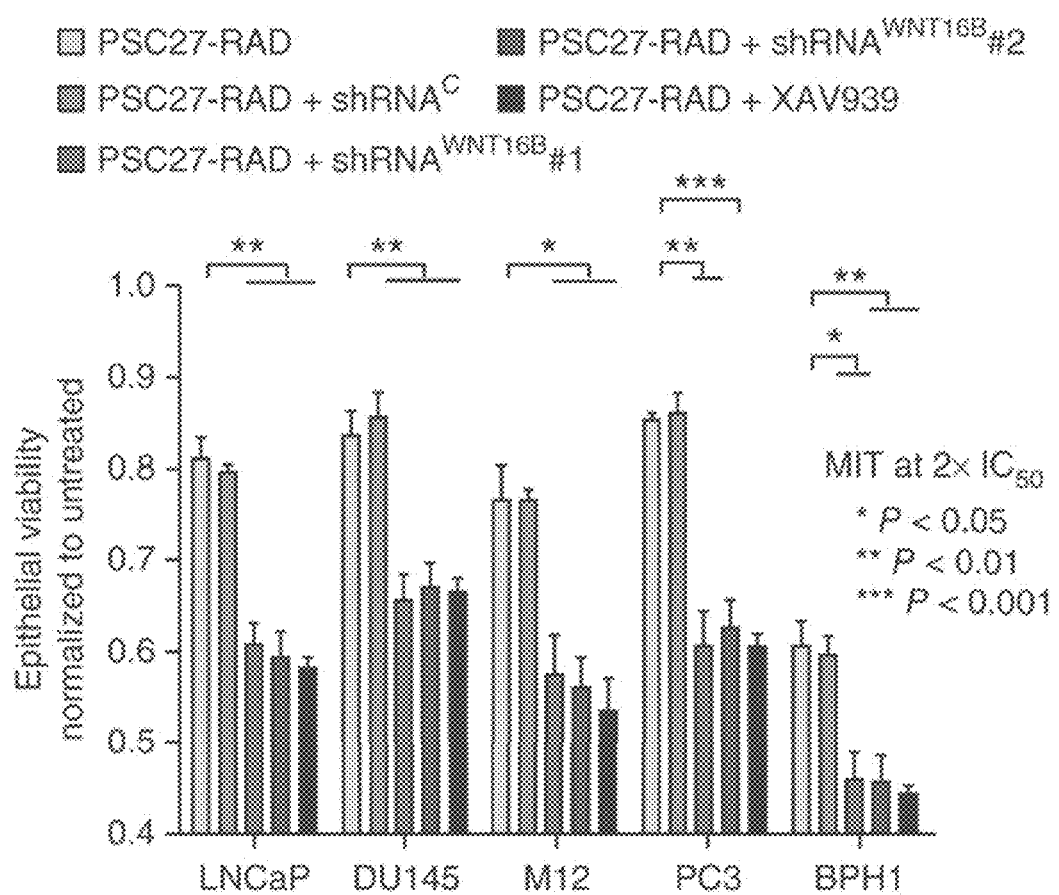
Figure 12C:
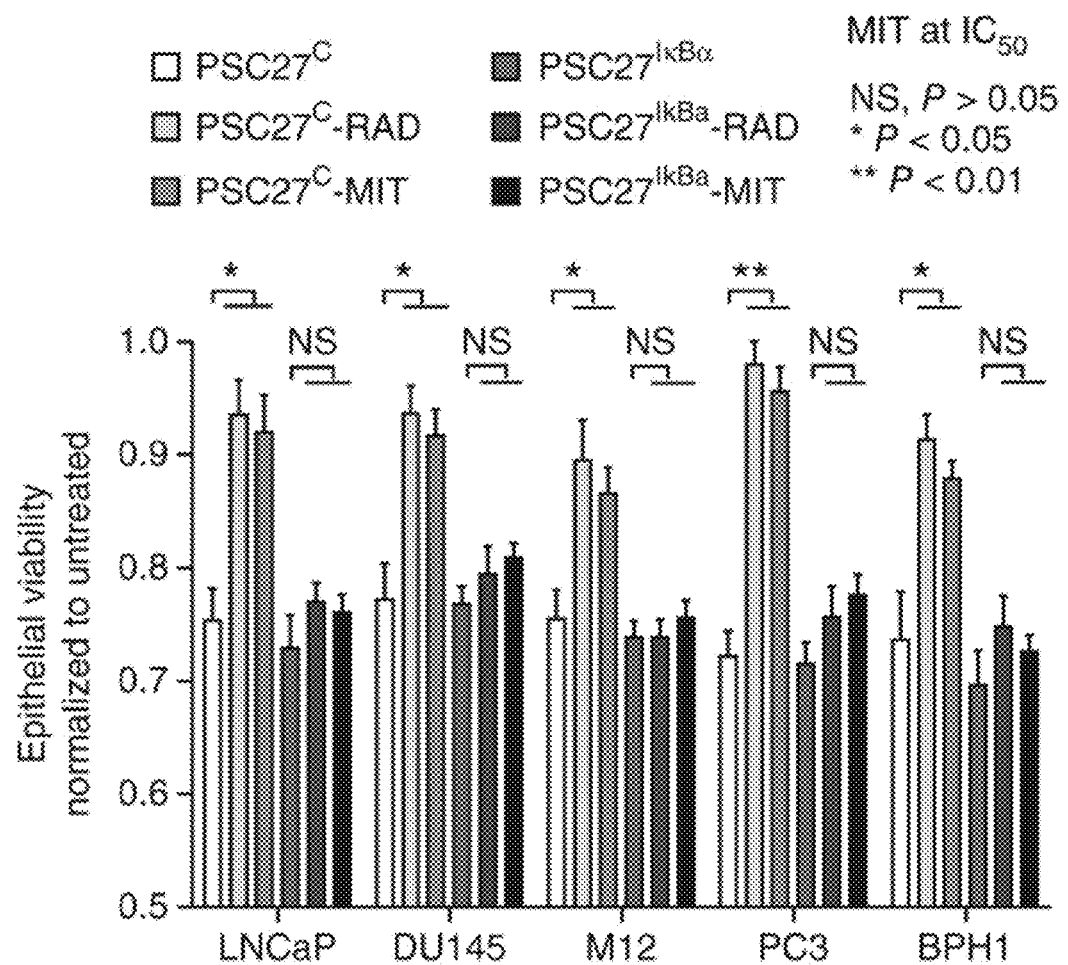
Figure 12D:
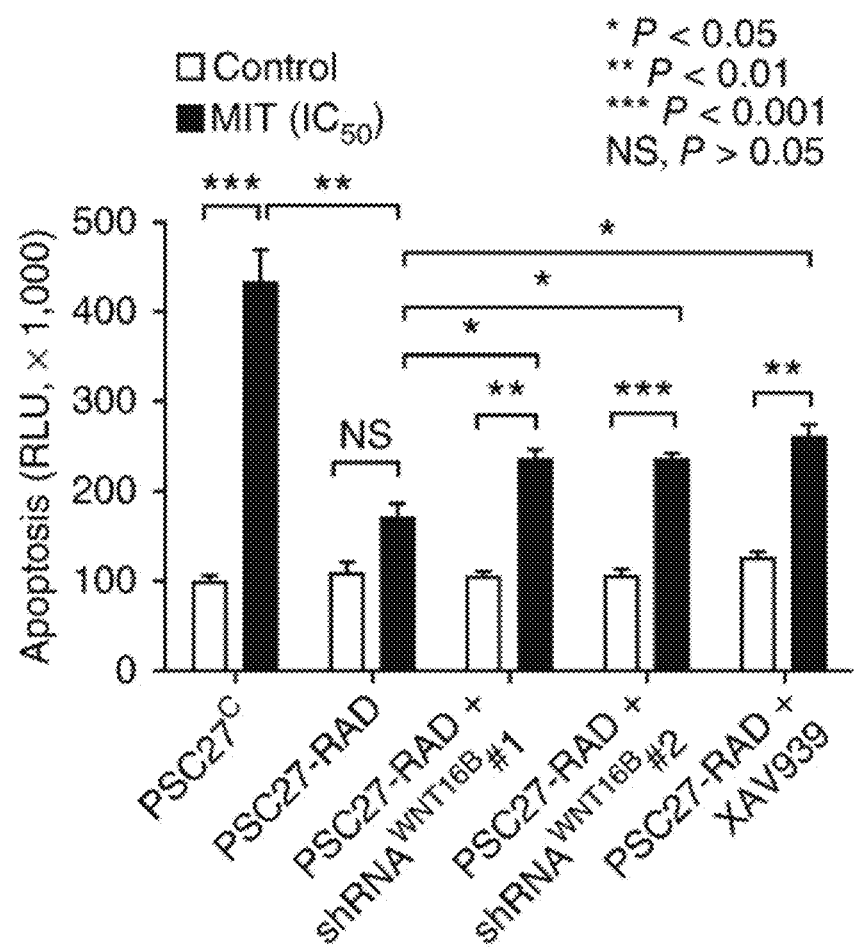
Figure 12E:
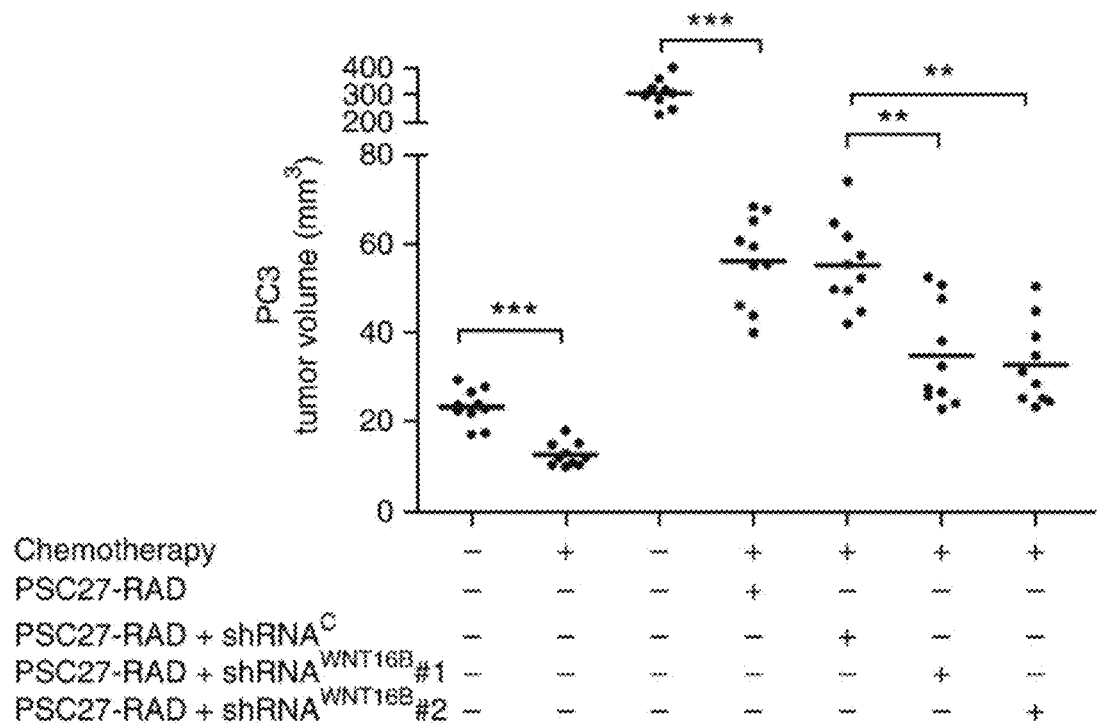
Figure 12F:
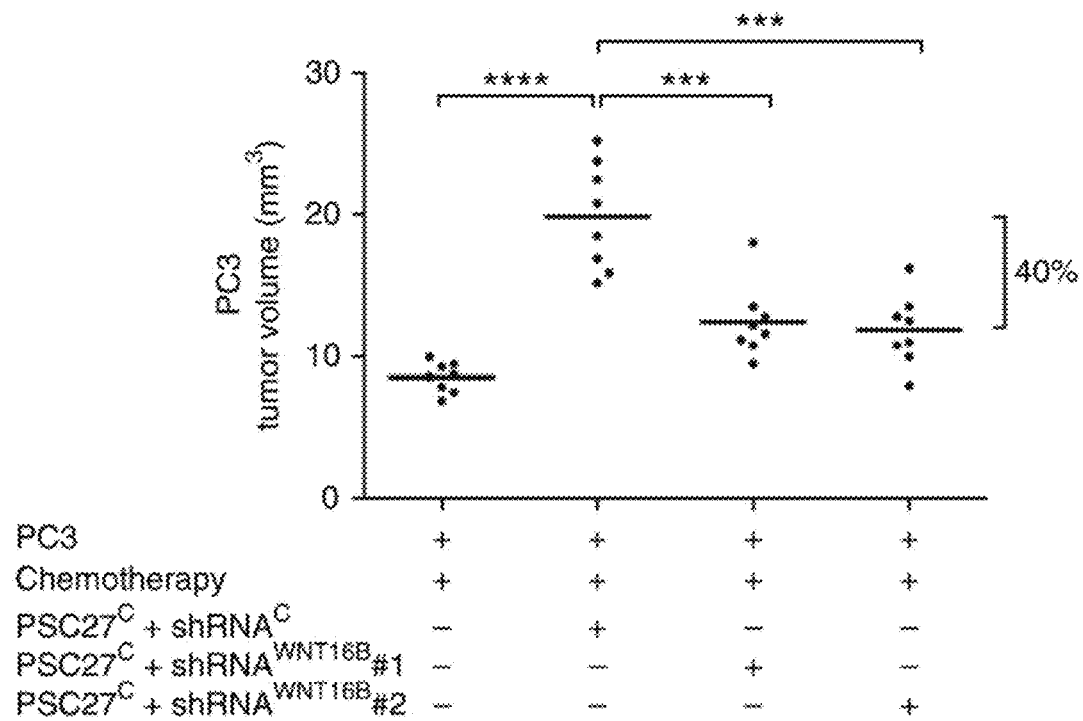
Figure 12G:
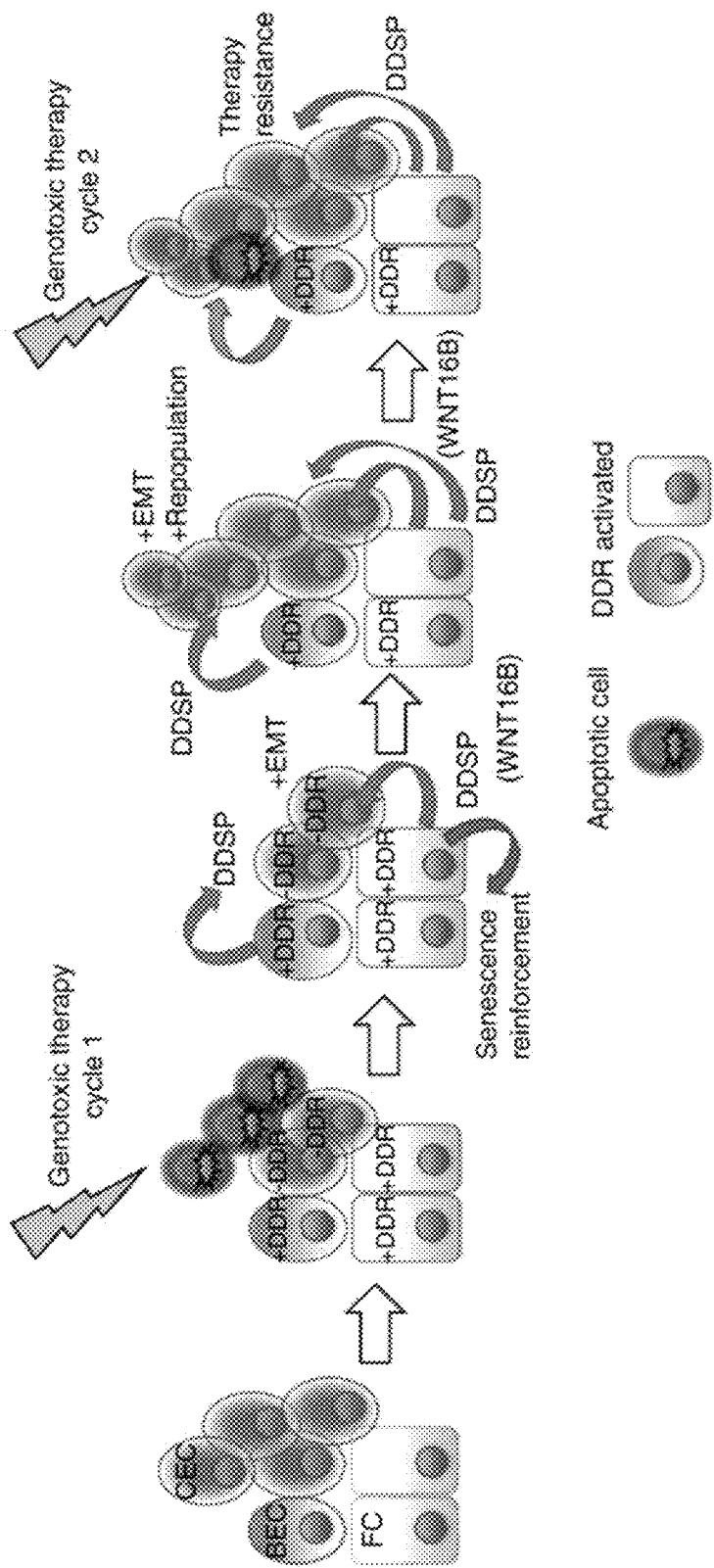
Figure 13A:
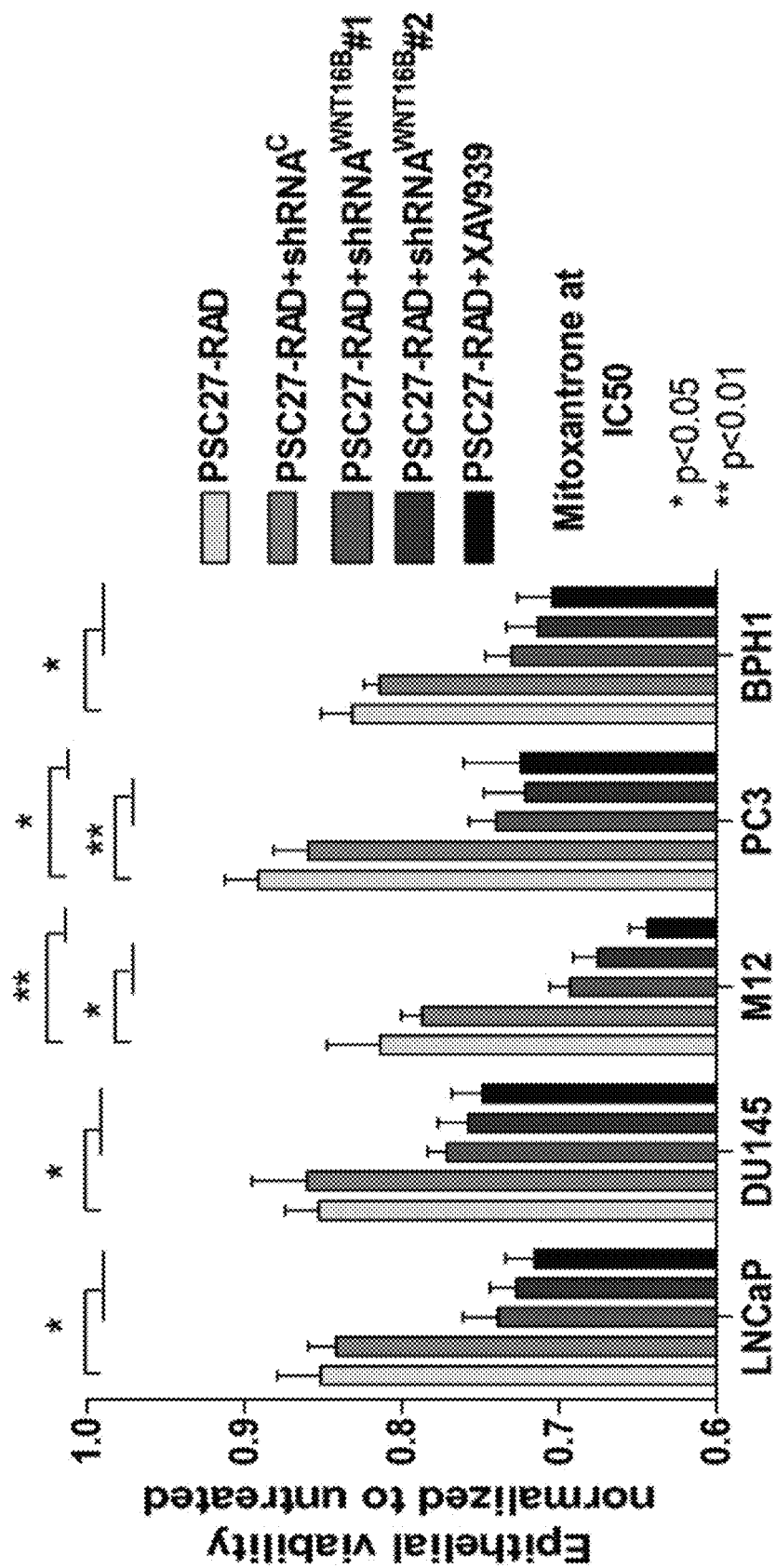
FIG. 13A through 13D demonstrate prostate, breast and ovarian carcinoma therapy resistance promoted by damaged fibroblasts is attenuated by blocking WNT16B or β-catenin signaling.
Figure 13B:
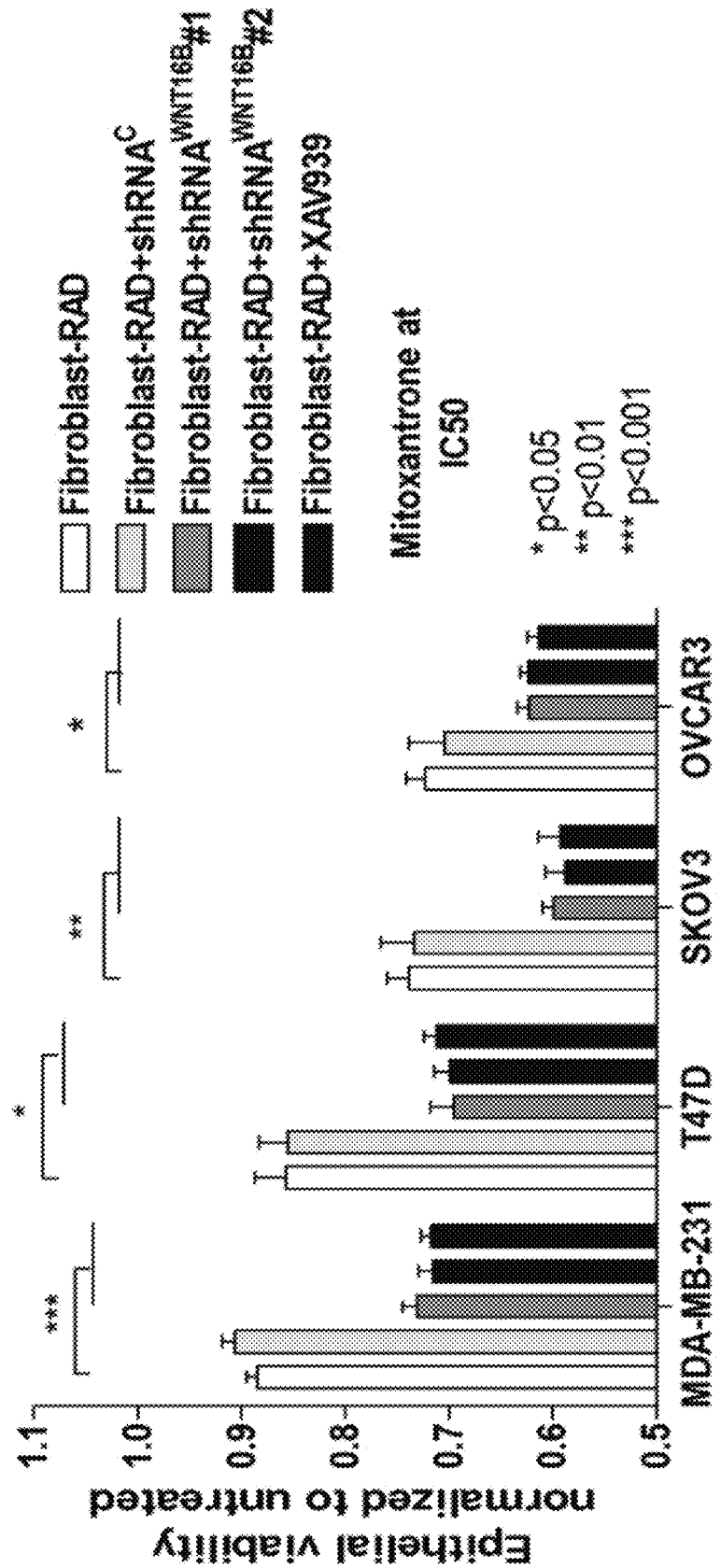
Figure 13C:
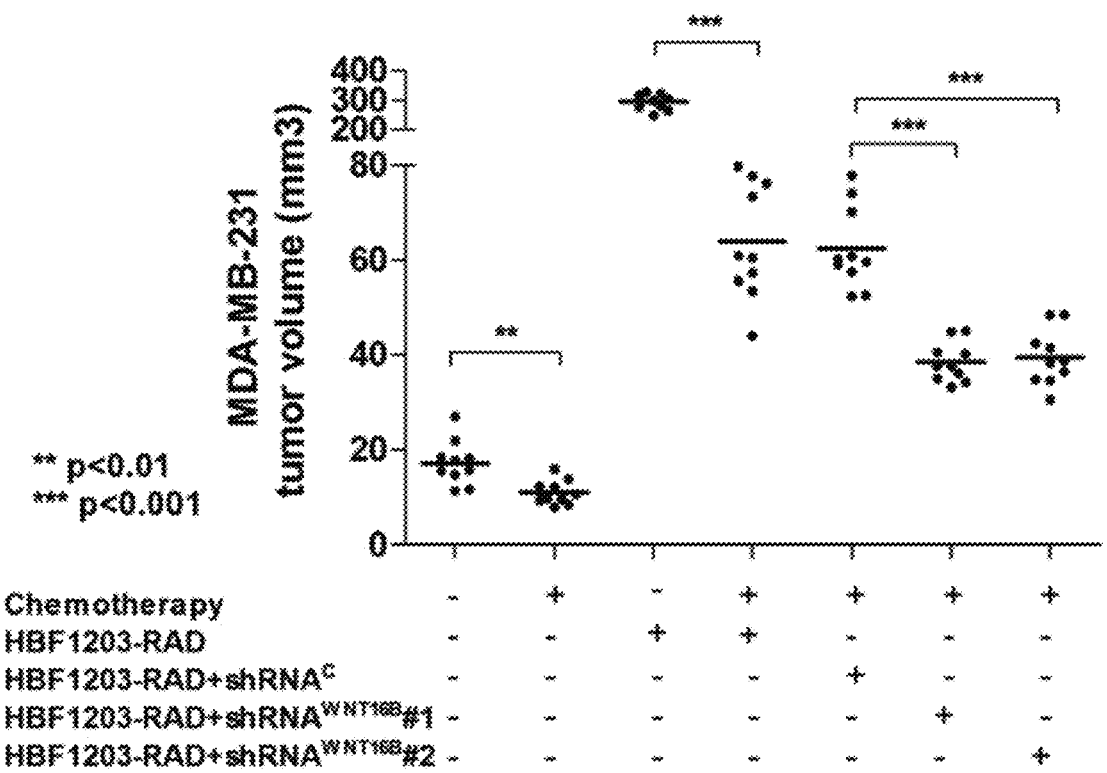
Figure 13D:
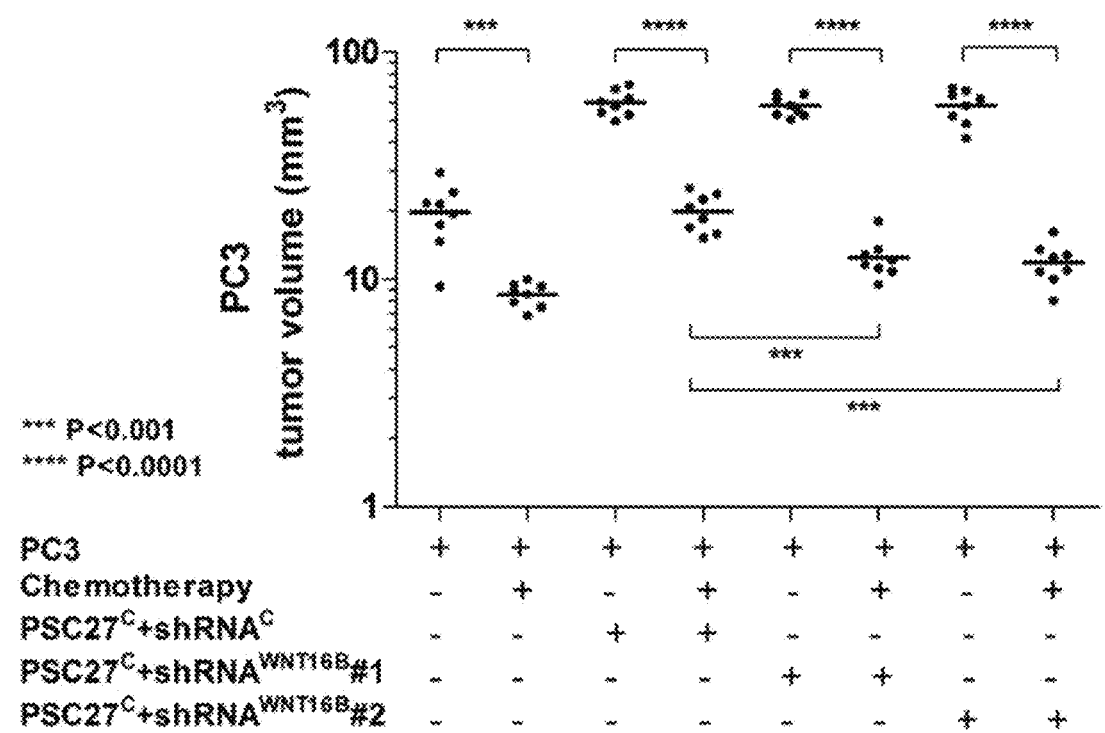

The conditioned medium from PSC27-RAD cells, representing the full fibroblast DDSP, significantly increased the viability of PC3 cancer cells exposed to MIT concentrations ranging between 0.1 to 1 μM in vitro ($P<0.01$) (FIG. 12). In comparison to PSC27-RAD-conditioned medium, PSC27-RAD+shRNA$^{WNT16B}$ or PSC27$^{IκBα}$RAD fibroblasts, engineered to suppress WNT16B expression or NF-κB activation, respectively, substantially augmented the effects of MIT, further increasing apoptosis and reducing tumor cell viability by 30 to 40%. Blocking β-catenin signaling in carcinoma cells with XAV939 also attenuated the effects of PSC27-RAD-conditioned medium on promoting tumor cell survival (FIGS. 12B through 12D and FIGS. 13A and 13B). This effect of WNT16B was also evident in vivo. PC3+ PSC27-RAD tumor grafts averaged 300 mm$^3$ in size compared to 25 mm$^3$ for grafts of PC3 cells alone ($P<0.001$). MIT chemotherapy suppressed the growth of the PC3+ PSC27-RAD grafts, 55 mm$^3$ in size (FIG. 12E). However, after MIT treatment, grafts of PC3 tumor cells with PSC27-RAD+shRNA$^{WNT16B}$ fibroblasts, with attenuated WNT16B induction, were on average about 33% smaller than PC3+ PSC27-RAD tumors ($P<0.001$) (FIG. 12E). Experiments with MDA-MD-231 cells and breast fibroblasts produced similar results (FIG. 13C). To more accurately mimic the clinical situation of cancer therapy, grafted tumor cells with unirradiated PSC27 fibroblasts (PSC27$^C$) were grafted and the same treatment schema of three MIT cycles was followed. Tumors from mice treated with MIT were substantially smaller than tumors from untreated mice ($P<0.001$). Attenuating the induction of WNT16B further enhanced the effects of chemotherapy: after MIT treatment, grafts of PC3 cells and PSC27$^C$+shRNA$^{WNT16B}$ were on average 40% smaller than grafts of PC3 cells combined with PSC27$^C$ cells without shRNA$^{WNT16B}$ ($P<0.001$) (FIG. 12F and FIG. 13D).

The mTOR Inhibitor Rapamycin Suppresses the DDSP and Enhances Tumor Responses to Genotoxic Chemotherapy The above data, and recent reports in the literature, provide strong evidence that signals initiated by genotoxic stress are propagated via NFκB, p38MAPK, mTOR, and potentially influenced by poly-ADP ribose polymerase (PARP). Inhibiting a key master regulator has the potential to simultaneously suppress major components of the DDSP, which is complex and likely exhibits substantial redundancy. Recent reports implicate the involvement of MDM2 in linking DNA damage to metabolic/energy regulation, and potentially the DDSP. DDR signals, independent of ATM/ATR, transiently activates mTOR-S6K1, which phosphorylates MDM2, allowing retention in the cytoplasm, leading to loss of p53 ubiquitination and p53 stabilization. mTOR is a serine/threonine protein kinase that governs highly-conserved nutrient- and growth factor-sensing pathways, and is a component of two distinct complexes: mTORC1 and mTORC2. DNA damage induced by UV irradiation can induce the mTOR target p70S6 kinase concomitant with the up-regulation of DDSP members MMP1 and MMP3. While a systematic analysis of mTOR's role in DDSP is lacking, the data suggest that mTOR inhibitors (e.g., RAD001 and Rapamycin) may regulate DDSP effection proteins.

The effects of inhibiting mTOR signaling in the context of genotoxic stress was evaluated. PSC27 fibroblasts were treated with Rapamycin (RAPA) prior to ionizing radiation. RAPA treatment markedly attenuated the induction of most of the DDSP factors analyzed, including SPINK1 and WNT16B. RAPA treatment also substantially reduced the MIT-resistance effects of the fibroblast DDSP toward prostate cancer cells. in vivo, systemic RAPA significantly enhanced the tumor inhibitory effects of MIT toward subcutaneous grafts of PC#/PSC27 cells. The RAPA was administered at concentrations that produced no individual anti-tumor effects, but used with MIT produced substantial responses (approximately 60% reduction in tumor volumes; p<0.001).

Optimizing radiotherapy and chemotherapy for the treatment of malignant neoplasms has relied on the iterative development and testing of models involving tumor growth dynamics, mutation rates and cell-kill kinetics. However, the most theoretically effective tumoricidal strategies must usually be tempered because of detrimental effects to the host. This reality has led to the development of regimens in which therapies are administered at intervals or cycles to avoid irreparable damage to vital host functions. However, the recovery and repopulation of tumor cells between treatment cycles is a major cause of treatment failure (Kim and Tannock, *Nat. Rev. Cancer* 5:516-525, 2005; Tredan et al., J. Natl. Cancer Inst. 99:1441-1454, 2007). Interestingly, rates of tumor cell repopulation have been shown to accelerate in the intervals between successive courses of treatment, and solid tumors commonly show initial responses followed by rapid regrowth and subsequent resistance to further chemotherapy. Our results indicate that damage responses in benign cells comprising the tumor microenvironment may directly contribute to enhanced tumor growth kinetics (FIG. 12G).

The autocrine- and paracrine-acting influences of genotoxic stress responses can exert complex and potentially conflicting cell nonautonomous effects (Kuilman and Peeper, Nat. Rev. Cancer 9:81-94, 2009; Fumagalli and d'Adda di Fagagna, Nat. Cell Biol. 11:921-923, 2009). Overall, the above findings are in agreement with studies of DNA damage in which the execution of a signaling program culminating in a senescence phenotype is accompanied by elevated concentrations of specific extracellular proteins termed a 'senescence messaging secretome' or a 'senescence-associated secretory phenotype' (Kuilman and Peeper, Nat. Rev. Cancer 9:81-94, 2009; Fumagalli and d'Adda di Fagagna, Nat. Cell Biol. 11:921-923, 2009). DNA damage responses and senescence programs can clearly operate in a cell autonomous 'intrinsic' manner to arrest cell growth and inhibit tumor progression, as has been observed in premalignant nevi (Michaloglou et al., Nature 436:720-724, 2005). Secreted factors such as insulin-like growth factor binding protein 7 (IGFBP7) and the chemokine (C-X-C motif) receptor 2 (CXCR2) ligands IL-6 and IL-8 participate in a positive feedback loop to fortify the senescence growth arrest induced by oncogenic stress and also promote immune responses that clear senescent cells and enhance tumor regression (Acosta et al., Cell 133:1006-1018, 2008; Kuilman et al., Cell 133:1019-1031, 2008; Xue et al., Nature 445:656-660, 2007; Wajapeyee et al., Cell 132:363-374, 2008). However, in addition to proinflammatory cytokines, the damage response program comprises proteases and mitogenic growth factors, such as MMPs, hepatocyte growth factor (HGF), vascular endothelial growth factor (VEGF) and epidermal growth factor receptor (EGFR) ligands that have clear roles in promoting tumor growth, inhibiting cellular differentiation, enhancing angiogenesis and influencing treatment resistance (Bavik et al., Cancer Res. 66:794-802, 2006; Coppe et al., PLoS Biol. 6:2853-2868, 2008; Coppe et al., J. Biol. Chem. 281:29568-29574, 2006). This concept is supported by reports of tissue-specific chemoresistant survival niches involving hematopoietic neoplasms, such as lymphomas (Gilbert and Hemann, Cell 143:355-366, 2010). The situation also has parallels with studies of radiation and chemotherapy paradoxically promoting tumor dissemination (Biswas et al., J. Clin. Invest. 117:1305-1313, 2007).

Collectively, the above support several conclusions: first, the outcomes of genotoxic exposures to any specific benign or neoplastic cell depend on the integration of innate damage response capabilities and the context that is dictated by the composition of the tumor microenvironment; second, although intrinsic drug resistance is clearly operative in some cancers, acquired resistance can also occur without alterations in intrinsic cellular chemosensitivity (Davis and Tannock, Lancet Oncol. 1:86-93, 2000), and the above results provide strong support for previous studies that implicate constituents of the tumor microenvironment as important contributors to this resistance (Meads et al., Clin. Cancer Res. 14:2519-2526, 2008; Shree et al., Genes Dev. 25:2465-2479, 2011; DeNardo et al., Cancer Discov. 1:54-67, 2011); third, the composition of the microenvironment damage response indicates the potential to promote resistance to pathway-targeted agents such as EGFR inhibitors, as these drugs must contend with damage-enhanced local concentrations of competing ligands such as SPINK1 and amphiregulin; and fourth, specific microenvironment DDSP proteins that promote therapy resistance such as WNT16B are attractive targets for augmenting responses to more general genotoxic therapeutics. However, the complexity of the damage response program also supports strategies that are focused on inhibiting upstream master regulators, such as NF-κB (Chien et al., Genes Dev. 25:2125-2136, 2011), that may be more efficient and effective adjuncts to cytotoxic therapies, provided their side effects are tolerable.

Example 2

In this example, it is demonstrated that SFRP2 is expressed by fibroblasts following genotoxic treatment and that the expression of SFRP2 can be modulated to effect cancer therapy.

It has been established that anticancer treatments cause DNA damage, which leads to tumor regression through the activation of apoptosis and senescence programs. To assess the damage responses of human benign stromal cells comprising the tumor microenvironment, a primary prostate stromal cell line, PSC27 (Bavik et al., Cancer Res. 66:794-802, 2006) was examined. PSC27 cells were exposed to a 10Gy ionizing radiation, cell lysates were collected for RNA preparation. Expression of both SFRP2 and WNT16B were analyzed by RT-PCR reactions. PSC27 stable line over-expressing SFRP2 or WNT16B was examined in parallel as positive control. Data was averaged from three independent experiments. Following this ionizing radiation, the expression of SFRP2 was found to be dramatically up-regulated in the PSC27 line, as evidenced by SRFP2 over-expression in these cells upon genotoxic treatment.

Since radiation caused such a remarkable influence to SFRP2 expression, the consequences of several other treatments was next examined, including the use of hydrogen peroxide ($H_2O_2$), DNA damaging agents including bleomycin (BLEO) and mitoxantrone (MIT). The latter are chemicals frequently used in clinical therapies of human cancer patients.

In particular, PSC27 cells were treated with 0.6 mM hydrogen peroxide, 10 μg/mL bleomycin, or 1 μM mitoxantrone in PSC medium as previously described above. After treatment, the cells were rinsed thrice with PBS and left to recover 3 days in PSC medium. Following recovery, cells were designated PSC27-$H_2O_2$, PSC27-BLEO, PSC27-MIT or PSC27-RAD, while normally proliferating PSC27 cells as PSC27-Pre. After treatment, cells were maintained in medium for 7 to 10 days before cell lysis for RNA or protein analysis. (A), quantitative RT-PCR of SFRP2 expression at transcription level, amplified signals normalized to the interior reference gene RPL13A; (B), Immunoblot analysis of SFRP2 with samples collected as either conditioned media about 7 to 10 days after in vitro treatments, or as the whole cell lysates collected in the same time period. Not surprisingly, a consistent pattern of SFRP2 was observed, indicating that the over-expression was not specific to ionizing radiation, but comprehensive to multiple DNA damaging treatments.

To determine the intracellular localization of SFRP2, immunofluorescence staining with an anti-SFRP2 antibody was applied. Subsequent to treatments under in vitro conditions, PSC27 cells were rinsed, subjected to fixation in 4% paraformaldehyde and permeabilization with 0.1% Triton- X100 prior to immunostaining A rabbit polyclonal anti-SFRP2 (Santa Cruz, clone no. H-140) and secondary antibody Alexa Fluor® 488 (or 594)-conjugated F(ab')$_2$ goat anti-rabbit IgG (Invitrogen) were sequentially applied. Nuclei were counterstained with 2 µg/ml of 4',6-diamidino-2-phenylindole (DAPI) and coverslips were mounted onto glass slides. Interestingly, the majority of SFRP2 signals were found in the cytoplasm, while the untreated cells had barely detectable expression. Although the appearance of SFRP2 was visible only after 7 to 10 days upon treatment, this paralleled with most of other secreted factors, including WNT16B, MMP3, GM-CSF, Groa and IL-8.

In one of the previous study above, the expression of another factor, WNT16B, a Wnt family member that participates in paracrine actions from stromal areas to the prostate epithelial populations and alters multiple epithelial phenotypes, was found to be markedly enhanced upon chemotherapy and have the potential to propagate cellular DNA damage signals to other residents of the tissue microenvironment. In this work, chemotherapy-induced SFRP2 expression changes in human prostate cancer associated stroma was measured by qRT-PCR after microdissection. Each data point represented the measurements from an individual patient and the results were determined as PCR cycle number relative to the reference gene, ribosomal protein L13 (RPL13), which served as the base control. The P values were calculated by Student's t test. The expression level of SFRP2 was measured in both pre- and post-treatment patients, and found its transcripts increased significantly ($p<0.05$). It is therefore interesting to interrogate whether many of the DDSP factors share a similar expression pattern, or only a small handful of them exhibit this feature.

Since SFRP2 has been found to be over-expressed in the vasculature of 85% human breast tumors (Courtwright et al., Cancer Res. 69: 4621-4628, 2009), it was determined whether its expression has a similar or special pattern in human prostate populations, including the well characterized cell lines. The primary prostate stromal line PSC27 and several established prostate epithelial lines were exposed to 5Gy ionizing radiation. Total RNAs were prepared, with cDNA synthesized by reverse transcription. Values on the Y axis are based on the $Log_2$ of fold change of SFRP2 transcript expression, as post-treatment signal against pre-treatment signal. Data are the average of three independent experiments. Treatment to PSC27 and several typical prostate epithelial cell lines with radiation demonstrated that this Frizzled-related protein was more susceptible to be induced in prostate fibroblasts, while epithelial cells only had a minor response, even when the cells received the same dose of radiation.

SFRP2 belongs to a large family of SFRPs that are implicated in the Wnt signaling cascade and are involved in cancer progression. Some studies suggest that SFRP2 inhibits the Wnt-β-catenin pathway thus acts as a tumor suppressor (Kawano and Kypta, J. Cell Sci. 116: 2627-2634, 2003; Suzuki et al., Br. J. Cancer 98:1147-1156, 2008). In contrast, recent reports suggest that SFRP2 can induce tumor growth and it is produced by certain tumor types including glioma (Roth et al., Oncogene 19: 4210-420, 2000) and stimulates angiogenesis via a calcineurin/NFAT signaling pathway (Courtwright et al., Cancer Res. 69:4621-4628, 2009; Siamakpour-Reihani et al., PloS One 6:e20412, 2011). In the present disclosure, the first choice was to silence SFRP2 expression through the application of shRNA. In particular, the primary prostate stromal line PSC27 and several established prostate epithelial lines were exposed to 5Gy ionizing radiation. Total RNAs were prepared, with cDNA synthesized by reverse transcription. Data were calculated as the average of three independent experiments. From these data it was found that the activated β-catenin pathway by stromal conditioned media collected post-DNA damage which was mainly mediated by WNT16B, became significantly attenuated. When the conditioned media from PSC27 cells made to over-express SFRP2, the β-catenin signals remained unchanged, indicating SFRP2 itself does not activate this pathway. However, when SFRP2 and WNT16B were co-expressed, the conditioned media caused significantly higher activation of the β-catenin axis.

Figure 14:
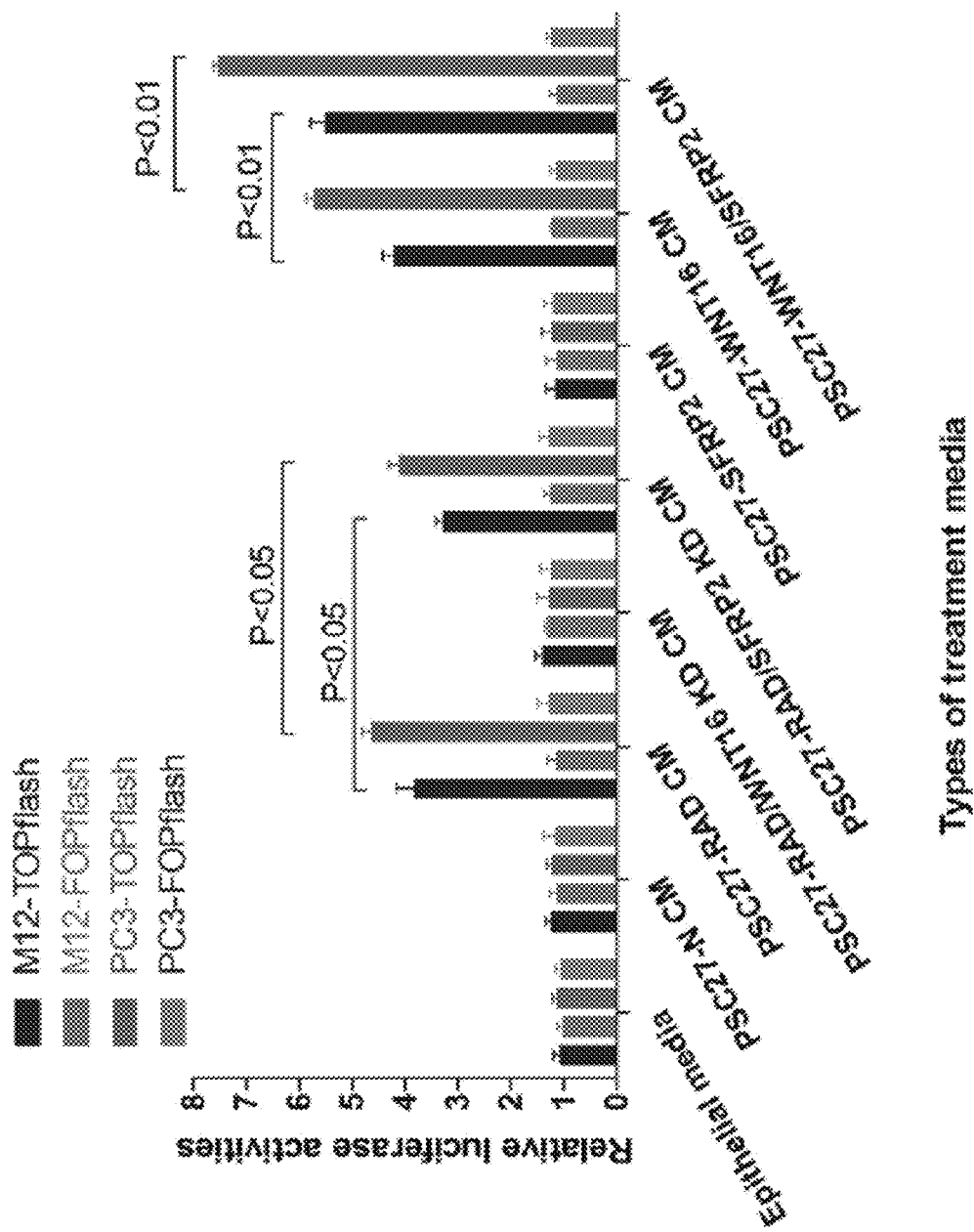
FIG. 14. Activation of the Wnt-β-catenin pathway by conditioned media from PSC27 cells, either after ionizing radiation, upon over-expression or knock-down of target genes. Data are mean±s.e.m. of triplicates, and P values were determined by ANOVA followed by t test.

In another study an assay of canonical Wnt pathway signaling through activation of a TCF/LEF luciferase reporter construct (TOPflash) or a control reporter (FOPflash) was conducted. In particular, epithelial cells were exposed to conditioned medium (CM) from PSC27 prostate fibroblasts over-expressing or silencing SFRP2, or WNT16B against their corresponding vector controls. These data were examined as the mean±s.e.m. of triplicates, and P values were determined by ANOVA followed by t test. (FIG. 14).

Figure 15:
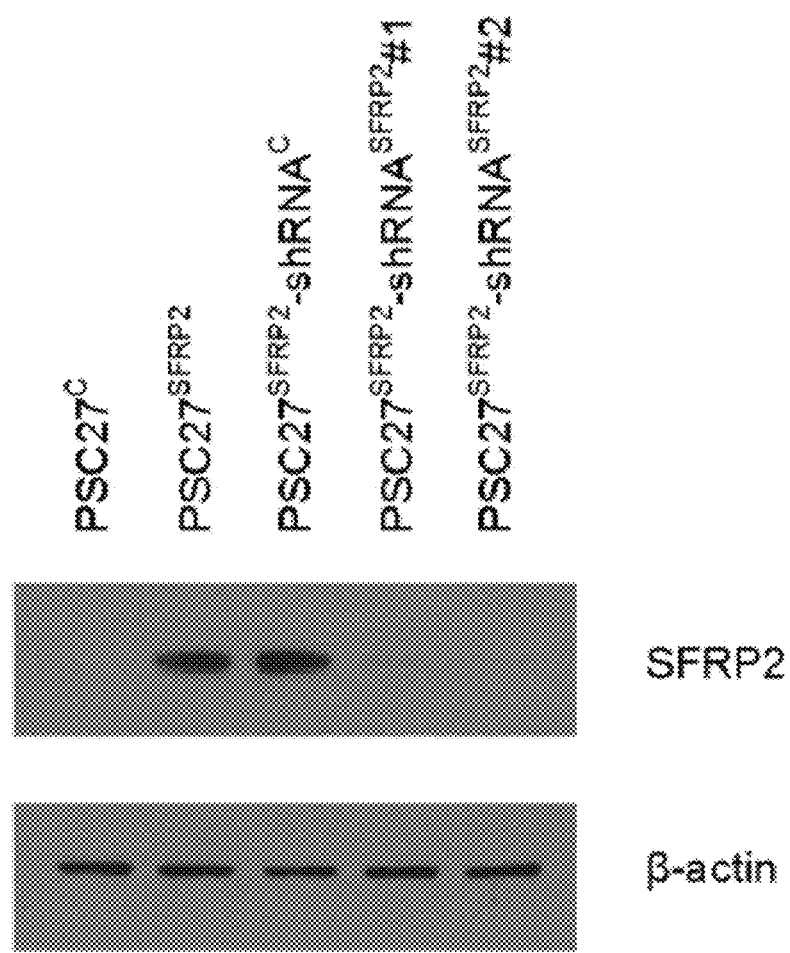
FIG. 15. Immunoblots of SFRP2 expression in PSC27 stable cell lines and shRNA silencing efficacy. Samples were loaded to the gel, from left to right: PSC27 vector control ((PSC27$^C$); PSC27 cells expressing SFRP2 (PSC27$^{SFRP2}$); PSC27$^{SFRP2}$ cells infected with non-specific shRNA; PSC27$^{SFRP2}$ cells infected with SFRP2-specific shRNAs (#1 and #2, respectively).

Similarly, immunoblot was used for confirmation of SFRP2 expression in PSC27 stable cell line and shRNA silencing efficacy. In this study, samples were loaded to the gel, from left to right: PSC27 vector control (PSC27C); PSC27 cells expressing SFRP2 (PSC27SFRP2); PSC27SFRP2 cells infected with non-specific shRNA; PSC27SFRP2 cells infected with SFRP2-specific shRNAs (#1 and #2, respectively). See FIG. 15.

Example 3

The present example demonstrates that quiescent cells retain their proliferative potential and "DNA damage secretory program" (DDSP) development capacity one the cells are allowed or induced to exit from their $G_0$ phase.

Components of the tumor microenvironment (TME) are now well-established to strongly influence the development and progression of malignancies. A robust secretory phenotype that occurs during the process of cellular senescence primarily results from damage to DNA, and such a phenotype is regulated by a mechanism termed "DNA damage secretory program (DDSP)" (See above). The DDSP is remarkable in several respects. First, the program is complex, with several hundred proteins induced to varying levels. Second, the program is robust, many transcripts, and their attendant proteins, are induced more than 10-fold. Third, there is both consistency and variability in the program depending on the cell type, e.g., fibroblast or epithelium. Fourth, a number of the DDSP proteins are well-known to promote tumor progression. These include proteases (MMPs), growth factors (SPINK1, amphiregulin, epiregulin), pro-angiogenic factors (ANGPTL4, ANGPT1), and pro-inflammatory cytokines (IL-1β, IL6, IL8) (Coppe et al. PLoS Biol. 6:e301: 2853-2868 2008; Bavik et al., supra, 2006; Kuilman et al., Cell 133:1019-1031, 2008; Krtolica et al., Proc. Natl. Acad. Sci. USA 98:12072-12077, 2001; Parrinello et al., J. Cell Sci. 118:485-496, 2005; and Examples above).

It is clear that current clinical therapeutics do not exclusively engage tumor cells, but rather also damage benign host 'bystander' cells, which are competent to activate damage responses including the DDSP. With preclinical animal models, it has been demonstrated above that following initial treatment, a robust DDSP derived from the TME, acts in a paracrine fashion to promote the survival and proliferation of adjacent neoplastic cells. In support of this concept, tumor growth kinetics has been shown to accelerate during the treatment intervals (Kim and Tannock, *Nat. Rev. Cancer* 5:516-525, 2005). This rapid tumor repopulation is viewed as major cause of treatment failure in some malignancies, and therapies designed to suppress repopulation by using cytostatic agents in a metronomic fashion have improved clinical outcomes.

On the other hand, many cells in human exist in the state of quiescence, which is characterized by reversible exit from the cell cycle. Quiescent cells used to be described to have reduced size, nucleotide synthesis, and metabolic activity. However, recent studies reported that primary human fibroblasts continue to exhibit high metabolic rates when induced into quiescence via contact inhibition (Coller et al., *PLoS Biol.* 4:e83, 2006). By monitoring isotope labeling through metabolic pathways and quantitatively identifying fluxes from the data, some laboratories have shown that contact-inhibited fibroblasts utilize glucose in all branches of central carbon metabolism at rates similar to those of proliferating cells, with greater overflow flux from the pentose phosphate pathway back to glycolysis (Lemons et al., *PLoS Biol.* 8:e1000514, 2010). The high metabolic activity of the fibroblasts was partially directed to breakdown and re-synthesis of protein and lipid, and partially to excretion of extracellular matrix proteins. Thus, reduced metabolic activity per se is actually not a hallmark of the quiescent state. Quiescent fibroblasts, relieved of the biosynthetic requirements associated with generating progeny, maintain their metabolic activity to preservation of self-integrity and alternative functions beneficial to the organism as a whole.

Quiescent cells sustain DNA damage and a unique gene expression program is induced upon DNA damage in quiescent cells. Cells that have withdrawn from the cell cycle do not proliferate. Such cells, which are in the $G_0$ phase of the cell cycle, are also termed post-mitotic cells, non-cycling cells, or resting cells.

Results

Figure 16:
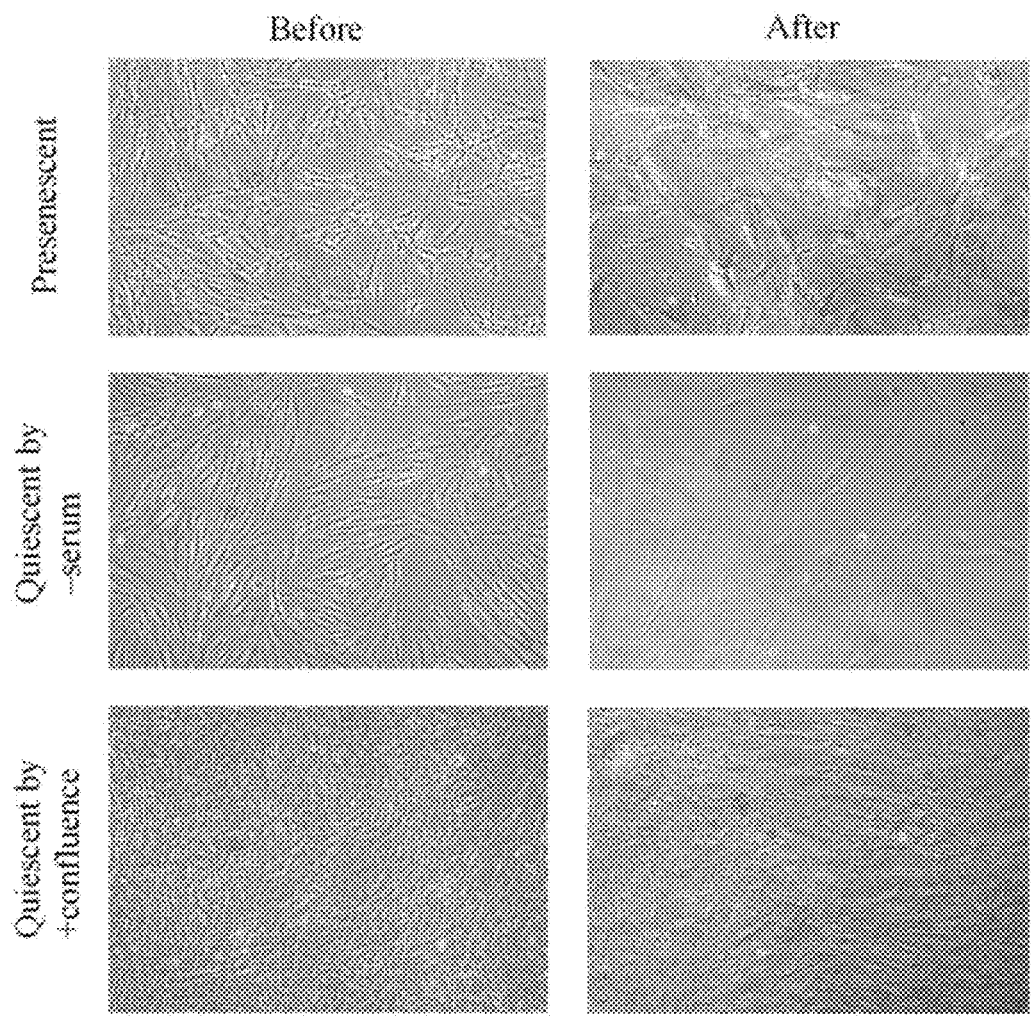
FIG. 16. Generation of quiescent cells in culture and cell morphology upon genotoxic treatment. Photographs of cells in proliferation, cells arrested by mitogen withdrawal for 4 days or contact inhibition for about 7 to 10 days. PSC27 cells in either case were exposed to a 10 Gy ionizing radiation, maintained in stromal media for 7 days. Bright field pictures were taken at a magnification of 10×. Photos are representative of three independent experiments.
Figure 17:
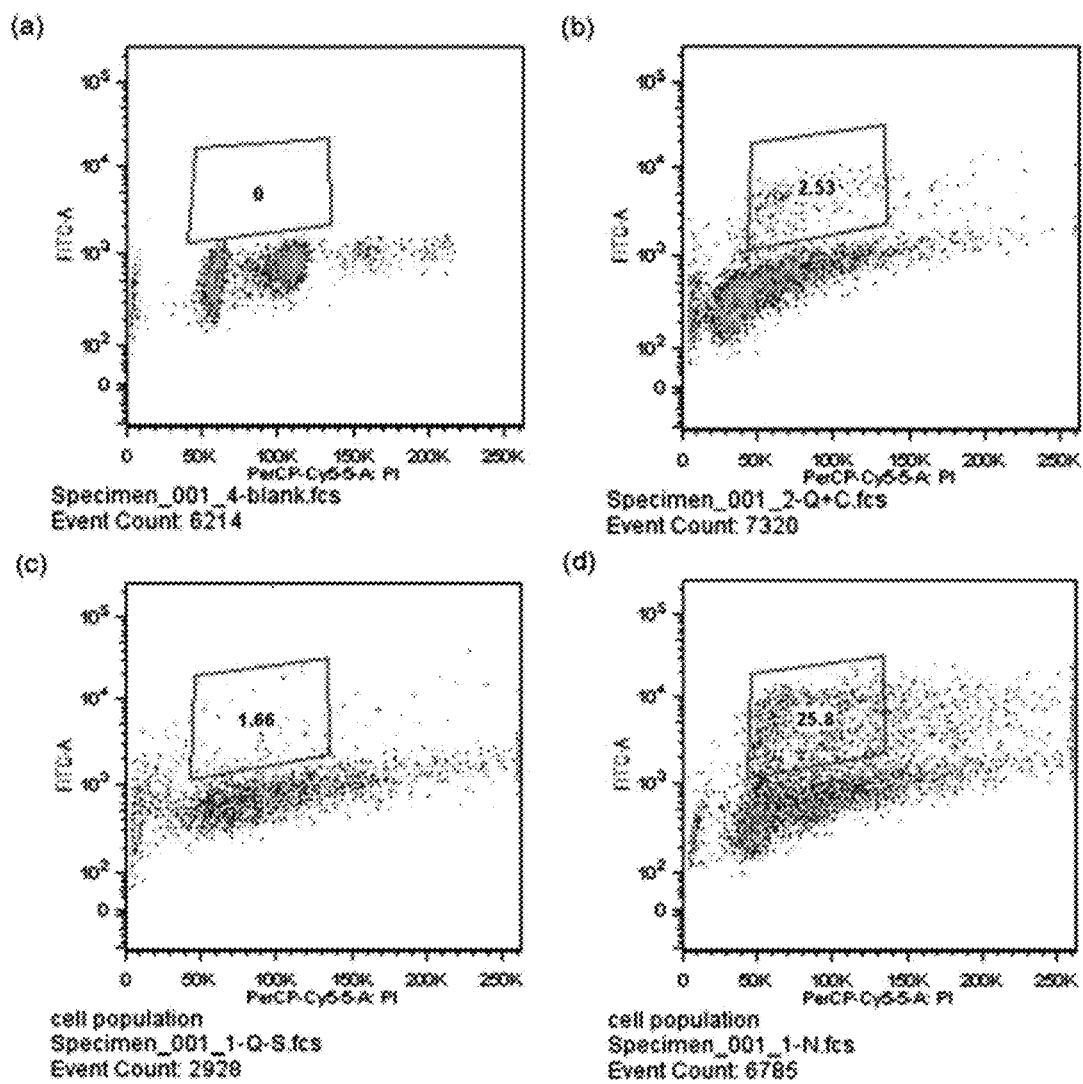
FIG. 17. Experimental model system: proliferating and quiescent cells. Proliferating cells and quiescent cells were incubated with bromodeoxyuridine (BrdU) for 6 hours. Cell nuclei were labeled with an anti-BrdU antibody and propidium iodide, and analyzed by FACS. DNA content was plotted along the x-axis, and BrdU intensity was plotted along the y axis. Percentage of cells that incorporated BrdU into their nuclei during the incubation is indicated in each case. Data are representative of three independent experiments.

Quescent Cells Sustain DNA Damage and Unique Gene Expression Program Upon DNA Damage in Quiescent Cells Cell that have withdrawn from the cell cycle do not proliferate. Such cells, which are in the $G_0$ phase of the cell cycle, are also termed post-mitotic cells, non-cycling cells, or resting cells. In this Example, human primary prostate fibroblast line, PSC27, was induced to quiescence by exposure to mitogen deprivation, or growth to maximal confluency ("contact inhibition") (FIG. 16, left panel). Each of these arrest protocols caused greater than a 90% decrease in the fraction of cells undergoing DNA synthesis, as indicated by flow cytometry of collected cells (FIG. 17). Not surprisingly, about 7 to 10 days after proliferating fibroblasts were exposed to ionizing radiation, cells exhibited typical senescence morphology, including enlarged, flattened shape, expanding nuclei and nucleoli, with multiple granular vacuoles present in the cytoplasm. In contrast, when quiescent cells generated by mitogen withdrawal were treated the same way, they exhibited elongated spindle shape, while those induced quiescent by contact inhibition remained in compact and compressed state, not in line with damaged cells that were proliferation (FIG. 16, right panel).

Figure 21:
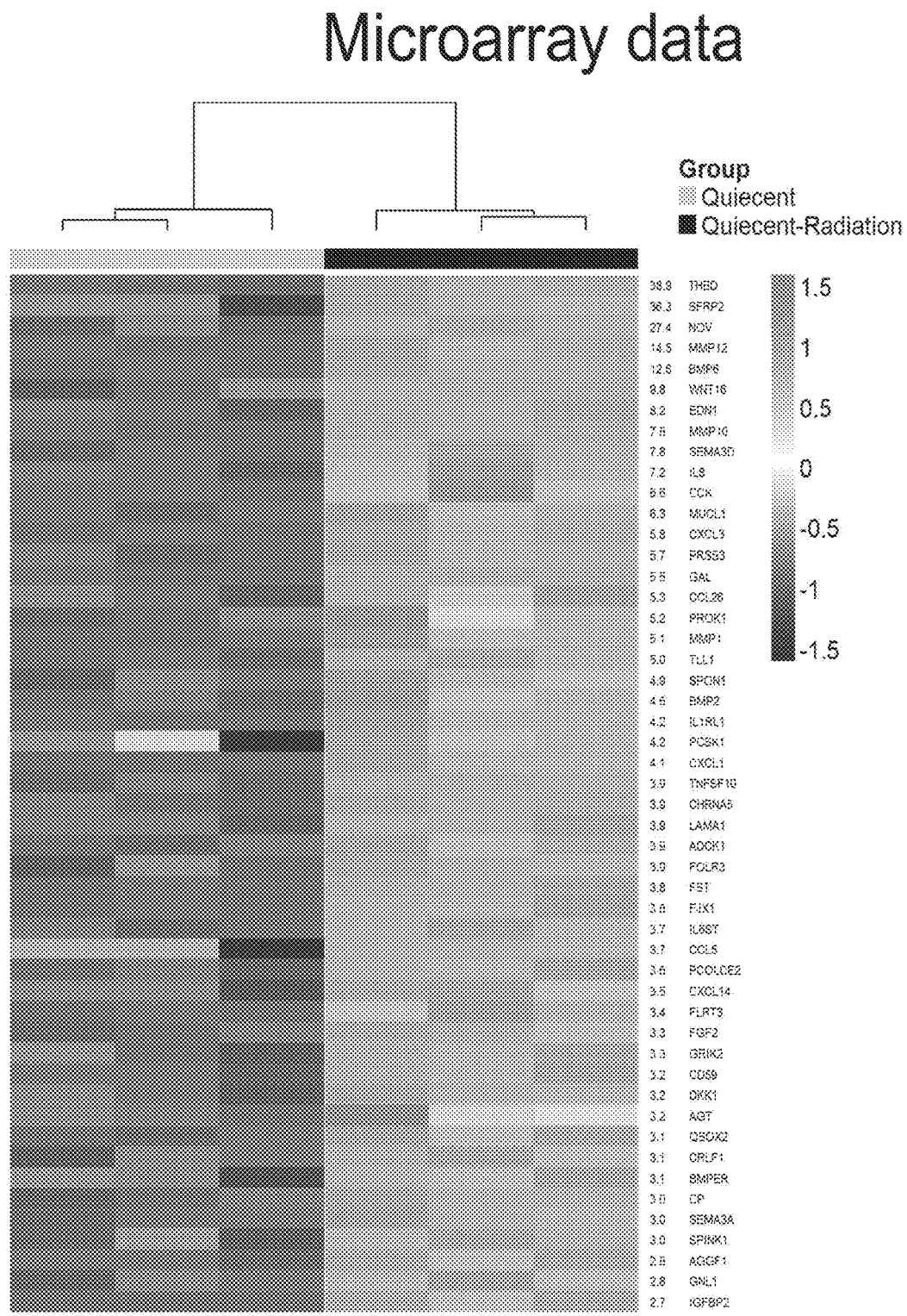
FIG. 21. Microarray patterns of gene expression in growing cells and cells arrested upon contact inhibition under the culture conditions.

Example 1 describes a stroma-specific, DNA damage secretory phenotype (DDSP) that is unique, robust and universal in human fibroblasts, and such phenotype exert profound influences to the tumor microenvironment, including but not limited to increased epithelial growth, migration, invasion and resistance to anticancer treatments. Many cells in the human body are in a reversible state of quiescence, where they have exited the cell cycle but retain the capacity to re-enter it and divide again under in vivo conditions. Quiescent fibroblasts remain highly metabolically active even though they are not dividing, and they degrade and re-synthesize protein and fatty acid, and secrete large amounts of protein into the extracellular environment (Lemons et al., *PLoS Biol* 8:e1000514, 2010). The goal of this example was to determine whether there is a novel set of genes whose expression is specifically associated with DNA damage response in the quiescent fibroblasts, as is similar to or distinct from what we have found for proliferating human prostate fibroblasts. DNA microarrays were used to compare patterns of gene expression in growing cells and cells arrested upon contact inhibition under the culture conditions (FIG. 21).

Figure 18:
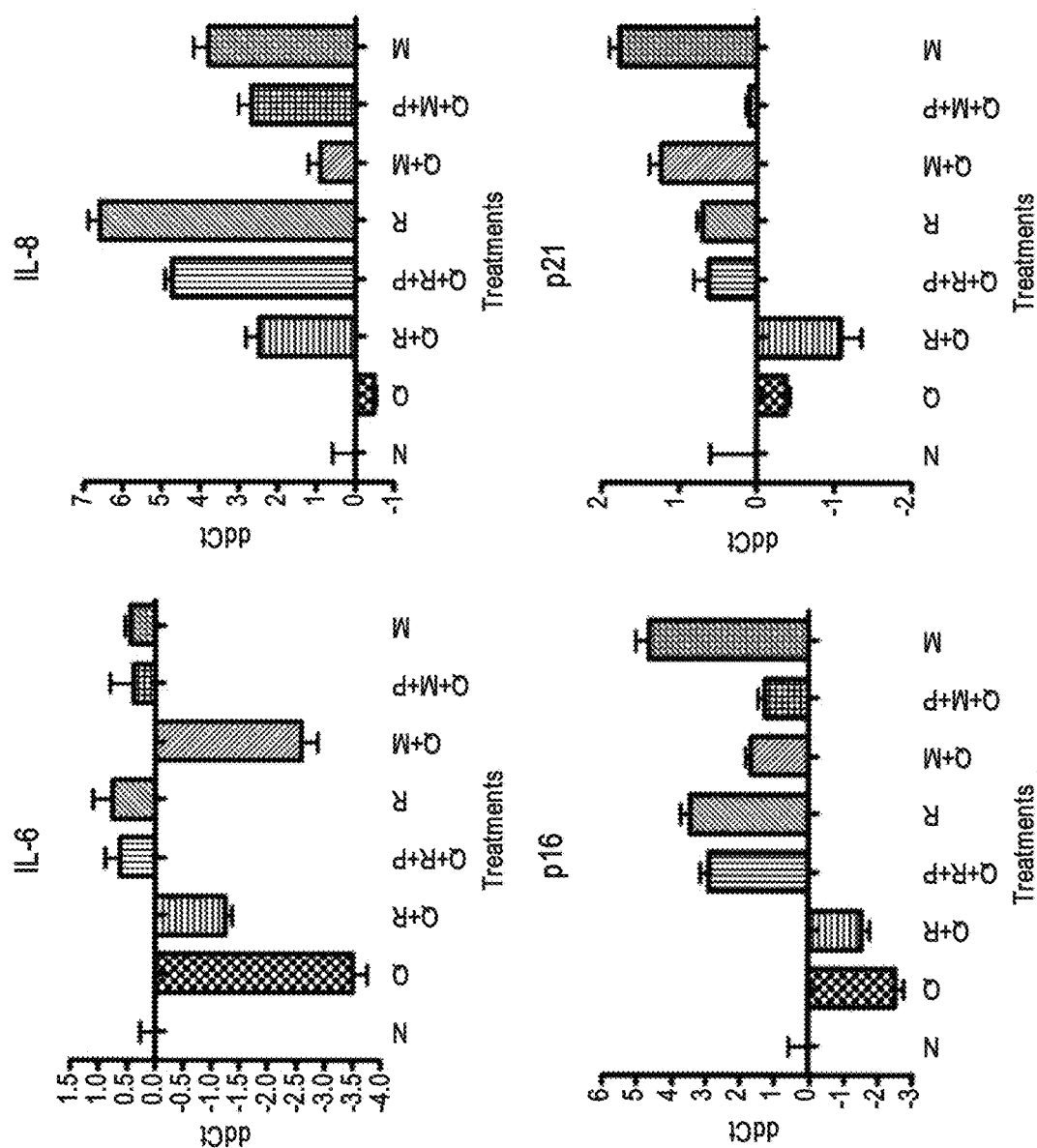
FIG. 18. Genotoxic influence on expression of senescence and proliferation-related genes in pre-senescent or quiescent PSC27 cells. Designation: N, untreated or pre-senescent cells; Q, quiescent cells; Q+R, quiescent cells exposed to ionizing radiation; Q+R+P, quiescent cells exposed to ionizing radiation, allowed to stay for 7~10 days, and released into larger vessels or sub-cultured into multiple flasks to allow resumed proliferation; R, proliferative PSC27 cells treated by ionizing radiation; Q+M, quiescent cells subject to Mitoxantrone (MIT) treatment in culture; Q+M+P, quiescent cells exposed to Mitoxantrone treatment, allowed to stay for 7 to 10 days, and released into larger vessels or subcultured into multiple flasks to allow resumed proliferation; M, proliferative PSC27 cells treated by Mitoxantrone in culture.
Figure 18:
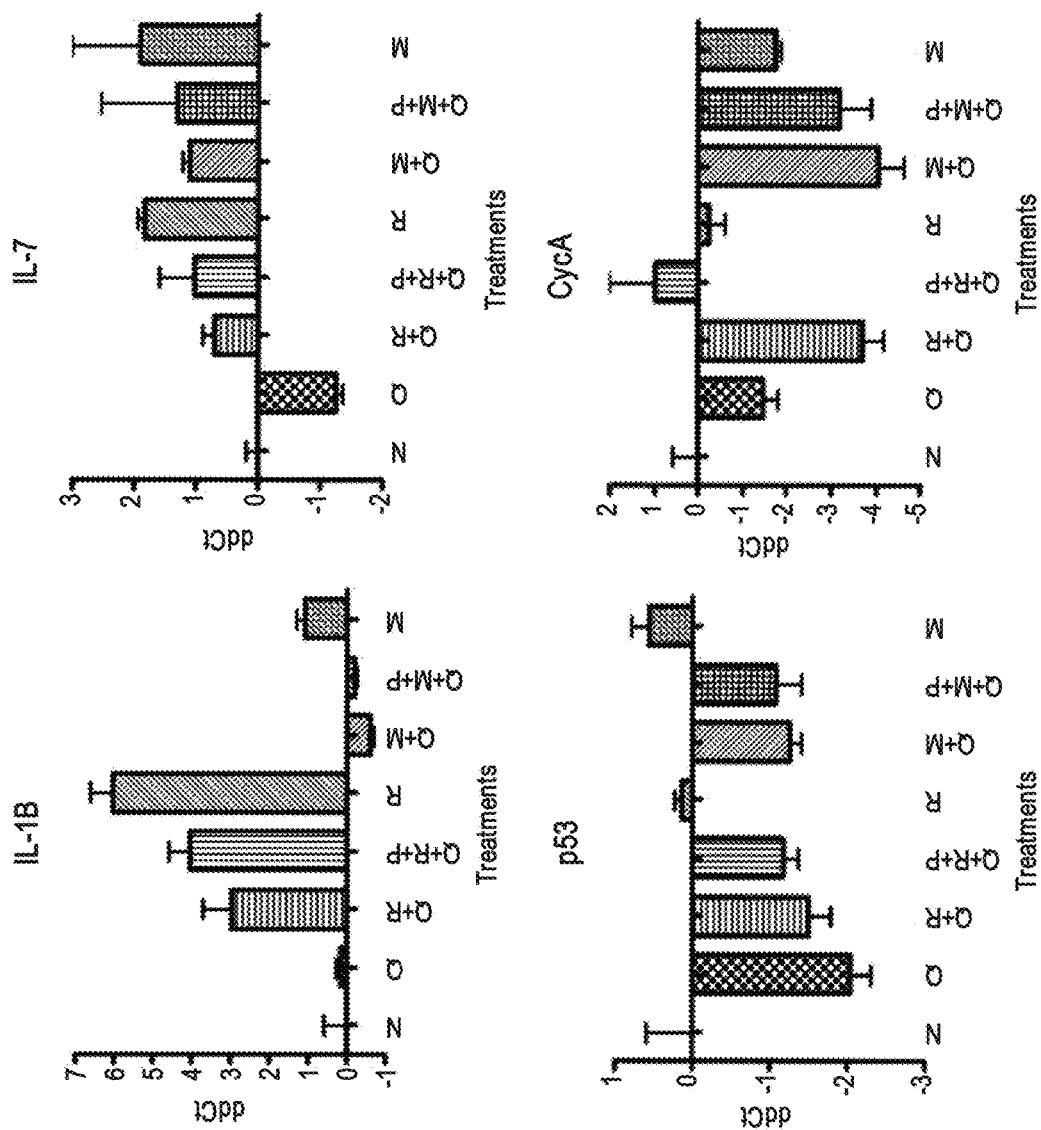
Figure 18:
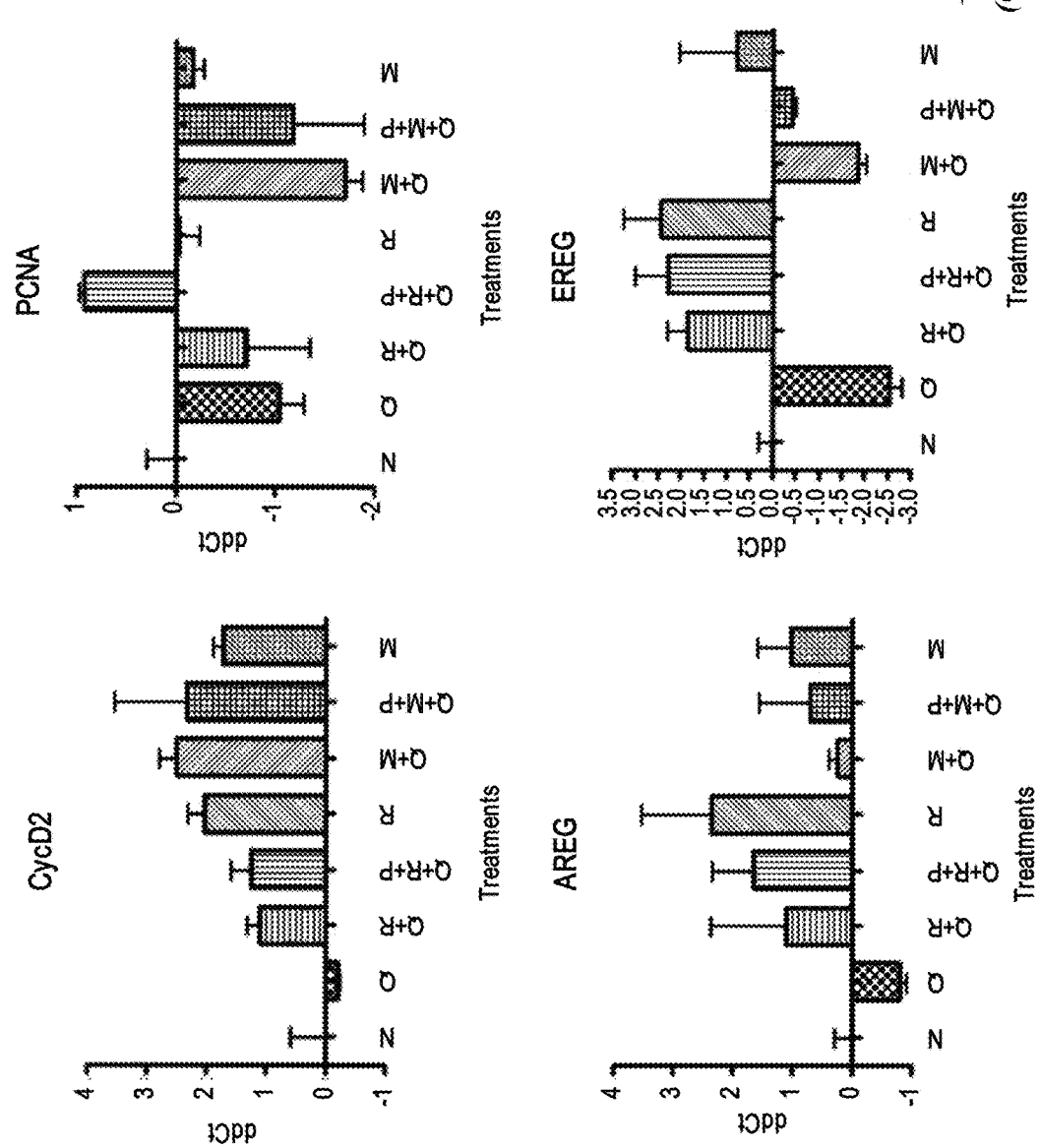
Figure 18:
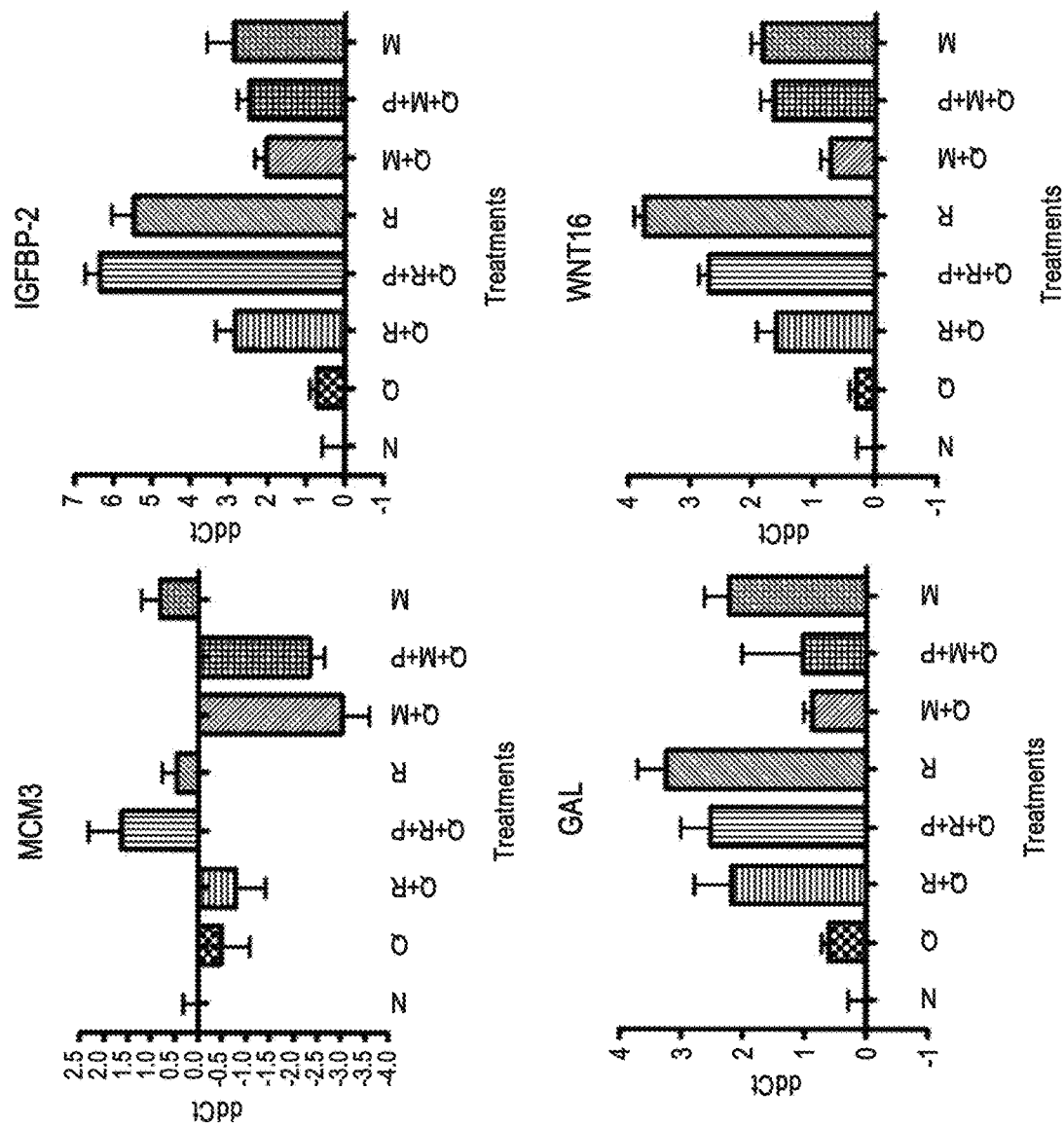
Figure 18:
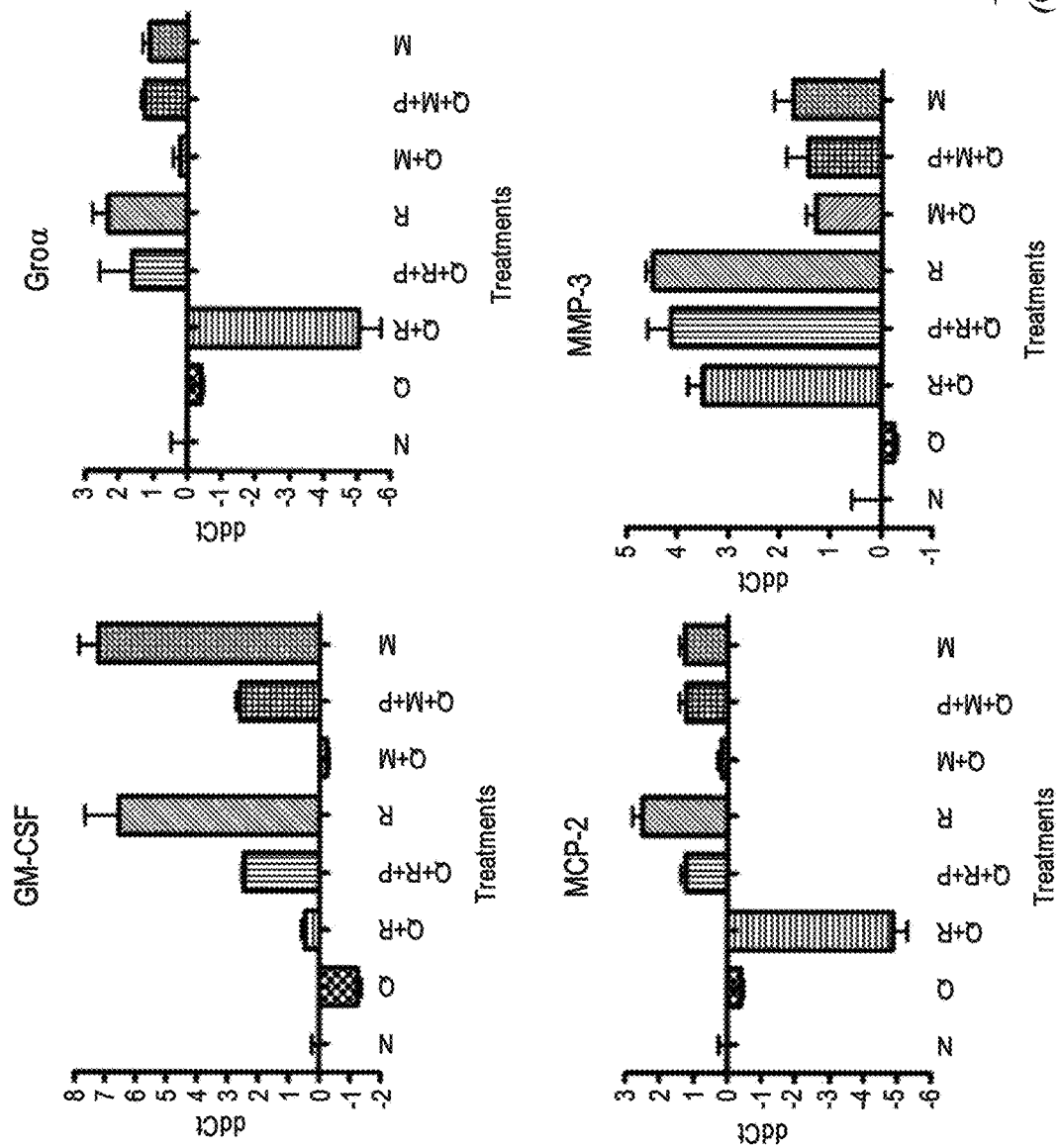
Figure 18:
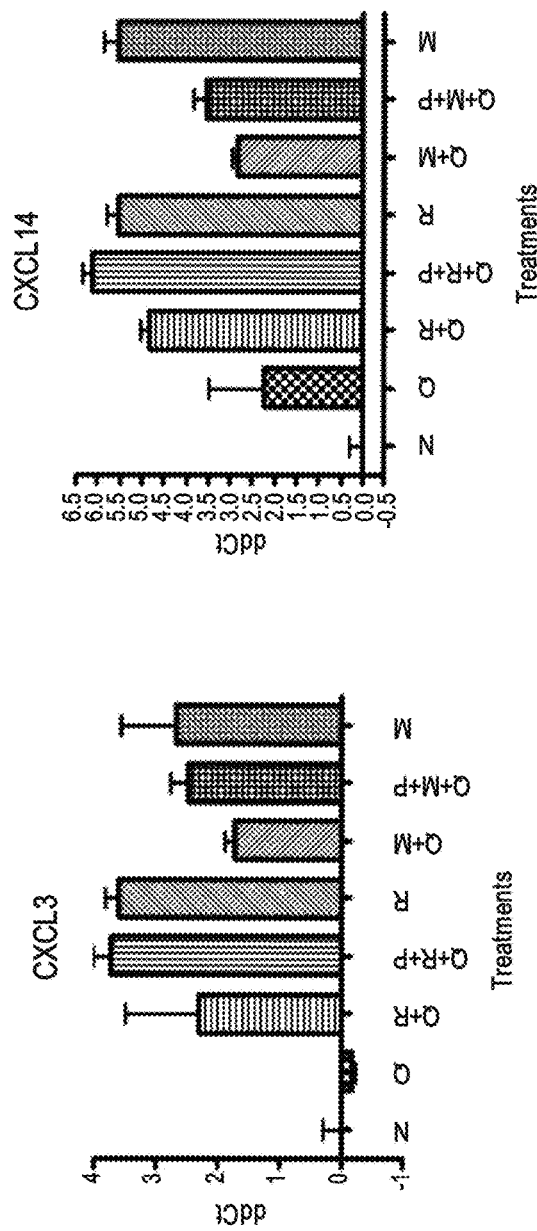
Figure 18:
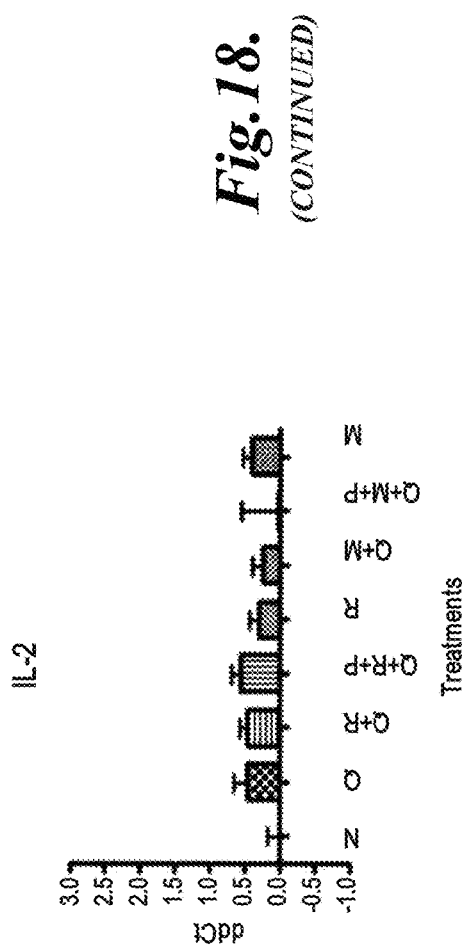

Interestingly, many of DDSP-associated genes had similar expression pattern change in quiescent cells as compared with those occurring in proliferating cells. However, their expression fold change was mostly less than that in proliferating fibroblasts, in particular IL-8, IL-1B and IL-7 (FIG. 18). In addition, atypical alteration was observed for some genes implicated in cell proliferation or cell cycle arrest, including p16, p21, p53, Cyclin A, Cyclin D2, PCNA and MCM3. Some soluble factors, including AREG, EREG, GAL, MMP3 and WNT16B exhibited similar tendency with cytokines, although GM-CSF, Groa and MCP2 were differentially regulated, potentially by some other mechanisms. As a negative control, IL-2 expression did not change substantially, suggesting the DNA damage-induced gene expression change does not cover the entire spectrum of cytokines or secreted factors, instead, only a handful of the total extracellular proteins.

It is established that quiescent cells are reversibly growth-arrested, and can be induced to resume proliferation under certain conditions including exposure to growth factors, cytokine, hormones, or chemical agents, thus distinct from terminally differentiated cells that are definitively withdrawn from the cell cycle. To examine whether such cells are able to follow the complete expression fold change as proved by stromal cells damaged in the proliferative phase, the quiescent cells were released from $G_0$ after they were subject to DNA damage, by allowing them to reestablish in vessels of larger growth area or subcultured into multiple vessels. Interestingly, majority of them were able to reach a full expression fold change when normalized to their basic status, quiescence, as compared with proliferating stromal cells exposed to DNA damaging agents. Clearly, this demonstrates that quiescent cells retain their proliferative potential and DDSP development capacity once allowed to exit from their $G_0$ phase.

Figure 19:
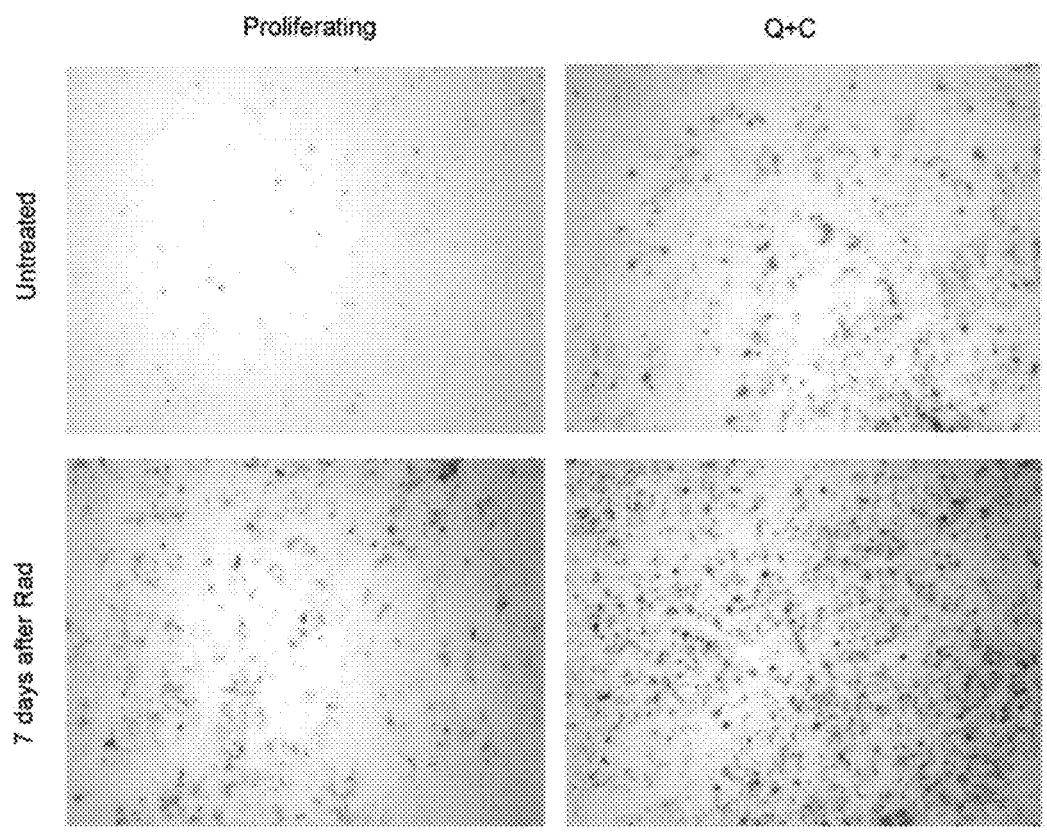
FIG. 19. Senescence associate β-Gal staining of prostate fibroblasts and senescence of quiescent cells. PSC27 cells were either untreated or treated by 10Gy radiation, processed for typical senescence associated β-Gal staining. For each case, cells were stained for 12 hours under culture conditions, and the photos are representative of three independent experiments.

Quiescent Cells can be Senescent and Reserve Intact DNA Damage Response Although quiescent cells are not proliferating, do they respond by entering senescence when exposed to DNA damaging agent? To address this, the phenotype of PSC27 cells was examined after treatment with ionizing radiation by applying senescence-associated β-Gal (SA-B-Gal) staining, an indicator of cellular senescence, and found quiescent cells demonstrated significantly enhanced staining about 7 to 10 days after DNA damage (FIG. 19). Not only the percentage of positively stained quiescent cells before treatment as a basal control is close to that of proliferating cells, but the ratio of SA-B-Gal stained cells resembles that of the PSC27 fibroblasts upon radiation.

Figure 20:
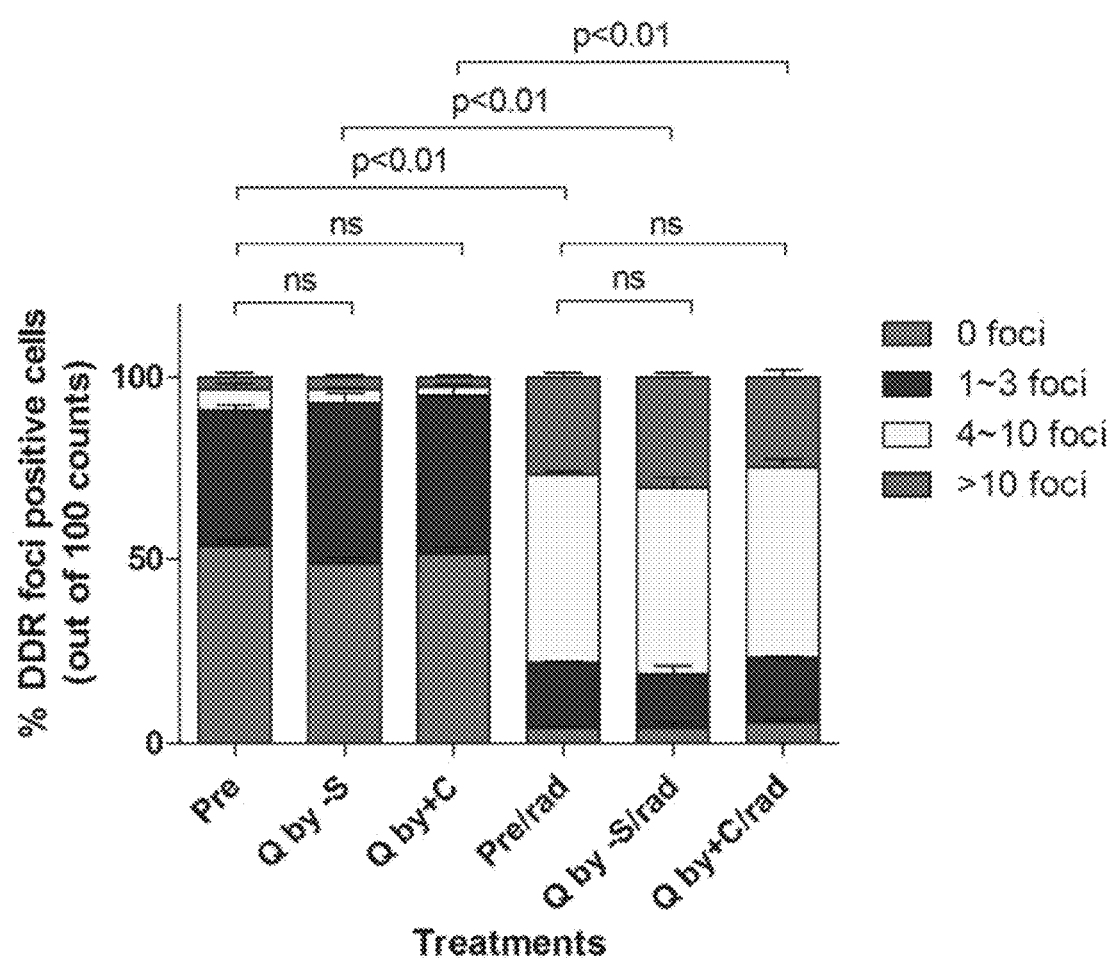
FIG. 20. Characterization of DNA damage response by immunofluorescence staining on DNA double strand lesions. PSC27 fibroblasts on coverslips were rinsed, subjected to fixation in 4% paraformaldehyde and permeabilization with 0.1% Triton-X100 prior to immunostaining Primary mouse monoclonal anti-phospho-Histone H2A.X (Ser139) (clone JBW301) and secondary antibody conjugated with Alexa Fluor® 488 (or 594) were sequentially applied. Nuclei were counterstained with DAPI and coverslips were mounted onto glass slides. Upon visual examination of the DNA damage extent with immunofluorescence microscopy, DDR foci were recorded with a 4-category counting strategy, namely 4 classes: 0 foci, 1 to about 3 foci, 4 to about 10 foci, and >10 foci as above in Example 1. Data from each cell line/treatment were averaged from a pool of 3 independent fields counting 100 nuclei per pool. P values are calculated by student's t test.

Following this, the extent of quiescent cells in activation of a typical DNA damage response (DDR) was examined by applying immunofluorescence staining with γ-H2AX antibody on cells maintained under culture conditions. Quiescent cells induced by either mitogen withdrawal or contact inhibition have similar formation of DNA damage foci, suggesting quiescence itself does not cause lesions to DNA strands; more importantly, once cells were exposed to radiation, quiescence cells exhibited robust DDR activation, and there was no significant difference between proliferating and quiescent fibroblasts (FIG. 20).

Example 4

In this example, the DDSP component, glial cell line-derived neurotrophic factor (GDNF), is examined for its growth promoting, pro-invasive, and resistance-inducing potential. Importantly, cancer stem cells are known to respond to specific molecular cues from their cellular niche. It is likely that the microenvironment-derived DDSP components, including GDNF, exert potent pro-survival and therapy-resistance phenotypes in prostate cancer stem cells and these effects will be determined using in vitro and in vivo assays. In proof-of-principle studies, Wnt16B was identified as the first active component in the DDSP with therapy-resistance activity. However, Wnt16B only accounted for about ⅓ of the DDSP induced effects. Thus, additional components secreted by the tumor microenvironment upon DNA-damage are being examined, which act in an additive or synergistic manner to Wnt16B and/or GDNF. Preliminary data from Example 1 demonstrated that GDNF exerted proliferation-inducing effects on both epithelial cancer cells as well as on the damaged tumor stroma itself.

Glial cell line-derived neurotrophic factor (GDNF) was identified as one of the secreted factors of the DDSP in human prostate tumor microenvironment upon DNA damage (See Example 1 above). It was also identified as activated in reactive prostate cancer associated tumor stroma in a cohort of grade 3 cancers in an independent study (Dakhova et al., *Clin. Cancer Res.* 15:3979-3989, 2009). GDNF was originally identified in glioma cell supernatant as a trophic factor for dopaminergic neurons. It signals via the GDNF family receptor alpha 1 (GFRA1) and the transmembrane receptor kinase RET, activating pro-survival and pro-proliferative signaling cascades via activation of Src family kinases (SFK) and the Ras/Raf/Erk pathway. GDNF binds to GFRA1 which can activate SFK signaling if GFRA1 is in its GPI anchored form and bound to the cell membrane. The GDNF/GFRA1 complex in both its soluble form and when GPI anchored binds to the RET receptor additionally activating the MEK/Erk pathway via RET trans-activation at its intracellular domain. Adult human stem cells are tightly regulated by their cellular niche which dictates self-renewal, proliferation and precursor differentiation. Adult spermatogonial stem cells (SSCs) up-regulate the expression of the transcription factor encoding genes bcl6b, etv5 and lhx1 upon GDNF stimulation, which regulate stem cell self-renewal and proliferation (Oatley and Brinster, *Annu. Rev. Cell Dev. Biol.* 24:263-286, 2008) indicating additional roles of GDNF in stem cell regulation. If GDNF is involved in PCSC regulation remains elusive.

The mechanism(s) that promote GDNF expression upon DNA damage in prostate cancer remains ill defined. However, several studies indicate that active FGF signaling via either PI3K/Akt or MEK/Erk and subsequent activation of the transcription factor CREB lead to the induction of GDNF expression in cancer cells (Tanabe et al., *Brain Res* 1463:21-29, 2010; Tsuchioka et al., *Brain Res.* 1384:1-8, 2011; Obara et al., *Cell Signal,* 23:666-672, 2011]. FGF expression and secretion is enhanced upon DNA damage in a variety of tissues including fibroblasts and adult stem cells (Haimovitz-Friedman et al., *Cancer Res.* 51:2552-8, 1991; Harfouche et al., *Stem Cells* 28:1639-48, 2010; Wondergem et al., *Atherosclerosis* 175:59-67, 2004), suggesting a DNA damage induced, FGF/CREB mediated GDNF inducing control mechanism. However, this mechanism awaits experimental verification in CaP.

Figure 22:
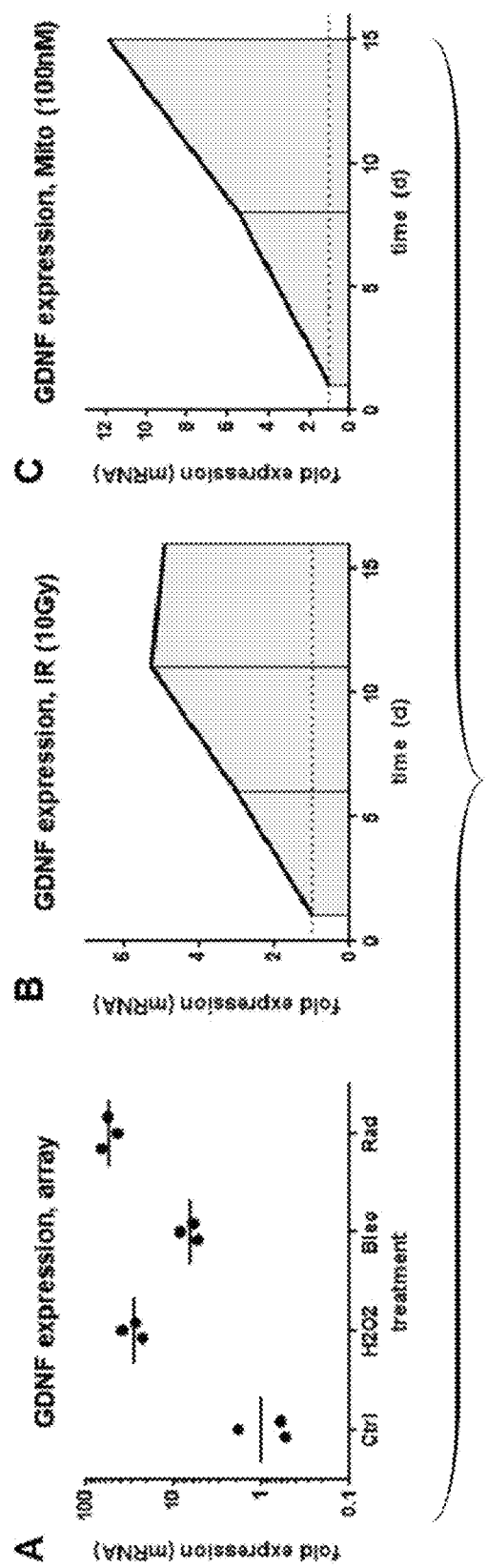
FIGS. 22A through 22C. Induced GDNF expression in PSC27 cells upon DNA damage.

GDNF expression was increased in these experiments by at least 6-fold in all of the three DNA damaging conditions (FIG. 22A). We confirmed the induction of GDNF expression was confirmed by qPCR in independent experiments in primary human prostate fibroblasts (PSC27 cells) and also included a treatment group with Mitoxantrone, a drug originally used in the neo-adjuvant study known to induce DNA damage by disrupting DNA synthesis and repair (FIGS. 22B and 22C). GDNF induction was consistently found upon DNA damage and GDNF expression levels gradually increase over time post treatment reaching an induction >3-fold after approximately 4 days and increasing afterwards.

Both components of the GDNF receptor complex, RET and GFRA1, are expressed in CaP in both epithelial and stromal cells as determined by IHC staining Expression of GDNF itself was only found in tumor stromal cells but not in the epithelial cancer cells in all samples analyzed, further supporting the concept that damage to components of the tumor microenvironment exerts paracrine-effects toward surviving tumor cells. An analysis of gene and protein expression showed that >95% of CaP express the RET receptor and >80% express GFRA1, indicating that the majority of CaP are, via at least one pathway, GDNF sensitive. The patient samples are being used from a neo-adjuvant study to confirm the up-regulation of GDNF in the CaP stroma by IHC and qPCR using RNA from microdissected tumor stroma after DNA damaging therapy.

Figure 23:
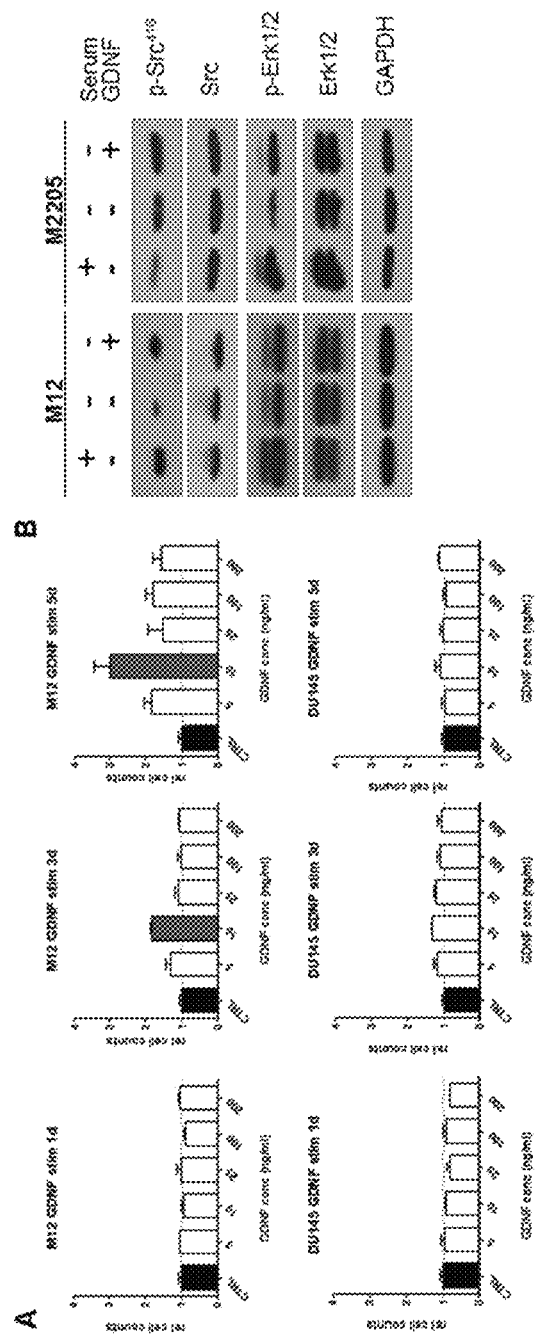
FIGS. 23A and 23B show that prostate cancer cell lines respond to GDNF stimulation and activate Src and Erk pathways.

To study the effect GDNF has on tumor growth, we have used two experimental approaches have been used. 1) the effect of purified GDNF on cell proliferation of epithelial cells was analyzed and 2) GDNF over-expressing and secreting human prostate fibroblasts were generated which can also be used in co-culture and in vivo experiments. Stimulation of epithelial CaP cells with increasing concentrations of GDNF induced cell proliferation in cell lines expressing GFRA1 alone or GFRA1 in combination with RET whereas double negative epithelial cell lines did not show any increase in proliferation (FIG. 23A). GDNF can act in the absence of RET via GFRA1 activating SFK pathways or through the activation of the RET/GFRA1 complex activating the Ras/Raf/Erk pathway. In our experiments we determined that both pathways were activated in GDNF sensitive cell lines (FIG. 23B). These data shows that the DNA damage in tumor stroma can cause increased proliferation and survival in prostate cancer cells via the secretion of GDNF. The number of epithelial cell lines are being expanded and analyzed after GDNF stimulation. GDNF-activated SFK and Erk pathways can lead to reduced sensitivity to pro-apoptotic treatments or decrease drug sensitivity.

Figure 24:
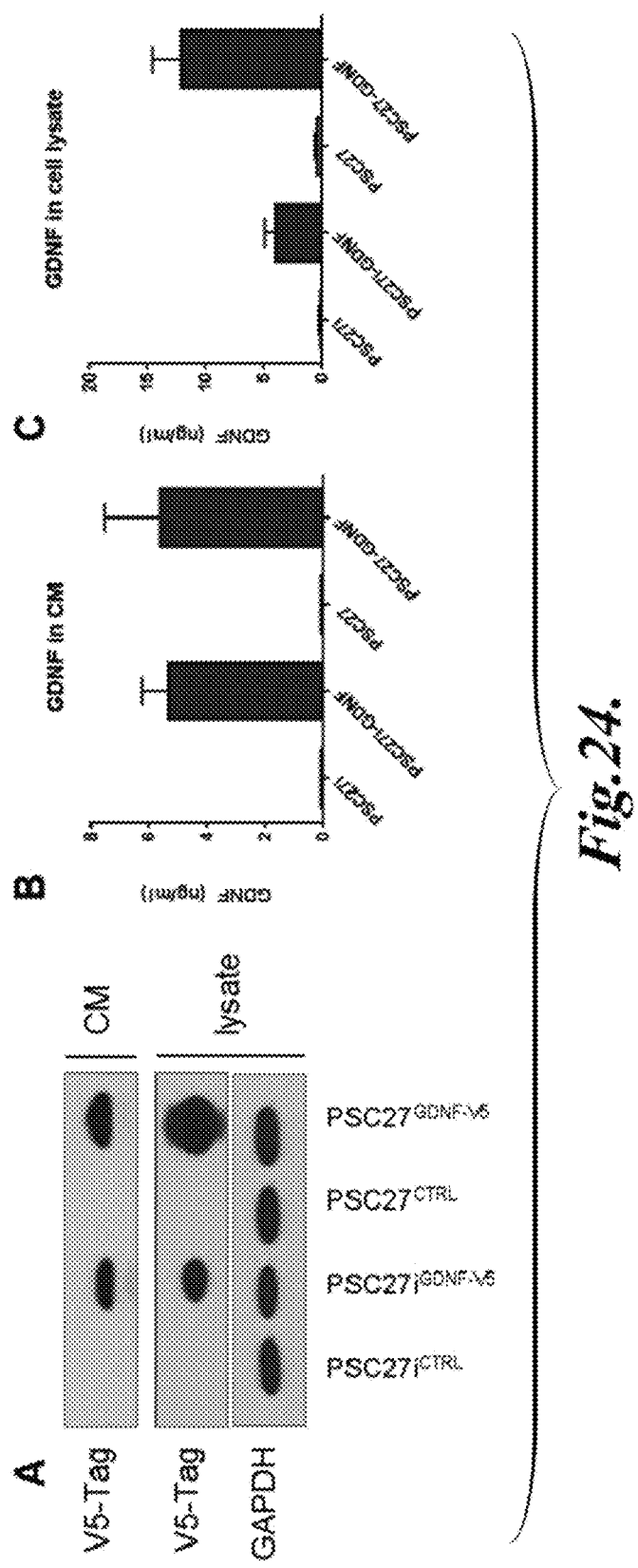
FIGS. 24A through 24C show human primary prostate stromal cells PSC27 over-expressing GDNF. PSC27 cell transduced with GDNF-V5 expression construct.
Figure 25:
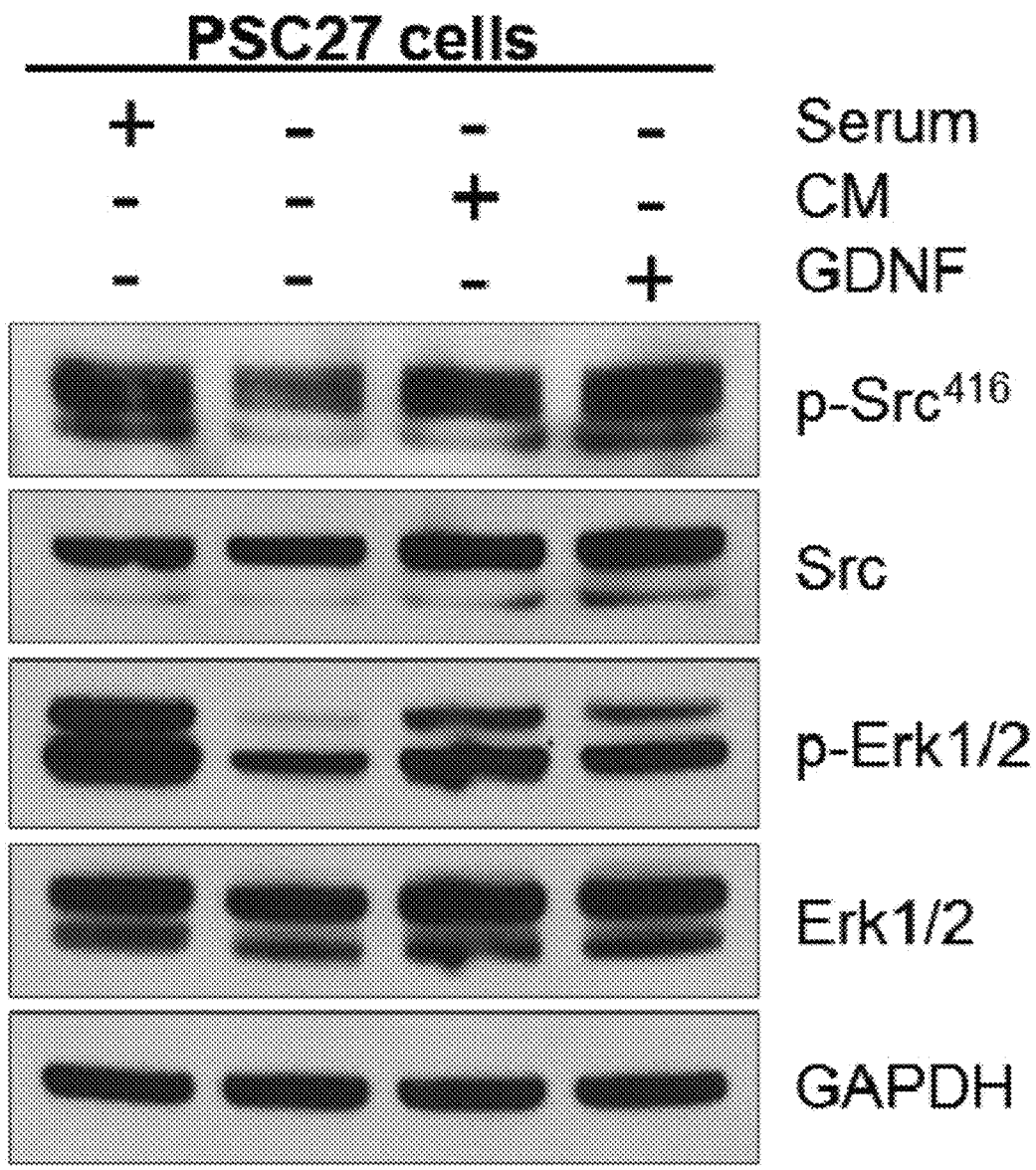
FIG. 25. GDNF induces mitotic signaling in human stromal cells PSC27. Human primary prostate fibroblast cell stimulated with human recombinant GDNF or conditioned medium from GDNF over-expressing cells show activation of the Ras/Raf/Erk and the SFK pathways, similar to the response in epithelial cancer cells.

Stimulation of epithelial CaP cells with GDNF leads to the activation of the SFK and the Ras/Raf/Erk pathways (FIG. 25). To determine if the same pathways are involved in the pro-proliferative effect on the PSC27 stromal cells, PSC27 cells were stimulated with hrGDNF or conditioned medium from PSC27/iGDNF-V5 cells. The results show, that the same pathways activated in epithelial cells are also stimulated by both purified GDNF and CM in stromal cells (FIG. 24). Additional more downstream effector proteins potentially involved in these effects are also being examined.

The GDNF over-expressing cell lines can be used to determine the role of this growth factor in prostate cancer progression and therapy resistance: i) co-cultures with epithelial cells can be used to determine the growth changing effect these cells have on prostate cancer. Based on these results, ii) epithelial CaP cells can be implanted in a mix with the PSC27/iGDNF-V5 cells either subcutaneously or into the renal capsule of immune-compromised mice to analyze in vivo growth differences. These tumors can be further used to analyze the effect GDNF has on the tumor micro-architecture, gene expression and vascularization. iii) the conditioned medium of these cells can be used to analyze the effect GDNF has on epithelial cell proliferation and in particular treatment resistance.

Figure 26:
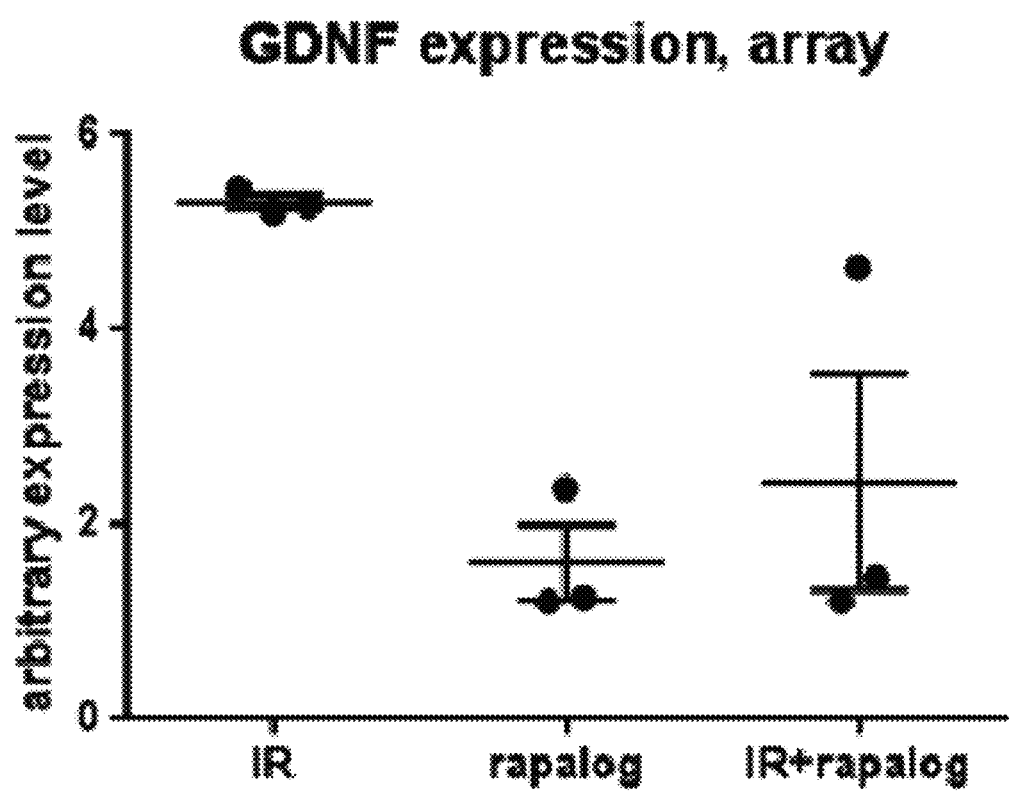
FIG. 26. GDNF induction upon DNA damage is mTOR dependent. Up-regulation of GDNF upon DNA damage is reduce when mTOR activity is blocked by rapalogs. Gene expression data from microarray comparing GDNF mRNA levels post irradiation (IR), after rapalog treatment and after irradiation and rapalog treatment. (lines: mean with SEM).

DNA damage activates multiple DNA repair, cell cycle arrest and signaling cascades. In the case of Wnt16B it was shown that the activation of the NF-kB pathway led to the induction and secretion of Wnt16B. (See Example 1 above). For GDNF, FGF signaling has been suggested to induce expression upon DNA damage. If primary prostate stromal cells are treated with a mTOR-inhibiting Rapamycin analog (rapalog), the induction of GDNF is greatly reduced or, in some cases, even completely blocked (FIG. 26). mTOR function is known to control translation initiation and this effect can be highly mRNA species specific, however, it also affects gene expression at the transcription level. Rapalog treatment does not block transcription in these cells in toto. For example, MYC expression is unaffected upon rapalog treatment in the above data set. Therefore, the mechanism(s) by which mTOR inhibition suppresses GDNF transcription will be evaluated. Further analysis of whether pre-treatment of stromal cells and stromal-epithelial cell mixtures with rapalogs blocks the induction of the DDSP or DDSP components and thereby would limit the growth stimulating effects of, among others, GDNF and Wnt16B can also be examined.

Wnt16B expression is induced by NF-kB signaling upon DNA damage (See Example 1 above). When human prostate stromal cells are treated with a NF-kB inhibitor, this blocks the induction of Wnt16B, however, GDNF gene expression is not affected. This indicates that there are at least two different, additive mechanisms controlling the expression of DDSP components after DNA damage. The two regulatory mechanisms via NFkB and mTOR control the DDSP can be examined.

GDNF and Wnt16B are but two out of >30 components of the DNA damage response program with the potential to influence tumor phenotypes. The above studies indicate that specifically co-targeting GDNF- and Wnt-mediated signaling in the context of conventional cytotoxic modalities has the potential to diminish therapy resistance.

Optimizing radiotherapy and chemotherapy for the treatment of malignant neoplasms has relied on the iterative development and testing of models involving tumor growth dynamics, mutation rates, and cell-kill kinetics. Unfortunately, the most theoretically-effective tumoricidal strategies must be tempered by detrimental effects toward the host. This reality has led to regimens in which therapies are administered at intervals or cycles to avoid irreparable damage to vital functions. However, the recovery and repopulation of tumor cells between treatment cycles is a major cause of treatment failure (Kim and Tannock, *Nat. Rev. Cancer* 5:516-525, 2005; Tredan et al., *J. Natl. Cancer Inst.* 99:1441-1454, 2007). Interestingly, rates of repopulation have been shown to accelerate in the intervals between successive courses of treatment, and it is common for solid tumors to show initial responses followed by re-growth and subsequent resistance to further chemotherapy. Previous results indicate that damage responses in benign cells comprising the tumor microenvironment may directly contribute to enhanced tumor growth kinetics. As outlined above, tumor repopulation probably occurs via activation and selection of resistant cells or PCSC. The accelerated re-growth after treatment cycles can indicate refined selection for cells not responding to treatment or for cells more responsive to DDSP components (or a combination of both). GDNF induces stem cell renewal and proliferation and anti-cancer treatment resistance in other cancer types, indicating a potential role for GDNF in the tumor repopulation of CRPC (Plaza-Menacho et al., *Oncogene,* 29:4648-4657, 2010; Hansford and Marshall, *Neurosci. Lett.* 389:77-82, 2005; Kubota Et al., *Proc. Natl. Acad. Sci. USA,* 101:16489-16494, 2004).

These findings support several conclusions: first, the outcomes of genotoxic exposures to any specific benign or neoplastic cell depend on the integration of innate damage response capabilities and the context of the TME; second, although intrinsic drug resistance is clearly operative in some cancers, acquired resistance can also occur without alterations in intrinsic cellular chemosensitivity (Davis and Tannock, *Lancet Oncol.* 1:86-93, 2000), and the results on GDNF and Wnt16B provide strong support for previous studies that implicate the tumor microenvironment as an important contributor (Meads, et al., *Clin. Cancer Res.* 14:2519-2526, 2008); third, the composition of the microenvironment damage response indicates a potential to promote resistance to pathway-targeted agents such as EGFR inhibitors as these drugs must contend with damage-enhanced local concentrations of competing ligands. Finally, specific effector proteins such as GDNF or Wnt16B represent attractive microenvironment targets that may avoid side-effects of more general therapeutics. However, the complexity of the damage response program also supports strategies focused on upstream master regulators, such as NFκB (Chien et al., *Genes Dev.,* 25:2125-2136, 2011.) and mTOR, that can be more efficient and effective adjuncts to cytotoxic therapies, provided side-effects are tolerable. The exact interplay between GDNF, Wnt16B and the remaining DDSP components can be defined by these methods.

The effect of GDNF and other individual key DDSP components on prostate cancer cell proliferation, migration and treatment resistance in vitro and in vivo can be determined.

The study performed on Wnt16B in Example 1 has served as a model for the analysis of GDNF and additional DDSP components. Using the above findings as a staring point, the analysis of GDNF (and other factors) can be analyzed. For example, GDNF expression and secretion in patient samples can be examined after treatment to confirm GDNF activation in an expanded cohort. In parallel, additional human primary fibroblasts can be tested for the up-regulation of GDNF after DNA damage, also expanding to stromal cells from other cancer types like breast cancer. The effect GDNF has on the $IC_{50}$ concentrations of standard chemotherapeutics and irradiation in both epithelial and stromal cells can be analyzed to determine a potential pro-resistance effect. The PSC27/iGDNF-V5 cells can be used to analyze the effects of GDNF through in vitro co-culture experiments, which form the basis for the subsequent in vivo analysis (as described below). The effect GDNF has on global gene expression in stromal and epithelial cells can be examined to identify factors of the DDSP controlled by GDNF or functionally related to the observed phenotypes (MMPs, MDR genes, and the like). The expression data shown above after rapalog treatment can be used to expand the analysis of how GDNF is regulated, primarily focusing on mTOR and FGF signaling. The analysis can also be expanded to other cancer types, primarily to breast cancer. A particular emphasis will be given to the analysis of the effects of GDNF and other DDSP components on PCSC. The Lin−; Trop2+; CD49f+ (LTC+) cell population has been shown to have PCSC characteristics in CaP. These cells can be analyzed in respect of prostasphere (indicative of stem cell differentiation) or cancersphere formation, matrigel 3D sphere formation capacity and trans-well invasion potential when inoculated with GDNF or using GDNF as chemo-attractant. PSC27 prostate fibroblasts can be transduced with shRNA targeting GDNF, RET and GFRA1 using a lenti-viral strategy. This will provide a more in depth analysis in co-culture experiments as well as in co-culture in vivo models. Co-cultures of CaP cells and stable target knock-down or over expression stromal cells (shRNA or pLX304-GDNF-V5) can be implanted into the renal capsule of immunocompromised SCID mice. Xenograft growth can be monitored at least bi-weekly for up to 12 weeks. At termination, tumors can be analyzed for mitotic figures, vascularization, weight, volume, and marker expression. Histological analysis and re-culturing can be done depending on the initial findings.

DDSP components can be analyzed for Wnt16B additive or synergistic effects. Based on our current data, Wnt16B contributes approximately ⅓ of the growth promoting effect of the DDSP. The effect of GDNF can be quantified as a fraction of the full DDSP. GDNF might also act in an additive or synergistic effect together with Wnt16B. For example, the initial screen performed above identified SFRP2 as substantially induced by DNA damage. SFRP2 has traditionally been thought to function as a Wnt-signaling antagonist, but the studies above indicate that SFRP2 promotes Wnt16B effects toward frizzled receptor signaling. Therefore, siRNA knock-down screen can be performed for active DDSP components on "benign" fibroblasts, PSC27shRNA-Wnt16B and PCS27shRNA-GDNF cells enabling the detection of elements which induce a significant change in this setting even if they are not detectable when knocked down alone. PSC27shRNA-Wnt16B and PCS27shRNA-GDNF cells can be transfected with siRNA targeting individual DDSP components leading to the simultaneous loss or down regulation of two DDSP components. Once achieved, these cells can then be used to generate conditioned medium after DDSP induction or for co-culture experiments. Since the effects of Wnt16B have been scrutinized before, the readout will be relatively simple as it will be de facto a single factor problem. All experimental approaches as outlined above are also applicable to this study.

Since these screens can be performed mostly using in vitro systems, it will be important to confirm DDSP component candidate expression in human tumor samples. A candidate component will be analyzed for expression by IHC in samples of prostate tumors after neoadjuvant therapy with DNA damaging agents with confirmed DDSP induction.

The effect of the full DDSP on PCSC and the potential to induce stem like characteristics in non-stem like cancer cells can be determined. Stem cells closely interact with their surrounding niche and reciprocal signal exchange is a key component of SC regulation. Thereby, the niche is both necessary and required to maintain the characteristics of non-transformed SC in various tissues and organs. Several components of the DDSP, including GDNF, likely modulate adult SC function, and the DDSP can likely also influence the differential survival of PCSC following genotoxic therapy. The expression levels of stem cell markers and PCSC markers can be determined in benign and neoplastic prostate epithelial cells with and without exposure to the stromal cell factors and separately, epithelial cell DDSP program from conditioned medium. Initial markers will include Nestin, Sox2, CD133, Trop2, CD49f, ALDH1A1, Bmi-1, integrin α2β1hi, c-Met and Lin.

Approaches have been developed for isolating, propagating and characterizing prostate cancer stem cells based on lineage markers (L), Trop2 expression (T) and CD49f (C) expression. These LTC$^+$ cells show distinct features including the potential of clonal expansion, unlimited replication, sphere formation including 3D matrigel cultures or in vivo tumorigenicity. To date, it is not clear how the tumor microenvironment, and more specifically, the altered microenvironment following genotoxic damage, influences this cell population. The PCSC enhancing effects the DDSP could have on both LTC$^+$ and LTC$^-$ cells of various CaP cell lines and ex vivo cells can be examined. These examinations can involve determining if the microenvironment DDSP will enhance the establishment of tumors from individual or small numbers of LTC$^+$ versus LTC$^-$ tumor cells and assessing whether the DDSP can modulate tumor growth and survival following cytotoxic therapeutics.

Identification and exploration of "drugable" DDSP activated pathways to block or reduce tumor promoting effects in vitro and in vivo: ultimately impact the survival of patients with advanced prostate cancer. Co-targeting components of the DDSP in the tumor microenvironment or blocking the DDSP-inducing pathways will enhance the response rates of conventional genotoxic treatments. Based on the targets identified in vitro and in vivo (see above), suitable inhibitors can be found to assess the efficiency of anti-DDSP or anti-DDSP component combination strategies (e.g., anti-Wnt/β-catenin signaling, RET inhibitors and/or rapalogs to block GDNF induction). GDNF represents an attractive DDSP target as pharmacological inhibitors of the RET tyrosine kinase have been developed and one, vandetanib, was recently approved for clinical use (REF). Studies can be conducted that involve co-administration of a vandetanib (and other RET TKI inhibitors) in conjunction with the genotoxic chemotherapeutic Mitoxantrone. The primary readout will be the reduction of proliferation rates, susceptibility to therapy (apoptosis), loss of LTC$^+$ cell population, and loss of tumorigenic potential. An anti-DDSP combination therapy can be examined in vivo and subsequently in combination with chemo-therapy and radiotherapy. The renal capsule in vivo model of CaP can be used to assess the in vivo applicability of regimens which have shown promising results in vitro. The corollary will involve the examination of antagonism of upstream 'master regulators' of the DDSP, rather than specific individual effector proteins that can be targeted. For example, evidence is provided above that mTOR regulates major components of the full DDSP, and not only GDNF, and that mTOR inhibitors such as rapamycin or RAD001 effectively suppress key DDSP proteins including Wnt16B. As such, RAD001 can be combined, to suppress the microenvironment DDSP with or prior to genotoxic therapy (e.g., mitoxantrone) to assess for enhanced tumor regression.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for enhancing the effectiveness of a genotoxic cancer therapeutic comprising:
   administering the genotoxic cancer therapeutic to a subject, wherein administration of the genotoxic cancer therapeutic induces activity of a gene encoding a DNA damage secretory polypeptide or protein (DDSP) into a tumor microenvironment by a benign cell; and
   administering an agent that inhibits the activity of the gene encoding the DDSP polypeptide or protein subsequent to treatment of the subject with the genotoxic cancer therapeutic.

2. The method according to claim 1, wherein the DDSP polypeptide or protein is matrix metallopeptidase 1 (interstitial collagenase) (MMP1), Wingless-type MMTV integration site family member 16B (WNT16B), secreted frizzled-related protein 2 (SFRP2), matrix metallopeptidase 12 (MMP12), serine peptidase inhibitor (Kazal type 1) (SPINK1), matrix metallopeptidase 10 (stromelysin 2) (MMP10), ectonucleotide pyrophosphatase/phosphodiesterase 5 (ENPP5), epiregulin (EREG), bone morphogenic protein 6 (BMP6), angiopoietin-like 4 (ANGPTL4), chondroitin sulfate N-acetylgalactosaminyltransferase (CSGAL-NACT), chemokine (C-C motif) ligand 26 (CCL26), amphiregulin (AREG), angioplastin 1 (ANGPT1), cholecystokinin (CCK), thrombomodulin (THBD), chemokine (C-X-C motif) ligand 14 (CXCL14), novoblastoma overexpressed protein (NOV), galanin prepropeptide (GAL), natriuretic peptide C (NPPC), family with sequence similarity 150, member B (FAM150B), cystatin SN (CST1), glial cell-derived neurotrophic factor (GDNF), mucin-like 1 (MUCL1), neuronal pentaraxin II (NPTX2), transmembrane protein 155 (TMEM155), endothelin 1 (EDN1), pregnancy specific beta-1-glycoprotein 9 (PSG9), ADAM metallopeptidase with thrombospondin type 1 motif, 3 (ADAMTS3), CD24, pro-platelet basic protein (chemokine (C-X-C motif) ligand 7) (PPBP), chemokine (C-X-C motif) ligand 3 (CXCL3), matrix metallopeptidase 3 (stromelysin 1, progelatinase (MMP3), cystatin SA (CST2), pregnancy specific beta-1-glycoprotein 8 (PSG8), procollagen C-endopeptidase enhancer 2 (PCOLCE2), pregnancy specific beta-1-glycoprotein 7 (PSG7), tumor necrosis factor (ligand) superfamily, member 15 (TNFSF15), chromosome 17 open reading frame 67 (C17orf17), calcitonin-related polypeptide alpha (CALCA), fibroblast growth factor 18 (FGF18), bone morphogenic protein 2 (BMP2), matrilin 3 (MATN3), transferring pseudogene 1 (TFP1), serpin peptidase inhibitor, clade 1, member 1 (neuroserpin) (SERPINI1), tumor necrosis factor receptor superfamily, member 25 (TNFRSF25), or interleukin 23, alpha subunit p19 (IL23A).

3. The method according to claim 2, wherein the DDSP extracellular protein is WNT16B, secreted frizzled-related protein 2 (SFRP2), serine peptidase inhibitor (Kazal type 1) (SPINK1), and/or glial cell derived neurotrophic factor (GDNF).

4. The method according to claim 1, wherein the agent that inhibits the activity of the gene encoding the DDSP polypeptide or protein subsequent to treatment of the subject with the genotoxic cancer therapeutic comprises an antisense nucleic acid that specifically binds to and inhibits the expression of the identified DDSP polypeptide or protein, a polypeptide comprising a portion of the identified DDSP polypeptide of protein that antagonizes its activity, an antibody or a fragment or derivative thereof that specifically binds to and inhibits the activity of the identified DDSP polypeptide or protein, or a chemical compound of natural or synthetic origin that modulates the expression or the activity of the identified DDSP polypeptide of protein.

5. The method according to claim 4, wherein the genotoxic cancer therapeutic is radiation, mitoxantrone or bleomycin.

* * * * *

SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
caggaaaggt catgacacac c                                              21

<210> SEQ ID NO 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
agagcagcct ggggatct                                                  18

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tctcagggac tgcaggaaat                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cccaccaaca tctgggttac                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ctccagggag taccctgcta                                                20

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
tgtgctctga tcttttctc ca                                              22

<210> SEQ ID NO 7
<211> LENGTH: 19
<212> TYPE: DNA
<213> ORGANISM: Artificial Sequence

```
<220> FEATURE:
<223> OTHER INFORMATION: Synthetic

<400> SEQUENCE: 7
aaatgcccaa cagaggtca                                                  19

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
cacggctcta ggctctgaat                                                 20

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
acagttgaaa actataggag ctacatt                                         27

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
tcgcttctgg gcaagtaca                                                  19

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
gctcctgtgc tgtgaaaaca                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tgcattctct gccttgtgtc                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gacatccccg attgaaagaa                                                 20
```

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
tttacggtag tgggggaagg                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
gacaccactg gagggtgact                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
caggtccaca tggtcttcct                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gtgcagtttt gccaaggagt                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ctctgcaccc agttttcctt                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
tgcccagaaa atgaaaaagg                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
gtgtatgtgg caatgcgttc                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
gacaatgccc ctcaagtgtt                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
ccattaagcc gagtgatggt                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gagaactttg ccgttgaagc                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
tccagcagct tcctgtaggt                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
gtccgcagtc ttacgaggag                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
ccagcttgag ggtctgaatc                                               20

<210> SEQ ID NO 27

<211> LENGTH: 20
<212> TYPE: DNA
<213> ORGANISM: Artificial Sequence
<220> FEATURE:
<223> OTHER INFORMATION: Synthetic

<400> SEQUENCE: 27 cttttcttg ccctcactgc                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
acagcagcca gattcctcat                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
agcaagaagt cgagcgaaga                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
cagcttgagc gtctggatct                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
cctgccacca agacctacat                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
cttcattcaa ggtggggaga                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
actttgcgca gtaccagagc                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
acgtcttccc gtacaccttg                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
ttcgggtagt ggaaaaccag                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
cagcagctcg aatttcttcc                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
aactacctgg accgcttcct                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
ccacttgagc ttgttcacca                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
gtacgctgtg aaggcatcaa                                               20

<210> SEQ ID NO 40
<211> LENGTH: 20
<212> TYPE: DNA

```
<213> ORGANISM: Artificial Sequence
<220> FEATURE:
<223> OTHER INFORMATION: Synthetic

<400> SEQUENCE: 40
cgctttttct tgtcgtaggg                                              20
```